United States Patent
Chambers et al.

(10) Patent No.: US 11,591,567 B2
(45) Date of Patent: Feb. 28, 2023

(54) SPECIFICATION OF FUNCTIONAL CRANIAL PLACODE DERIVATIVES FROM HUMAN PLURIPOTENT STEM CELLS

(71) Applicant: MEMORIAL SLOAN-KETTERING CANCER CENTER, New York, NY (US)

(72) Inventors: Stuart Chambers, San Francisco, CA (US); Lorenz Studer, New York, NY (US); Zehra Dincer, New York, NY (US); Bastian Zimmer, Hamburg (DE)

(73) Assignee: MEMORIAL SLOAN-KETTERING CANCER CENTER, New York, NY (US)

(*) Notice: Subject to any disclaimer, the term of this patent is extended or adjusted under 35 U.S.C. 154(b) by 0 days.

(21) Appl. No.: 16/373,026

(22) Filed: Apr. 2, 2019

(65) Prior Publication Data

US 2019/0225939 A1    Jul. 25, 2019

Related U.S. Application Data

(63) Continuation of application No. 15/159,351, filed on May 19, 2016, now Pat. No. 10,273,452, which is a
(Continued)

(51) Int. Cl.
  *C12N 5/0793* (2010.01)
  *A61K 35/12* (2015.01)
  (Continued)

(52) U.S. Cl.
  CPC ............ *C12N 5/0619* (2013.01); *A61K 35/12* (2013.01); *C07D 211/00* (2013.01);
  (Continued)

(58) Field of Classification Search
  CPC ............ C12N 5/0619; C12N 2501/155; C12N 2501/998; C12N 2506/02;
  (Continued)

(56) References Cited

U.S. PATENT DOCUMENTS

| 5,166,065 A | 11/1992 | Williams et al. |
| 5,340,740 A | 8/1994 | Petitte et al. |

(Continued)

FOREIGN PATENT DOCUMENTS

| CN | 101641436 A | 2/2010 |
| CN | 102165058 A | 8/2011 |

(Continued)

OTHER PUBLICATIONS

U.S. Appl. No. 15/159,351 (U.S. Pat. No. 10,273,452), filed May 19, 2016 (Apr. 30, 2019).

(Continued)

*Primary Examiner* — Sean C. Barron
(74) *Attorney, Agent, or Firm* — Baker Botts L.L.P.

(57) ABSTRACT

Cranial placodes are embryonic structures essential for sensory and endocrine organ development. The efficient derivation of cranial placodes from human pluripotent stem cells is disclosed where the timed removal of the BMP inhibitor Noggin, a component of the dual-SMAD inhibition strategy of neural induction, triggers placode induction at the expense of CNS fates. Further fate specification at the pre-placode stage enables the selective generation of placode-derived trigeminal ganglia capable of in vivo engraftment, mature lens fibers and anterior pituitary hormone-producing cells that upon transplantation produce hormones including, but not limited to, human growth hormone and adrenocortiocotropic hormone in vivo. Alternatively, ante- (Continued)

rior pituitary hormone-producing cells are generated in cell culture systems in vitro.

14 Claims, 120 Drawing Sheets

Specification includes a Sequence Listing.

Related U.S. Application Data continuation of application No. PCT/US2014/066952, filed on Nov. 21, 2014.

(60) Provisional application No. 61/907,302, filed on Nov. 21, 2013.

(51) Int. Cl.
  *C07D 211/00* (2006.01)
  *C07D 307/32* (2006.01)
  *C07D 243/36* (2006.01)

(52) U.S. Cl.
  CPC ......... *C07D 243/36* (2013.01); *C07D 307/32* (2013.01); *C12N 2501/119* (2013.01); *C12N 2501/13* (2013.01); *C12N 2501/155* (2013.01); *C12N 2501/41* (2013.01); *C12N 2501/415* (2013.01); *C12N 2501/727* (2013.01); *C12N 2501/734* (2013.01); *C12N 2501/998* (2013.01); *C12N 2501/999* (2013.01); *C12N 2506/02* (2013.01); *C12N 2506/45* (2013.01)

(58) Field of Classification Search
  CPC ........ C12N 2501/415; C12N 2501/119; C12N 2501/41; C12N 2501/13; C12N 2501/734; C12N 2501/999; A61K 35/12
  See application file for complete search history.

(56) References Cited

U.S. PATENT DOCUMENTS

| | | | |
|---|---|---|---|
| 5,453,357 | A | 9/1995 | Hogan |
| 5,523,226 | A | 6/1996 | Wheeler |
| 5,589,376 | A | 12/1996 | Anderson et al. |
| 6,833,269 | B2 | 12/2004 | Carpenter |
| 7,005,252 | B1 | 2/2006 | Thomson |
| 7,011,828 | B2 | 3/2006 | Reubinoff et al. |
| 7,211,434 | B2 | 5/2007 | Van Der Kooy et al. |
| 7,252,995 | B2 | 8/2007 | Fu et al. |
| 7,294,510 | B2 | 11/2007 | Okano et al. |
| 7,297,539 | B2 | 11/2007 | Mandalam et al. |
| 7,332,336 | B2 | 2/2008 | Ochiya et al. |
| 10,273,452 | B2 * | 4/2019 | Chambers .............. A61K 35/12 |
| 2005/0026747 | A1 | 2/2005 | Steen et al. |
| 2006/0078543 | A1 | 4/2006 | Reubinoff et al. |
| 2007/0037282 | A1 | 2/2007 | Takahashi |
| 2007/0270841 | A1 | 11/2007 | Badie |
| 2009/0035385 | A1 | 2/2009 | Bortz |
| 2010/0028882 | A1 | 2/2010 | Moreau |
| 2010/0062477 | A1 | 3/2010 | Yu |
| 2010/0105098 | A1 | 4/2010 | Frederiske et al. |
| 2012/0034692 | A1 | 2/2012 | D'Amour et al. |
| 2012/0094381 | A1 | 4/2012 | Chambers et al. |
| 2012/0276572 | A1 | 11/2012 | Shekdar et al. |

FOREIGN PATENT DOCUMENTS

| | | |
|---|---|---|
| JP | 2016-532598 A | 10/2016 |
| JP | 2016-538856 A | 12/2016 |
| WO | WO 2002/34286 A1 | 5/2002 |
| WO | WO 2005/017131 A2 | 2/2005 |
| WO | WO 2010/096496 A2 | 8/2010 |
| WO | WO 2013/166488 A1 | 11/2013 |

OTHER PUBLICATIONS

U.S. Appl. No. 15/159,351, Mar. 28, 2019 Issue Fee Payment.
U.S. Appl. No. 15/159,351, Dec. 28, 2018 Notice of Allowance.
U.S. Appl. No. 15/159,351, Jul. 24, 2018 Request for Continued Examination (RCE).
U.S. Appl. No. 15/159,351, Apr. 24, 2018 Notice of Allowance.
U.S. Appl. No. 15/159,351,Jan. 22, 2018 Response to Non-Final Office Action.
U.S. Appl. No. 15/159,351, Oct. 20, 2017 Non-Final Office Action.
U.S. Appl. No. 15/159,351, Aug. 25, 2017 Response to Restriction Requirement.
U.S. Appl. No. 15/159,351, Feb. 28, 2017 Restriction Requirement.
Abdelhak et al., "A human homologue of the *Drosophila* eyes absent gene underlies Branchio-Oto-Renal (BOR) syndrome and identifies a novel gene family," Nature Genetics 15:157-164 (1997).
Agarwal et al., "Efficient Differentiation of Functional Hepatocytes from Human Embryonic Stem Cells," Stem Cells, 26:1117-1127 (2008).
Ahrens et al., "Tissues and signals involved in the induction of placodal Six 1 expression in Xenopus laevis," Developmental Biology 288:40-59 (2005).
Amit et al., "Derivation and spontaneous differentiation of human embryonic stem cells," J. of Anat. 200:225-232 (2002).
Arkell et al., "BMP-7 influences pattern and growth of the developing hindbrain of mouse embryos," Development 124:1-12 (1997).
Bailey et al., "Lens Specification is the Ground State of All Sensory Placodes, from which FGF Promotes Olfactory Identity," Developmental Cell 11:505-517 (2006).
Baker et al., "Establishing neuronal identity in vertebrate neurogenic placodes," Development, 127:3045-3056 (2000).
Baker et al., "Vertebrate Cranial Placodes I. Embryonic Induction," Developmental Biology 232:1-61 (2001).
Balmer et al., "Noses and Neurons: Induction, Morphogenesis, and Neuronal Differentiation in the Peripheral Olfactory Pathway," Developmental Dynamics 234:464-481 (2005).
Barberi et al., "Derivation of engraftable skeletal myoblasts from human embryonic stem cells," Nat. Med., 13(5):642-648 (2007).
Barberi et al., "Derivation of Multipotent Mesenchymal Precursors from Human Embryonic Stem Cells," PLoS Med, 2(6):554-560 (2005).
Barberi et al., "Neural subtype specification of fertilization and nuclear transfer embryonic stem cells and application in parkinsonian mice," Nat Biotechnol. 21(10):1200-1207 (2003).
Barnett et al., "Herpes Simplex Encephalitis in the Temporal Cortex and Limbic System after Trigeminal Nerve Inoculation," J Infect Dis 169:782-786 (1994).
Bernardo et al., "Brachyury and CDX2 mediate BMP-Induced Differentiation of Human and Mouse Pluripotent Stem Cells into Embryonic and Extraembryonic Lineages," Cell Stem Cell 9:144-155 (2011).
Bhattacharyya et al., "Hierarchy of regulatory events in sensory placode development," Current Opinion in Genetics & Development 14:520-526 (2004).
Bouwmeester et al., "Cerberus is a head-inducing secreted factor expressed in the anterior endoderm of Spemann's organizer," Nature 382:595-601 (1996).
Bradley et al., "Formation of germ-line chimaeras from embryo-derived teratocarcinoma cell lines," Nature, 309:255-256 (1984).
Briscoe et al., "The specification of neuronal identity by graded sonic hedgehog signalling," seminars in Cell & Dev Biol. 10:353-362 (1999).
Callaerts et al., "PAX-6 in Development and Evolution," Annu. Rev. Neurosci., 20:483-532 (1997).
Chambers et al., "Combined small-molecule inhibition accelerates developmental timing and converts human pluripotent stem cells into nociceptors," Nat Biotechnol 30(7):715-720 (2012).
Chambers et al., "Highly efficient neural conversion of human ES and iPS cells by dual inhibition of SMAD signaling," Nat Biotechnology 27(3):275-280 (2009).
Charrier et al., "Dual origin of the floor plate in the avian embryo," Development 129:4785-4796 (2002).

(56) References Cited

OTHER PUBLICATIONS

Charron et al., "The Morphogen Sonic Hedgehog Is an Axonal Chemoattractant that Collaborates with Netrin-1 in Midline Axon Guidance," Cell 113:11-23 (2003).
Chen et al., "Chemically defined conditions for human iPSC derivation and culture," Nature Methods 8(5):424-429 (2011).
Chen et al., "Restoration of auditory evoked responses by human ES-cell-derived otic progenitors," Nature 490:278-282 (2012).
Colas et al., "Localization of cartilage linking protein 1 during primary neurulation in the chick embryo," Dev Brain Res 141:141-148 (2003).
D'Amour et al., "Efficient differentiation of human embryonic stem cells to definitive endoderm," Nat Biotechnology 23(12):1534-1541 (2005).
Dennis, Jr. et al., "DAVID: Database for Annotation, Visualization, and Integrated Discovery," Genome Biology 4:R60 (2003).
Dincer et al., "Specification of Functional Cranial Placode Derivatives from Human Pluripotent Stem Cells," Cell Reports 5:1387-1402 (2013).
Doetschman et al., "Establishment of Hamster Blastocyst-Derived Embryonic Stem (ES) Cells," Dev. Biol., 127:224-227 (1988).
Downey, T., "Analysis of a Multifactor Microarray Study Using Partek Genomics Solution," Methods in Enzymology 411:256-270 (2006).
Dupin et al. Isolation and Differentiation Properties of Neural Crest Stem Cells. Cytometry Part A (epub. Jul. 26, 2012), v83A, p. 38-47 (Year: 2012).
Dutta et al. pitx3 defines an equivalence domain for lens and anterior pituitary placode. Development (2005), vl32, Year: 2005).
Eiraku et al., "Self-Organized Formation of Polarized Cortical Tissues from ESCs and Its Active Manipulation by Extrinsic Signals," Cell Stem Cell 3:519-532 (2008).
Elkabetz et al., "Human ES cell-derived neural rosettes reveal a functionally distinct early neural stem cell stage," Genes & Development 22:152-165 (2008).
Erceg et al., "Human Embryonic Stem Cell Differentiation Toward Regional Specific Neural Precursors," Stem Cells, 27:78-87 (2009).
Ericson et al., "Two Critical Periods of Sonic Hedgehog Signaling Required for the Specification of Motor Neuron Identity," Cell 87:661-673 (1996).
Evans et al., "Derivation and Preliminary Characterization of Pluripotent Cell Lines From Porcine and Bovine Blastocysts," Theriogenology, 33(1):125-128 (1990).
Evans et al., "Establishment in culture of pluripotential cells from mouse embryos," Nature, 292:154-156 (1981).
Fasano et al., "Bmi-1 cooperates with Foxg1 to maintain neural stem cell self-renewal in the forebrain," Genes & Development 23:561-574 (2009).
Fasano et al., "shRNA Knockdown of Bmi-1 Reveals a Critical Role for p21-Rb Pathway in NSC Self-Renewal during Development," Cell Stem Cell 1:87-99 (2007).
Giles et al., "Pluripotency of Cultured Rabbit Inner Cell Mass Cells Detected by Isozyme Analysis and Eye Pigmentation of Fetuses Following Injection into Blastocysts or Morulae," Mol. Reprod. Dev., 36:130-138 (1993).
Glinka et al., "Dickkopf-1 is a member of a new family of secreted proteins and functions in head induction," Nature 391:357-362 (1998).
Graves et al., "Derivation and Characterization of Putative Pluripotential Embryonic Stem Cells from Preimplantation Rabbit Embryos," Mol. Reprod. Dev., 36:424-433 (1993).
Grigaliunas et al., "Distinctive Neurophysiological Properties of Embryonic Trigeminal and Geniculate Neurons in Culture," J. Neurophysiol 88:2058-2074 (2002).
Groppe et al., "Structural basis of BMP signaling inhibition by the cystine knot protein Noggin," Nature, 420:636-642 (2002).
Grotewold et al., "Bambi is coexpressed with Bmp-4 during mouse embryogenesis," Mechanisms of Development 100:327-330 (2001).

Hemmati-Brivanlou et al., "Follistatin, an Antagonist of Activin, is Expressed in the Spemann Organizer and Displays Direct Neuralizing Activity," Cell, 77:283-295 (1994).
Hima et al. Potency of Various Types of Stem Cells and their Transplantation. J. Stem Cell Res Ther (2011), vl(3), 1000115, 6 pages. (Year: 2011).
Huang et al., "Systematic and integrative analysis of large gene lists using DAVID bioinformatics resources," Nature Protocols 4(1):44-57 (2009).
Hunter et al., "LIM-homeodomain genes in mammalian development and human disease," Mol Biol Rep 32:67-77 (2005).
Hunter et al., "Retinoic acid stimulates neurite outgrowth in the amphibian spinal cord," PNAS 88:3666-3670 (1991).
Iannaccone et al., "Pluripotent Embryonic Stem Cells from the Rat Are Capable of Producing Chimeras," Dev. Biol., 163:288-292 (1994).
International Search Report and Written Opinion dated Apr. 17, 2015 in International Application No. PCT/US14/66952.
Ishihara et al., "Multiple Evolutionarily Conserved Enhancers Control Expression of Eya1," Developmental Dynamics 237:3142-3156 (2008).
Ivanova et al., "Dissecting self-renewal in stem cells with RNA interference," Nature 442:533-538 (2006).
Jeong et al., "A functional screen for sonic hedgehog regulatory elements across a 1 Mb interval identifies long-range ventral forebrain enhancers," Development 133:7761-7772 (2005).
Jeong et al., "Distinct regulators of Shh transcription in the floor plate and notochord indicate separate origins for these tissues in the mouse node," Development 130:3891-3902 (2003).
Jeong et al., "Regulation of a remote Shh forebrain enhancer by the Six3 homeoprotein," Nat Genet 40(11):1348-1353 (2008).
Jessell et al., "Polarity and patterning in the neural tube: the origin and function of the floor plate," Ciba Foundation Symposium 144:255-276; discussion 276-280, 290-295 (1989).
Jessell, "Neuronal Specification in The Spinal Cord: Inductive Signals and Transcriptional Codes," Nat Rev Genet 1:20-29 (2000).
Joksimovic et al., "Wnt antagonism of Shh facilitates midbrain floor plate neurogenesis," Nat Neurosci 12(2):125-131 (2009).
Kawasaki et al., "Induction of Midbrain Dopaminergic Neurons from ES Cells by Stromal Cell-Derived Inducing Activity," Neuron 28:31-40 (2000).
Kim et al., "Analysis of the Vertebrate Insulator Protein CTCF-Binding Sites in the Human Genome," Cell, 128:1231-1245 (2007).
Kimura-Yoshida et al., "Crucial roles of Foxa2 in mouse anterior-posterior axis polarization via regulation of anterior visceral endoderm-specific genes," PNAS 104(14):5919-59249 (2007).
Kittappa et al., "The foxa2 Gene Controls the Birth and Spontaneous Degeneration of Dopamine Neurons in Old Age," PLoS Biol 5(12):e325 (2007).
Koehler et al., "Generation of inner ear sensory epithelia from pluripotent stem cells in 3D culture," Nature 500:217-223 (2013).
Kudoh et al., "Combinatorial Fgf and Bmp signalling patterns the gastrula ectoderm into prospective neural and epidermal domains," Development 131:3581-3592 (2004).
Kwon et al., "Identification of Early Requirements for Preplacodal Ectoderm and Sensory Organ Development," PLoS Genet 6(9):e1001133 (2010).
Lafaille et al., "Impaired intrinsic immunity to HSV-1 in human iPSC-derived TLR3-deficient CNS cells," Nature 491:769-773 (2012).
Laflamme et al., "Cardiomyocytes derived from human embryonic stem cells in pro-survival factors enhance function of infarcted rat hearts," Nat. Biotechnol., 25(9): 1015-1024 (2007).
Lee et al., "Directed Differentiation and Transplantation of Human Embryonic Stem Cell-Derived Motoneurons," Stem Cells, 25:1931-1939 (2007).
Lee et al., "Isolation and directed differentiation of neural crest stem cells derived from human embryonic stem cells," Nat Biotechnol 25(12):1468-1475 (2007).
Lee et al., "Modeling Pathogenesis and Treatment of Familial Dysautonomia using Patient Specific iPSCs," Nature, 461(7262):402-406 (2009).
Leung et al. Differential BMP signaling controls formation and differentiation of multipotent preplacodal ectoderm progenitors

(56) References Cited

OTHER PUBLICATIONS from human embryonic stem cells. Developmental Biology (epub Apr. 30, 2013), v379, p. 208-220. (Year: 2013).
Leung et al., "Differential BMP signaling controls formation and differentiation of multi potent preplacodal ectoderm progenitors from human embryonic stem cells," Dev Biol 379:208-220 (2013).
Li et al., "Directed Differentiation of Ventral Spinal Progenitors and Motor Neurons from Human Embryonic Stem Cells by Small Molecules," Stem Cells 26(4):886-893 (2008).
Li et al., "Specification of motoneurons from human embryonic stem cells," Nat. Biotechnol., 23(2):215-221 (2005).
Litsiou et al., "A balance of FGF, BMP and WNT signalling positions the future placode territory in the head," Development 132:4051-4062 (2005).
Lois et al., Germline Transmission and Tissue-Specific Expression of Transgenes Delivered by Lentiviral Vectors, Science 295:868-872 (2002).
Love et al., "Trigeminal neuralgia: Pathology and Pathogenesis," Brain 124:2347-2360 (2001).
Lyuksyutova et al., "Anterior-Posterior Guidance of Commissural Axons by Wnt-Frizzled Signaling," Science 302:1984-1988 (2003).
Mackay et al., "The mouse Ovol2 gene is required for cranial neural tube development," Dev Biol 291:38-52 (2006).
Martin et al., "Competence of cranial ectoderm to respond to Fgf signaling suggests a two-step model of otic placode induction," Development 133:877-887 (2006).
Martin, "Isolation of a pluripotent cell line from early mouse embryos cultured in medium conditioned by teratocarcinoma stem cells," PNAS, 78(12):7634-7638 (1981).
Matise et al., "Gli2 is required for induction of floor plate and adjacent cells, but not most ventral neurons in the mouse central nervous system," Development 125:2759-2770 (1998).
McCabe et al., "Discovery of genes implicated in placode formation," Developmental Biology 274:462-477 (2004).
McCauley et al., "Conservation of Pax gene expression in ectodermal placodes of the lamprey," Gene 287:129-139 (2002).
Menendez et al., "Wnt signaling and a Smad pathway blockade direct the differentiation of human pluripotent stem cells to multipotent neural crest cells," PNAS 108(48): 19240-19245 (2011).
Mengarelli et al., "Derivation of Multiple Cranial Tissues and Isolation of Lens Epithelium-Like Cells from Human Embryonic Stem Cells," Stem Cells Transl Med 2:94-106 (2013).
Metcalfe et al., "Primary neurons that express the L2/HNK-1 carbohydrate during early development in the zebrafish," Development 110:491-504 (1990).
Mica et al., "Modeling Neural Crest Induction, Melanocyte Specification, and Disease-Related Pigmentation Defects in hESCs and Patient Specific iPSCs," Cell Rep 3:1140-1152 (2013).
Mizuseki et al., "Generation of neural crest-derived peripheral neurons and floor plate cells from mouse and primate embryonic stem cells," PNAS 100(10):5828-5833 (2003).
Mukhopadhyay et al., "Dickkopf1 Is Required for Embryonic Head Induction and Limb Morphogenesis in the Mouse," Dev Cell 1:423-434 (2001).
Mullor et al., "Pathways and consequences: Hedgehog signaling in human disease," Trends in Cell Biology 12(12):562-569 (2002).
Munoz-Sanjuan et al., "Neural Induction, The Default Model and Embryonic Stem Cells," Nat. Rev. Neurosci., 3:271-280 (2002).
Notarianni et al., "Maintenance and differentiation in culture of pluripotential embryonic cell lines from pig blastocysts," J. Reprod. Fertil., Suppl. 41:51-56 (1990).
O'Rahilly et al., "Developmental Stages in Human Embryos," vol. 637, (Washington, D.C.: Carnegie Institution of Washington) (1987).
Ono et al., "Differences in neurogenic potential in floor plate cells along an anteroposterior location: midbrain dopaminergic neurons originate from mesencephalic floor plate cells," Development 134:3213-3225 (2007).
Ooto et al., "Induction of the Differentiation of Lentoids from Primate Embryonic Stem Cells," Invest Ophthalmol & Vis Sci 44(6):2689-2693 (2003).

Oshima et al. "Mechanosensitive Hair Cell-like Cells from Embryonic and Induced Pluripotent Stem Cells," Cell 141:704-716 (2010).
Patten et al., "Distinct modes of floor plate induction in the chick embryo," Development 130:4809-4821 (2003).
Perrier et al., "Derivation of midbrain dopamine neurons from human embryonic stem cells," PNAS 101(34):12543-12548 (2004).
Pieper et al., "Differential distribution of competence for panplacodal and neural crest induction to non-neural and neural ectoderm," Development 139:1175-1187 (2012).
Placantonakis et al., "BAC Transgenesis in Human Embryonic Stem Cells as a Novel Tool to Define the Human Neural Lineage," Stem Cells, 27:521-532 (2009).
Placzek et al., "Induction of floor plate differentiation by contact-dependent, homeogenetic signals," Development 117:205-218 (1993).
Placzek et al., "The Floor Plate: Multiple Cells, Multiple Signals," Nat Rev Neurosci 6:230-240 (2005).
Placzek, M., "The role of the notochord and floor plate in inductive interactions," Curr Opin in Genet and Dev 5:499-506 (1995).
Reubinoff et al., "Neural progenitors from human embryonic stem cells," Nature Biotechnology 19:1134-1140 (2001).
Roelink et al., "Floor Plate and Motor Neuron Induction by vhh-1, a Vertebrate Homolog of hedgehog Expressed by the Notochord," Cell 76:761-775 (1994).
Ruf et al., "SIX1 mutations cause branchio-oto-renal syndrome by disruption of EYA1-SIX1-DNA complexes," PNAS 101(21):8090-8095 (2004).
Sasai et al., "Xenopus chordin: A Novel Dorsalizing Factor Activated by Organizer-Specific Homeobox Genes," Cell, 79(5):779-790 (1994).
Sasaki et al., "Differential expression of multiple fork head related genes during gastrulation and axial pattern formation in the mouse embryo," Development 118:47-59 (1993).
Schlosser, G., "Induction and specification of cranial placodes," Dev Biol 294:303-351 (2006).
Scully et al., "Pituitary Development: Regulatory Codes in Mammalian Organogenesis," Science 295:2231-2235 (2002).
Shen et al., "The timing of cortical neurogenesis is encoded within lineages of individual progenitor cells," Nat Neurosci 9(6):743-751 (2006)..
Shi et al., "BMP4 induction of sensory neurons from human embryonic stem cells and reinnervation of sensory epithelium," Eur J Neurosci 26:3016-3023 (2007).
Shirasaki et al., "Guidance of Cerebellofugal Axons in the Rat Embryo: Directed Growth toward the Floor Plate and Subsequent Elongation along the Longitudinal Axis," Neuron 14:961-972 (1995).
Sjödal et al., "Time of Exposure to BMP Signals Plays a Key Role in the Specification of the Olfactory and Lens Placodes Ex Vivo," Dev Cell 13:141-149 (2007).
Smith et al., "Expression Cloning of noggin, a New Dorsalizing Factor Localized to the Spemann Organizer in Xenopus Embryos," Cell, 70:829-840 (1992).
Smith et al., "Inhibition of Activin/Nodal signaling promotes specification of human embryonic stem cells into neuroectoderm," Dev. Biol., 313:107-117 (2008).
Stark et al., "Neural tube-ectoderm interactions are required for trigeminal placode formation," Development 124:4287-4295 (1997).
Streit, "Early development of the cranial sensory nervous system: from a common field to individual placodes," Dev. Biol., 276:1-15 (2004).
Suga et al., "Self-formation of functional adeno-hypophysis in three-dimensional culture," Nature 480:57-62 (2011).
Sukoyan et al., "Embryonic Stem Cells Derived from Morulae, Inner Cell Mass, and Blastocysts of Mink: Comparisons of Their Pluripotencies," Mol. Reprod. Dev., 36:148-158 (1993).
Sukoyan et al., "Isolation and Cultivation of Blastocyst-Derived Stem Cell Lines from American Mink (*Mustela vison*)," Mol. Reprod. Dev., 33:418-431 (1992).
Supplementary European Search Report dated Jun. 7, 2017 in EP Application No. 14863620.
Suter et al., "A Sox1 to Pax6 Switch Drives Neuroectoderm to Radial Glia Progression During Differentiation of Mouse Embryonic Stem Cells Stem Cells," 27:49-58 (2009).

(56) References Cited

OTHER PUBLICATIONS

Tabar, V., "Making a pituitary gland in a dish," Cell Stem Cell 9:490-491 (2011).
Takahashi et al., "Induction of Pluripotent Stem Cells from Adult Human Fibroblasts by Defined Factors," Cell 131:861-872 (2007).
Tesar et al., "New cell lines from mouse epiblast share defining features with human embryonic stem cells," Nature, 448:196-199 (2007).
Tomishima et al., "Production of Green Fluorescent Protein Transgenic Embryonic Stem Cells Using the GENSAT Bacterial Artificial Chromosome Library," Stem Cells, 25:39-45 (2007).
Tremblay et al., "The pan-Pituitary Activator of Transcription, Ptxl (Pituitary Homeobox 1), Acts in Synergy with SF-1 and Pit1 and Is an Upstream Regulator of the Lim-Homeodomain Gene Lim3/Lhx3," Mol Endocrinol 12(3):428-441 (1998).
Valenzuela et al., "Identification of Mammalian Noggin and Its Expression in the Adult Nervous System," J. Neurosci., 15(9):6077-6084 (1995).
Vallier et al., "Nodal inhibits differentiation of human embryonic stem cells along the neuroectodermal default pathway," Dev. Biol., 275:403-421 (2004).
Venezia et al., "Molecular Signatures of Proliferation and Quiescence in Hematopoietic Stem Cells," PLoS Biol 2(10):e301 (2004).
Wang et al., "Noggin and bFGF cooperate to maintain the pluripotency of human embryonic stem cells in the absence of feeder layers," Biochem. Biophys. Res. Commum., 330:934-942 (2005).
Watanabe et al., "Directed differentiation of telencephalic precursors from embryonic stem cells," Nat Neuro 8(3):288-296 (2005).
Weinstein et al., "Neural Induction," Annu Rev Cell Dev Biol 15:411-433 (1999).
Wichterle et al., "Directed Differentiation of Embryonic Stem Cells into Motor Neurons," Cell 110:385-397 (2002).
Wilson et al., "Concentration-dependent patterning of the Xenopus ectoderm by BMP4 and its signal transducer Smad 1," Development 124:3177-3184 (1997).
Xu et al. "Basic FGF and suppression of BMP signaling sustain undifferentiated proliferation of human ES cells," Nat. Methods, 2(3):185-190 (2005).
Xu et al., "BMP4 initiates human embryonic stem cell differentiation to trophoblast," Nat Biotechnol 20:1261-1264 (2002).
Xu et al., "NANOG Is a Direct Target of TGFβ/Activin-Mediated SMAD Signaling in Human ESCs," Cell Stem Cell, 3:196-206 (2008).
Yanagisawa et al. Expression of GD2 and GD3 gangliosides in human embryonic neural stem cells. ASN Neuro. (2011), 7;3(2), pii:e00054, p. 69-74. (Year: 2011).
Zhang et al., "Pax6 is a Human Neuroectoderm Cell Fate Determinant," Cell Stem Cell 7:90-100 (2010).
Zhang, et al., "In vitro differentiation of transplantable neural precursors from human embryonic stem cells," Nature Biotechnology 19:1129-1133 (2001).
Zoltewicz et al., "oto is a homeotic locus with a role in anteroposterior development that is partially redundant with Liml," Development 126:5085-5095 (1999).

\* cited by examiner

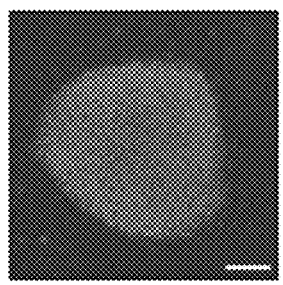 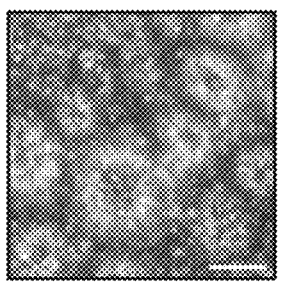 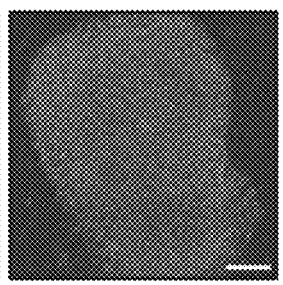 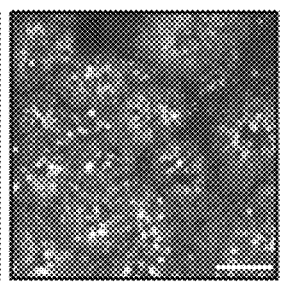
FIG. 9A    FIG. 9G    FIG. 9B    FIG. 9H
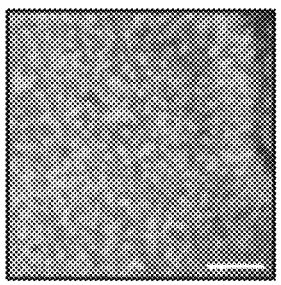 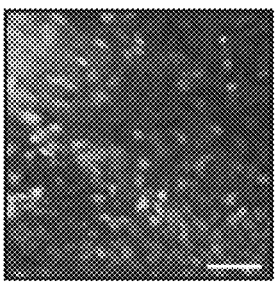 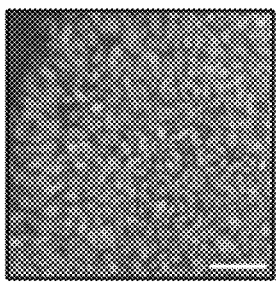 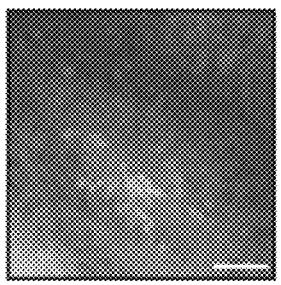
FIG. 9C    FIG. 9I    FIG. 9D    FIG. 9J
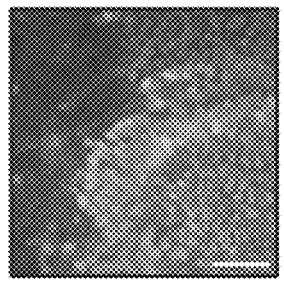 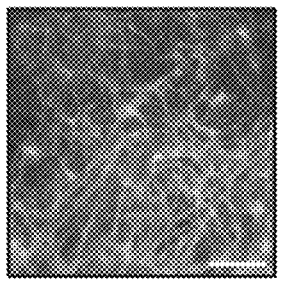 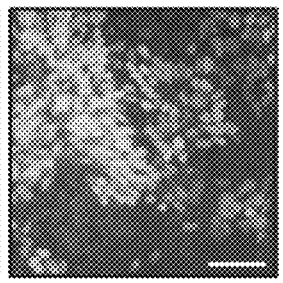 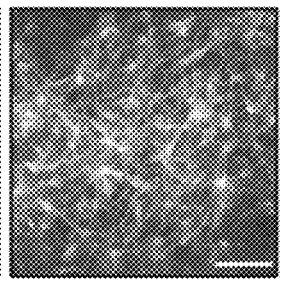
FIG. 9E    FIG. 9K    FIG. 9F    FIG. 9L
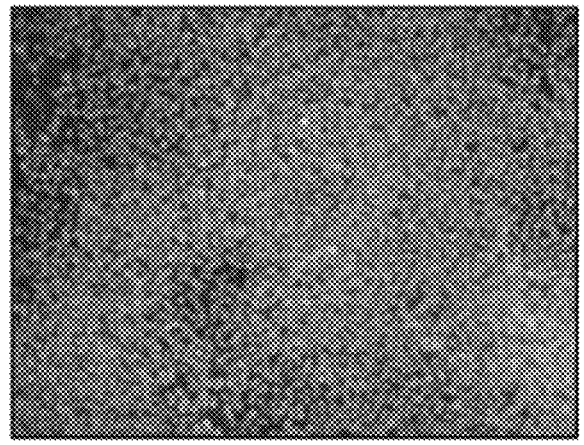
FIG. 10

FIG. 13A  FIG. 13B  FIG. 13C
Six1/Tuj1/DAPI  Six1/Tuj1/DAPI  Six1/Tuj1/DAPI
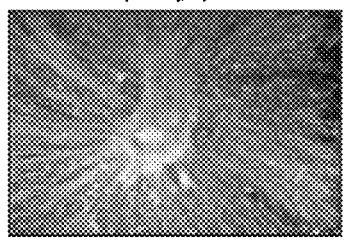 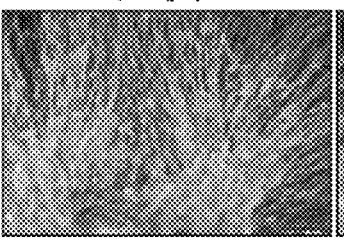 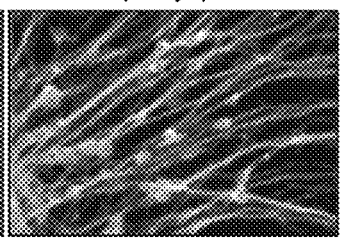
Brn3A/DAPI  Isl1/HNK1/DAPI  Peripherin/Tuj1
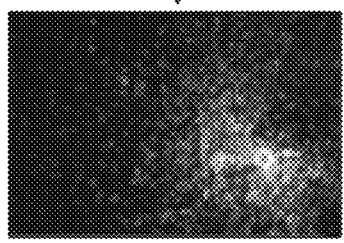 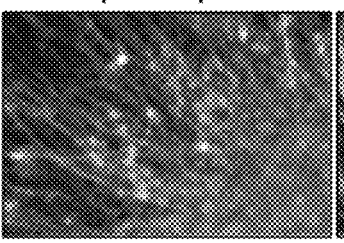 
FIG. 13D  FIG. 13E  FIG. 13F
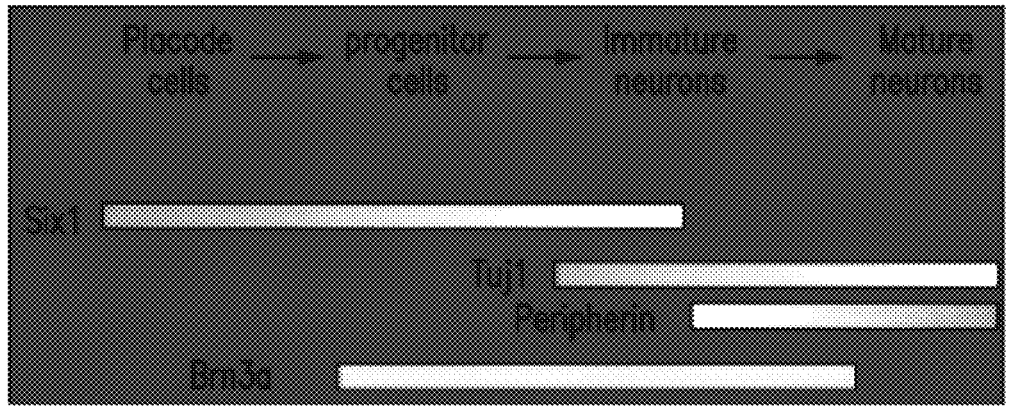
FIG. 13G

DAPI/FOXA2

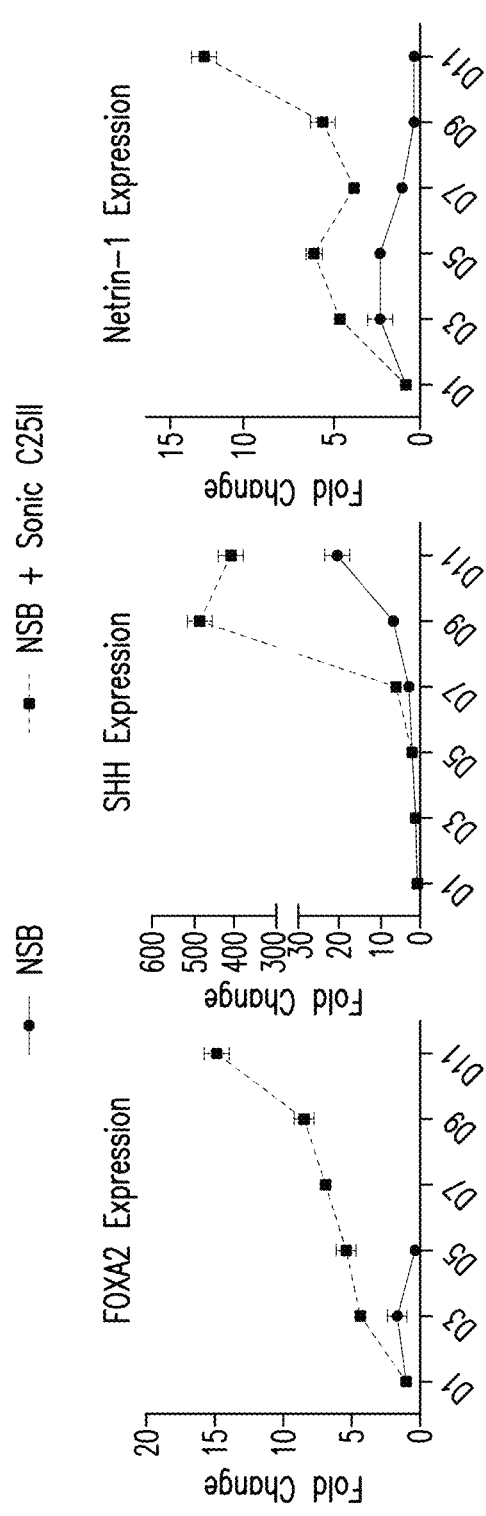
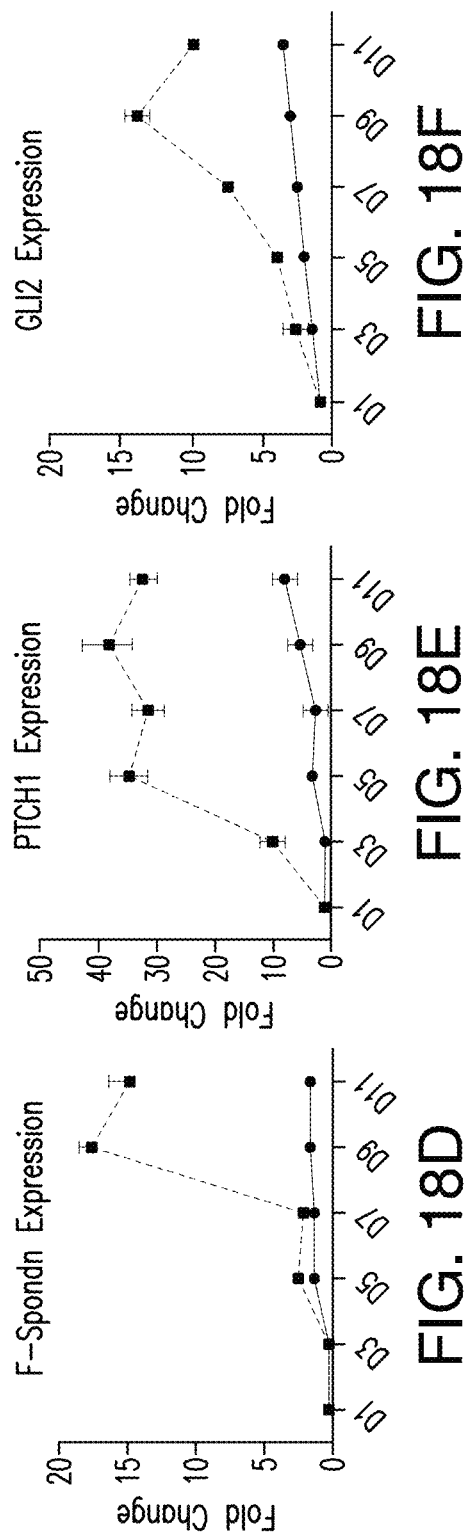

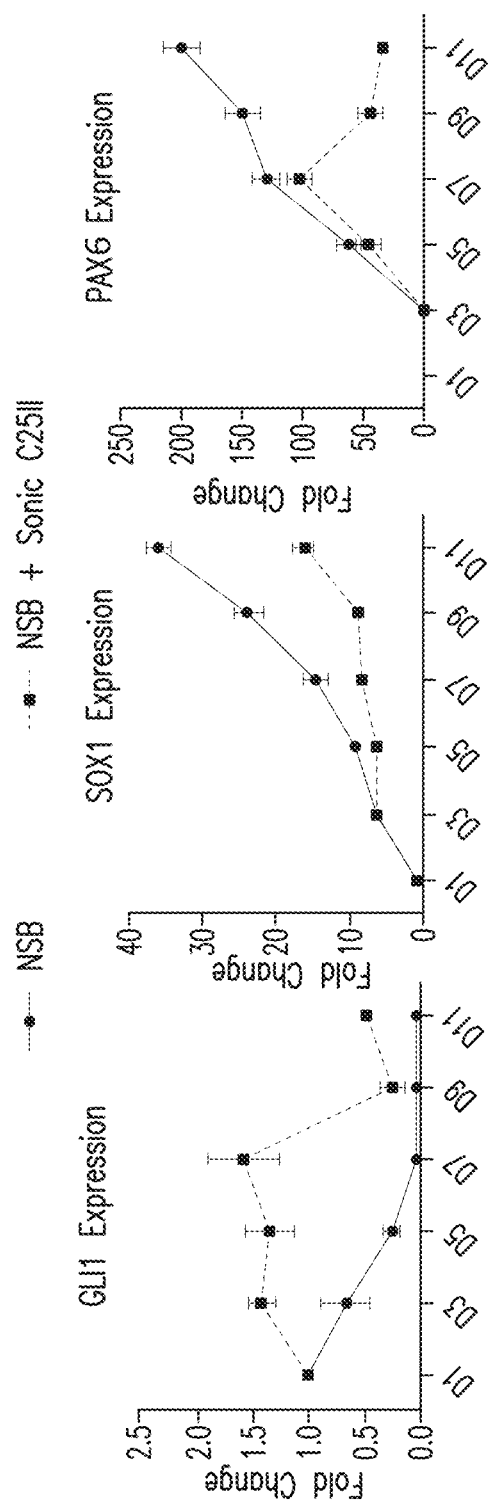
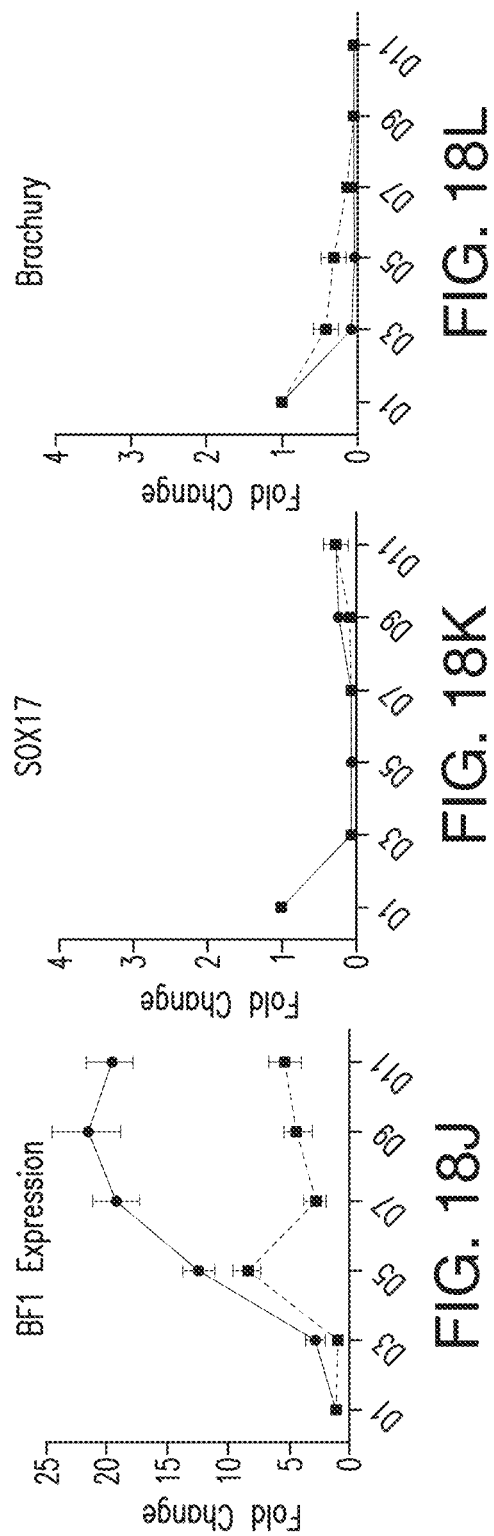
FIG. 18I, FIG. 18H, FIG. 18G, FIG. 18L, FIG. 18K, FIG. 18J

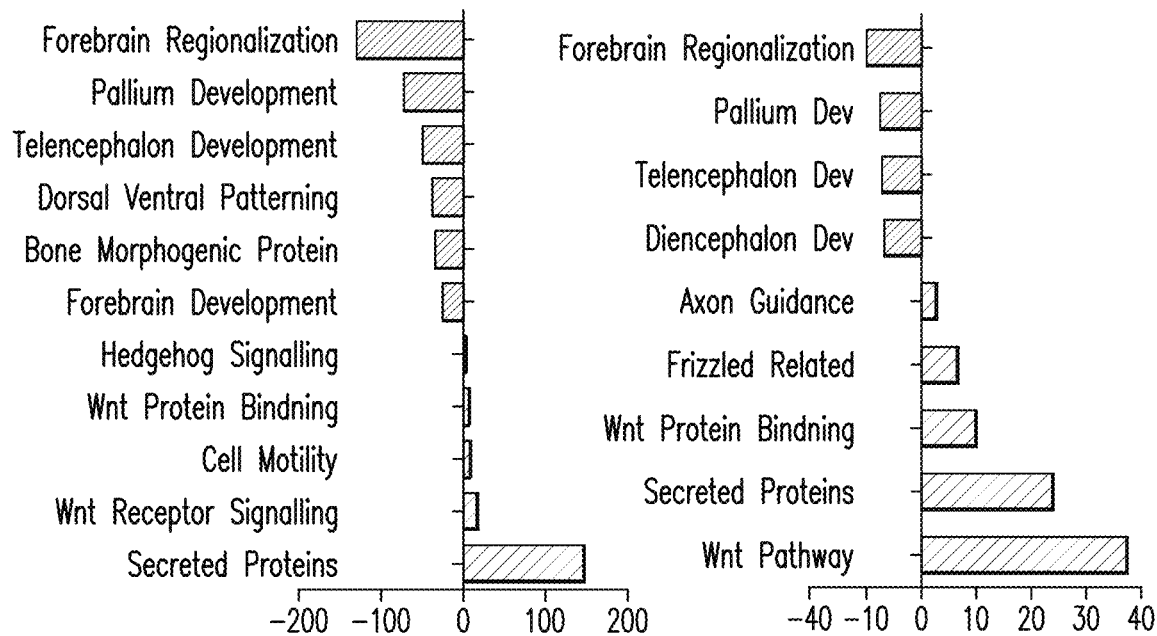
FIG. 18M
FIG. 18N
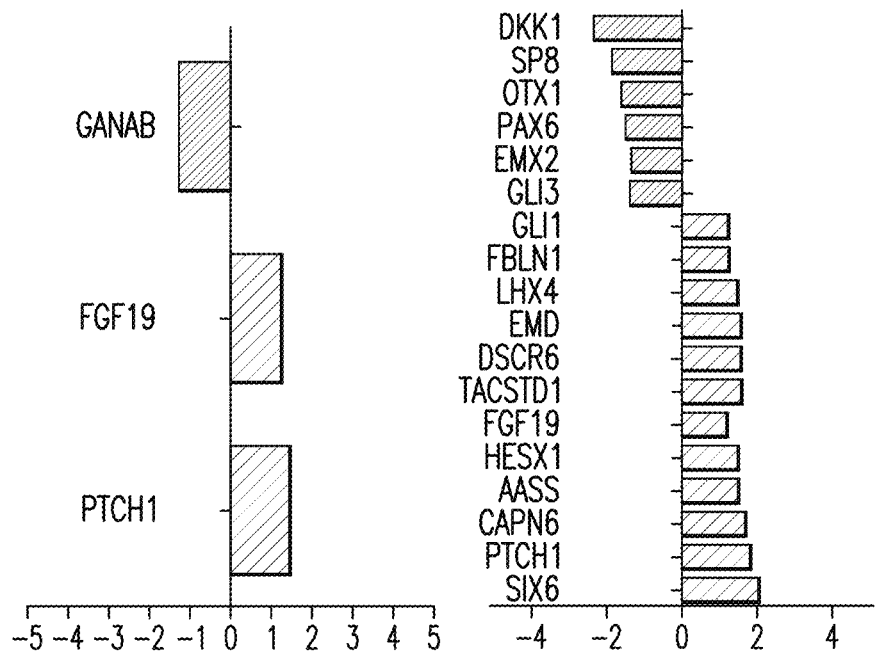
FIG. 18O
FIG. 18P

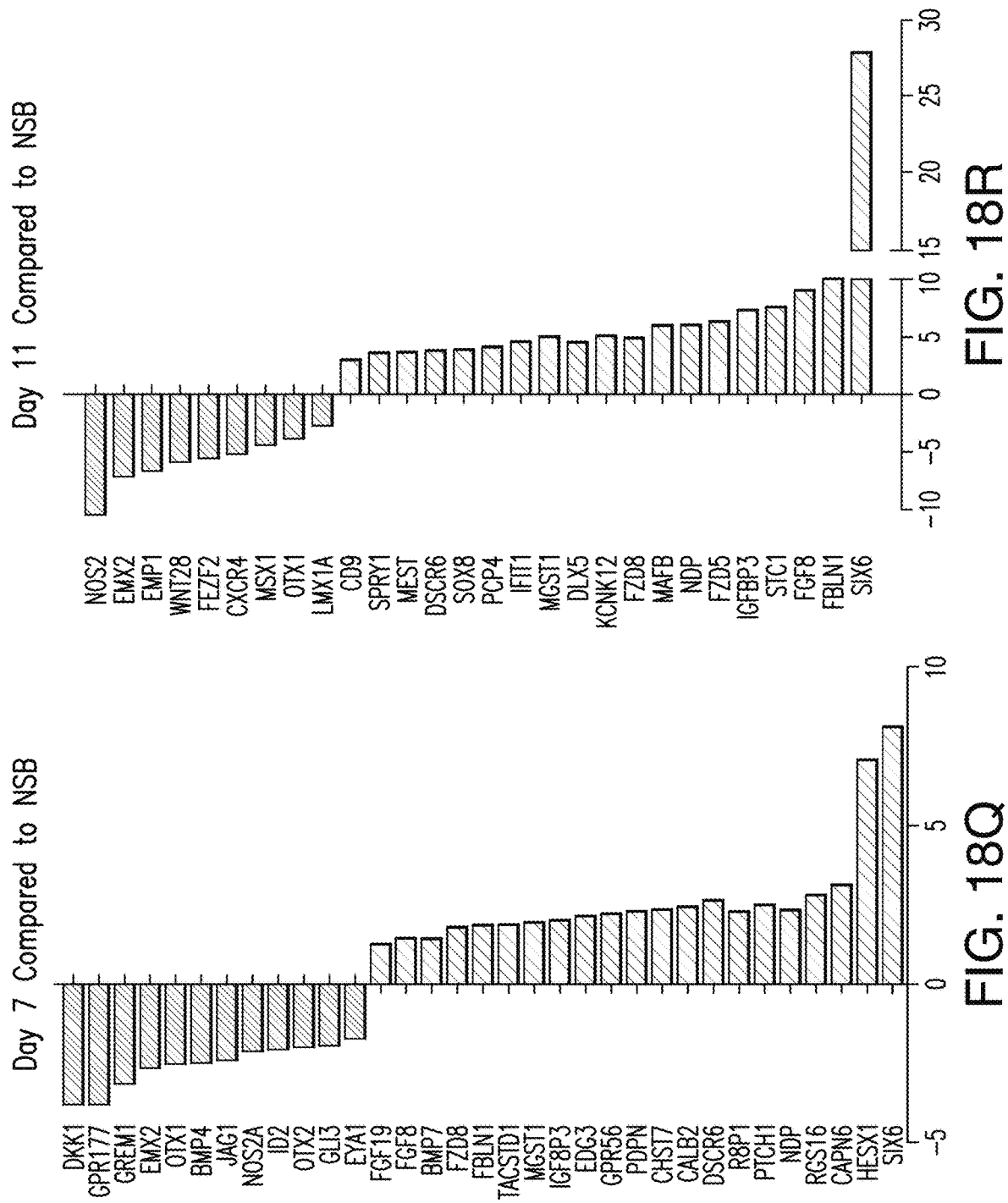

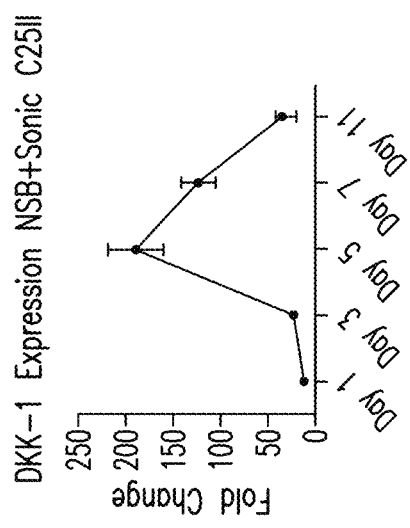
FIG. 19A
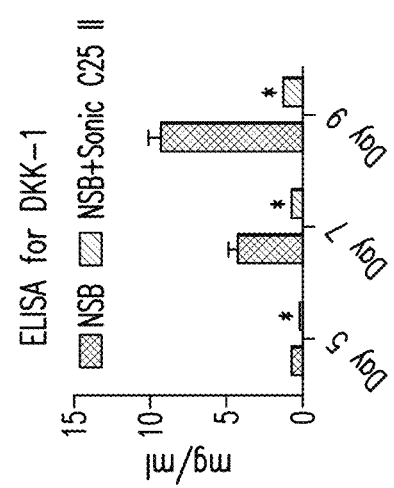
FIG. 19B
FIG. 19C
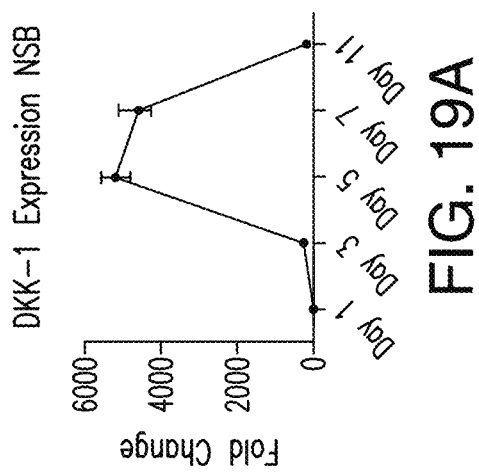
FIG. 19D
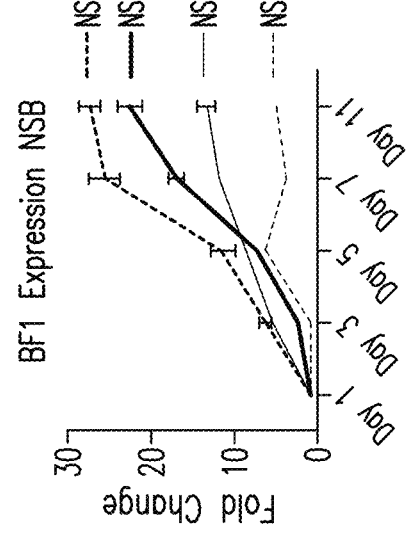
FIG. 19E
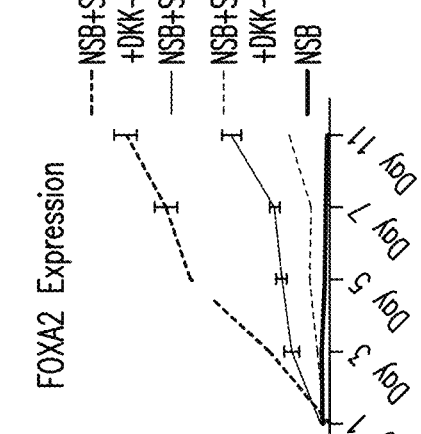

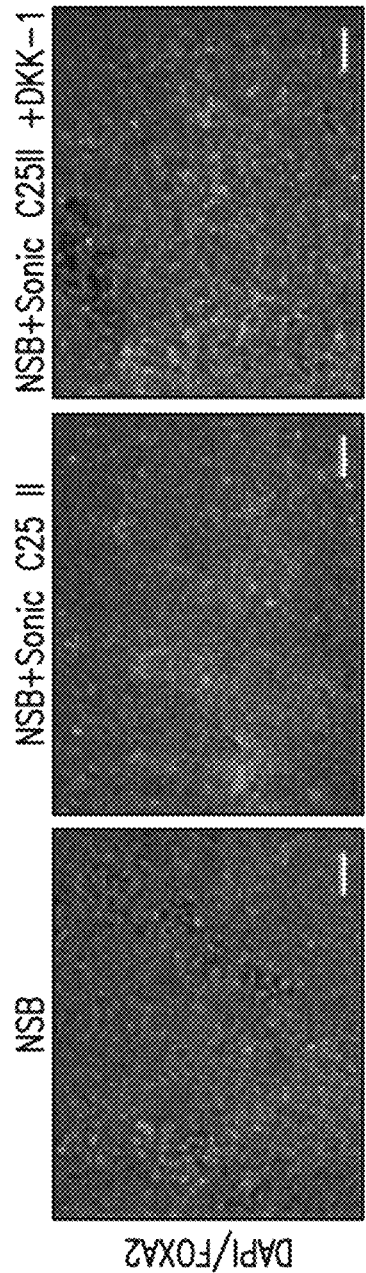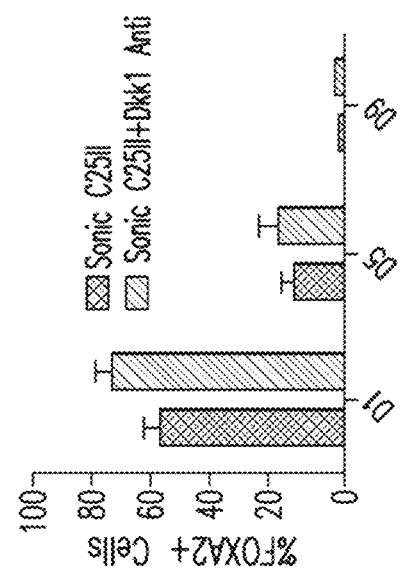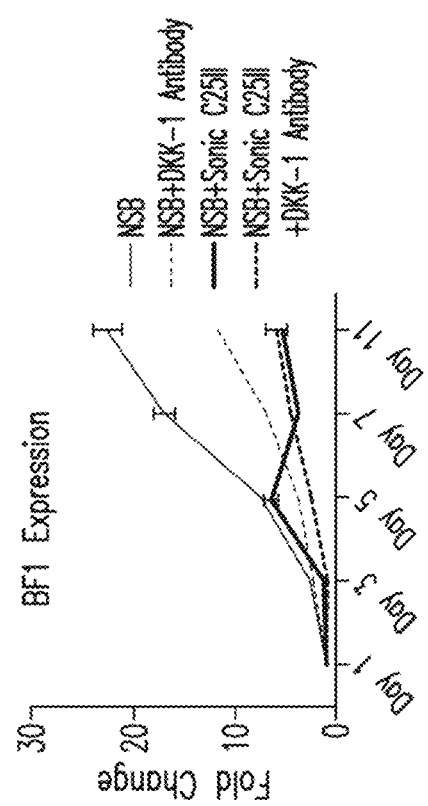
FIG. 19F
FIG. 19G
FIG. 19H

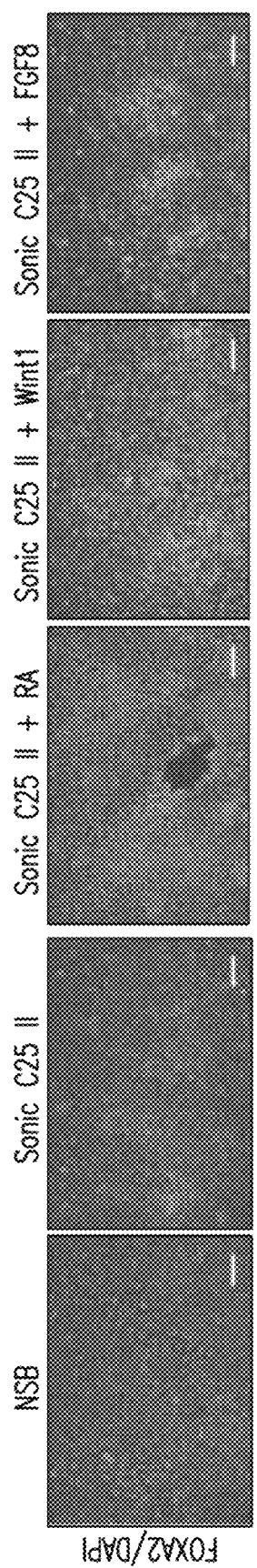
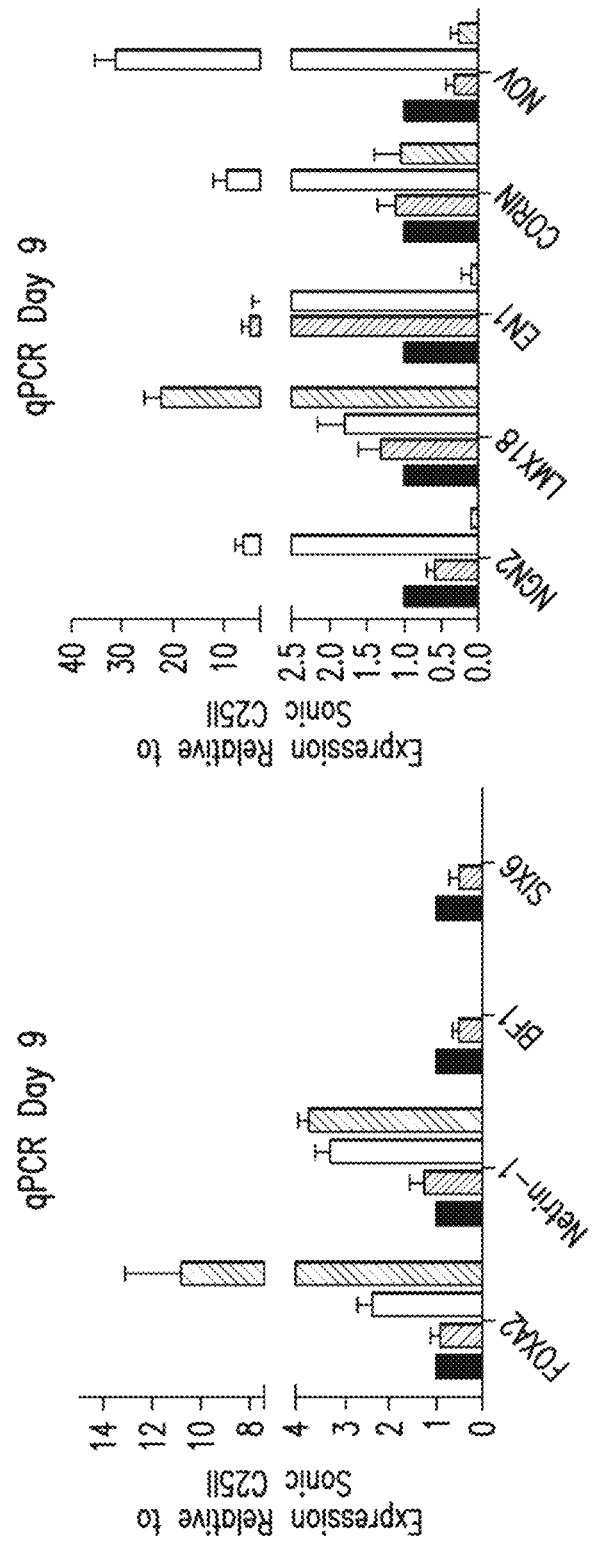
FIG. 20A
FIG. 20B
FIG. 20C

| Antibody Name | Staining | Percentage |
|---|---|---|
| Nestin | +++ | 86 ± 6 |
| Tuj1 | ++ | 37 ± 7 |
| Nkx2.2 | + | 13 ± 4 |
| TH | + | 4 ± 1 |
| SOX2 | + | 17 ± 5 |
| SOX17 | − | |
| AFP | − | |
| Albumin | − | |
| BF1 | − | |
| DCX | − | |
| S100B | − | |
| PAX6 | − | |
| SOX1 | − | |
| Brachury | − | |
| Musashi | − | |

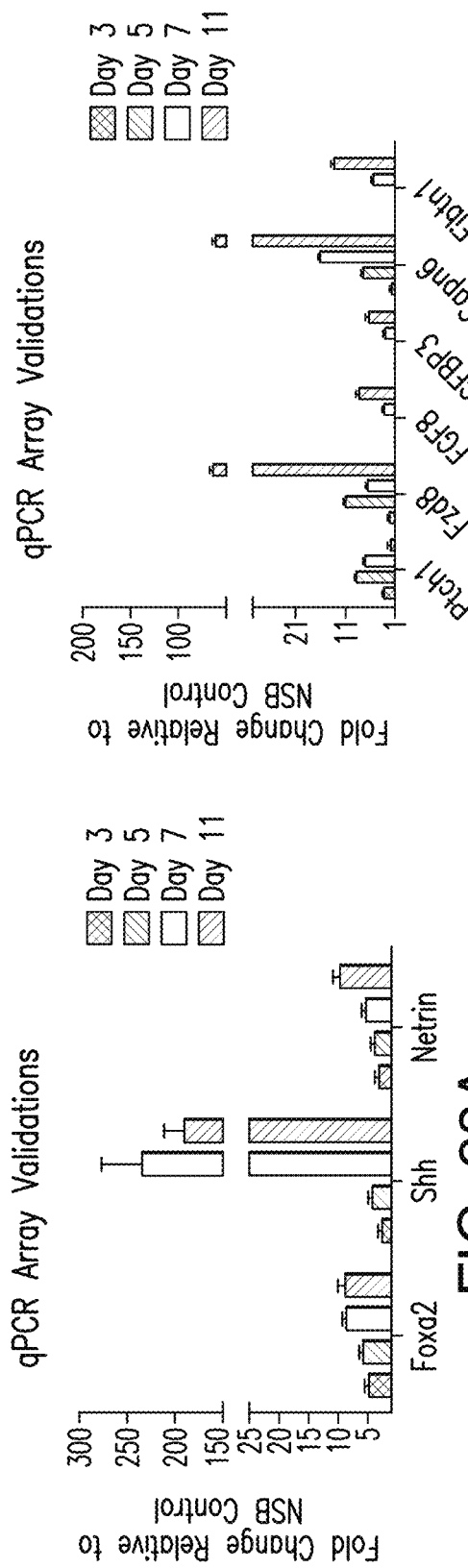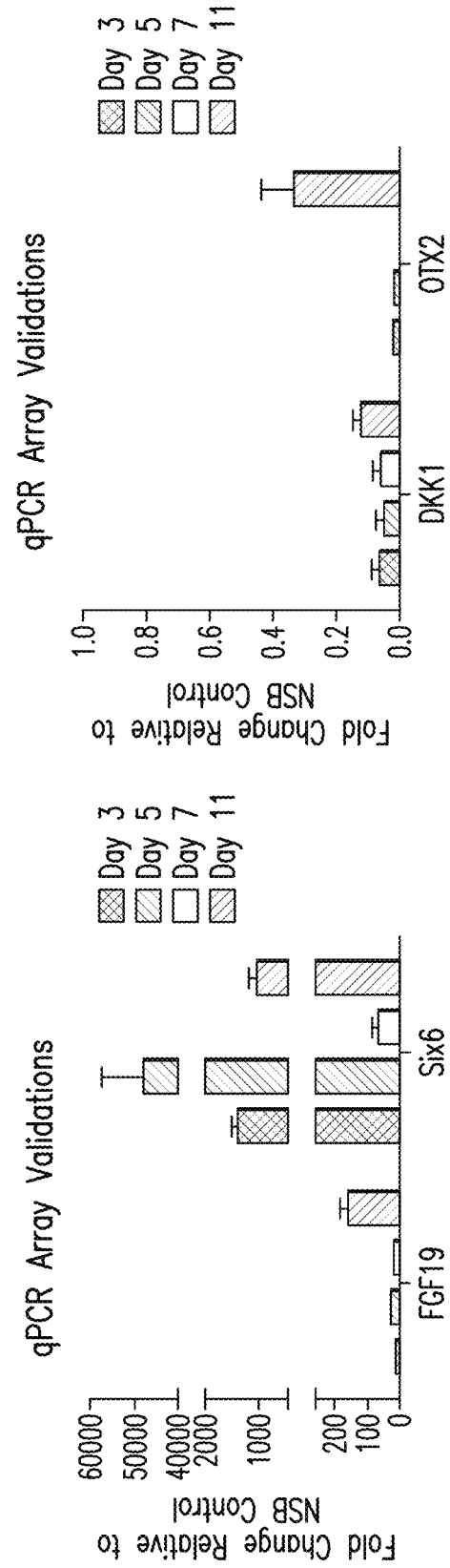
FIG. 23A, FIG. 23B, FIG. 23C, FIG. 23D

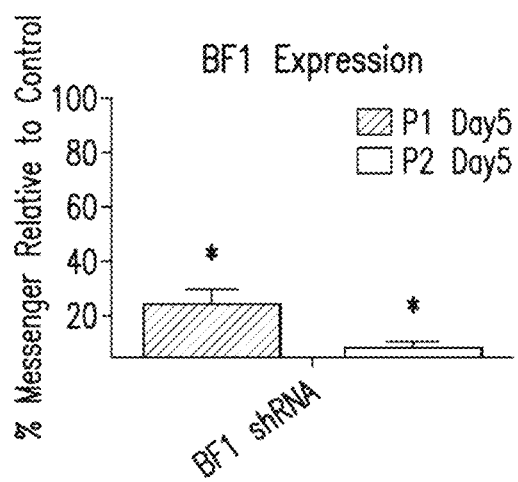
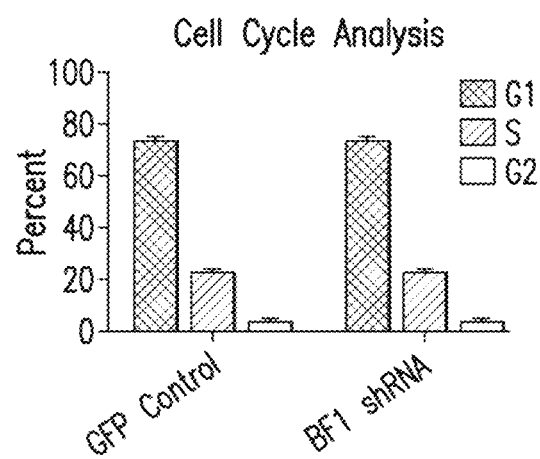
FIG. 24A   FIG. 24B
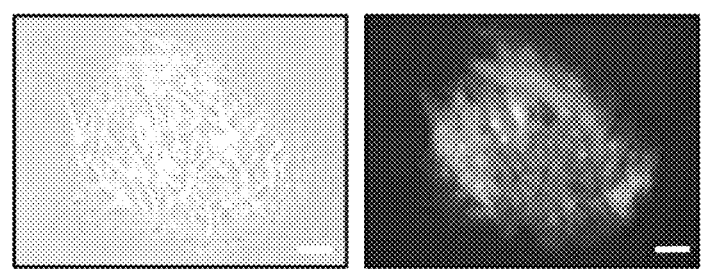
FIG. 24C
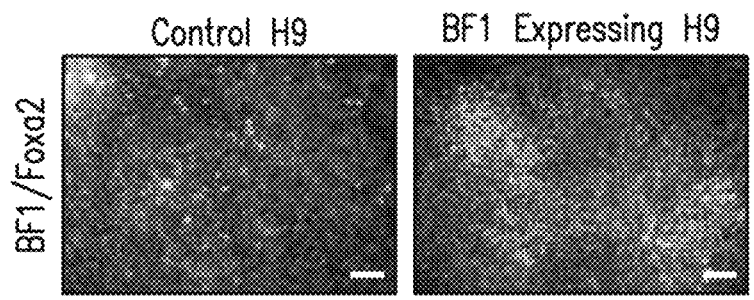
FIG. 24D

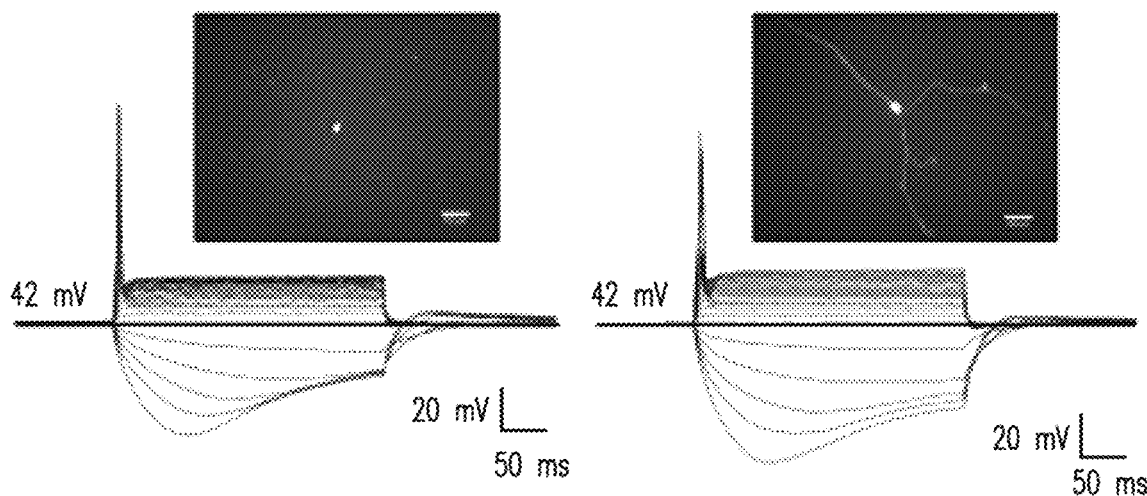
FIG. 34L   FIG. 34M
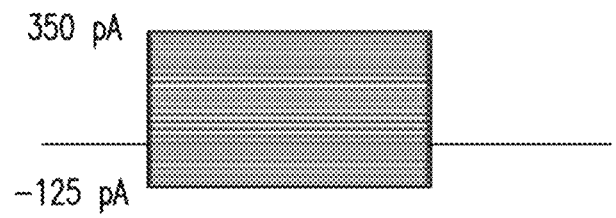
FIG. 34N
|  | Bipolar (N=7) | Tripolar (n=6) |
| --- | --- | --- |
| RMP (mv) | −66.0 ± 3.3 | −65.2 ± 1.8 |
| Threshold (mV) | −18.9 ± 4.6 | −23.2 ± 4.3 |
| Threshold (pA) | 317.9 ± 44.2 | −275.0 ± 53.2 |
| Peak (mV) | 24.9 ± 6.3 | 30.8 ± 6.2 |
| AP (mV) | 90.9 ± 7.4 | 96 ± 6.8 |
| Input Rt (MΩ) | 325.4 ± 92.3 | 388.2 ± 123.0 |
| Rm (MΩ) | 281.4 ± 81.8 | 349.2 ± 113.2 |
| Cm (pF) | 30.0 ± 5.60 | 37.2 ± 10.5 |
FIG. 34O Trigeminal anlage (chick embryo)

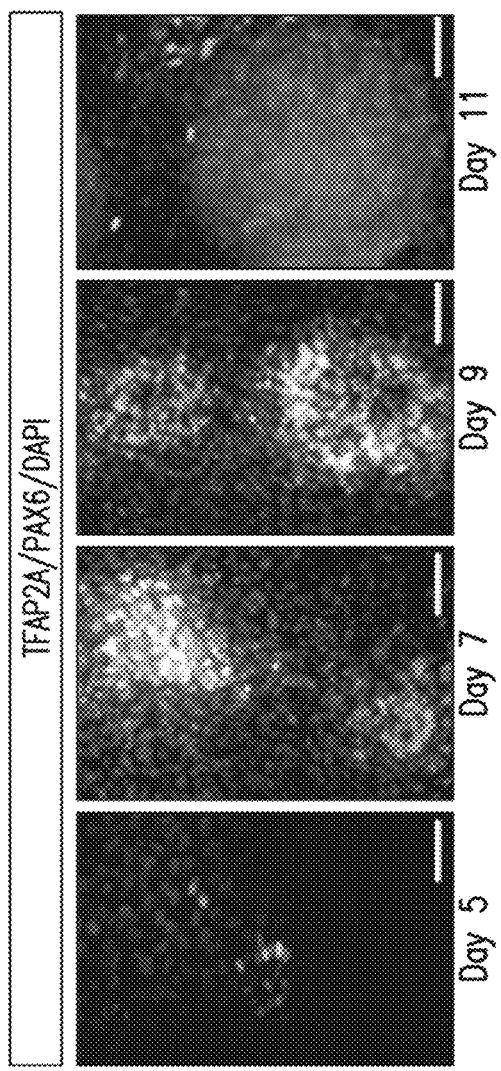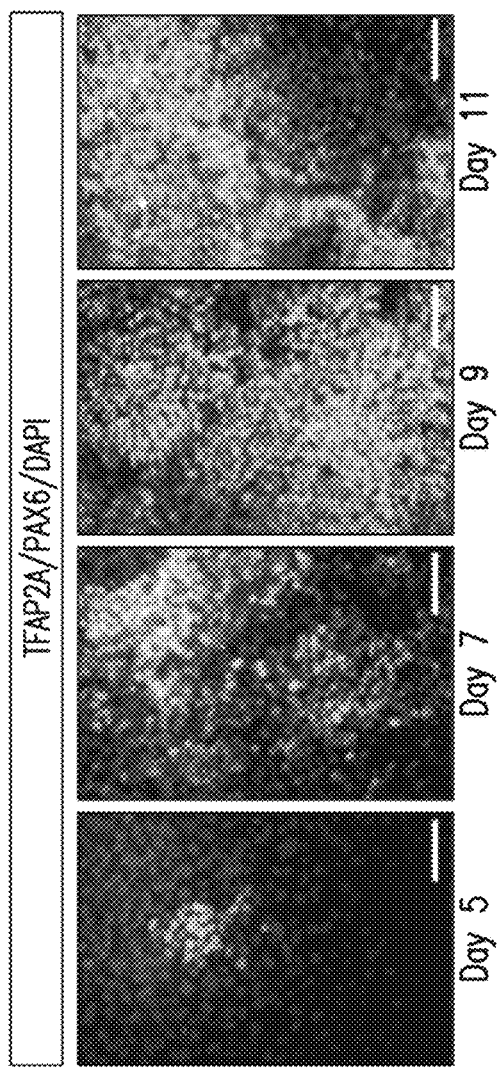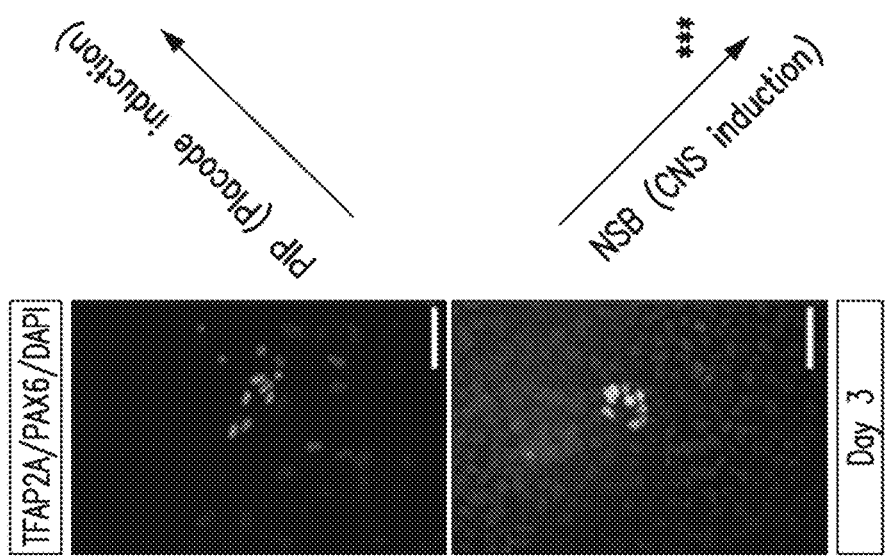
FIG. 36B
FIG. 36C
FIG. 36A

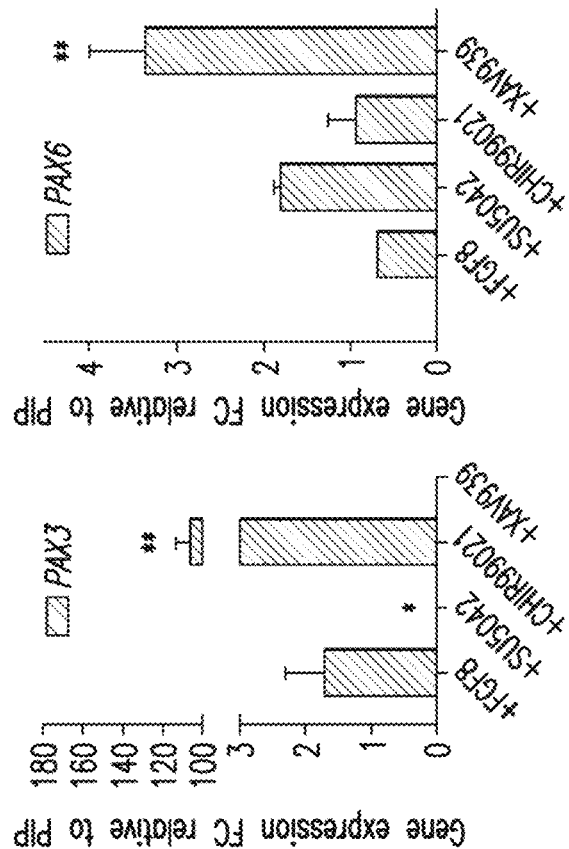
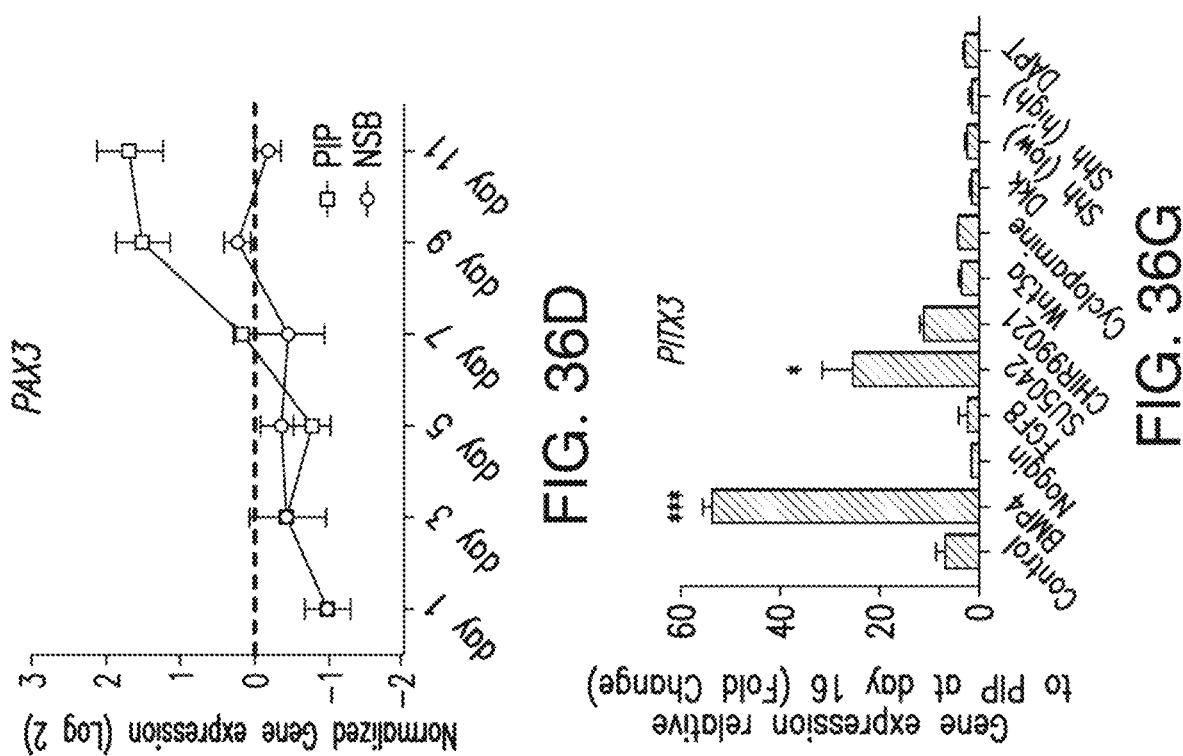

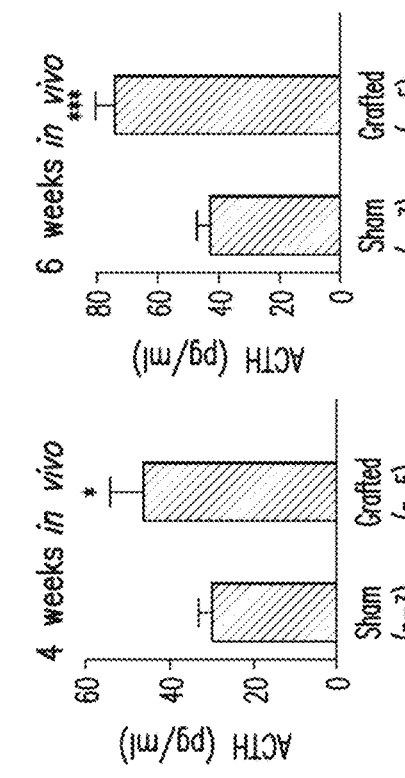
FIG. 38L
FIG. 38M
FIG. 38N
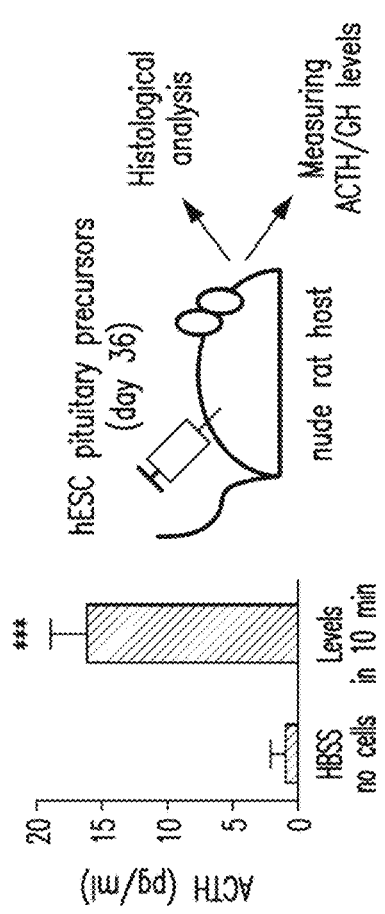
FIG. 38O
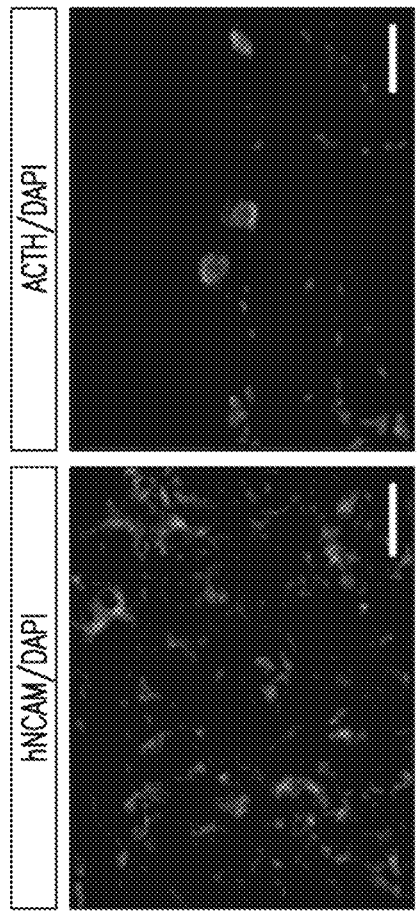
FIG. 38P
FIG. 38Q
FIG. 38R
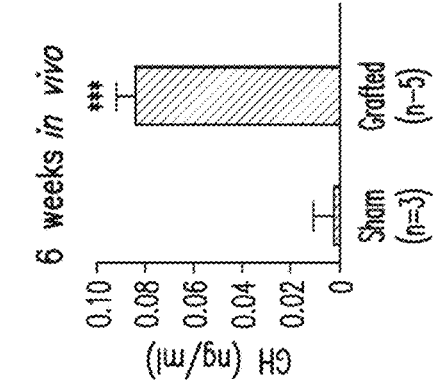

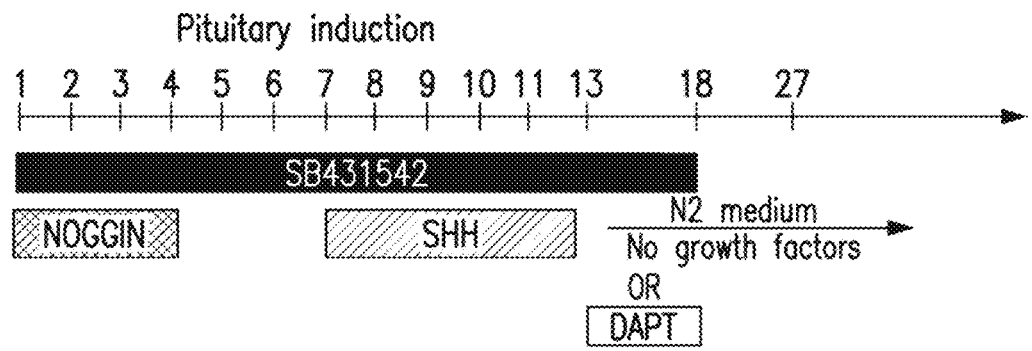
FIG. 39A
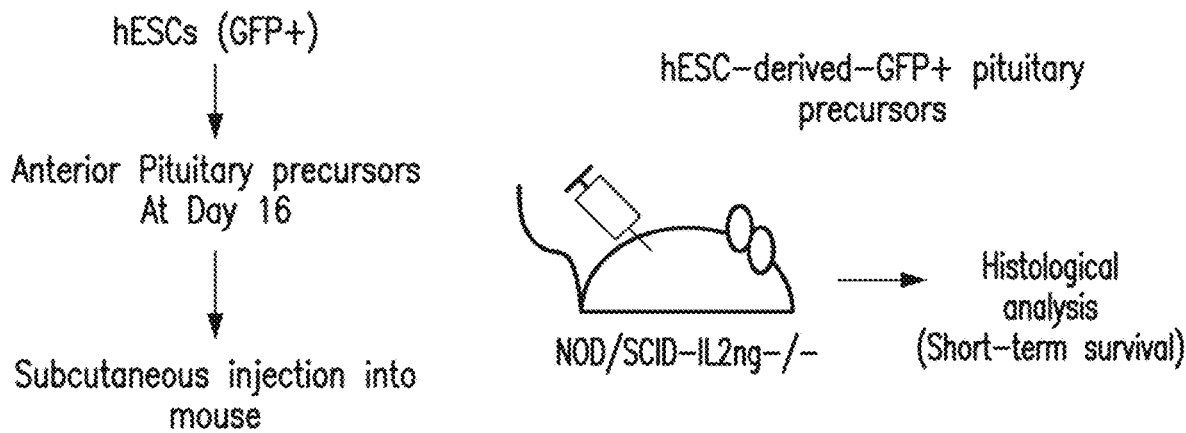
FIG. 39B
FIG. 39C
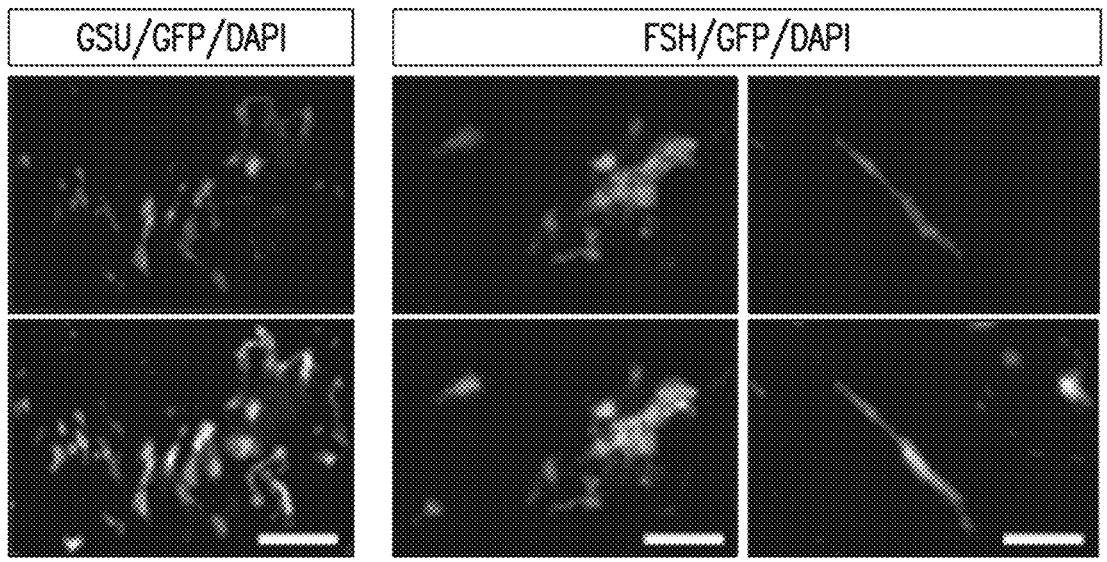
FIG. 39D
FIG. 39E

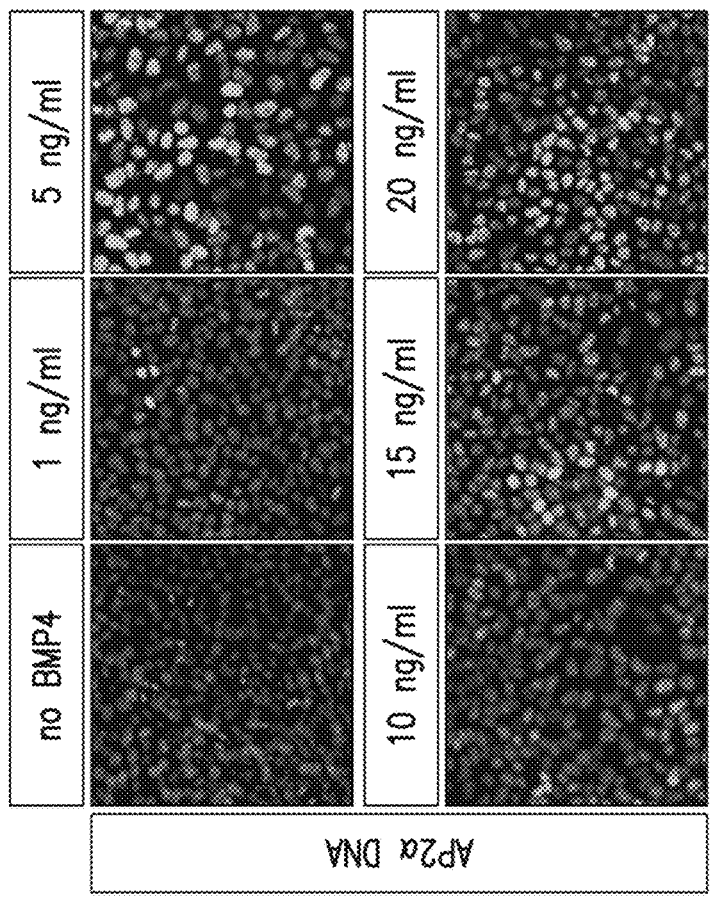
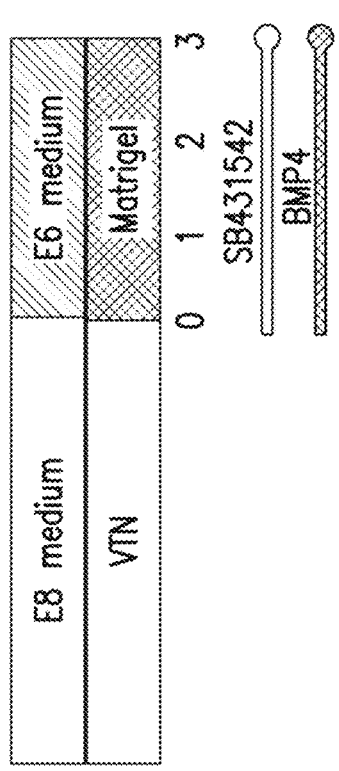
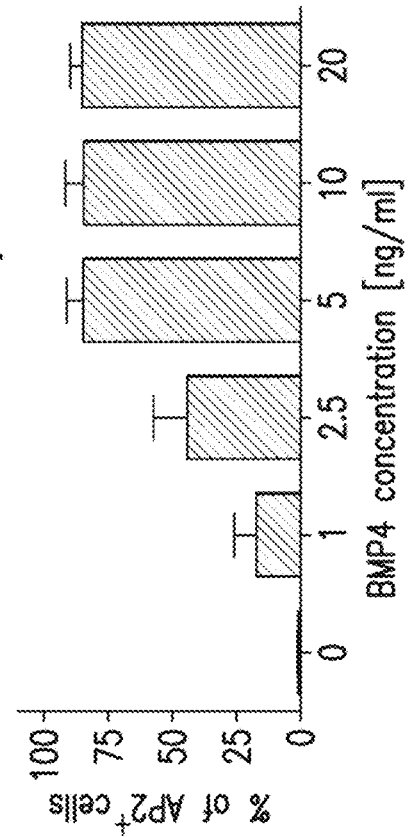
FIG. 43A
FIG. 43B
FIG. 43C

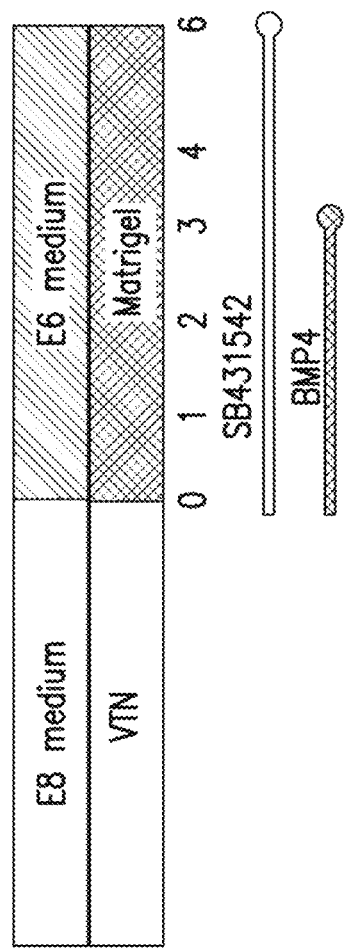
FIG. 44A
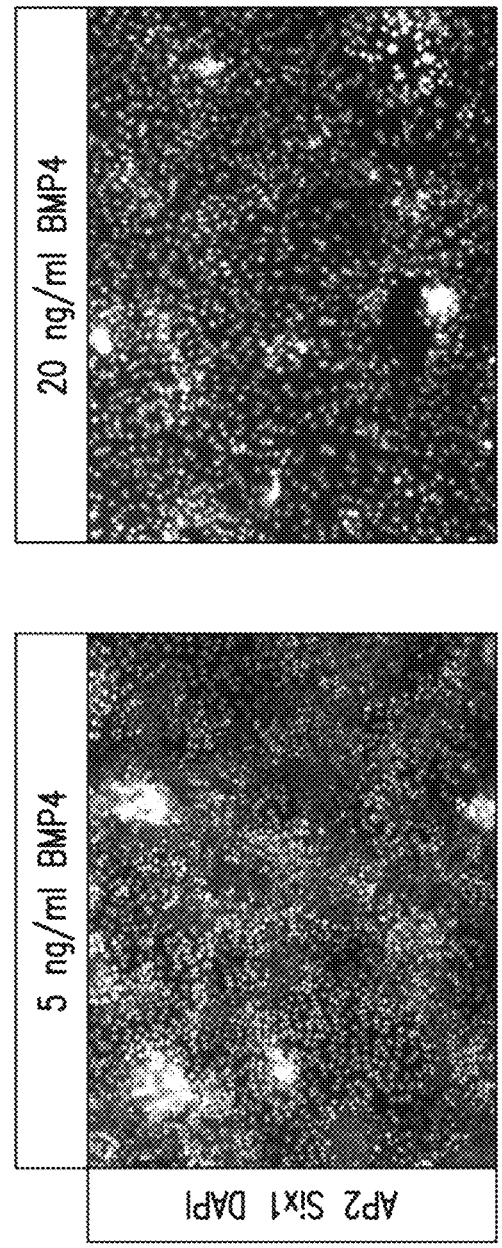
FIG. 44C
FIG. 44B

SPECIFICATION OF FUNCTIONAL CRANIAL PLACODE DERIVATIVES FROM HUMAN PLURIPOTENT STEM CELLS

CROSS-REFERENCE TO RELATED APPLICATIONS

This application is a continuation of U.S. patent application Ser. No. 15/159,351 filed May 19, 2016, which is a continuation of International Patent Application No. PCT/US2014/066952, filed Nov. 21, 2014, which claims priority to U.S. Provisional Application No. 61/907,302, filed Nov. 21, 2013, priority to each of which is claimed, and the contents of each of which are incorporated by reference in their entireties herein.

GRANT INFORMATION

This invention was made with government support under grant number NS072381 awarded by the National Institutes of Health. The government has certain rights in the invention.

FIELD OF THE INVENTION

The present invention relates generally to the field of cell biology of stem cells, more specifically the directed differentiation of pluripotent or multipotent stem cells, including human embryonic stem cells (hESC), somatic stem cells, and induced human pluripotent stem cells (hiPSC) using novel culture conditions. In particular, cranial placodes are derived from human pluripotent stem cells by a dual-SMAD inhibition strategy of neural induction coupled with further fate specification at the pre-placode stage. The method generates placode-derived trigeminal ganglia, mature lens fibers and anterior pituitary hormone-producing cells. Applications of these cells include, but are not limited to, human cell-based therapies in sensory and endocrine disease.

SEQUENCE LISTING

The specification further incorporates by reference the Sequence Listing submitted herewith via EFS on Apr. 2, 2019. Pursuant to 37 C.F.R. § 1.52(e)(5), the Sequence Listing text file, identified as 072734_0760SL, is 2,739 bytes and was created on Apr. 2, 2019. The Sequence Listing, electronically filed herewith, does not extend beyond the scope of the specification and thus does not contain new matter.

BACKGROUND OF THE INVENTION

The differentiation capacity of embryonic and somatic stem cells have opened possibilities for cell replacement therapies for genetic, malignant, and degenerative diseases. Neurodegenerative disorders, conditions, and diseases, and their treatment by cell-based therapies represent a promising means of preventing, reducing or eliminating the symptoms. Such disorders include Huntington's disease, Alzheimer's, Parkinson's, and amyotrophic lateral sclerosis. They also provide a source of cells for screening for critical small molecules (i) that could be useful in for treatment of disease; or (ii) for determining the cell fate of neural tissue. Further, these cells were studied in order to characterize key genes, mRNA transcripts, and proteins relevant in normal or pathological lineages.

Neural development is dictated in time and space by a complex set of signals that instruct neural precursor identity. While significant progress was made in animal models, human neural development remains much less understood. Previous studies reported directed differentiation of mouse (Wichterle et al., 2002; Barberi et al., 2003; Watanabe et al., 2005) and human (Perrier et al., 2004; Li et al., 2008; Eiraku et al., 2008) ESCs into specific neuron types in response to patterning factors defining anterior/posterior (A/P) and dorso-/ventral (D/V) CNS identity. These studies demonstrate evolutionary conservation of signaling systems that specify the major CNS regions. In mammals, sonic hedgehog (SHH) is a ventralizing factor acting in a dose-dependent manner to specify the various ventral cell types including cells expressing floor plate (FP) in primary neural explants (Briscoe and Ericson, 1999) and in mouse ES cells (Mizuseki et al., 2003). While application of SHH to hESC-derived neural cells was shown to induce various ventral neuron types, the derivation of floor plate (FP) tissue itself was not reported. As FP is one signaling center for inducing differentiation pathways and subsequent committed cell lineage, the ability to produce FP from human ES cells would be a major step forward in furthering studies of early human neural development. Furthermore, little is known about FP development in humans, due to lack of accessibility to tissue.

In animals, the FP is a major site of SHH production and several human developmental disorders are related to alterations in midline SHH signaling (Mullor et al., 2002) including certain forms of holoprosencephaly and microphthalmia, skeletal disorders including various cleft plate syndromes, and tumor conditions such as Gorlin's syndrome; a rare genetic disorder caused by a mutation in the SHH receptor Patched 1. However it is not known whether similar alterations in midline SHH signaling would induce these diseases in humans.

Therefore there is a critical need for inducing human floor plate tissue from human embryonic stem cells (hESCs) for providing a source of human floor plate cells. These human floor plate cells are necessary for use in medical research for determining causes and treatments of developmental diseases in humans and for comparative developmental studies of human neural patterning and axonal pathfinding.

SUMMARY OF THE INVENTION

The present invention relates generally to the field of cell biology of stem cells, more specifically the directed differentiation of pluripotent or multipotent stem cells, including human embryonic stem cells (hESC), somatic stem cells, and induced human pluripotent stem cells (hiPSC) using novel culture conditions. In particular, cranial placodes are derived from human pluripotent stem cells by a dual-SMAD inhibition strategy of neural induction coupled with further fate specification at the pre-placode stage. The method generates placode-derived trigeminal ganglia, mature lens fibers and anterior pituitary hormone-producing cells. Applications of these cells include, but are not limited to, human cell-based therapies in sensory and endocrine disease.

In one embodiment, the present invention contemplates a method, comprising: a) providing or plating a plurality of cranial placodal precursor cells in an N2 cell culture medium; b) contacting said plurality of placodal precursor cells with a composition comprising brain-derived neurotrophic factor, wherein a plurality of trigeminal placode cells are created. In one embodiment, the method further comprises incubating the trigeminal placode cells under conditions such that trigeminal neurons are created. In one embodiment, the cranial placodal precursor cell expresses SIX1, PAX6 and TFAP2A. In one embodiment, the trigeminal placode cells express SIX1 and PAX3. In one embodiment, the trigeminal placodal precursor cells may be used to identify pharmacological agents to inhibit sensory neuron infectious agents. In one embodiment, the sensory neuron infectious agent comprises Varicella zoster virus (e.g., whose infection results in chicken pox). In one embodiment, the infected sensory neuron is a trigeminal neuron.

In one embodiment, the present invention contemplates a method, comprising: a) providing or plating a plurality of cranial placodal precursor cells in a cell culture medium; and b) contacting said plurality of placodal precursor cells with a composition comprising sonic hedgehog, purmorphamine and a γ-secretase inhibitor, wherein a plurality of pituitary placode cells are created. In one embodiment, the method further comprises incubating said pituitary placode cells under conditions such that a plurality of pituitary cells including, but not limited to, gonadotrophs, corticotrophs and somatotrophs are created that are capable of secreting hormones. In one embodiment, the secreted hormones include, but are not limited to, steroid hormones, adrenocorticotropic hormone and/or growth hormone. In one embodiment, the cranial placodal precursor cell expresses SIX1, PAX6 and TFAP2A. In one embodiment, the pituitary placode cells express SIX1 and PITX1.

In one embodiment, the present invention contemplates a method, comprising: a) providing or plating a plurality of cranial placodal precursor cells in a cell culture medium; and b) contacting said plurality of placodal precursor cells with a composition comprising sonic hedgehog, purmorphamine, a γ-secretase inhibitor and an FGF-inhibitor, wherein a plurality of lens placode cells are created. In one embodiment, the method further comprises incubating the lens placode cells under conditions such that lens fibers are created. In one embodiment, the cranial placodal precursor cell expresses SIX1, PAX6 and TFAP2A. In one embodiment, the lens placode cells express SIX1 and PITX3.

In one embodiment, the present invention contemplates a method, comprising grafting a trigeminal placode cell to a subject expressing at least one symptom of a pain syndrome, wherein said at least one symptom of the pain syndrome is reduced. In one embodiment, the pain syndrome includes, but is not limited to trigeminal nerve palsy, trigeminal neuralgia and/or migraine pain. In one embodiment, the grafting is performed on the pons. In one embodiment, the trigeminal placode cells migrate to the trigeminal nuclei.

In one embodiment, the present invention contemplates a method comprising grafting a pituitary placode cell to a subject expression at least one symptom of a neuroendocrine disorder, wherein said at least one symptom of the neuroendocrine disorder is reduced. In one embodiment, the grafted pituitary placode cells secrete growth hormone. In one embodiment, the grafted pituitary placode cells secrete adrenocortiotrophic hormone. In one embodiment, the engraftment is on a leg muscle.

In one embodiment, the engraftment is on the hypothalamic-pituitary axis. In one embodiment, the engraftment is on the hypothalamus. In one embodiment, the engraftment is on the sella. In one embodiment, the neuroendocrine disorder comprises diabetes. In one embodiment, the neuroendocrine disorder comprises hypopituitarism. In one embodiment, the neuroendocrine disorder comprises a pituitary tumor. In one embodiment, the neuroendocrine disorder comprises radiation therapy.

In one embodiment, the present invention contemplates a method comprising grafting a lens placode cell to a subject expression at least one symptom of an ocular disorder, wherein said at least one symptom of the ocular disorder is reduced. In one embodiment, the at least one symptom of an ocular disorder comprises blindness. In one embodiment, the at least one symptom of an ocular disorder comprises macular degeneration. In one embodiment, the at least one symptom of an ocular disorder comprises a cataract. In one embodiment, the at least one symptom of an ocular disorder comprises astigmatism. In one embodiment, the at least one symptom of an ocular disorder comprises near sightedness. In one embodiment, the at least one symptom of an ocular disorder comprises far sightedness. In one embodiment, the grafted lens placode cell secretes a plurality of lens fiber protein. In one embodiment, the plurality of lens fiber protein comprises an αβ-crystalline lens fiber protein. In one embodiment, the plurality of lens fiber protein is layered.

In one embodiment, the present invention contemplates a method, comprising: a) providing or plating a cell culture comprising human pluripotent stem cells in a culture medium; b) contacting said cell culture with a first inhibitor of Small Mothers Against Decapentaplegic (SMAD) protein signaling and 4-[4-(1,3-benzodioxol-5-yl)-5-(2-pyridinyl)-1H-imidazol-2-yl] benzamide (SB431542); c) removing said first SMAD inhibitor under conditions such that cranial placode precursor cells are formed. In one embodiment, the first SMAD inhibitor is selected from the group consisting of Noggin, a disulfide-linked homodimer of Noggin, Dorsomorphin, LDN-193189, and mixtures thereof. In one embodiment, the cranial placode precursor cells express SIX1, PAX6 and TFAP2A. In one embodiment, the culture medium comprises an N2 medium. In one embodiment, the culture medium comprises a knockout serum replacement medium. In one embodiment, the removing is performed at least 48 hours after the contacting.

The present inventions provide a method of producing a human neural cell (neural stem cells, neuronal subtypes, mature neurons, cells of a neural lineage) by (i) obtaining stem cells (hESCs, hiPSCs, somatic stem cells, cancer stem cells, human or mammalian pluripotent or multipotent cells); and (ii) culturing the human stem cell under conditions that block SMAD signaling. In a preferred embodiment, the methods for culture include conditions in a feeder-free system. In a preferred embodiment, the stem cells are cultured in a monolayer. A preferred embodiment contemplated the use of media that is supplemented with compounds Noggin and/or Dorsomorphin and SB431542.

In one embodiment the inventions provide a kit comprising a first inhibitor of Small Mothers Against Decapentaplegic (SMAD) protein signaling and a second inhibitor of Small Mothers Against Decapentaplegic (SMAD) protein signaling. In one embodiment, said first inhibitor is selected from the group consisting of a disulfide-linked homodimer of Noggin (SEQ ID NO:1), Dorsomorphin, LDN-193189, combination thereof and mixture thereof. In one embodiment, said Noggin is selected from mouse, human, rat, and *xenopus*. In one embodiment, said is Noggin is (SEQ ID NO:1) In one embodiment, said second inhibitor inhibits an anaplastic lymphoma kinase signaling pathway. In one embodiment, said second inhibitor inhibits a signaling pathway selected from the group consisting of Lefty, Activin, and TGFbeta. In one embodiment, said second inhibitor inhibits both activins and nodal signaling. In one embodiment, said second inhibitor is 4-[4-(1,3-benzodioxol-5-yl)-5-(2-pyridinyl)-1H-imidazol-2-yl]benzamide (SB431542) and derivatives thereof. In one embodiment, said kit further comprises a human stem cell. In one embodiment, the kit further comprises instructions.

In one embodiment the inventions provide a composition comprising a stem cell, a first inhibitor of Small Mothers Against Decapentaplegic (SMAD) protein signaling and a second inhibitor of Small Mothers Against Decapentaplegic (SMAD) protein signaling. In one embodiment, said first inhibitor is selected from the group consisting of a disulfide-linked homodimer of Noggin, Dorsomorphin, LDN-193189, combination thereof and mixture thereof. In one embodiment, said is Noggin is selected from mouse, human, rat, and *xenopus*. In one embodiment, said is Noggin is (SEQ ID NO:1) In one embodiment, said second inhibitor inhibits the Lefty/Activin/TGFbeta pathways by blocking phosphorylation of the ALK4, ALK5 and ALK7 receptors. In one embodiment, said second inhibitor inhibits activin/nodal signaling. In one embodiment, said second inhibitor is 4-[4-(1,3-benzodioxol-5-yl)-5-(2-pyridinyl)-1H-imidazol-2-yl]benzamide (SB431542) and derivatives thereof. In one embodiment, said stem cell is selected from the group consisting of human embryonic stem cells (hESC), somatic stem cells, and induced human pluripotent stem cells (hiPSC).

In one embodiment the inventions provide a method for inducing differentiation in stem cell, comprising, a) providing: i) a cell culture comprising human stem cells, ii) a first inhibitor of Small Mothers Against Decapentaplegic (SMAD) protein signaling, iii) a second inhibitor of Small Mothers Against Decapentaplegic (SMAD) protein signaling, and b) contacting said stem cells with said first inhibitor of Small Mothers Against Decapentaplegic (SMAD) protein signaling and said test compound under conditions for inducing differentiation in a stem cell into a non-default differentiated cell. In one embodiment, said first inhibitor is selected from the group consisting of a disulfide-linked homodimer of Noggin, Dorsomorphin, LDN-193189, combination thereof and mixture thereof. In one embodiment, said is Noggin is selected from mouse, human, rat, and *xenopus*. In one embodiment, said is Noggin is (SEQ ID NO:1) In one embodiment, said second inhibitor is a ALK4 receptor inhibitor. In one embodiment, said second inhibitor is 4-[4-(1,3-benzodioxol-5-yl)-5-(2-pyridinyl)-1H-imidazol-2-yl]benzamide (SB431542) and derivatives thereof. In one embodiment, said non-default differentiated cell is a neural progenitor cell. In one embodiment, said non-default differentiated cell is a part of a population of cultured cells. In one embodiment, said non-default differentiated cell is at least 10% up to 100% of said population of cultured cells. In one embodiment, said non-default differentiated cell in a population of cultured cells expresses paired box gene 6 protein. In one embodiment, said paired box gene 6 protein is expressed in at least 10% of said population of cultured cells. In one embodiment, said stem cell is selected from the group consisting of human embryonic stem cells (hESC), human somatic stem cells, and induced human pluripotent stem cells (hiPSC). In one embodiment, said non-default differentiated cell is a neural cell. In one embodiment, said neural cell is selected from the group consisting of dopamine positive neurons and floor plate cells.

In one embodiment the inventions provide a composition comprising isolated human embryonic neural cells. In one embodiment, said isolated human embryonic neural cells were derived from human embryonic cells. In one embodiment, said human embryonic neural cells are cultured in vitro. In one embodiment, said human embryonic neural cells are attached cells. In one embodiment, said composition is a co-culture further comprising a second cell type.

In one embodiment the inventions provide a method for screening biological agents, comprising, a) providing: i) a cell culture comprising human embryonic stem cells (hESCs), and ii) a test compound, and b) contacting said stem cells with said test compound under conditions for inducing neural floor plate cells. In one embodiment, said test compound is sonic hedgehog or fragment thereof. In one embodiment, said human embryonic stem cells are rosette-stage neural cells.

In one embodiment the inventions provide a method for providing differentiated cells, comprising, a) providing: i) a cell culture of human embryonic stem cells (hESCs), and ii) a compound for inducing differentiation, and b) contacting said stem cells with said test compound under conditions for inducing neural floor plate cells. In one embodiment, said compound is sonic hedgehog protein or fragment thereof. In one embodiment, said inducing consists of increasing a characteristic selected from the group consisting of flat cellular morphology, expressing sonic hedgehog, expressing forkhead box protein A2 (FOXA2), expressing Netrin-1, and expressing F-Spondin compared to said characteristic expressed in said human embryonic stems cells cultured without said test compound. In one embodiment, said inducing consists of decreasing a characteristic selected from the group consisting of rosette structures, BF1 expression, paired box homeotic gene-6 (PAX6) expression, NK6 homeobox 1 (NKX6.1), homeobox protein SIX6 expression compared to said characteristic in said human embryonic stems cells cultured without said test compound. In one embodiment, the method further provides and comprises a Noggin protein and an agent for blocking phosphorylation of a receptor selected from the group consisting of activin receptor-like kinase 4 (ALK4), activin receptor-like kinase 5 (ALK5) and activin receptor-like kinase 7 (ALK7) receptors and contacting said human stem cells with said noggin and said agent to human stem cells before adding said compound. In one embodiment, the method further provides an antibody, wherein said antibody is dickkopf homolog 1 (DKK-1) antibody, and contacting said stem cells with said antibody for reducing DKK-1 protein function. In one embodiment, the method further provides and comprises a caudalizing factor selected from the group consisting of wingless-type MMTV integration site family, member 1 (Wnt-1), and Retinoic Acid (RA). In one embodiment, the method further provides and comprises a neuron inducing compound and step c) adding said neuron inducing compound for inducing progenitor neurons. In one embodiment, said dopamine neurons express a marker selected from the group consisting of corin, serine peptidase (CORIN) and nephroblastoma overexpressed gene (NOV). In one embodiment, said progenitor neurons are dopamine neurons express a marker selected from the group consisting of LIM homeobox transcription factor 1, beta (LMX1B) and neurogenin 2 (NGN2). In one embodiment, the method further provides and comprises a stem cell, and step d) co-culturing said human neural floor plate cells with said stem cells for producing neurite outgrowth from said stem cells.

In one embodiment the inventions provide a neural floor plate cell produced by the methods described herein. In one embodiment the inventions provide a placode cell produced by the methods described herein. In one embodiment the inventions provide a lens cell produced by the methods described herein.

The invention contemplates methods for assessing the neural identity of the derived neural cells. This method may be through morphological means, functional assessment, and measurement of expression or downregulation of proteins associated with certain lineages. In a preferred method, dopaminergic activity or functional assays for motor neurons are utilized.

The present method can by employed to deliver agents or neural cells to the brain in an effective amount for diagnosis, prevention, treatment of disease, disorders, or for patients suffering from nerve damage form stroke. Such cells were co-committed towards a neural fate.

In one embodiment, the present invention contemplates a composition comprising isolated human embryonic floor plate cells. In one embodiment, the isolated human embryonic floor plate cells were derived from human embryonic cells. In one embodiment, the human embryonic floor plate cells are cultured in vitro. In one embodiment, the human embryonic floor plate cells are attached cells. In one embodiment, the composition is a co-culture further comprising a second cell type.

In one embodiment, the present invention contemplates a method for screening biological agents, comprising, a) providing: i) a cell culture comprising human embryonic stem cells (hESCs), and ii) a test compound, and b) contacting said stem cells with said test compound under conditions for inducing neural floor plate cells. In one embodiment, the test compound is sonic hedgehog or fragment thereof. In one embodiment, the human embryonic stem cells are rosette-stage neural cells.

In one embodiment, the present invention contemplates a method for providing differentiated cells, comprising, a) providing: i) a cell culture of human embryonic stem cells (hESCs), and ii) a compound for inducing differentiation, and b) contacting said stem cells with said test compound under conditions for inducing neural floor plate cells. In one embodiment, the compound is sonic hedgehog protein or fragment thereof. In one embodiment, the inducing consists of increasing a characteristic selected from the group consisting of flat cellular morphology, expressing sonic hedgehog, expressing forkhead box protein A2 (FOXA2), expressing Netrin-1, and expressing F-Spondin compared to said characteristic expressed in said human embryonic stems cells cultured without said test compound. In one embodiment, the inducing consists of decreasing a characteristic selected from the group consisting of rosette structures, BF1 expression, paired box homeotic gene-6 (PAX6) expression, NK6 homeobox 1 (NKX6.1), homeobox protein SIX6 expression compared to said characteristic in said human embryonic stems cells cultured without said test compound. In one embodiment, the method further provides Noggin protein and an agent for blocking phosphorylation of a receptor selected from the group consisting of activin receptor-like kinase 4 (ALK4), activin receptor-like kinase 5 (ALK5) and activin receptor-like kinase 7 (ALK7) receptors and contacting said human stem cells with said noggin and said agent to human stem cells before adding said compound. In one embodiment, the method further provides an antibody, wherein said antibody is dickkopf homolog 1 (DKK-1) antibody, and contacting said stem cells with said antibody for reducing DKK-1 protein function. In one embodiment, the method further provides a caudalizing factor selected from the group consisting of wingless-type MMTV integration site family, member 1 (Wnt-1), and Retinoic Acid (RA). In one embodiment, the further comprises, providing, a neuron inducing compound and step c) adding said neuron inducing compound for inducing progenitor neurons. In one embodiment, the dopamine neurons express a marker selected from the group consisting of corin, serine peptidase (CORIN) and nephroblastoma overexpressed gene (NOV). In one embodiment, the progenitor neurons are dopamine neurons express a marker selected from the group consisting of LIM homeobox transcription factor 1, beta (LMX1B) and neurogenin 2 (NGN2). In one embodiment, the method further comprises, providing, stem cells, and step d) co-culturing said human neural floor plate cells with said stem cells for producing neurite outgrowth from said stem cells.

BRIEF DESCRIPTION OF THE FIGURES

FIGS. 9A-9L show exemplary induced pluripotent stem cells (IPS) that were differentiated to neural tissue using dual SMAD inhibition and are patternable to dopaminergic neurons and motor neurons. (A, B) Two IPS clones (IPS$^{C14}$, IPS$^{C27}$) were generated and screened for OCT4 (red) as well as additional pluripotency factors (Tra-1-81, Tra-1-60, SSEA-4 and Nanog). (C, D) The two clones were neuralized by dual SMAD inhibition (PAX6 expression, green), and neural crest could be observed by HNK1 staining (E, F). Neural tissue from the IPS clones could be induced to form rosette-NSCs (G, H) based on KI-67 (red) and phospho-histone H3 (green) expression, motor neurons (I, J) based on HB9 expression (green), and dopaminergic neurons (K, L) based on TUJ1 (green) and TH (red) co-expression. Scale bars: 200 μm—(A, B); 50 μm—(C, D, E, F, G, H, I, J, K, L).

FIG. 10 shows exemplary combined SMAD inhibition during the first 5 days of neural-induction. Homogeneous PAX6 expression was observed on day 11 when SB431542 and Noggin, supplemented in the media, were withdrawn on day 5.

Figure 1A:
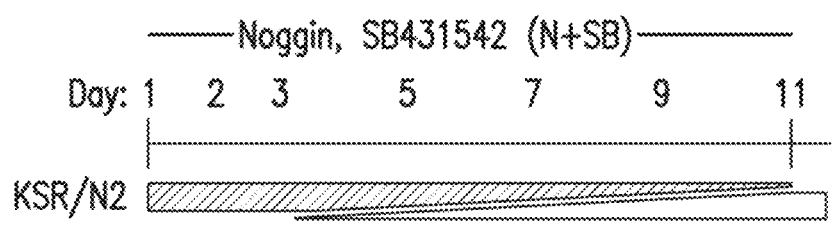
FIGS. 1A-1G show exemplary dual SMAD inhibition that allowed for a highly efficient feeder-free neural induction in adherent cultures within seven days. (A) Differentiation scheme used for achieving neural induction was achieved with the combination of SB431542, an ALK inhibitor, and Noggin, a BMP inhibitor. (B) The dual SMAD inhibition greatly improves neural differentiation (PAX6 expression, green) to greater than 80%. Infrequent neural differentiation (<10% PAX6$^+$ cells) were observed when the single factors are used. (C) Real-Time PCR for early germ layer markers CDX2, SOX1, SOX17 and Brachyury. (D) Immunoflourescence for OCT4 (red) and PAX6 (green) expression indicates rapid neutralization occurs by day 7. (E) Real-Time PCR for PAX6, OTX2, FGF5, OCT4 during dual SMAD inhibition reveals an epistem cell intermediate at day 5. (F) Real-Time PCR for neural and neuronal markers during dual SMAD inhibition differentiation towards neuroectoderm. (G) A BAC reporter line (HES5-GFP) was used to quantify the percentage of neural induction for the method using MS5 stromal cells (with Noggin) or dual SMAD inhibition (SB431542 and Noggin). Error bars represent S.E.M. and the p-value was determined using Student's T-test. Abbreviations: N, Noggin; SB, SB431542; KSR, knock-out serum replacement medium; N2, N2 medium. Scale bars: (B)—200 µm; (D)—50 µm.

A) Schematic illustration of timed noggin withdrawal paradigm to determine temporal requirement for endogenous BMP signaling in placode cell specification.

B) Relative induction of placodal markers (Dlx3, Eya1, and Six1) comparing modified N-SB protocol as described in (A) to N-SB treatment maintained throughout differentiation (SBN condition). Optimal co-expression of Dlx3, Eya1, and Six1 was observed when the cells are treated with noggin for 48 hours. Data represent fold changes of mRNA expression measured by qRT-PCR at day 11.

C) Immunocytochemical analyses showing Six1 (placodal marker) and Pax6 (anterior neuroectoderm marker) expression at day 11 of differentiation. Cells treated with the modified N-SB protocol (noggin withdrawal after 2 days of differentiation) show high percentages of Six1+ cells.

D) Approximately seventy percent of cells generated using modified N-SB conditions (2 days of noggin) are Six1+ compared to standard (anterior neurectoderm-inducing) 11 days of noggin treatment.

FIGS. 12A-12F show exemplary temporal global gene expression profiles during human ES cell derived placode specification. (A-D) Pair-wise comparison at day 5, day 7, day 9 and day 11 of differentiation of most the differentially expressed genes in hESC progeny subjected to the modified (placode-inducing) versus standard (anterior neuroectoderm-inducing) N-SB protocol. (E) Unsupervised clustering of microarray data segregates data according to replicates, temporal sampling and treatment conditions. (F) Principal component analysis of data confirms close temporal correlation of samples during human ES cell differentiation with increasing separation of modified versus standard N-SB treated cells at later differentiation stages.

FIGS. 13A-13G show exemplary derivation of hESC placode derived sensory neurons. (A-C) Immunocytochemical analysis at day 20 of differentiation demonstrates that placodal precursor cells efficiently yield neurons that initially retain Six1 expression. (D and E) Sensory neuron identity is confirmed by expression of Brn3A and Isl1 in the majority of neurons derived from Six1+ clusters. (F) At day 40 differentiation neurons show increased expression of peripherin and decreased levels of Tuj1 staining characteristic of a mature peripheral neuron fate. (G) Schematic illustration of marker expression during sensory neuron specification from hESC derived placodal cells.

FIGS. 14A-14D show exemplary prospective isolation of hESC derived placodal precursors. (A) At day 11 of differentiation hESC derived cells are segregated into mutually exclusive p'75+ and a Forsel+ precursor cell domains. (B) FACS analysis at day 11 of differentiation for expression of p75 and HNK1. (C) qRT-PCR data for Six1 mRNA expression following separation of cells based on the expression of p75 and HNK1. Cells single positive for p75 but negative for HNK1 (prospective placodal precursors) showed a dramatic increase in Six1 mRNA expression compared to other groups. (D) An increase in the fraction of cells that are positive for p75 and negative for HNK1 is observed when precursors are derived under modified (placode-inducing) compared to the standard (anterior neuroectoderm-inducing) N-SB induction conditions.

FIGS. 15A-15G show exemplary high SHH levels, increased FOXA2 and decreased BF1 expression. (A) Passage 1, Day 21 of neural differentiation shows no effect of SHH treatment when added at Day 15. Results quantified on right, *p<0.01 N=3. Scale bar, 200 um. (B) Day 21 of neural differentiation shows a reduction of rosette like structures after Sonic C25II treatment Day 9. Loss of rosettes quantified on right, *p<0.01 N=4. Scale bar, 100 um. (C) Sonic C25II treatment results in a decrease of BF1 and an increase in Foxa2 at Day 21. Quantified on right, *p<0.05 N=4. Scale bar, 200 um. (D) Day 21 of neural differentiation reveals a decrease in ZO1/BF1+ rosette structures. This decrease is quantified, *p<0.01 N=4. Scale bar, 50 um. (E) Decrease in PAX6 expression at Day 21 after Sonic C25II treatment. This decrease is quantified, *p<0.01 N=4. Scale bar, 200 um. (F) Dose response curve comparing Sonic and Sonic C25II efficacy on FOXA2 induction. (G) Dose response curve of Sonic C25II comparing the induction of FP markers (FOXA2 and Netrin-1) to another SHH responsive gene NKX6.1.

FIGS. 16A-16E show exemplary floor plate induction that has an early, short temporal patterning window (A) Schematic showing different time points of Sonic C25II additions during neural induction protocol. (B-C) Heading on the left delineates the day Sonic C25II was added, heading on the top delineates when the assay was stopped. The earlier Sonic C25II is added, and the longer the cells are exposed to it, leads to very high percentages of FOXA2. (C) This result is quantified, *p<0.01 N=3. Scale bars, 200 um, high magnification, 50 um. (D) Extended treatment with Sonic C25II (9 days of exposure) does not yield increased FOXA2 induction. (E) Schematic of optimal protocol for FOXA2 induction to be used for the rest of the study.

FIGS. 17A-17F show exemplary hESC derived FP that is functional (A) Schematic showing when conditioned media was collected. (B) ELISA showing an increase in levels of Netrin-1 secreted into the media at Days 9 and 11 when Sonic C25II is added early to the neural induction, *p<0.01 N=3. (C) Conditioned media from NSB and NSB+Sonic C25II was collected and placed on cultures containing NSB derived neural precursor cells qRT-PCR showing an induction of ventral genes (NKX6.1 and NKX2.1) as well as the SHH responsive gene (GLI2). These inductions are repressed in the presence of the SHH antagonist cyclopamine. (D) The induction of NKX6.1 is shown at the level of the protein using a GFP expressing line. *p<0.01 compared to NSB CM, #p<0.05 compared to FP CM, N=3. Scale bar, 200 um. (E and F) Neural explants isolated from E8.5 neurectoderm co-cultured with NSB+Sonic C25II tissue show ectopic FOXA2 staining. Inset shows co-localization of M6 (Green) and FOXA2 (Red). (F) This data is quantified, *p<0.001 N=4 explants. Scale bar, 50 um.

FIGS. 18A-18R show exemplary transcriptional analysis that revealed novel genes involved in FP development. (A-J) qRT-PCR data showing time course of expression over the length of the 11 day protocol. The genes looked at represented different populations including FP markers (A-D), SHH responsive genes (E-G), neural markers (H), AN markers (I and J), and genes involved in mesodermal and endodermal commitment (K and L). (M-R) Detailed time course microarray analysis (M-N) GO terms for Day 7 (M) and Day 11 (N) showing increase or decrease compared to NSB control. FP condition shows enrichment in genes associated with axon guidance and secreted proteins, while showing a decrease in genes associated with anterior neurectoderm development. (O-R) Pair wise comparisons showing genes up and down regulated compared to NSB control condition at Day 3 (O), Day 5 (P), Day 7 (Q), and Day 11 (R).

FIGS. 19A-19M show exemplary DKK-1 inhibition of FP induction. (A) qPCR for DKK-1 expression in control NSB condition over time. (B) ELISA measuring DKK-1 protein levels in the media at Day 5, 7, and 11 showing a decrease in Dkk-1 levels after Sonic C25II treatment, *p<0.05 N=3. (C) qPCR for DKK-1 expression in NSB+Sonic C25II condition over time. (D and E) qPCR for BF1 (D) and FOXA2 (E) showing an increase in BF1 and decrease of FOXA2 after DKK-1 addition, and an increase in FOXA2 when DKK-1 antibody is added. (F) Immunostaining for FOXA2 showing a decrease in FOXA2+ cells when DKK-1 is added. Scale bar, 200 um. (G) qPCR for BF1 expression showing that DKK-1 antibody treatment leads to a decreased expression at earlier time points (Day 3-Day 5). (H and I) Early addition of DKK-1 antibody leads to an increase of FOXA2 expression, but has no effect when added at later timepoints. (I) Immunocytochemical data demonstrating that DKK-1 treatment starting at day 5 of differentiation (or later) does not enhance SHH-mediated FOXA2 expression. (J-K) hESC transduced with either control or BF1 shRNA (J and K, left panels), GFP is a marker of transduction (J and K, middle panels). When differentiated to neural tissue, a reduction of BF1 is seen at the level of the protein compared to control (J and K, right panels). Scale bar, 100 um, (L) qRT-PCR analysis at Day 11 showed an increase in FP markers (FOXA2, SHH, Netrin-1 and F-Spondin) in the BF1 shRNA line compared to the control, p<0.01 N=3. (M) BF1 shRNA leads to an upregulation of FOXA2 seen at the level of the protein. Scale bar, 200 um.

FIGS. 20A-20E show exemplary hESC derived FP was shifted along the A/P axis (A) Immunostaining reveals an increase in FOXA2 in response to FGF8, Wnt-1, and Retinoic Acid. Scale bar, 200 um. (B) qPCR showing caudilizing agents such as FGF8, Wnt-1, and Retinoic Acid (RA) lead to an increase in FOXA2 and a reduction in SIX6 compared to NSB+Sonic C25II. (C) qPCR for a panel of midbrain FP markers (CORIN and NOV) and midbrain DA progenitor markers (LMX1B, NGN2, and EN1). In particular, Wnt-1 treatment causes an upregulation of both midbrain FP markers as well as midbrain DA progenitor markers. (D) FP cells were transfected with Shh enhancer that drives expression to the anterior ventral axis (SBE2) or midbrain ventral axis (SBE1). The default FP exhibits SBE2 activity indicating an anterior location. This is abolished upon Wnt1 and FGF8 addition and SBE1 activity is now seen suggesting a shift from anterior identity to midbrain. Scale bar, 200 um. (E) Schematic of FP versus AN specification during hESC differentiation. Neural differentiation is initiated upon exposure to Noggin and 0431542. SHH exposure, starting at day 1 of differentiation, induces FP differentiation and via inhibition of DKK-1 and BF1 suppresses AN specification. The regional identity of the resulting FP cells is anterior by default but posterior FP tissue were induced in the presence of caudalizing factors such as Wnt-1, FGFF8 or RA.

FIGS. 21A-21H show exemplary hESC derived FP that expresses appropriate markers (A) qRT-PCR data at Day 11 showing an increase in floor plate markers FOXA2, SHH, Netrin-1, and F-Spondin relative to control NSB conditions. (B) Table quantifying results of immunostaining experiments. (C-F) Immunostaining of FOXA2+ cells reveals co-labelling with few markers such as (C) Nestin, (D) SOX2, (E) Nkx2.2, and (F) Tuj1. Scale bar, (D and F, 50 um) (E and G, 100 um). (G-H) qRT-PCR data at Day 11 showing levels of FOXA2 and SOX17 cells differentiated with NSB+Sonic C25II treatment and cells differentiated towards an endodermal lineage. SOX17 is not expressed in Sonic C25II conditions but is highly expressed in the endoderm. This is shown at the level of the protein by immunostaining (H). Scale bar, 200 um.

Figure 22:
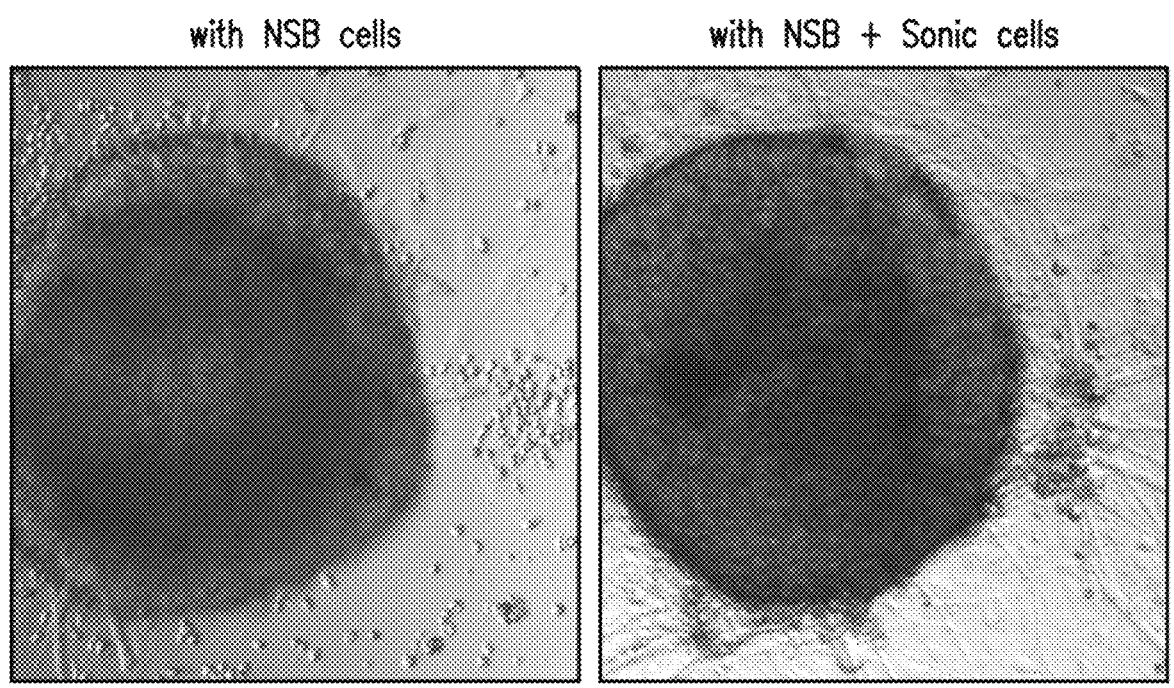

FIG. 22 shows exemplary co-culture of cerebellar plate explants on FP cells that induces neurite outgrowth. Cerebellar explants from E8.5 mouse were plated on NSB neural cells or NSB+Sonic (FP) cells. After 3 days considerable neurite outgrowth was observed in the NSB+Sonic (FP) condition compared to control.

FIGS. 23A-23D show exemplary qPCR that validates genes changing in microarray. (A) qPCR for FP genes showing an enrichment in Sonic C25II condition compared to NSB control. (B-D) qPCR validating novel genes that changes in the Sonic C25II condition compared to NSB control condition.

FIGS. 24A-24E show exemplary BF1 expression that inhibits FP induction (A) qRT-PCR at two points during neural differentiation showing a decrease in BF1 levels in the BF shRNA hESC line compared to control, *p<0.01 N=3. (B) Cell cycle analysis revealed no differences in the cell cycle kinetics of the two lines. (C) hESC expressing BF1 visualized by GFP. Scale bar, 20 um. (D) Cells overexpressing BF lack FOXA2+ expression. Scale bar, 200 um. (E) qRT-PCR data at Day 11 showing a lack of FP induction in BF1 expressing hESC after Sonic C25II treatment.

Figure 25A:
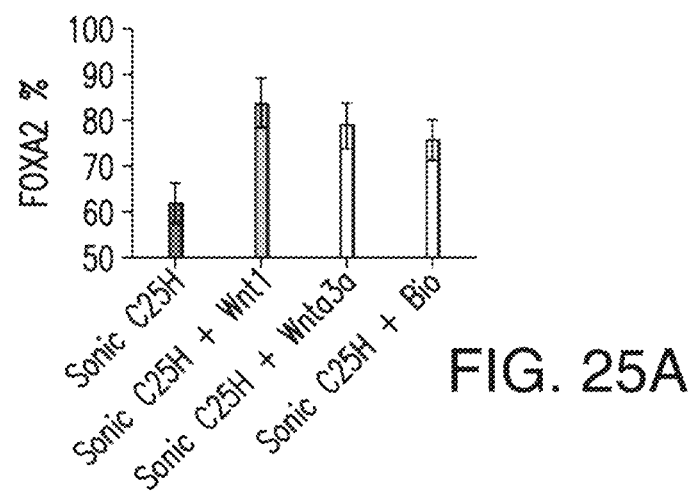
Figure 25B:
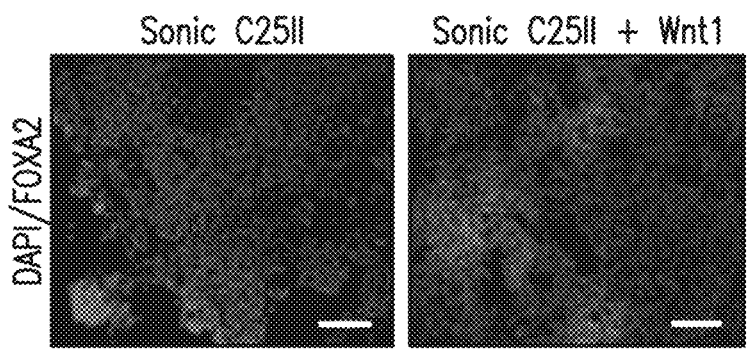
Figure 25C:
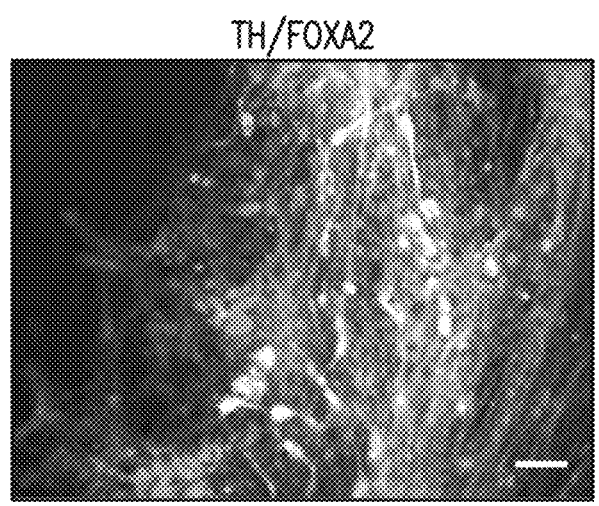

FIGS. 25A-25C show exemplary early WNT1 addition along FP differentiation that can cause DA neuron differentiation (A) Adding WNTs or GSK3β-Inhibitor (BIO 100 nM) early can increase FOXA2 expression. (B) Addition of WNT1 to later stage neural rosette cells has no effect on FOXA2 induction, scale bar 200 um. (C) WNT1 treated FP cultures can give rise to DA Neurons expressing FOXA2, scale bar 50 um.

Figure 26:
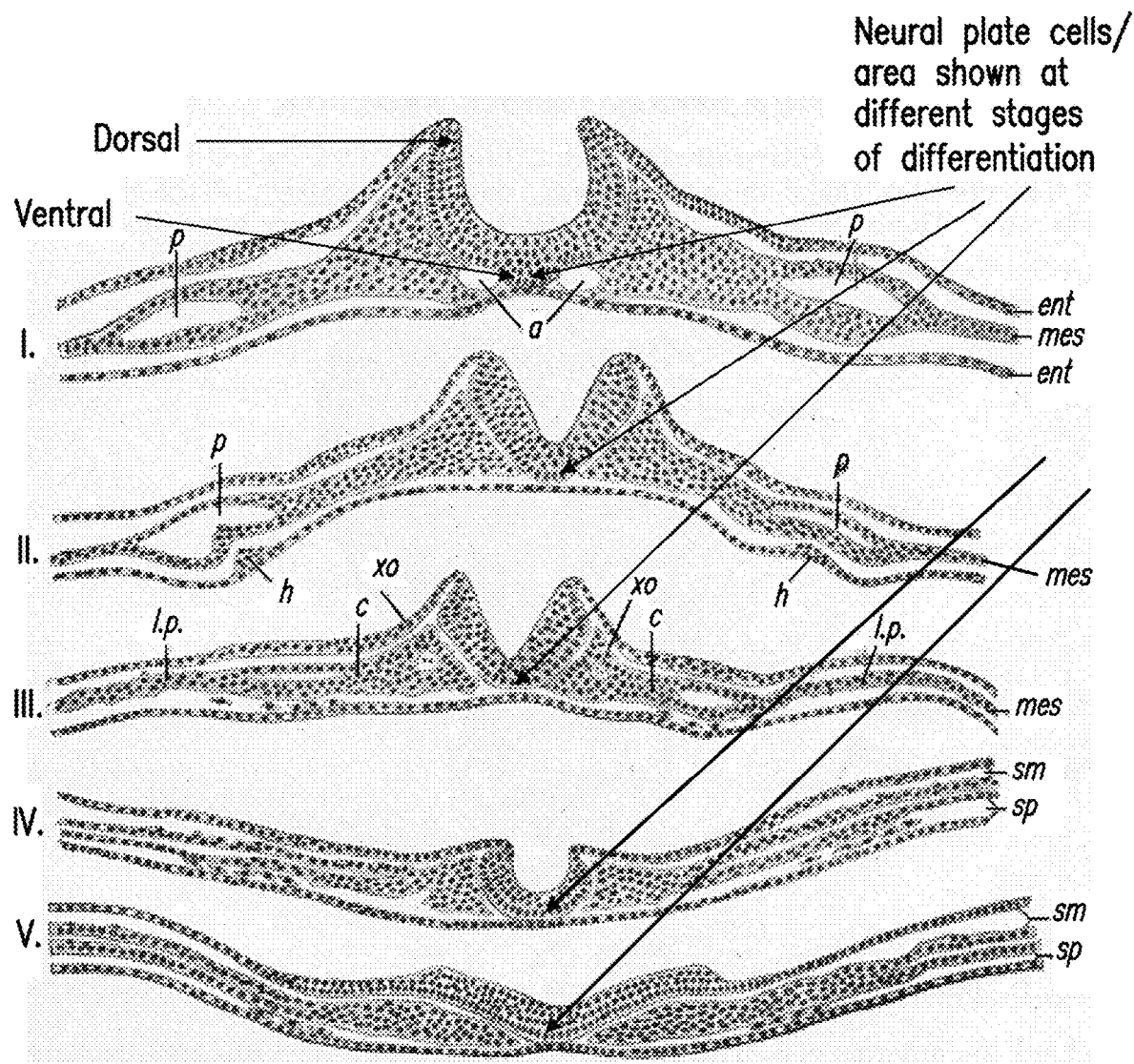

FIG. 26 presents an illustrative Gray's Anatomy plate A: series of transverse sections through an embryo of the dog, anterior to posterior, I-V. Section I is the most anterior. In V the neural plate is spread out nearly flat. Gray's Anatomy by Henry Gray.

FIGS. 27A-27K present exemplary data of placode induction, characterization and validation of protocol across various human ESC and iPSC lines. Error bar represents SEM. (*) P<0.05; () P<0.01; (*) P<0.001 compared with control N-SB condition (n=3 independent experiments). Scale bars correspond to 50 μm.

A) Schematic illustration of the dorsal view of a human neural plate stage embryo (based on (O'Rahilly, 1987)). Fate studies in model organisms have identified a unique horseshoe-shaped territory in the head ectoderm that contains all placode precursors, called the pre-placodal region (PPR; marked here in red). The neuroectoderm forms the neural plate (marked light blue). The most lateral aspects of the neural plate form the neural folds (marked in pink) that give rise to the future neural crest cells.

B) BMP4 treatment induces trophectoderm-like lineage by morphology

C) CDX2 expression at day 11 following BMP4 treatment or SB+BMP4 treatment. Data represent fold changes of mRNA expression by qRT-PCR as compared to N-SB condition.

D) SIX1 (red) and PAX6 (green) expression at day 11 of differentiation.

E) Immunocytochemistry for DACH1 (red) expression in N-SB and PIP conditions.

F) Flow analysis for SOX10 expression at day 11 of PIP using a SOX10::GFP hESC reporter line.

G, H) The placode induction protocol (PIP) was robust across multiple hESC (H9, 16 and Hs293) and hiPSC lines (C14, M3X, and C27). Representative images of SIX1/PAX6 immunocytochemistry are shown in (G) for each line with higher magnification insets and with quantification of the percentage of SIX1+ cells under PIP condition in (H).

I) Scheme of experimental design to test specificity of EYA1::GFP enhancer in the mammalian system. The primary cultures olfactory (OLF) area and midbrain (MB) area from E11.5 mouse embryo were isolated and nucleofected with placode specific EYA1::GFP enhancer J) Only the primary olfactory culture (OLF) showed activation of EYA1 enhancer, while midbrain primary cultures showed no GFP expression.

K) The GFP expression is quantified by FACS analysis under PIP and N-SB condition.

FIGS. 28A-28H show exemplary data of the derivation of Six1+ placodal precursors using a modified dual-SMAD inhibition protocol Error bar represents SD. (*) P<0.05; () P<0.01; (*) P<0.001 compared with control N-SB condition (n=3 independent experiments).

A) Schematic illustration of timed Noggin withdrawal paradigm to determine temporal requirement for endogenous BMP signaling during placode specification. The protocol is based on modifying the Noggin+SB431542 (NSB) protocol developed for CNS induction (Chambers et al., 2009).

B) Relative induction of placodal markers comparing modified NSB protocol (various time points of Noggin withdrawal) to N-SB treatment maintained throughout differentiation (NSB condition). Data represent fold changes of mRNA expression measured by qRT-PCR at day 11.

C) Immunocytochemical analyses of SIX1 and PAX6 expression at day 11 of differentiation. Inset shows a confocal section to demonstrate SIX1 expression within clusters. Scale bars correspond to 50 μm.

D) Quantification of the percentage of Six1+ cells generated under modified N-SB (SB3=placode induction (PIP) protocol) versus N-SB condition.

E) Immunocytochemical analysis of placodal markers, EYA1, DACH1, and FOXG1 in placodal clusters. Insets show higher magnification images for respective marker. Scale bars correspond to 50 μm F-H) Temporal analysis of gene expression in PIP versus N-SB protocol. Values are normalized to the expression observed in undifferentiated hESCs.

F) Loss of expression of pluripotency (NANOG, OCT4/POU5F1) and trophectodermal (TE) markers;

G) Lack of expression of mesodermal marker T;

H) of non-neural fates and induction of placodal fates by monitoring time course expression of pluripotency markers (NANOG, OCT4), trophectoderm (CDX2), mesoderm (T), endoderm (SOX17), and placodal markers (DLX3, SIX1, FOXG1).

FIGS. 29A-29E show exemplary data of a temporal gene expression analysis of placodal (PIP condition) versus CNS (NSB condition) fates:

A) Principal component analysis of data confirms close temporal correlation of samples during hESC differentiation with increasing separation of PIP versus N-SB treated cells at later differentiation stages.

B) Confirmation of the microarray data by qRT-PCR.

C) Gene ontology analysis of genes that are upregulated at day 7 of PIP protocol.

D) Venn Diagram of comparison of the genes that are upregulated at day 5, 7, and 9 in PIP.

E) Venn Diagram of comparison of the genes that are upregulated at day 7, 9, and 11 in PIP.

FIGS. 30A-30I show exemplary data of a temporal global gene expression profiles during hESC-derived placode specification.

A) Clustering of the differentially regulated genes during PIP versus N-SB protocol.

B-E) The top twenty most significant up (red) and down-regulated (blue) genes in PIP versus N-SB protocol by fold change at day 5, 7, 9 and 11.

F-G) Confirmation of ISL1 and TFAP2A expression at the protein level under PIP conditions (day 11).

H) Confirmation of OVOL2 expression by immunocytochemistry (day 11).

I) Time course analysis of OVOL2 gene expression during PIP, N—SB and neural crest (NC) protocol. Scale bars in F, G and H correspond to 50 µm.

FIGS. 31A-31E show exemplary data of the induction of epidermal versus placodal fates upon modulating FGF signaling and the role of BMP and WNT signaling during human placode induction: Error bar represents SEM. (*) $P<0.05$; () $P<0.01$; (*) $P<0.001$ (n=3 independent experiments).

A) Schematic summary of differentiation condition used for early keratinocyte induction.

B) Patches of keratinocyte co-express E-CADHERIN (green) and KRT14 (red) at day 42.

C) The center of the patches expresses KI67 at day 42, while KI67 positive cells diminish by day 60. KRT14 positive cells are negative for KI67. Scale bars correspond to 50 µm.

D) Analysis of SIX1 and SOX10 expression at day 11 following treatment with pharmacological inhibitor (XAV939) and activator (CHIR99021) of WNT signaling starting at day 3 of PIP.

E) Analysis of CDX2 and SIX1 expression at day 11 following treatment with inhibitor (Noggin) and activator (BMP4) of BMP signaling starting at day 3 of PIP.

FIGS. 32A-32G show exemplary data where FGF signaling determines placodal versus non-neural ectoderm/epidermal fate. Error bar represents SD. Error bar represents SD. (*) $P<0.05$; () $P<0.01$; (*) $P<0.001$ compared with control PIP condition (n=3 independent experiments). Scale bars in C and G correspond to 50 µm.

A-B) Time course of the induction of TFAP2A and SIX1 under PIP conditions. C) TFAP2A (green) is expressed in placodes and surface ectoderm, while SIX1 (red) is only expressed in placode cells. Blocking PIP via pharmacological inhibition of endogenous FGF signaling, blocks the formation of SIX1+ cells.

D) Quantification of the loss of SIX1 gene expression following treatment with the FGF inhibitor SU5402.

E) Expression of early epidermal marker KRT8. Data represent fold changes of mRNA expression by qRT-PCR at day 11 compared to PIP condition.

F) Expression of late epidermal marker KRT14 during keratinocyte differentiation. Data represent fold changes of mRNA expression by qRT-PCR at day 11 and day 42 compared to hESC.

G) Long-term SU5402 treated cultures are expressing KRT 14 protein suggesting epidermal/keratinocyte fate.

FIGS. 33A-33H show exemplary data of a characterization of placode-derived trigeminal sensory neuron lineage across multiple human ESC and iPSC lineages: Error bar represents SEM (n=3 independent experiments)

A) Immunocytochemical analysis at day 20 of differentiation demonstrates that SIX1+ placodal clusters efficiently yield large numbers of TUJ1 positive neurons that initially retain SIX1 expression.

B) At day 42 differentiated neurons express Peripherin (green).

C-E) Short (day 23) and long term (day 55) cultures of trigeminal neuron mRNA expression of C) RUNX1 D) RET1 E) TRK receptors, Data represent fold changes (FC) of mRNA expression, normalized to hESC.

F) Trigeminal neurons stain for TRKA (live stains)

G) Schematic representation of differentiation protocol for trigeminal sensory neurons. The clusters are manually passaged at day 13-17

H) Trigeminal-type sensory neurons can be obtained under the same PIP conditions at high efficiencies from various hESC (16) and hiPSC (C27, M3X, J1-5)

Figure 34A:
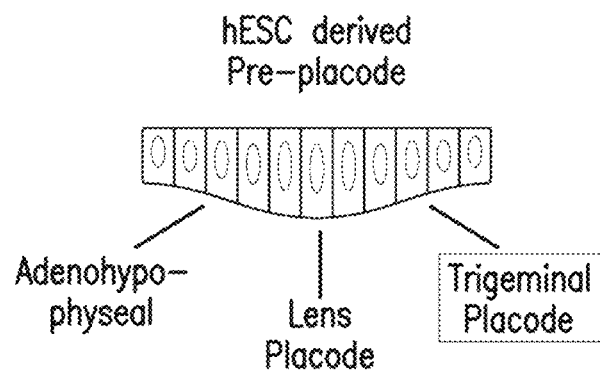
Figure 34B:
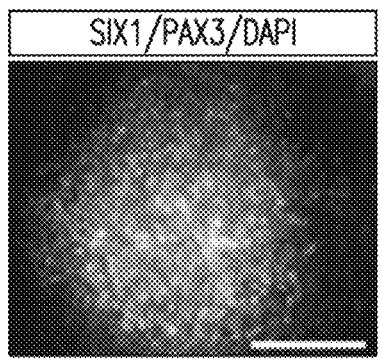
Figure 34C:
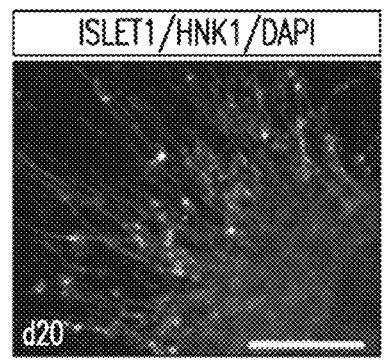
Figure 34D:
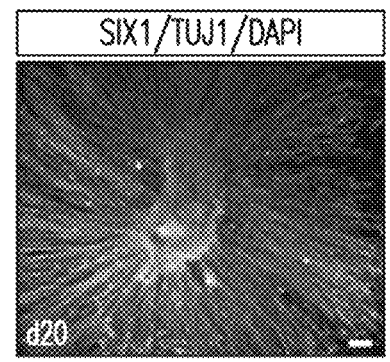
Figure 34E:
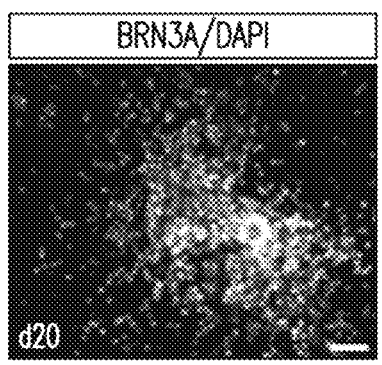
Figure 34F:
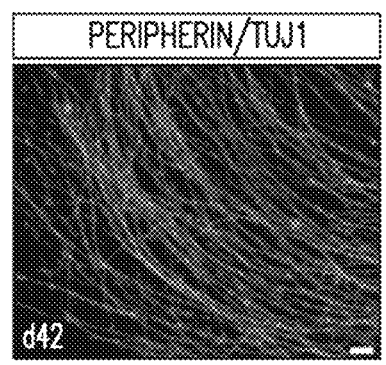
Figure 34G:
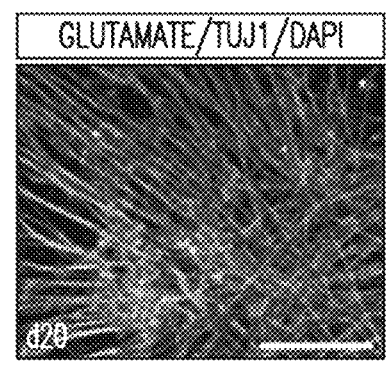
Figure 34H:
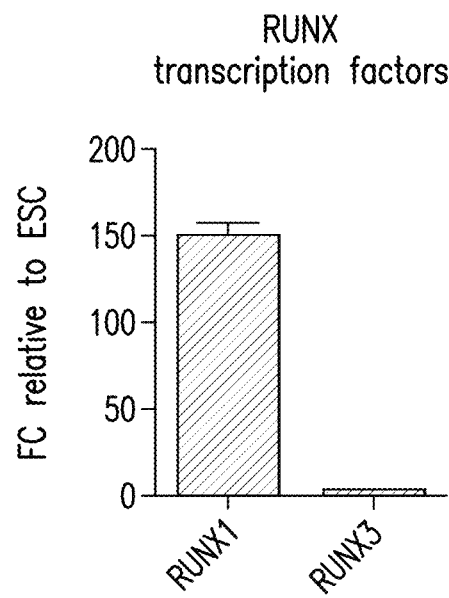
Figure 34I:
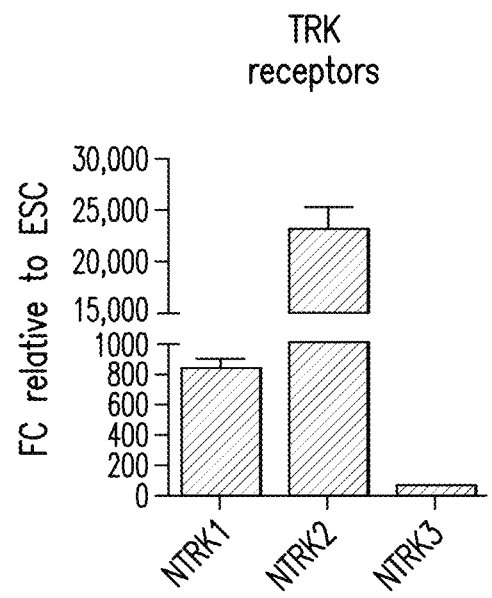
Figure 34J:
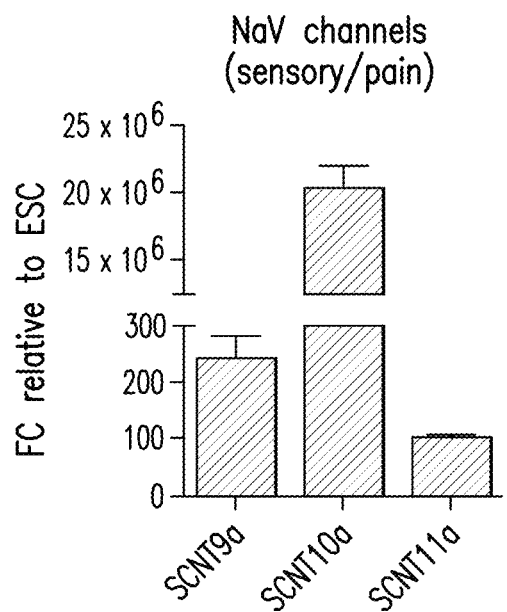
Figure 34K:
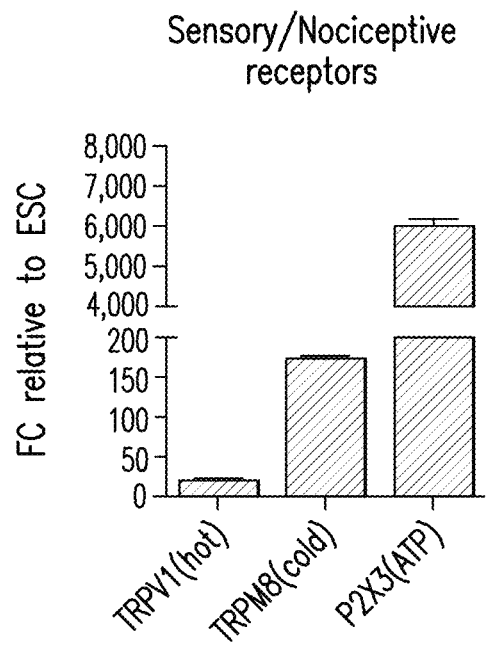
Figures 34P, 34Q, 34R, 34S:
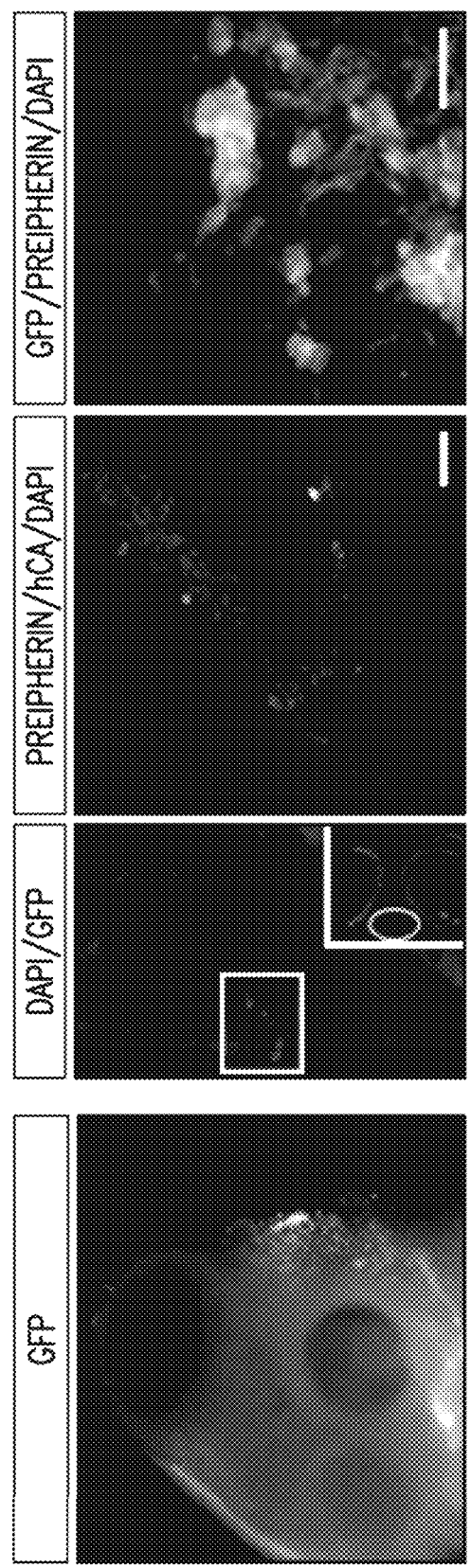

FIGS. 34A-34S show exemplary data of a derivation, characterization and transplantation of hESC-derived trigeminal type sensory neurons. All scale bars correspond to 50 µm.

A) Schematic representation of various placodes derived during development for pre-placode cells including hormone producing cells (pituitary placode), structural cells such as lens fibers (lens placode) and sensory neurons (trigeminal placode). Trigeminal placode fate (highlighted in orange) appears to be a default under PIP conditions.

B) PAX3, a trigeminal placode marker is expressed in SIX1+ placode clusters at the placode stage at day 11.

C) Placode clusters by default rapidly yield cells expressing sensory neuron makers such as ISL1 and HNK1.

D) Immunocytochemical analysis at day 20 of differentiation demonstrates that SIX1+ placodal clusters efficiently yield large numbers of TUJ1 positive neurons that initially retain SIX1 expression.

E) Sensory neuron identity is further confirmed by expression of BRN3A in the majority of neurons derived from SIX1+ clusters.

F) At day 42 of differentiation, neurons show increased expression of Peripherin and decreased levels of TUJ1 staining suggesting adoption of a more mature peripheral neuron fate.

G) Trigeminal neurons stain for glutamate.

H) Expression of RUNX factors,

I) TRK receptors,

J, K) nociceptor-specific channels and receptors in trigeminal neurons responsible for hot (TRPV1) and cold (TRPM8) sensation and for inflammatory pain (P2X3; n=3 independent experiments).

L, M) Examples of single cell patch clamp electrophysiological analysis in hESC-derived trigeminal-type neurons at day 53 of differentiation.

N) The intensity of the stimulus was started from −125 pA and increased by 25 pA until a single action potential was observed. Steps shown correspond to 25 pA increments.

O) Summary of quantitative electrophysiological parameters showed comparable patterns for both bipolar and tripolar type neurons.

P-S) Transplantation into trigeminal anlage in chick embryo. P) GFP labeled cells and graft morphology 2 days after transplantation.

Q) Low power image shows GFP+ fiber bundles: GFP (green) and DAPI (blue). Insert, section at midbrain level shows GFP+ fiber bundles adjacent to trigeminal anlage.

R) The human fiber bundles express human cytoplasmic marker (green) and the sensory neuron marker, Peripherin (red).

S) GFP+/PERIPHERIN+ cells bodies are arranged in ganglia-like clusters in vivo.

FIGS. 35A-35D show exemplary data of a paradigm for assessing the in vivo properties of hESC-derived trigeminal neuron precursors:

A) hESC-derived trigeminal neurons form bundles in vitro during differentiation (day 30) as shown by white circles.

B) Schematic of chick and mouse transplantation experiments.

C) Transplantation time and collection time of chick embryo experiments

D) The negative staining control for transplantation in the chick sections at neural plate region.

Transplantation of trigeminal neuron precursors into the adult mouse pons to test the ability of grafted hESC-derived trigeminal neuron axonal arbors to reach targets in trigeminal nuclei. Location and morphology of GFP (green) labeled human trigeminal neurons grafted within the pontine nuclei (Pn) after 1 month transplantation. Human GFP neuronal processes traveling towards the trigeminal nuclei Aqueduct (Aq). Immunohistochemistry for co-expression of BRN3A (red), GFP (green) and DAPI (blue) in grafted cells. Human neuronal fiber bundles co-express hNCAM and GFP.

FIGS. 36A-36H show exemplary data of an identification of putative pre-placode and directed differentiation towards human lens placode lineage. Scale bars in (G) correspond to 50 µm. Error bar represents SD. (*) P<0.05; () P<0.01; (*) P<0.001 compared with control PIP condition (n=3 independent experiments).

A) Immunocytochemical analysis for TFAP2A and PAX6 at day 3 of differentiation.

B) Time course analysis at day 5, 7, 9 and 11 of PIP differentiation show co-expression of TFAP2A and PAX6 at days 7 and 9 of differentiation.

C) Time course analysis at day 5, 7, 9 and 11 of N-SB differentiation shows lack of TFAP2A expression but expression of PAX6 in CNS neuroectodermal cells. Scale bars in A-C correspond to 25 µm.

D) Temporal analysis of PAX3 gene expression during PIP versus NSB protocol.

E) PAX3 expression levels following treatment (days 7-11) with activators or inhibitor of FGF (FGF8, SU5402) and WNT signaling (CHIR99021, XAV939) during PIP.

F) PAX6 expression levels using same treatment as in (E).

G) Results of a four signaling pathway screen (modulators of BMP, FGF, WNT and SHH signaling added at days 7-11 of PIP). Induction of the lens placode marker PITX3 by qRT-PCR was observed upon treatment with activators of BMP signaling (BMP4) or inhibitors of FGF signaling (SU5402).

H) Modified placode cultures differentiating into Crystalline+ cells with mature lens fiber morphologies by day 57 of differentiation.

Figure 37A:
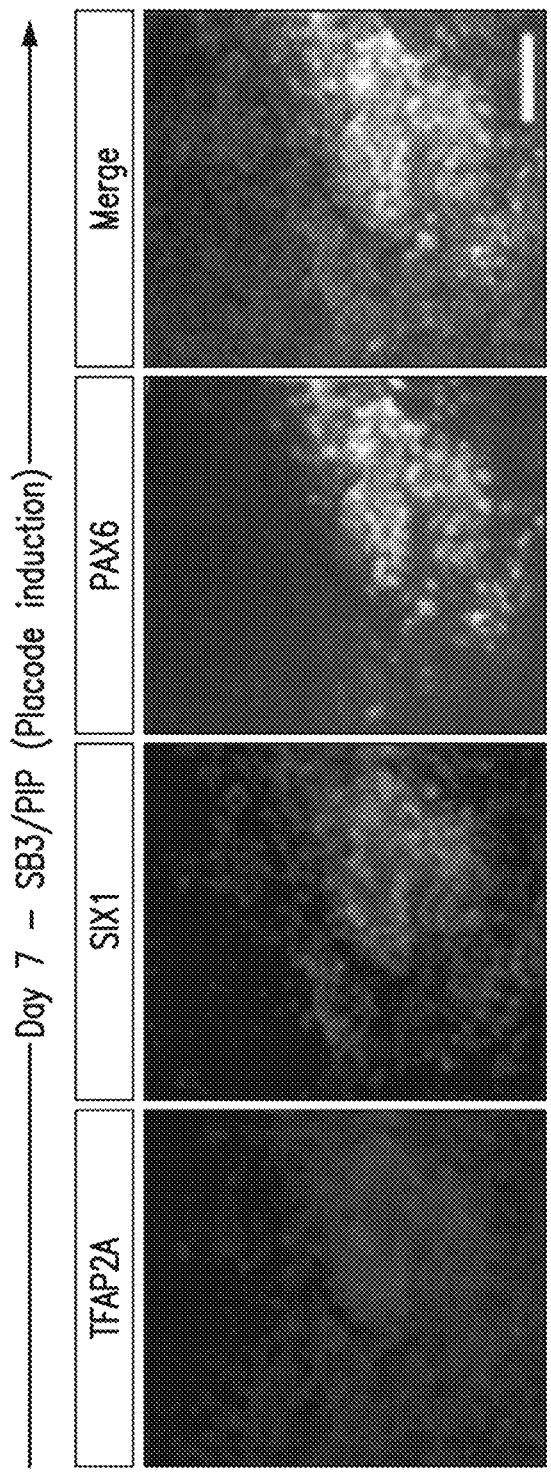
Figure 37B:
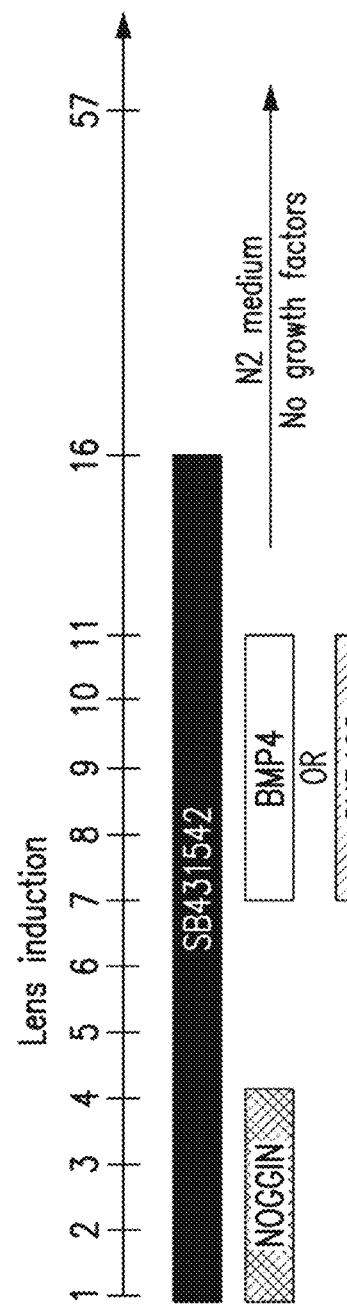

FIGS. 37A-37B show exemplary data that pre-placodal cells can be further differentiated into lens placode upon treatment with BMPs. Scale bars correspond to 50 µm.

A) TFAP2A, PAX6 and SIX1 co-expression mark a transient putative pre-placode stage under PIP conditions. Immunocytochemical analysis for SIX1 (red), TFAP2A (blue) and PAX6 (green) at day 7 of differentiation under PIP condition. Scale bars correspond to 50 µm.

B) Schematic representation of the differentiation condition used for early lens induction.

Figure 38A:
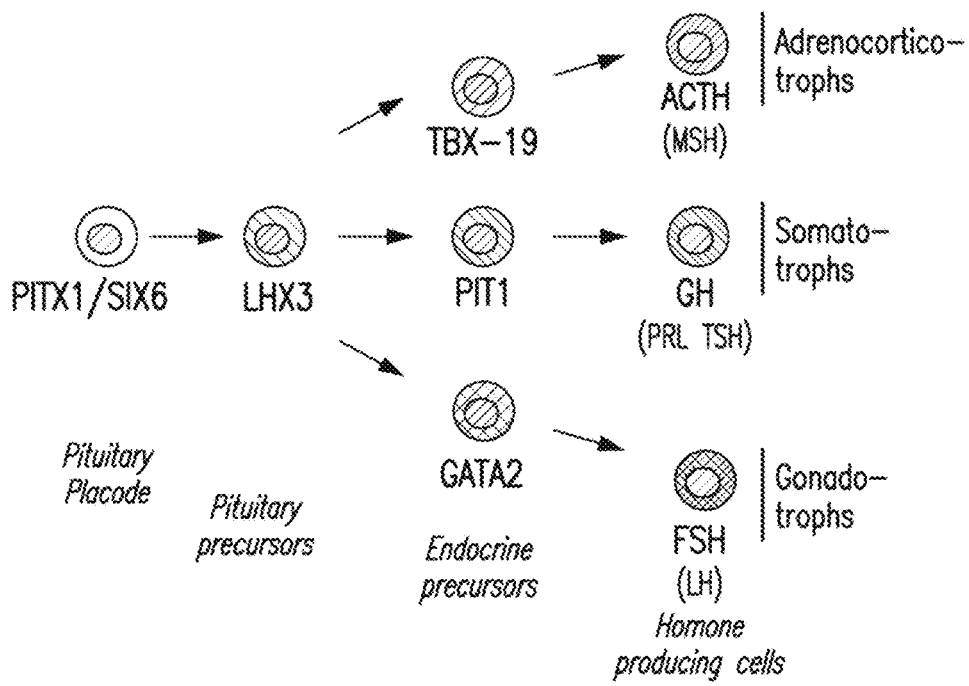

FIGS. 38A-38R show exemplary data of a specification and functional characterization of hormone-producing pituitary placode derivatives. Scale bars are: 100 µm in (C, P), 50 µm in (D, H, I, J, Q, R, S) and 10 µm in (K). Error bar represents SEM (*) P<0.05; () P<0.01; (*) P<0.001 compared with controls PIP condition in (B), hESC in (E, F, G; n=3 independent experiments), HBSS without cells in (L), and plasma samples from matrigel-only injected (Sham) animals in (N, O; n=3 and n=5 animals).

A) Schematic illustration of normal pituitary lineage development in vivo (Tabar, 2011). Examples of hormone producing cells generated using our modified PIP are listed in bold (ACTH, GH, FSH).

B) Treatment with SHH from day 7-11 of PIP differentiation induced PITX1 and SIX6 expression as assessed by qRT-PCR. PITX1 and SIX6 mark the pituitary anlage. Low SHH: 20 ng/ml C25II SHH; high SHH: 100 ng/ml C25II SHH+1 µM purmorphamine.

C) Immunocytochemical analysis showed expression of SIX6 at the protein level in a subset of clusters in the presence of SHH treatment.

D) Immunocytochemical analysis for expression of LHX3 at day 16 (upon SHH treatment).

E-G) Induction of defined endocrine precursor lineages: E) TBX19 expression was highly induced by day 20. F) PIT1 expression at day 20 and 32 of differentiation (see FIG. 39A for treatment paradigm). G) GATA2 expression at day 20 and 32 of differentiation.

H-L) Immunocytochemical evidence of hormone production H) CGA expression was readily detected by day 16 in SHH-treated PIP cultures. I) FSH, was expressed by day 27.

J) ACTH expression was most abundant in SHH-treated PIP culture by day 30 of differentiation.

K) GH expression at day 30 of differentiation.

L) ELISA measurement of in vitro hormone production after 10 min exposure in HBSS.

M) Schematic illustration of transplantation paradigm in nude rat host.

N) ACTH plasma levels in grafted adult nude rats and sham-grafted controls at 4 and 6 weeks after transplantation.

O) GH plasma levels using a human specific ELISA (6 weeks after transplantation).

P-R) Histological analysis 6 weeks after transplantation: P) Robust survival of hNCAM+ human cells. Q) ACTH expressing and (R) GH expressing cells in vivo.

FIGS. 39A-39E show exemplary data of a protocol to generate anterior pituitary placode and hormone producing cells for in vivo transplantation studies.

A) Schematic representation of the differentiation condition used for early pituitary induction.

B, C) Short-term in vivo analysis upon subcutaneous injections of hESC-derived GFP+ early pituitary cells in NOD-SCID mice.

D) Coexpression of GSU (CGA) and GFP labeled cells in mouse grafts.

E) Co-expression of FSU and GFP labeled cells in mouse grafts.

Figure 40:
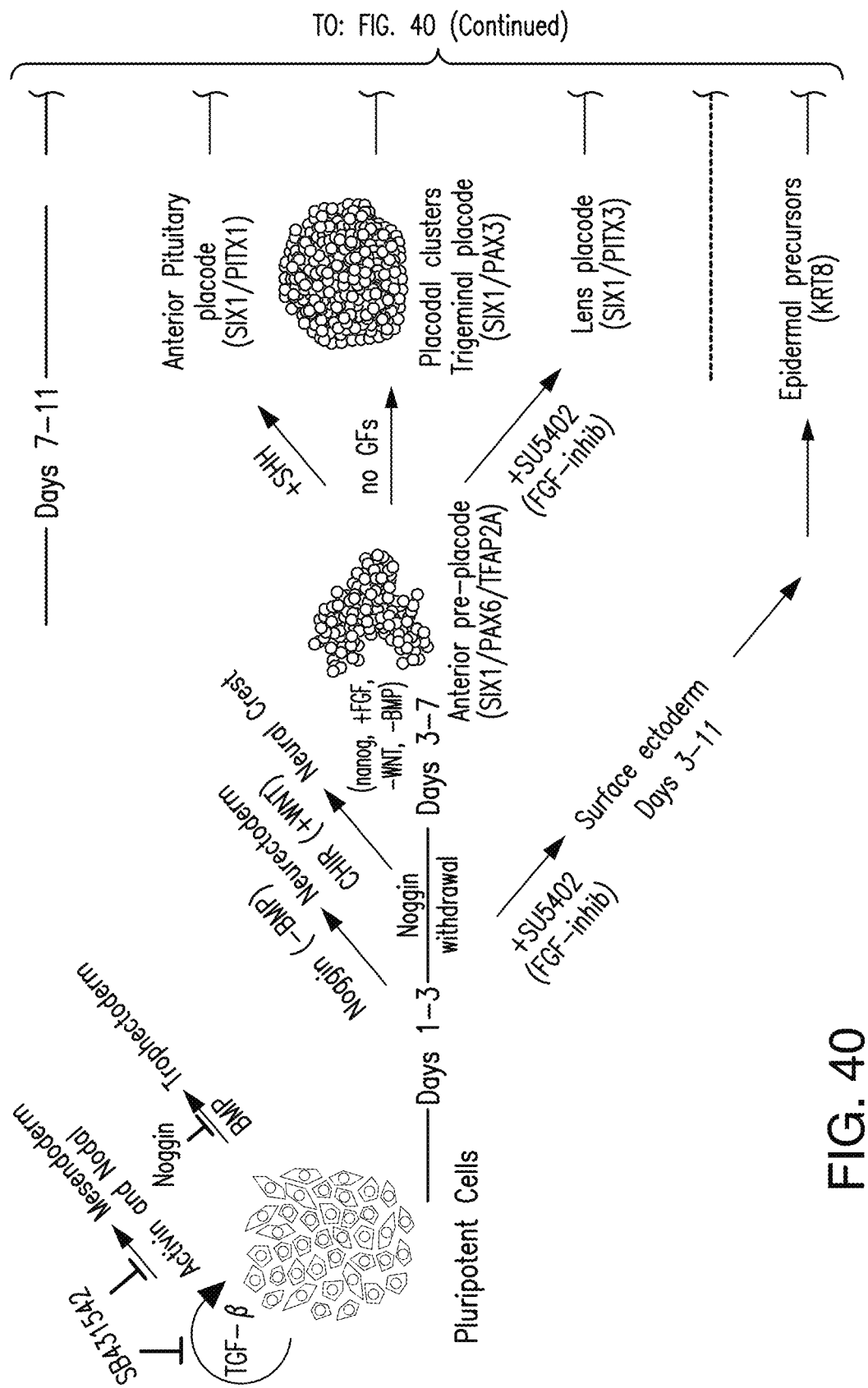
Figure 40:
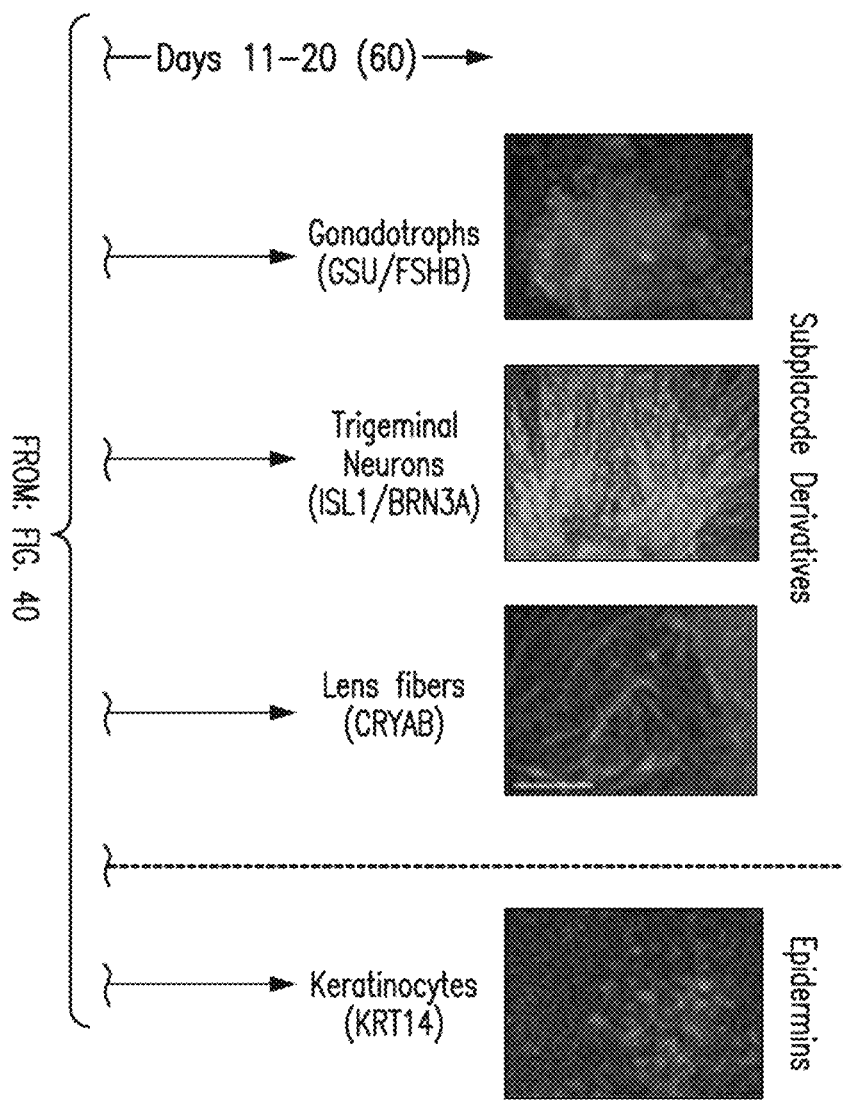
Figure 41A:
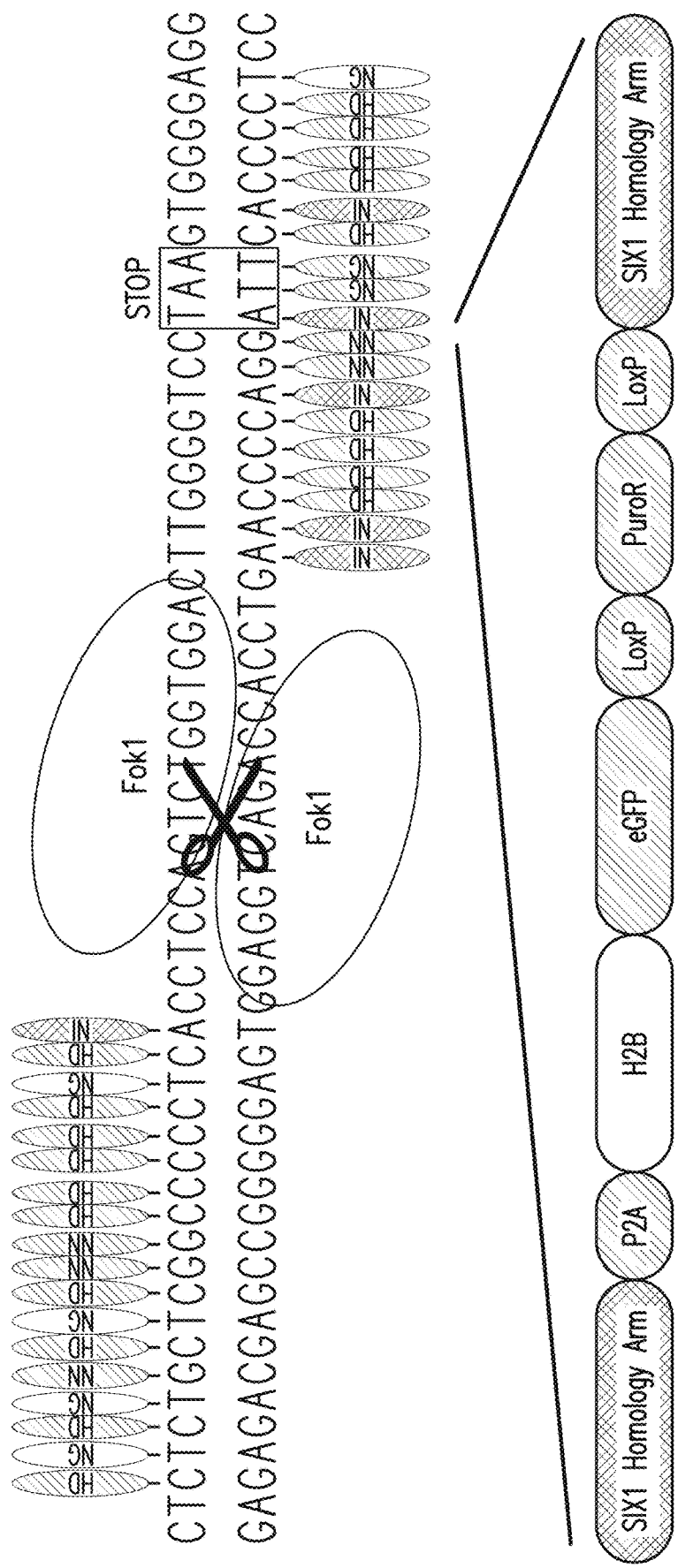
Figures 41B, 41C:
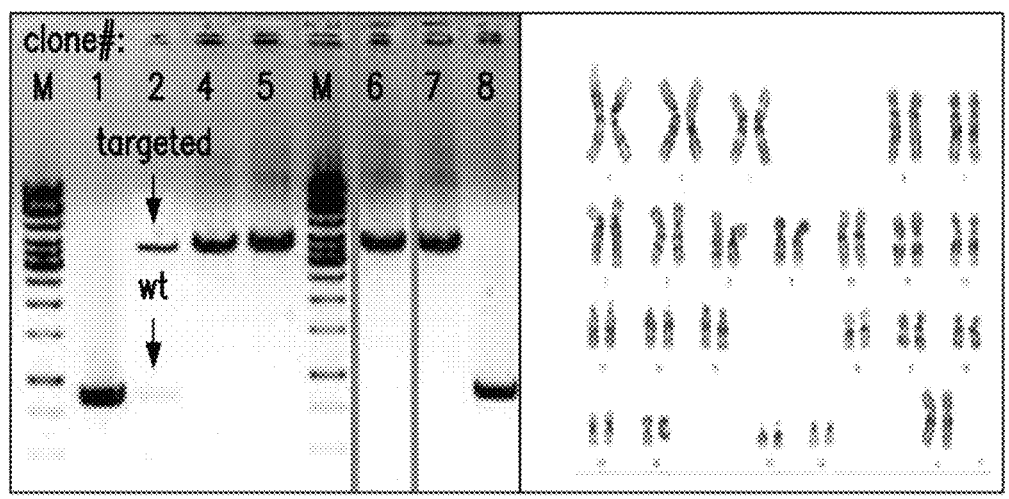
Figure 41D:
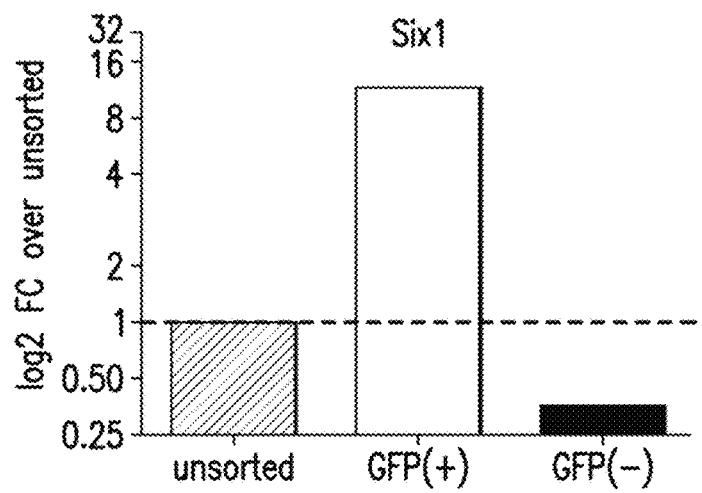
Figure 41E:
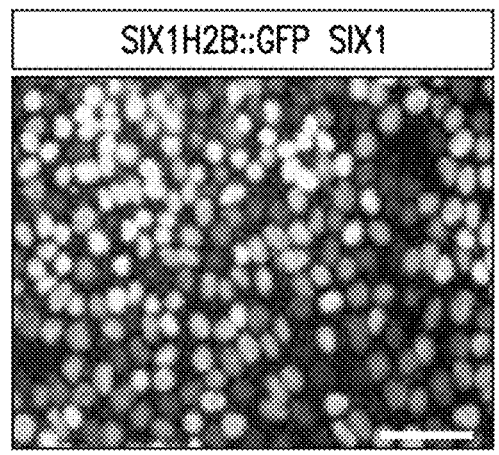

FIG. 40 shows exemplary data of a proposed model for the derivation of human placodes from hPSCs. Placode induction is dependent on de-repression of BMP signaling using dSMADi protocol. Continuous BMP repression induced CNS fates, de-repression of BMP in combination with the inhibition of FGF signaling by SU5402 triggers epidermal fates. Pre-placodal cells can be further patterned towards specific placode fates by modulating FGF, BMP or SHH signaling at day 7 of differentiation leading to functional lens, trigeminal neuron and anterior pituitary derivatives.

FIGS. 41A-41E show (A-C) a schematic depicting the protocol used to generate a SIX1::H2B-GFP reporter cell line; and (D-E) placode cell expressing the SIX1::H2B-GFP reporter construct.

Figure 42A:
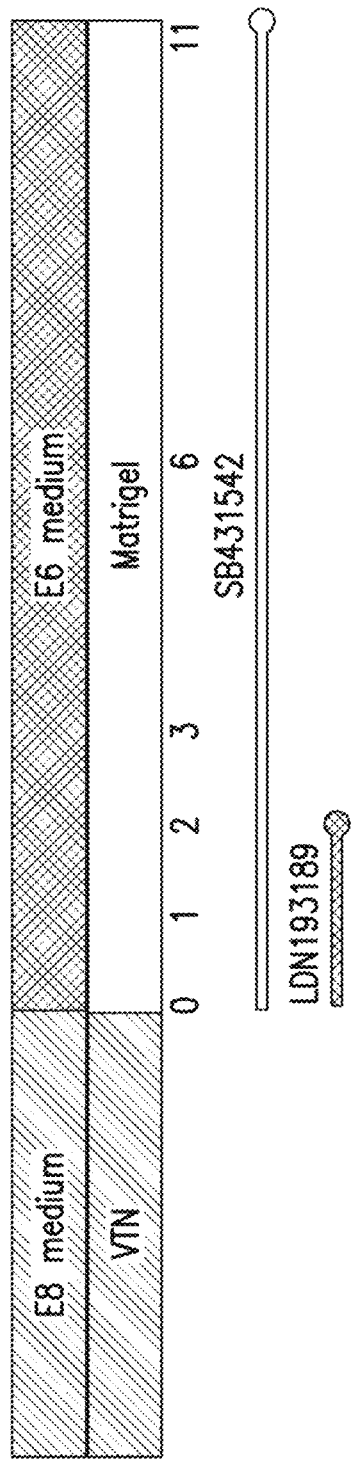
Figure 42B:
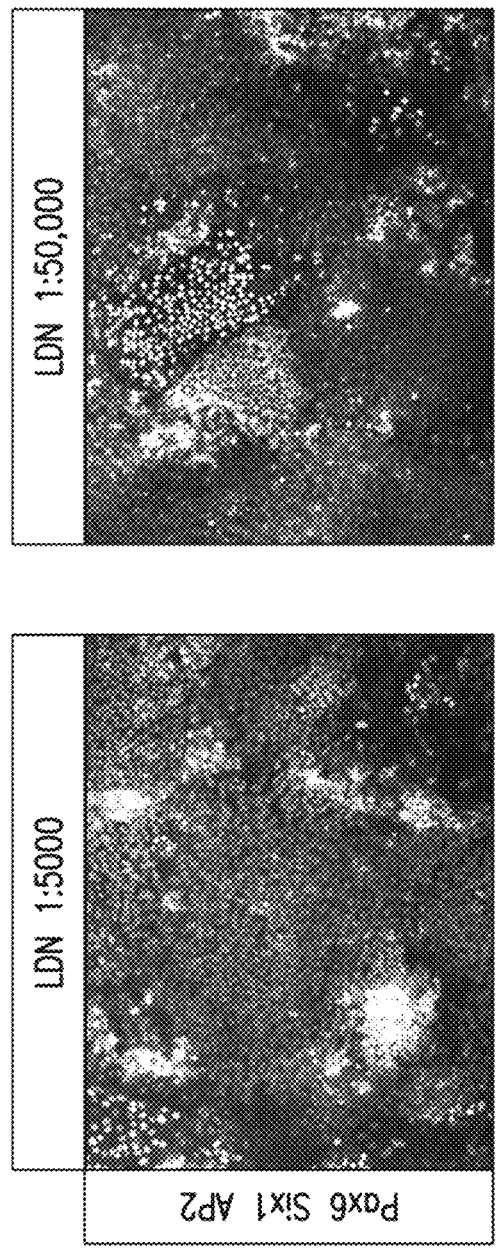

FIGS. 42A-42B show (A) the PIP protocol used to culture cells in E8/E6 cell culture media, wherein the culture media was supplemented with SMAD inhibitor SB431542 for culture days 0-11, and SMAD inhibitor LD193189 for days 0-2. (B) shows the expression of placode precursor markers SIX1 and PAX6 in the cells induced using the PIP protocol and E8/E6 media.

FIGS. 43A-43C show (A) the protocol for the modified PIP-E6 protocol which supplements the E8/E6 media with BMP4 and the single SMAD inhibitor SB431542 during days 0-3 of the culture; (B-C) shows AP2 expression in cells cultured according to the PIP-E6 protocol with 0, 1, 5, 10, 15 and 20 ng/ml BMP4.

FIGS. 44A-44C show (A) the PIP-E6 protocol used for culturing SIX1::H2B-GFP cells; (B) expression of AP2 and SIX1 in cells induced when BMP4 was present in the culture media for days 0-3 at a concentration of 5 ng/ml BMP4 and (C) expression of AP2 and SIX1 in cells induced when BMP4 was present in the culture media for days 0-3 at a concentration of 20 ng/ml BMP4.

Figure 45A:
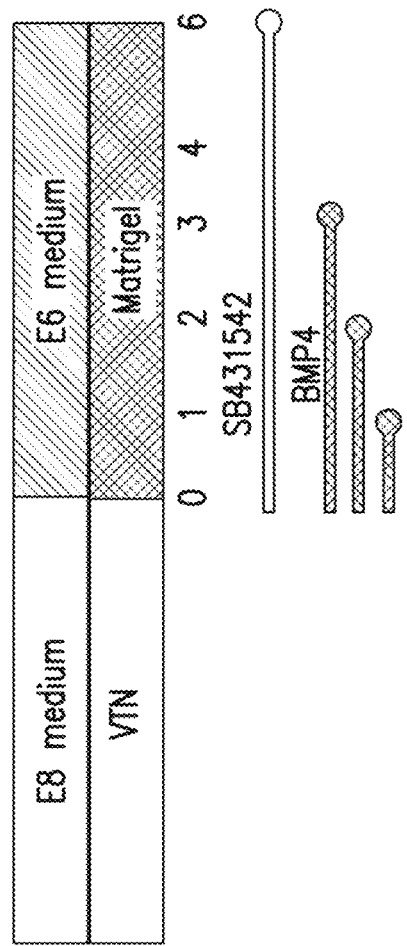
Figure 45B:
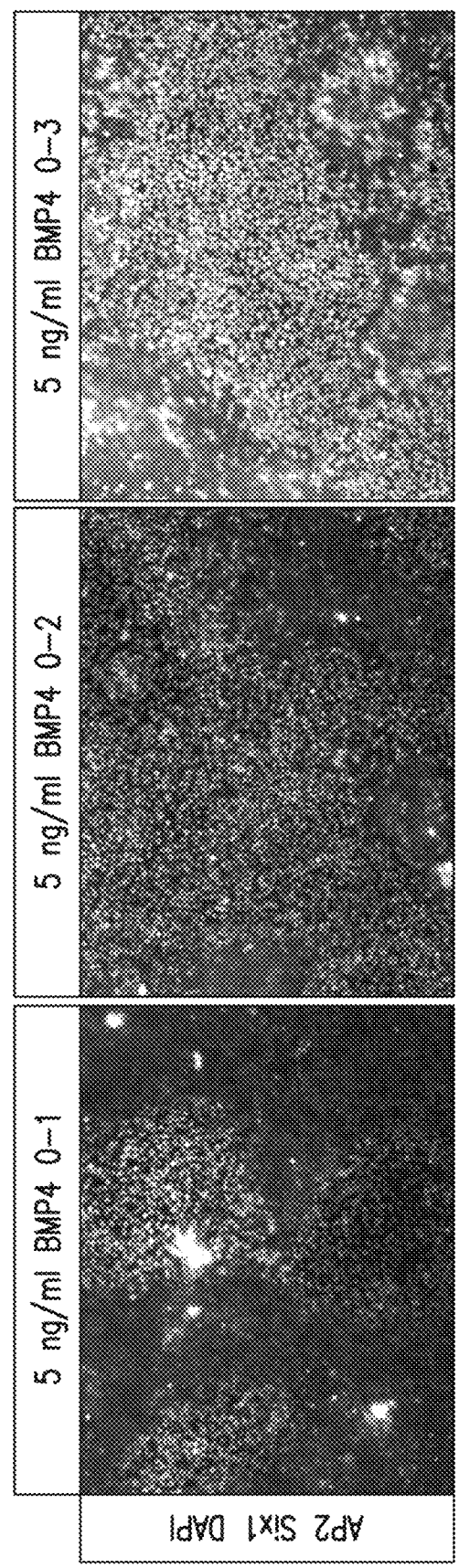

FIGS. 45A-45B show (A) the PIP-E6 protocol used for culturing SIX1::H2B-GFP cells using (B) 5 ng/ml BMP4 for 0-1, 0-2 and 0-3 days of culture days of culture, and the resulting expression of SIX1 and AP2. The highest level of SIX1 and AP2 expression occurred after the 0-3 day protocol.

Figure 46:
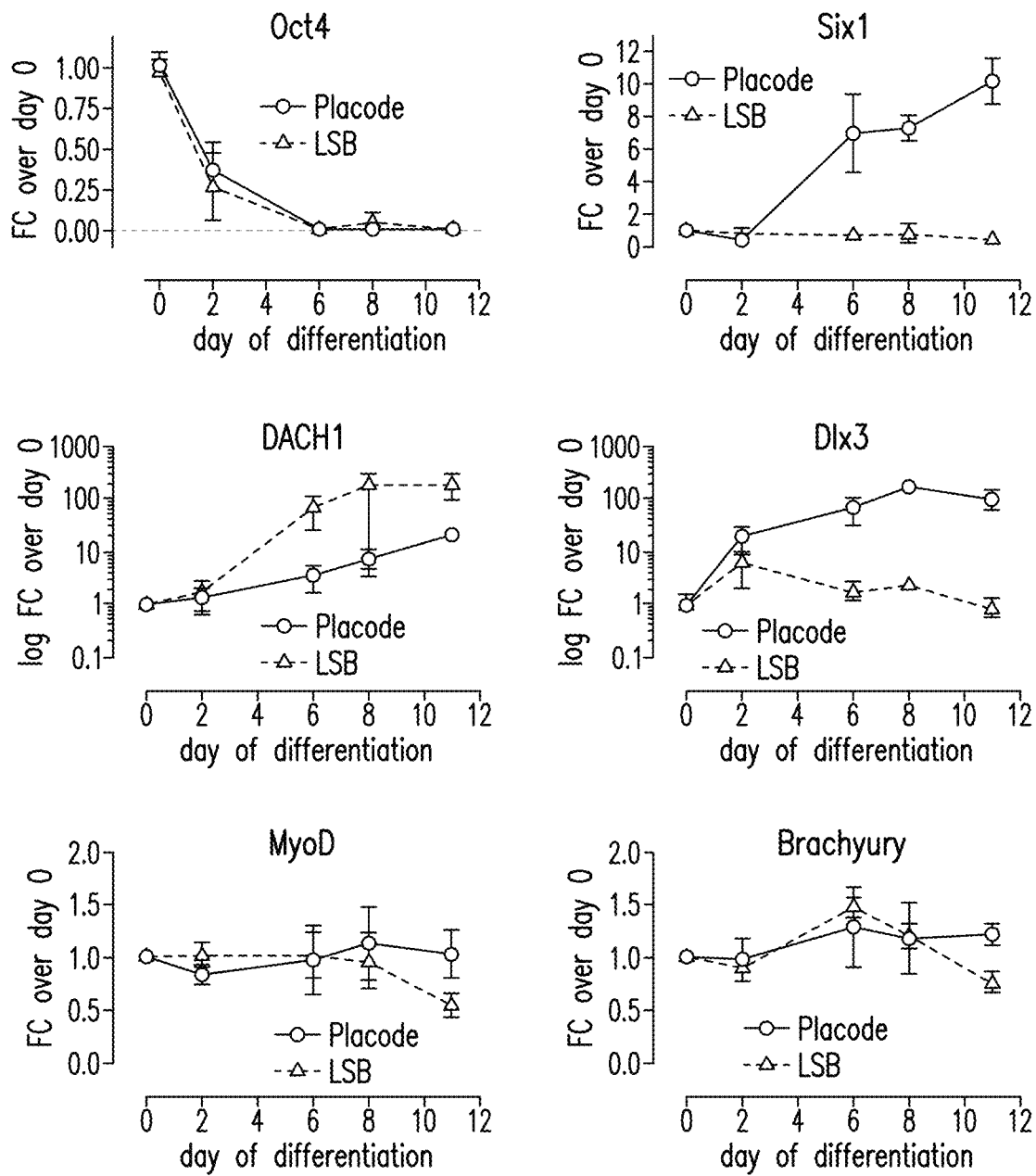
Figure 46:
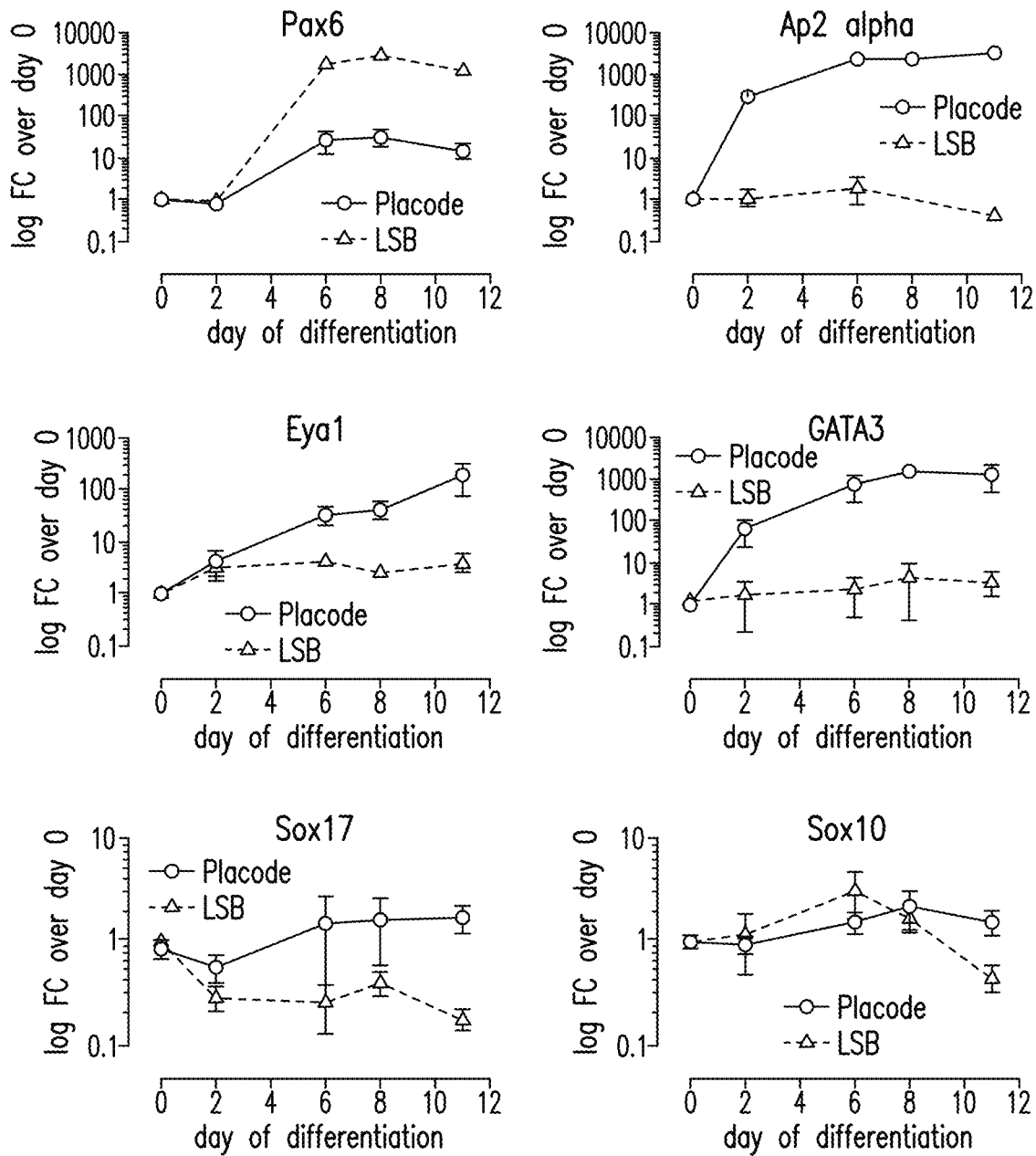

FIG. 46 shows the gene expression level of various placode markers over time during culture of SIX::H2B-GFP cells according to the PIP-E6 protocol (BMP4 withdrawn after culture day 3). Also shown are the loss of pluripotency (OCT4), lack of muscle (MyoD) or general mesoderm (Brachyury) induction, and the lack of endoderm (SOX17) or neural crest (SOX10) induction.

Figure 47:
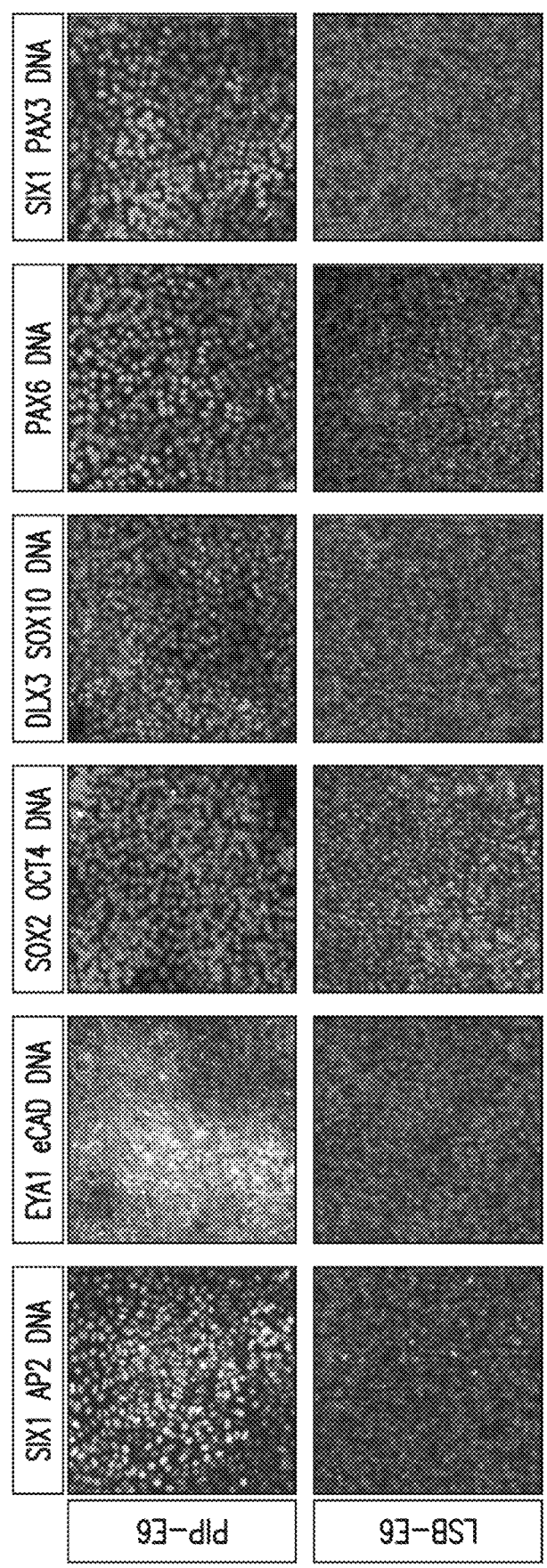

FIG. 47 shows staining of various proteins confirming placode identity in cells cultured in E8/E6 media using the PIP-E6 protocol (BMP4 withdrawn after culture day 3).

Figure 48:
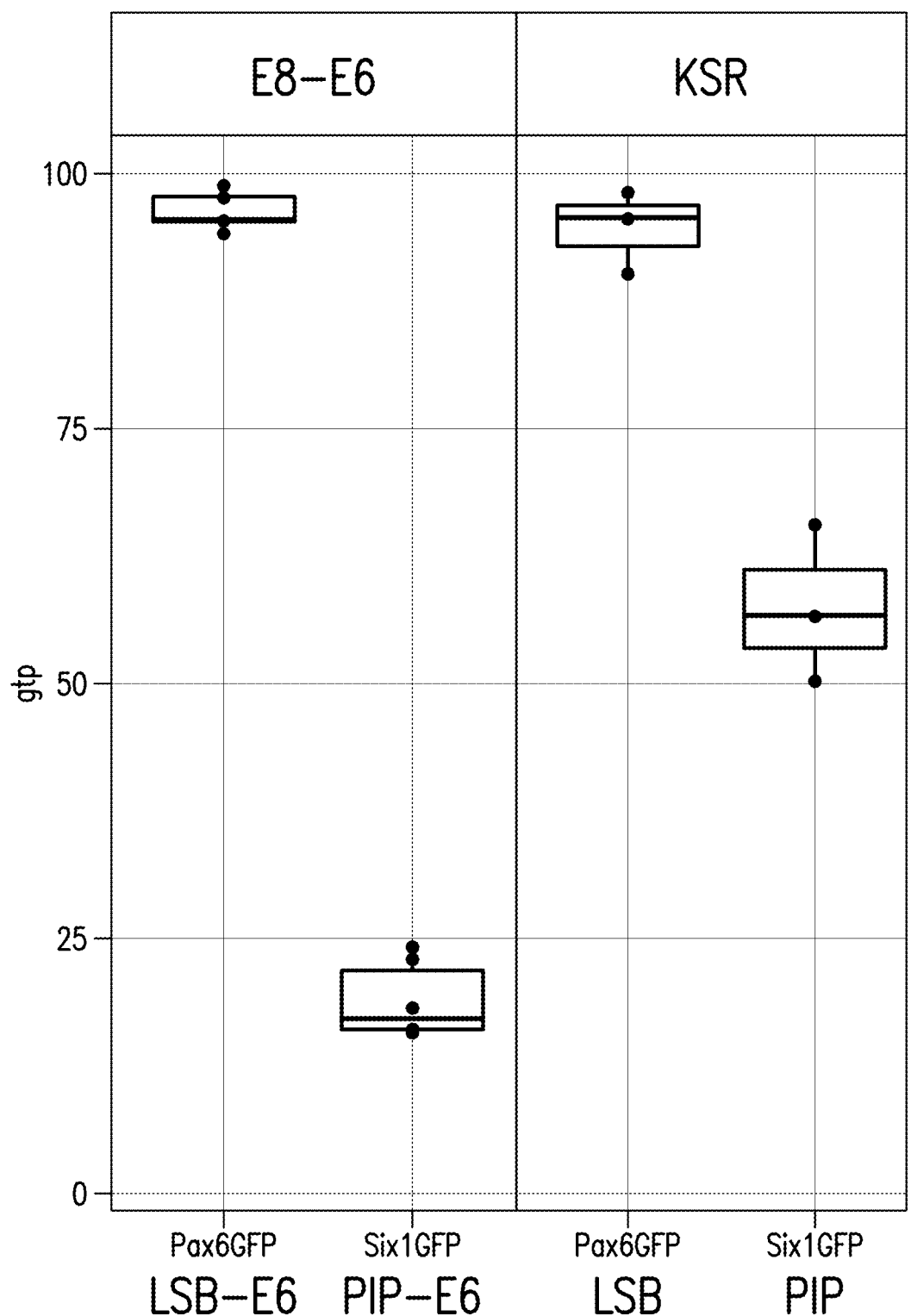

FIG. 48 shows the yield and variability of placode precursor cells generated using the PIP-E6 (E8/E6 media) and PIP (KSR media) protocols. PIP-E6 yielded fewer placode precursor cells, but with less variability compared to PIP.

Figure 49A:
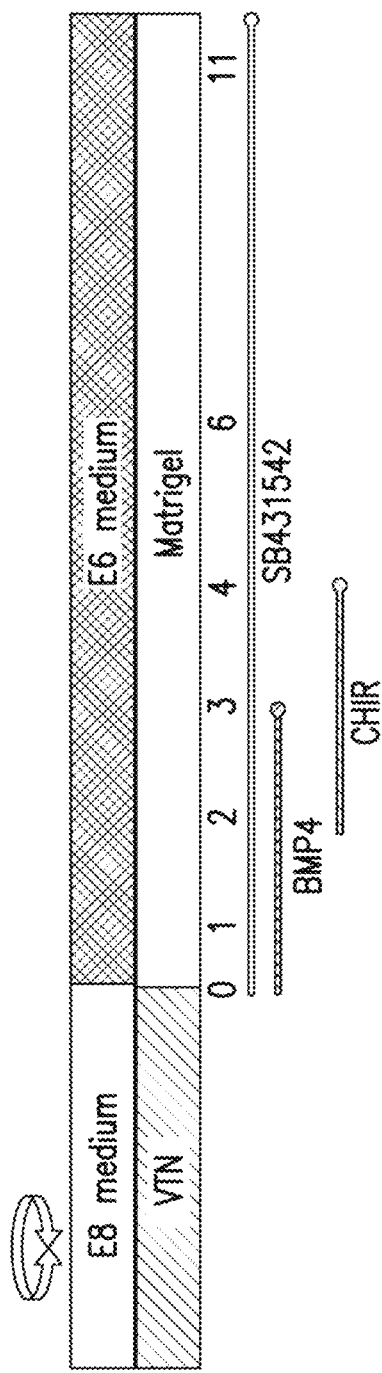
Figure 49B:
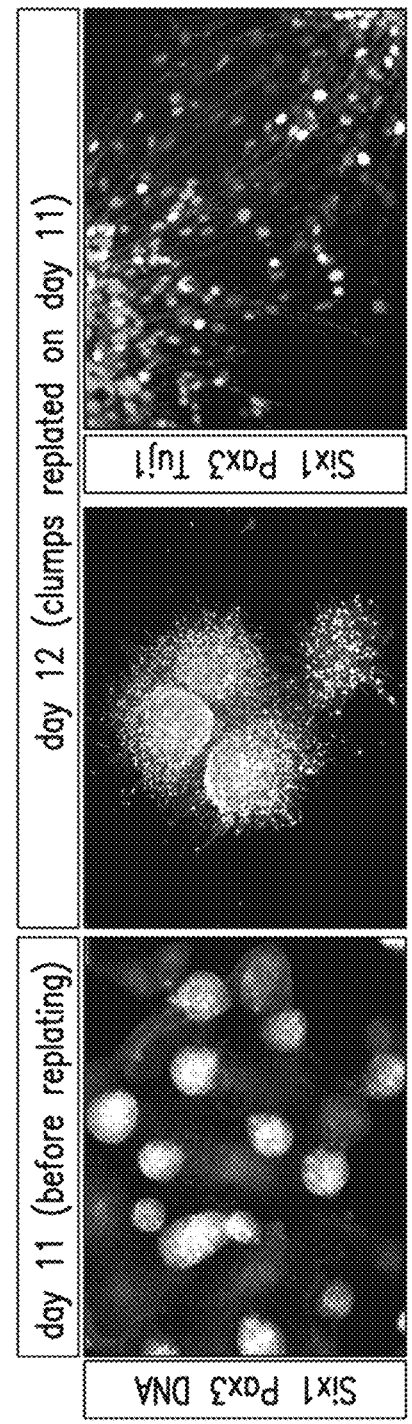

FIGS. 49A-49B show (A) the PIP-E6 protocol supplemented with CHIR (Wnt activator) to induce trigeminal placode as the default placode (supplemented during culture days 2-4); and (B) trigeminal placode markers SIX1 and PAX3 expressed by cells cultured according to the modified PIP-E6 protocol after 11 and 12 days of culture.

Figure 50:
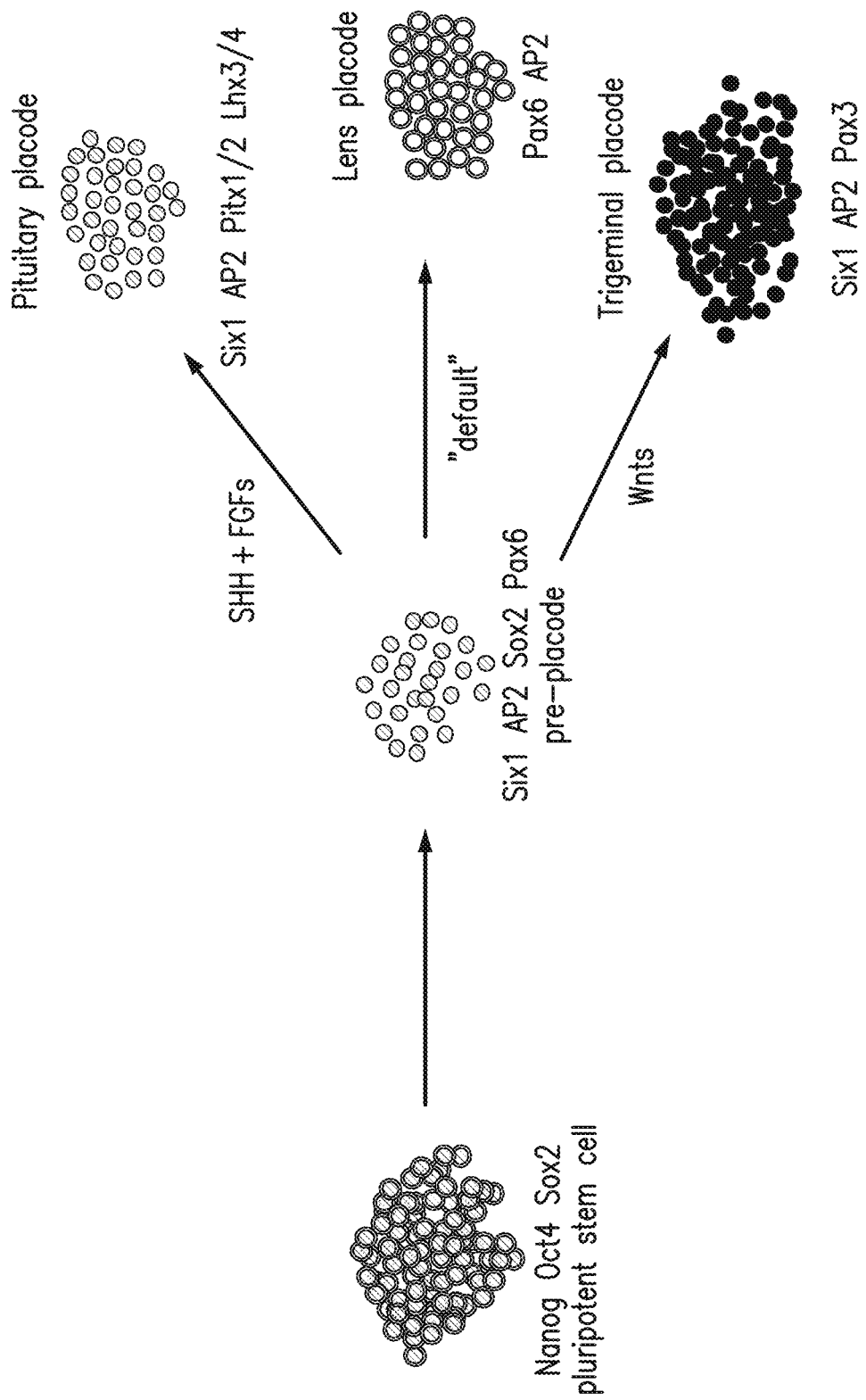

FIG. 50 shows the pituitary, lens and trigeminal placodes that can be induced using the PIP-E6 culture protocol.

Figure 51:
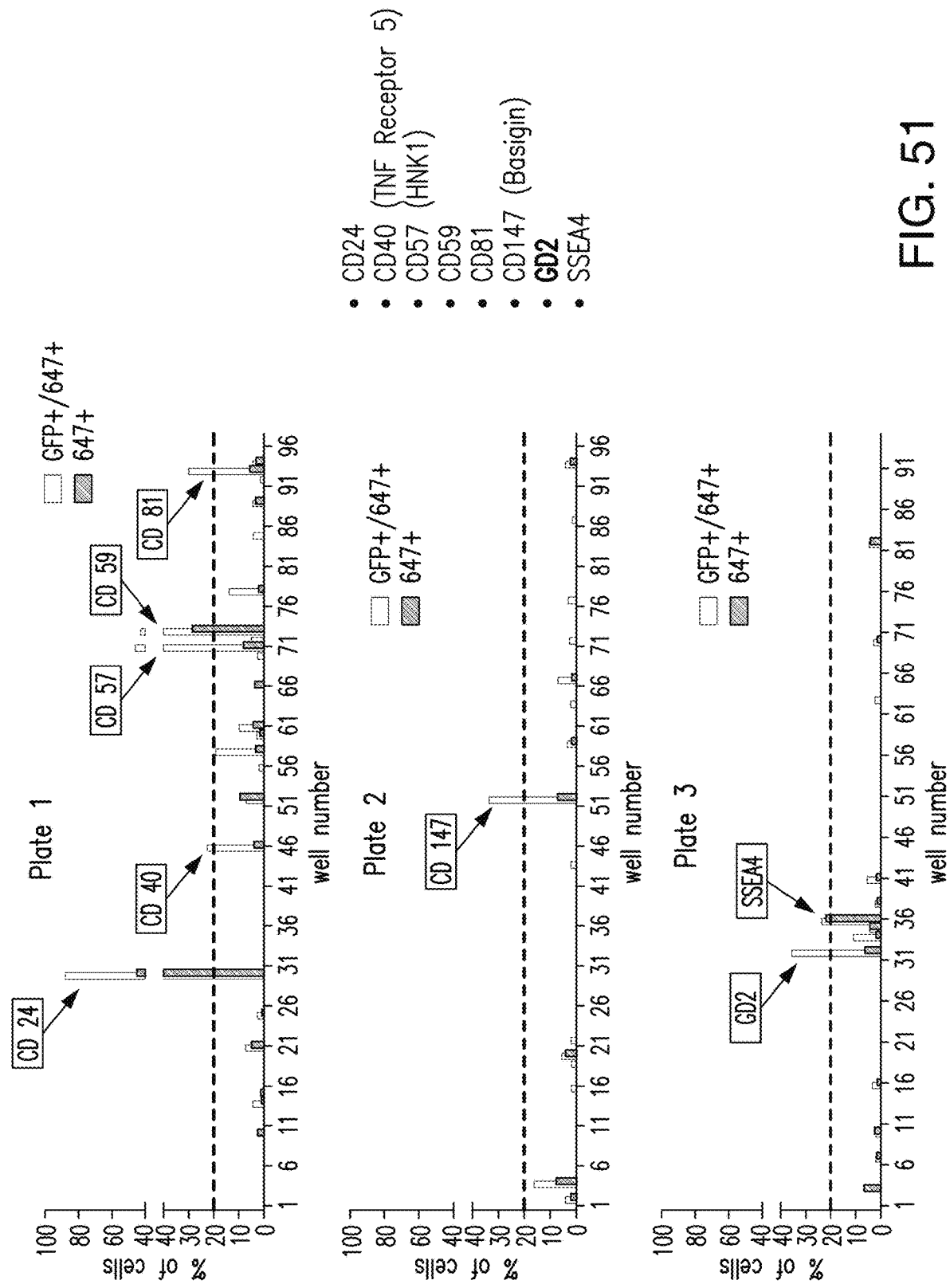

FIG. 51 shows the cell surface marker GD2 which is enriched in trigeminal placode cells induced using the PIP-E6 protocol supplemented with CHIR during culture days 2-4.

Figure 52:
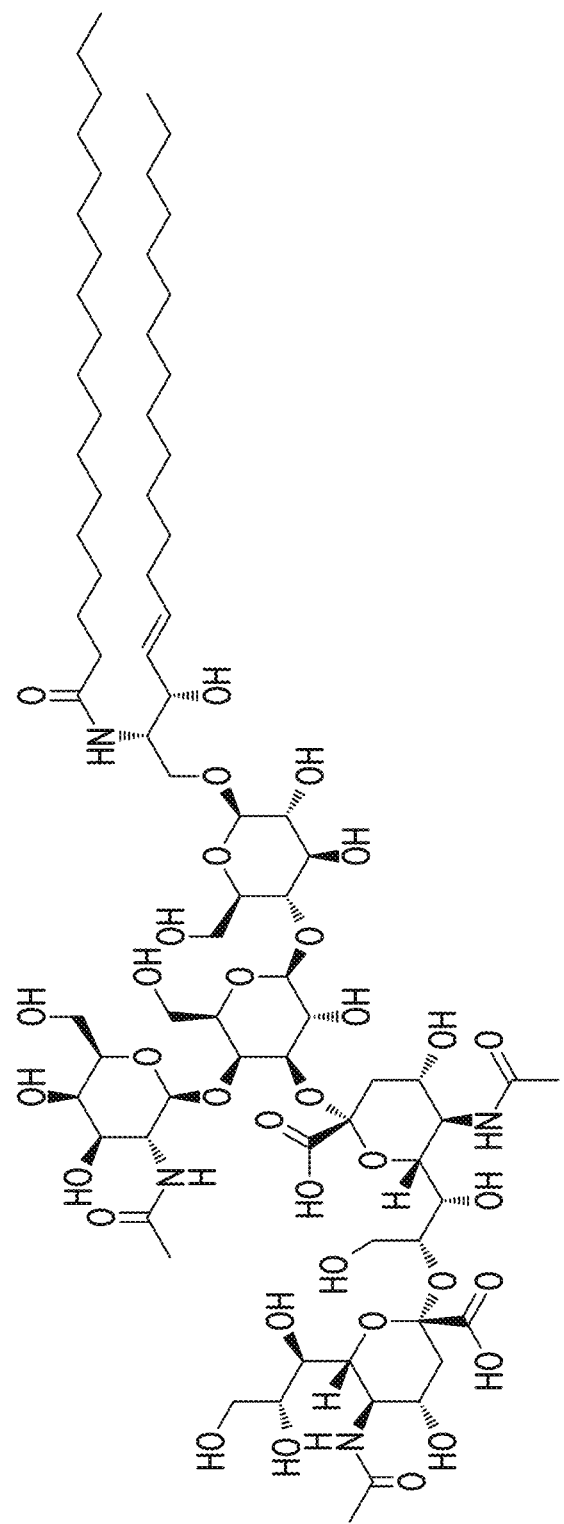

FIG. 52 shows the chemical structure of GD2.

Figure 53A:
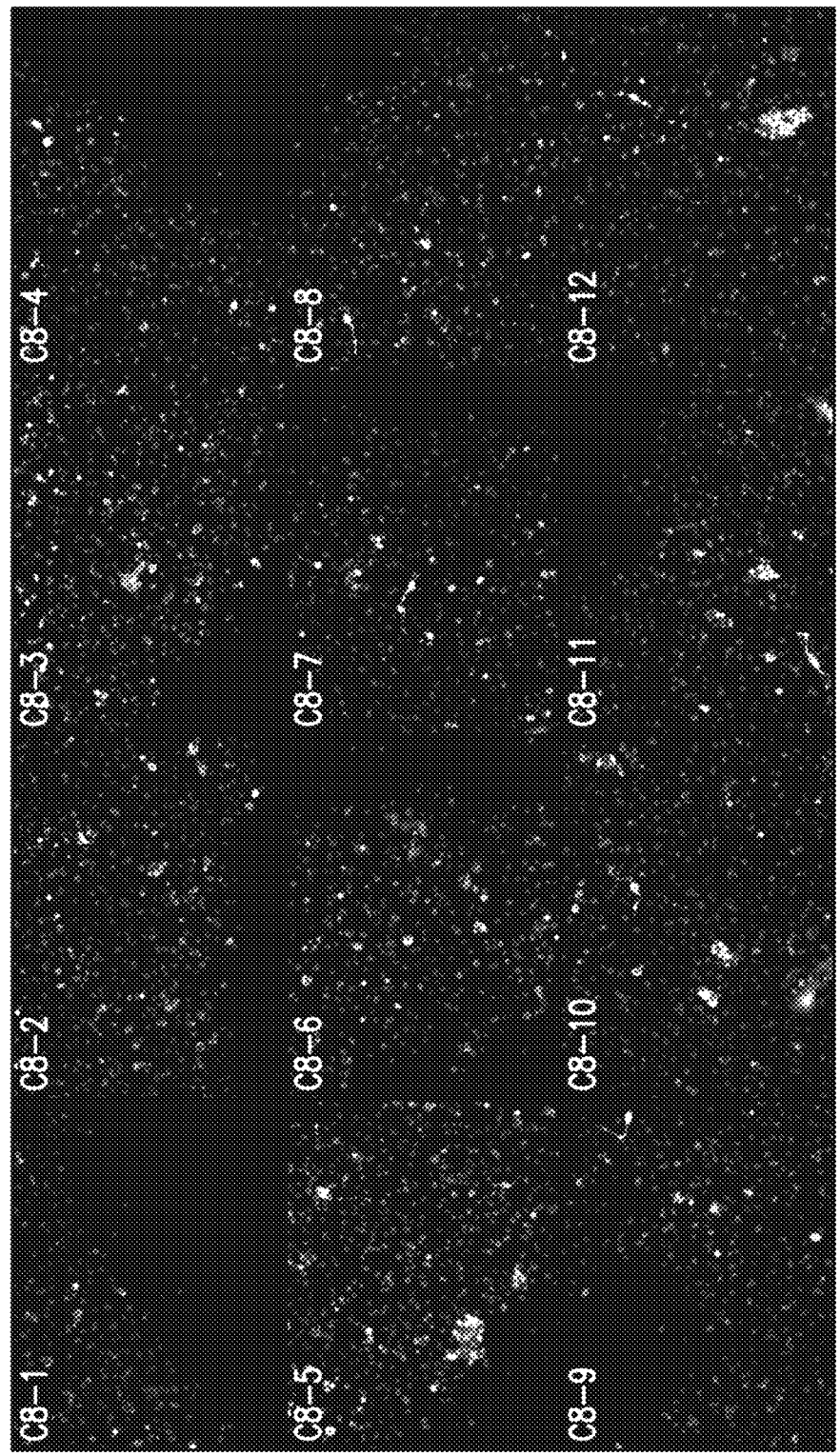
Figure 53B:
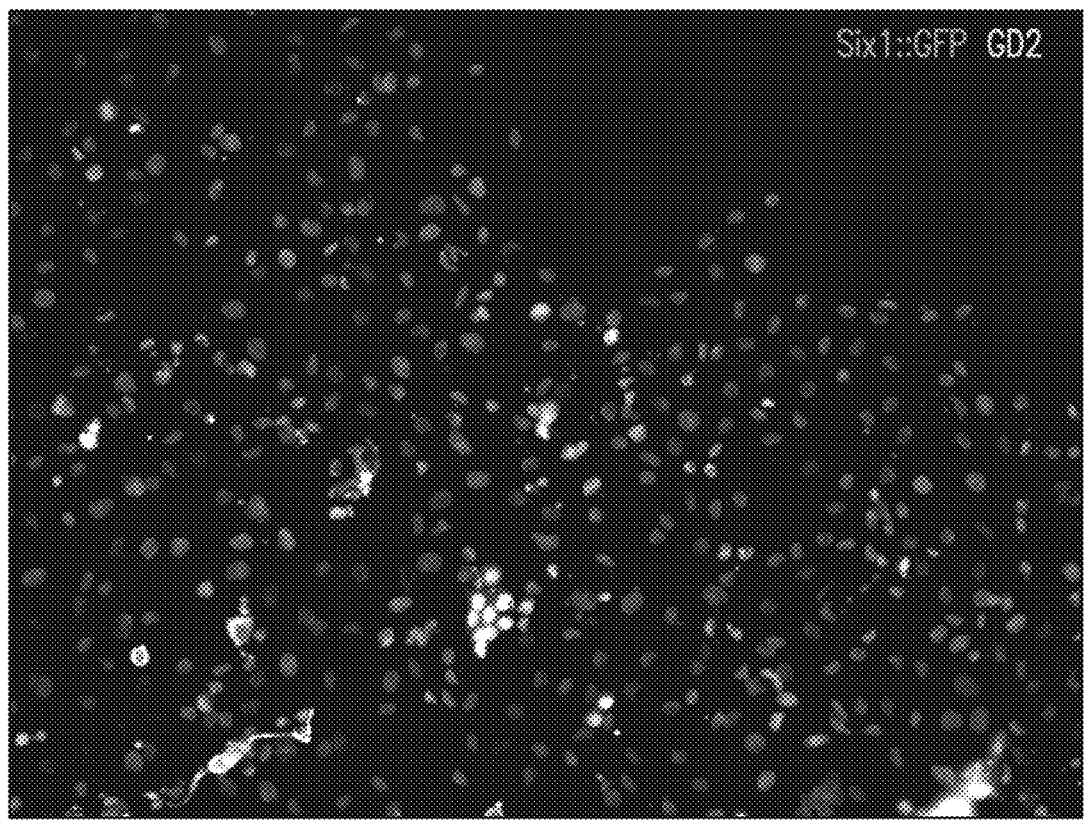

FIGS. 53A-53B show the co-expression of GD2 and the placode marker SIX1::GFP in trigeminal placode cells induced using the PIP-E6 protocol supplemented with CHIR during culture days 2-4.

Figure 54A:
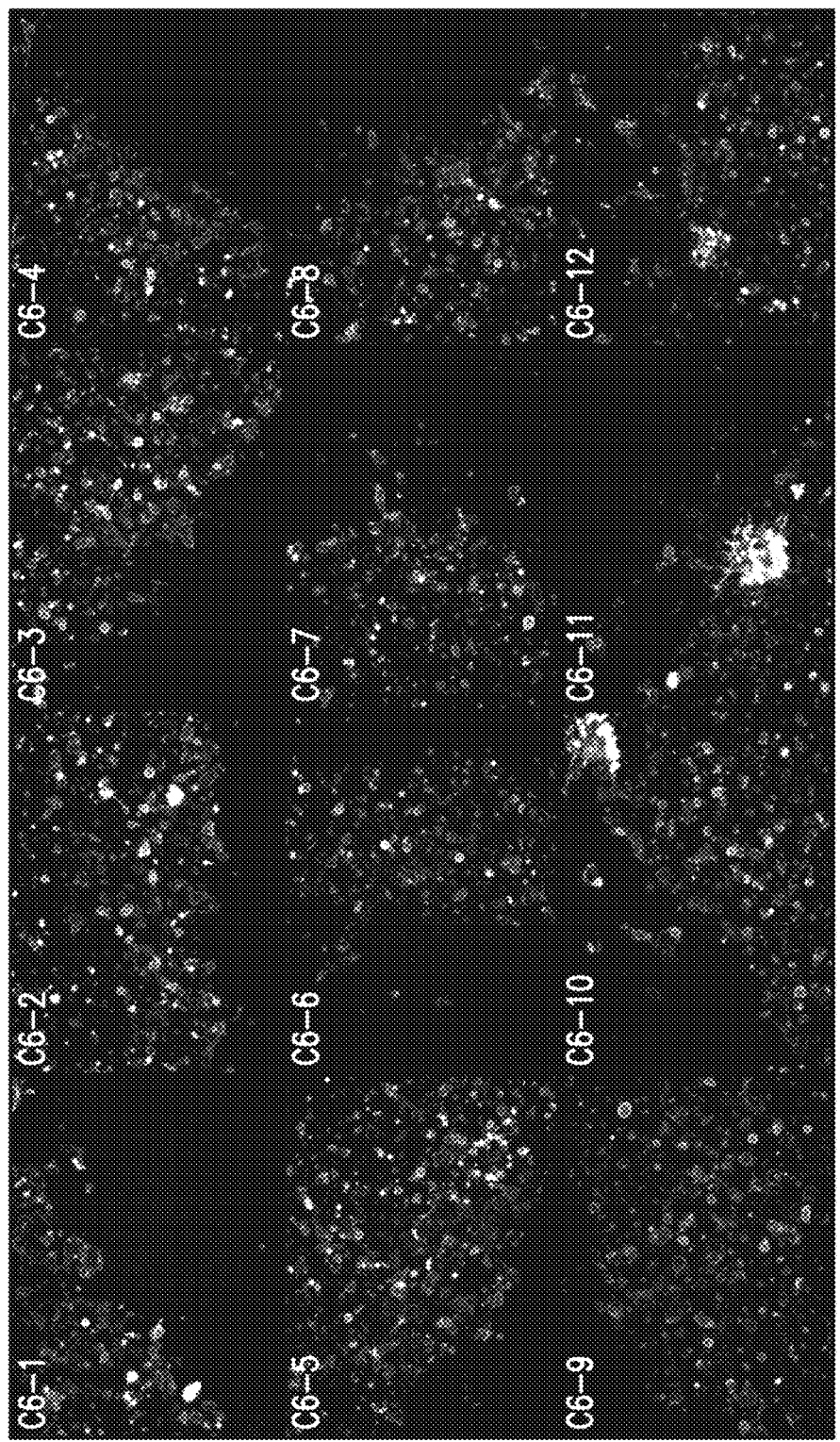
Figure 54B:
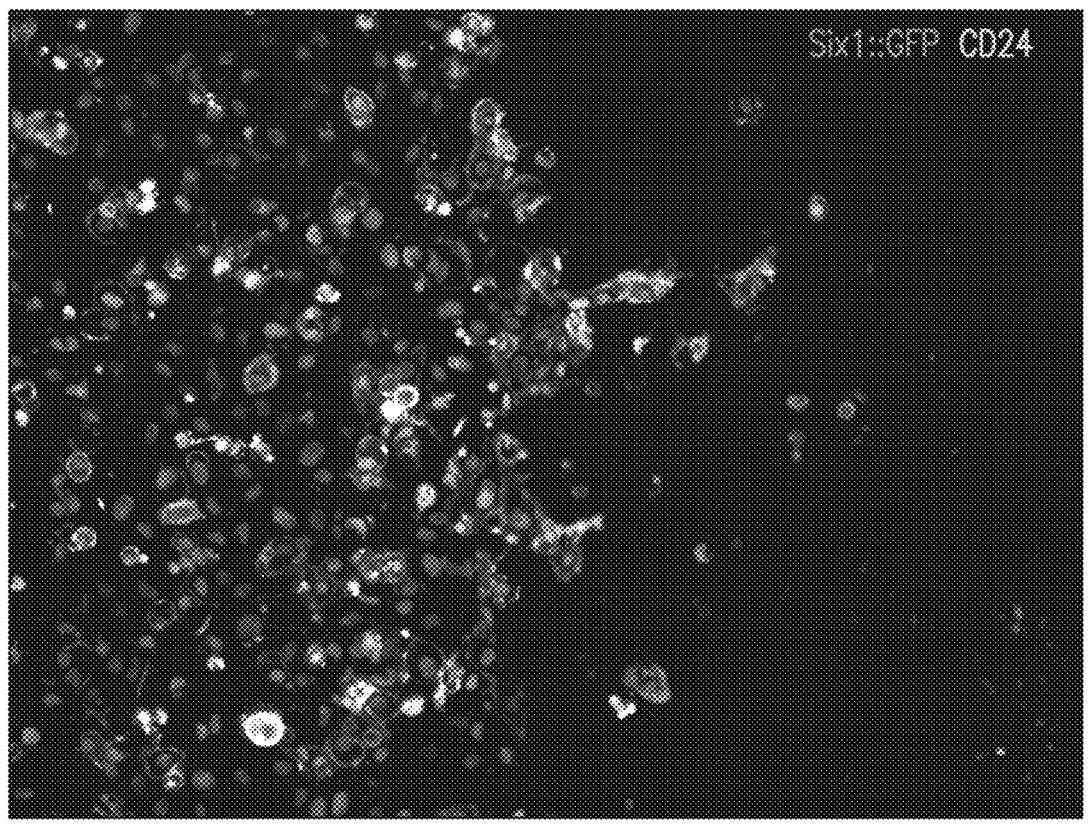

FIGS. 54A-54B show positive control cells in which CD24 and SIX1::GFP are expressed in all neural cells, including trigeminal placode cells induced using the PIP-E6 protocol supplemented with CHIR during culture days 2-4.

Figure 55:
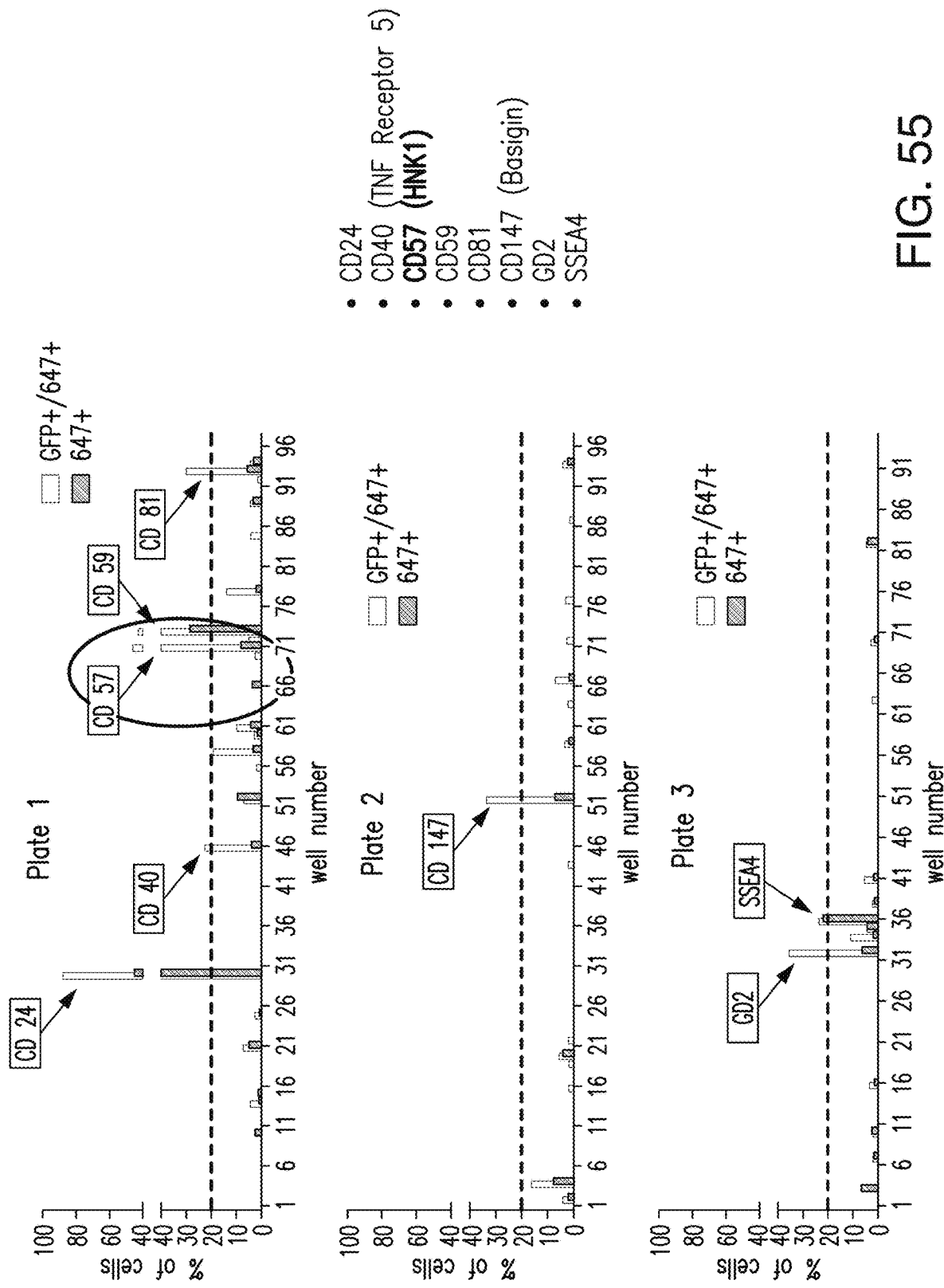

FIG. 55 shows the cell surface marker CD57 (HNK1) which is enriched in trigeminal placode cells induced using the PIP-E6 protocol.

Figure 56A:
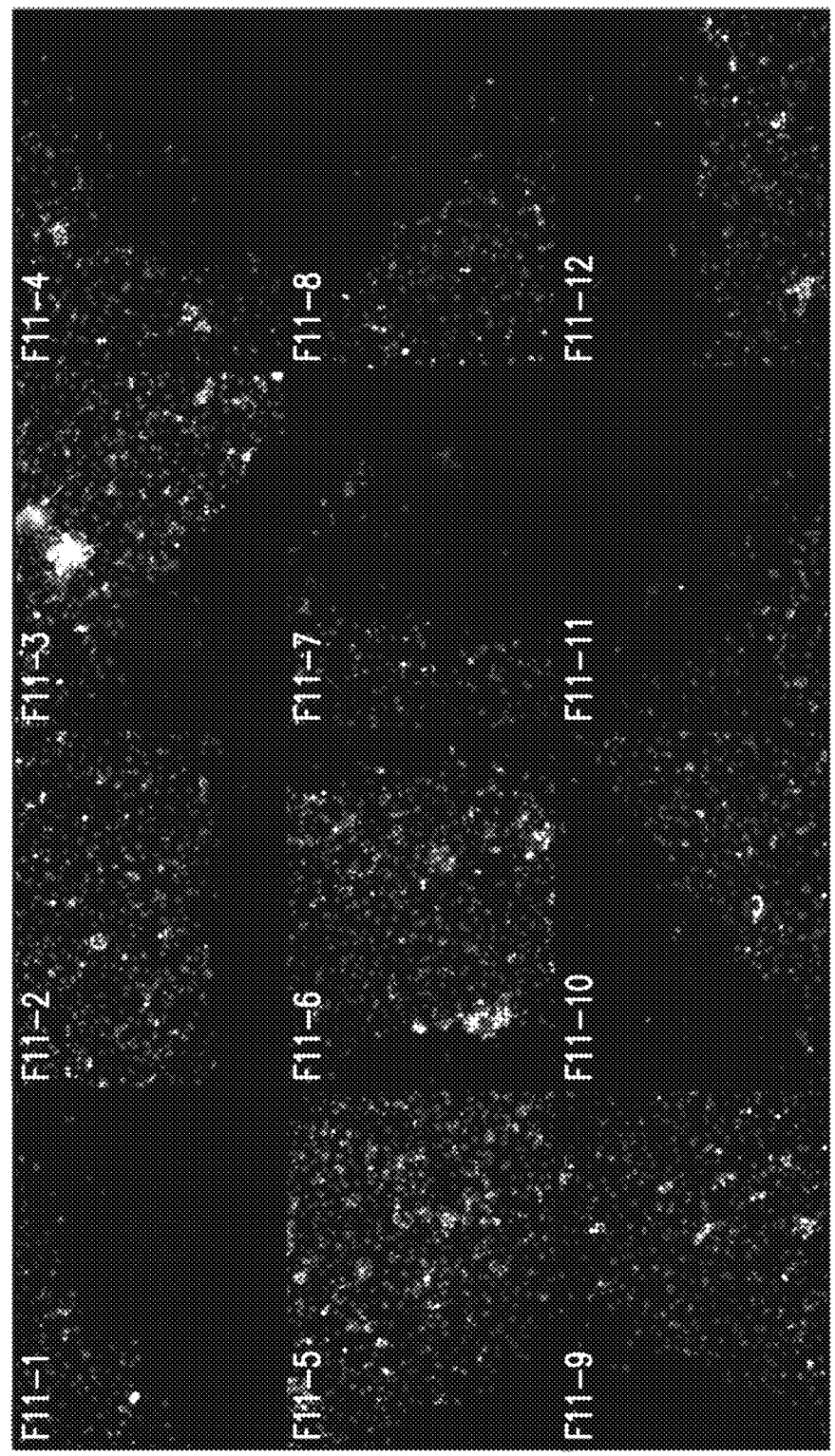
Figure 56B:
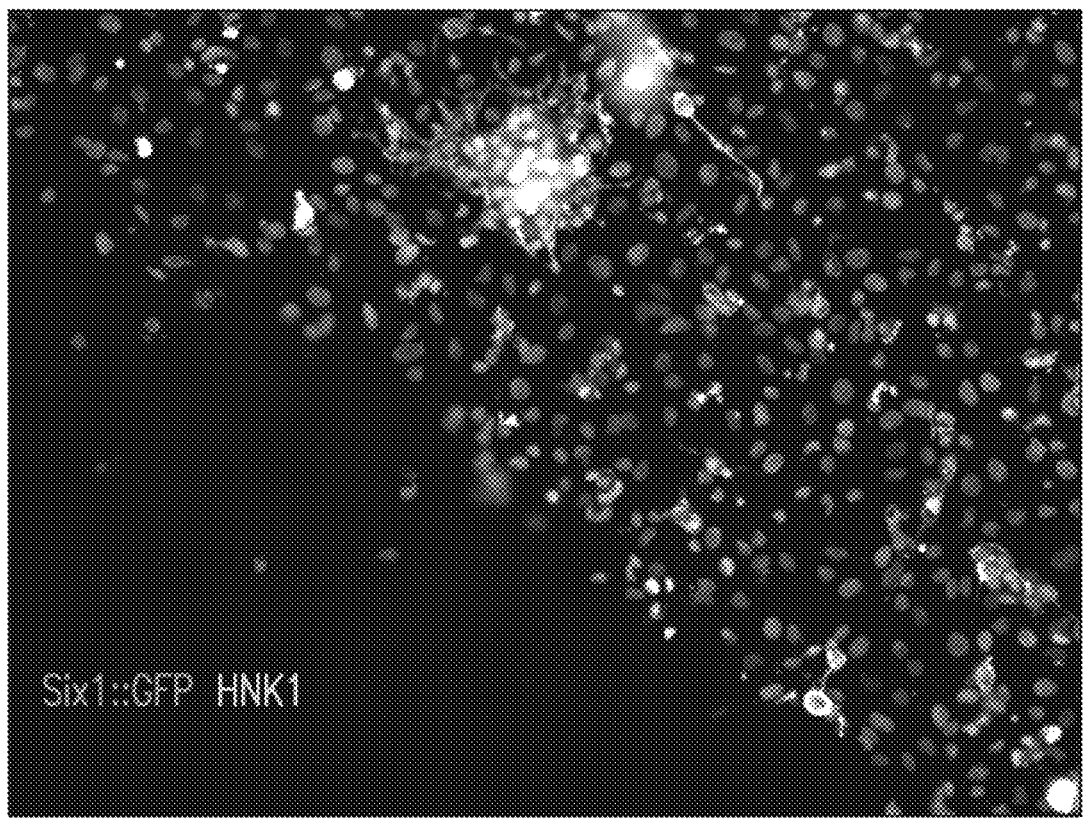

FIGS. 56A-56B show the co-expression of CD57 (HNK1) and SIX1::GFP in trigeminal placode cells induced using the PIP-E6 protocol supplemented with CHIR during culture days 2-4.

Figure 57:
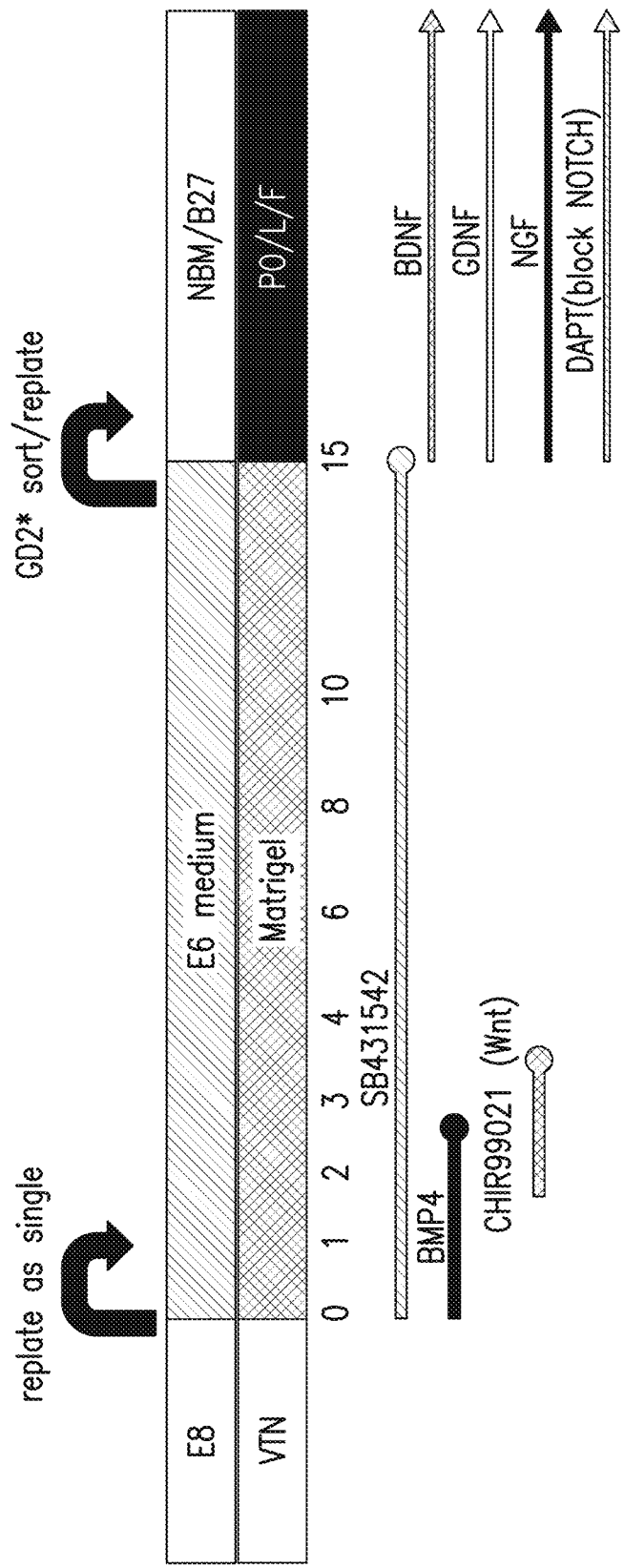

FIG. 57 shows a PIP-E6 protocol that can be used to generate trigeminal placode as the default placode fate, wherein placodes are isolated and sorted based on their expression of the GD2 marker.

Figure 58:
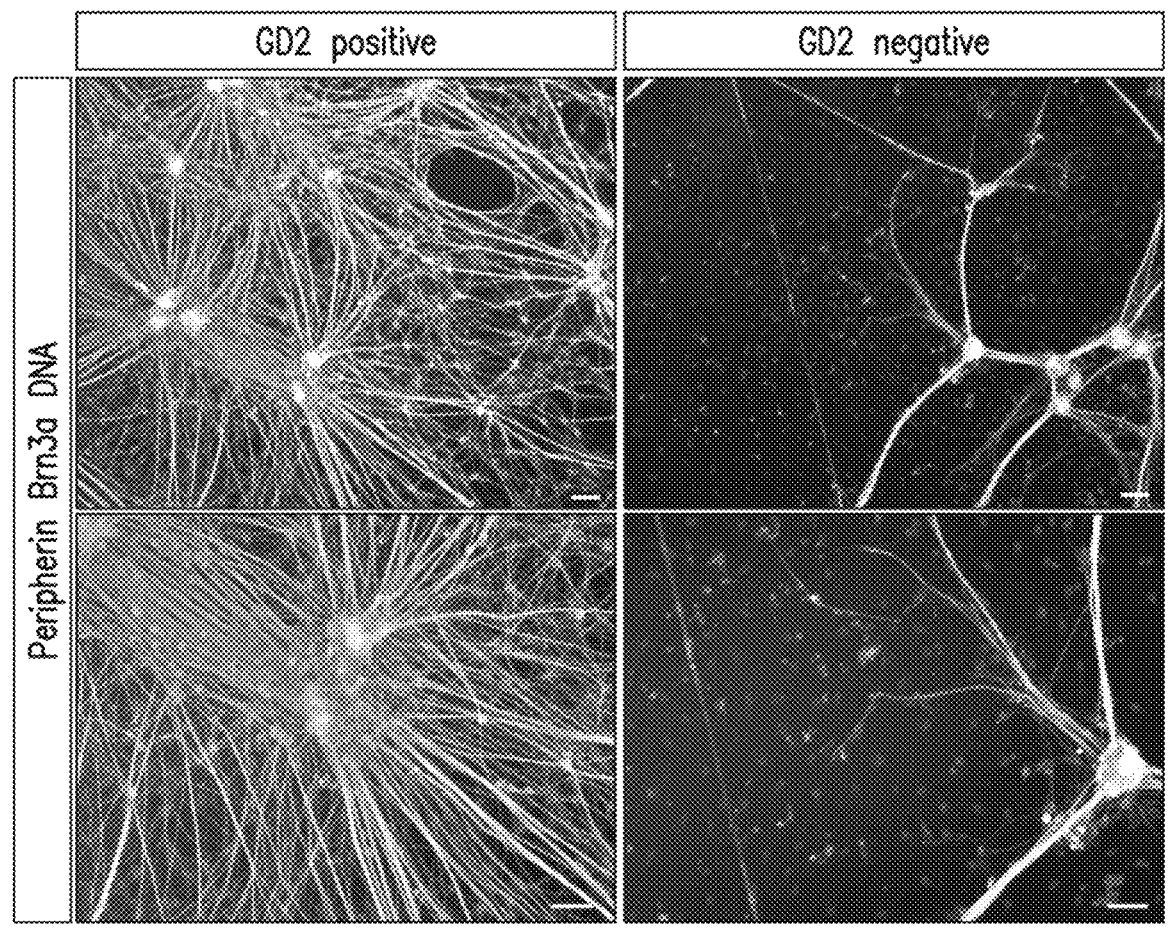

FIG. 58 shows the morphology of GD2 positive trigeminal cells induced using the modified PIP-E6 protocol (supplemented with CHIR) after 28 days of differentiation (14 days after GD2 sorting) compared to GD2 negative cells.

Figure 59:
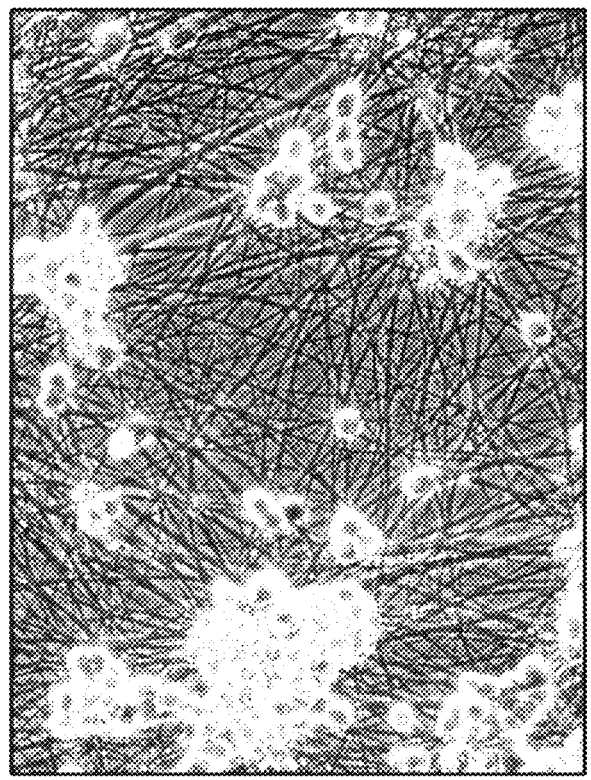
Figure 59:
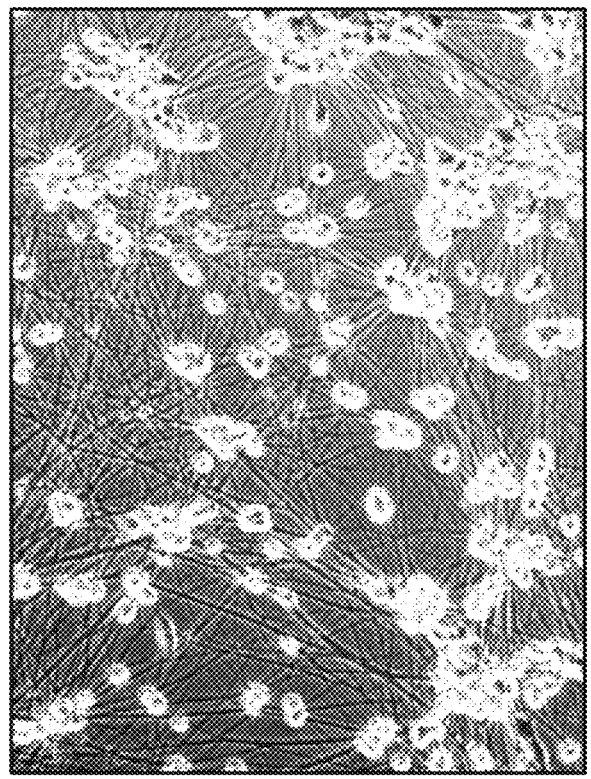

FIG. 59 shows the trigeminal neurons induced using the modified PIP-E6 protocol (supplemented with CHIR) after 48 days of differentiation (33 days after GD2 sorting).

Figure 60:
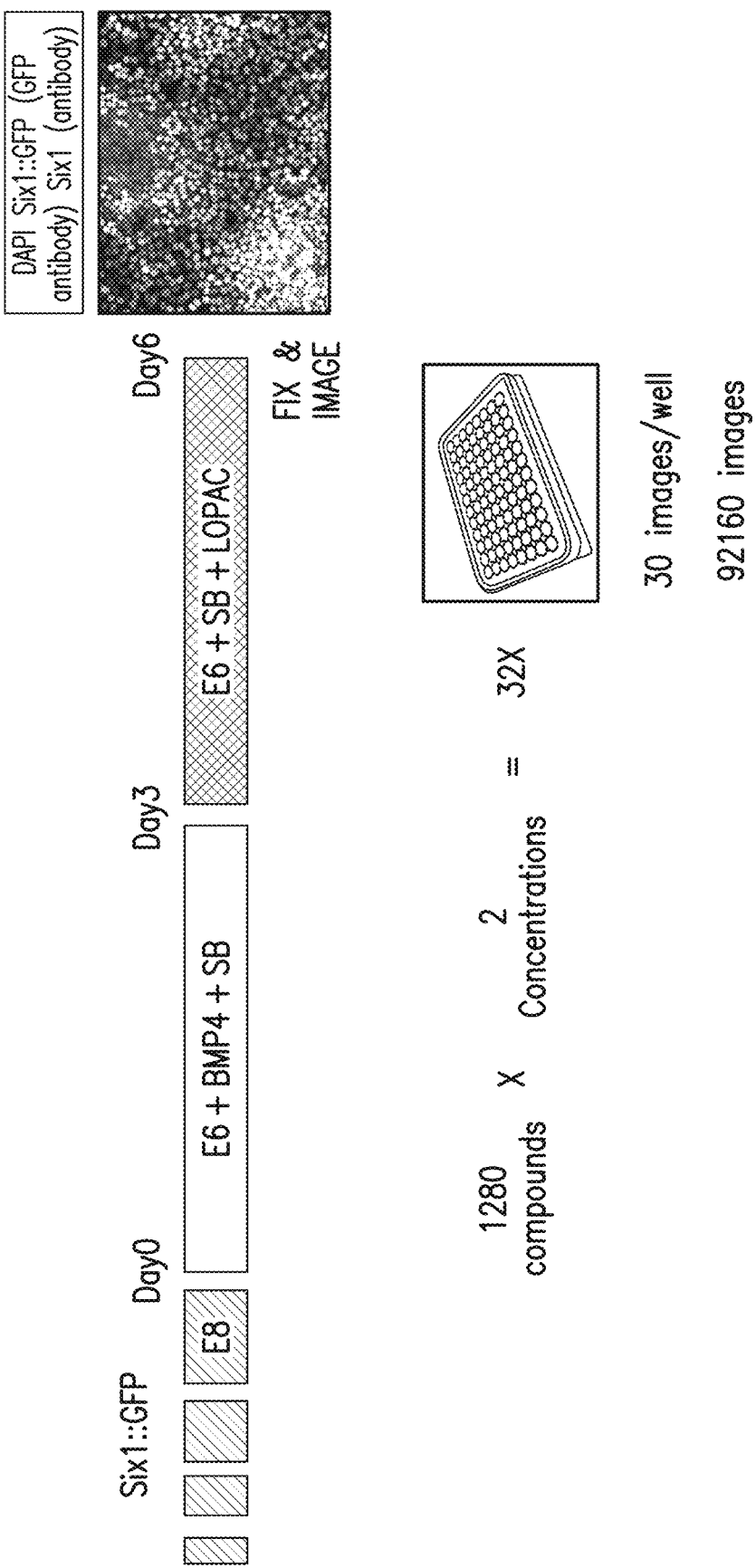

FIG. 60 shows a schematic of a high throughput screen for compounds that promote placode induction using the PIP-E6 protocol wherein test compounds are added to the culture media at day 3 of the PIP-E6 protocol.

Figure 61:
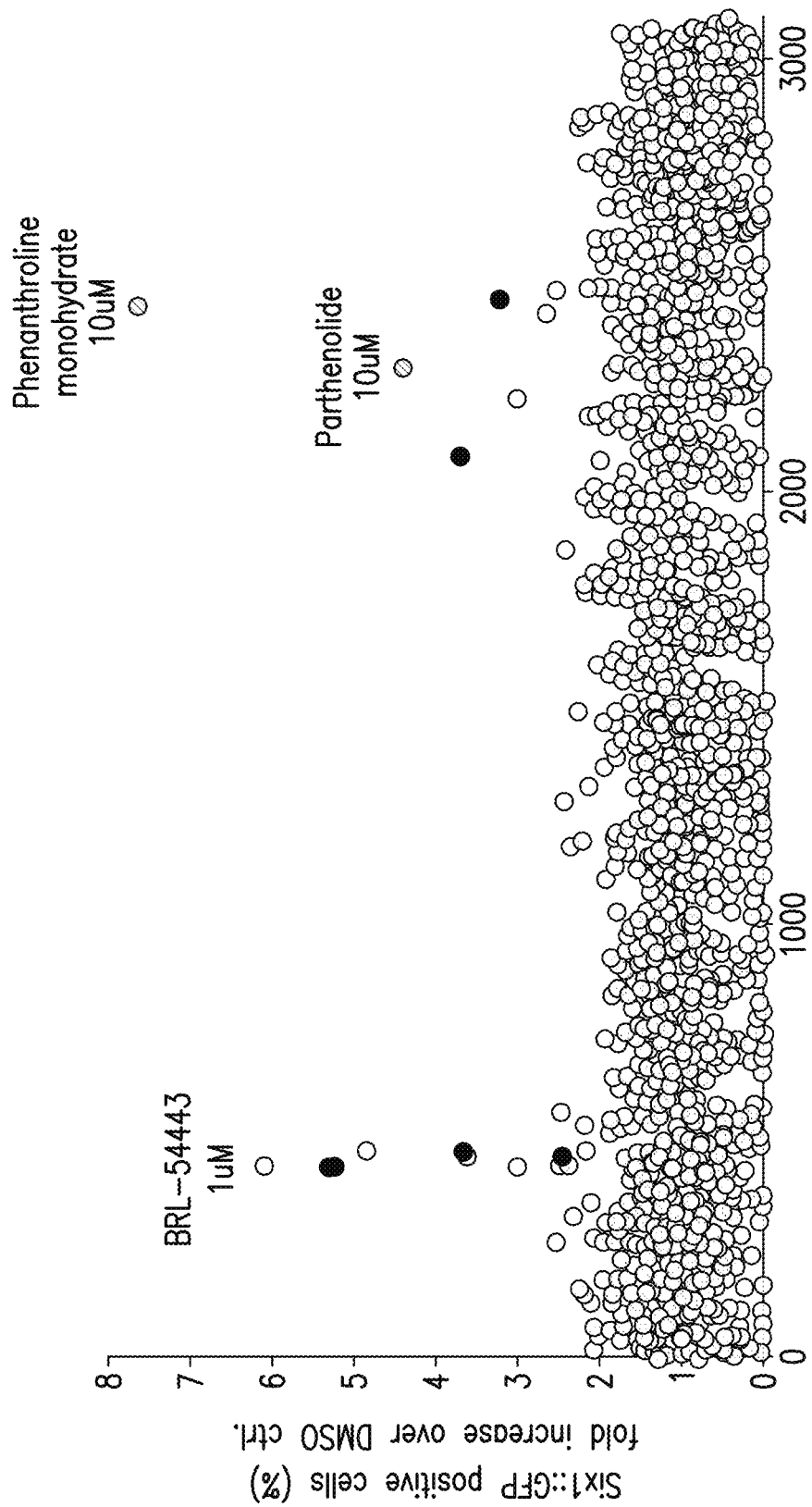

FIG. 61 shows results of the high throughput screen for compounds that promote placode induction. Three candidate compounds were identified in the screen as induction enhancers: BRL-54443, Phenanthroline monohydrate, and Parthenolide.

Figure 62:
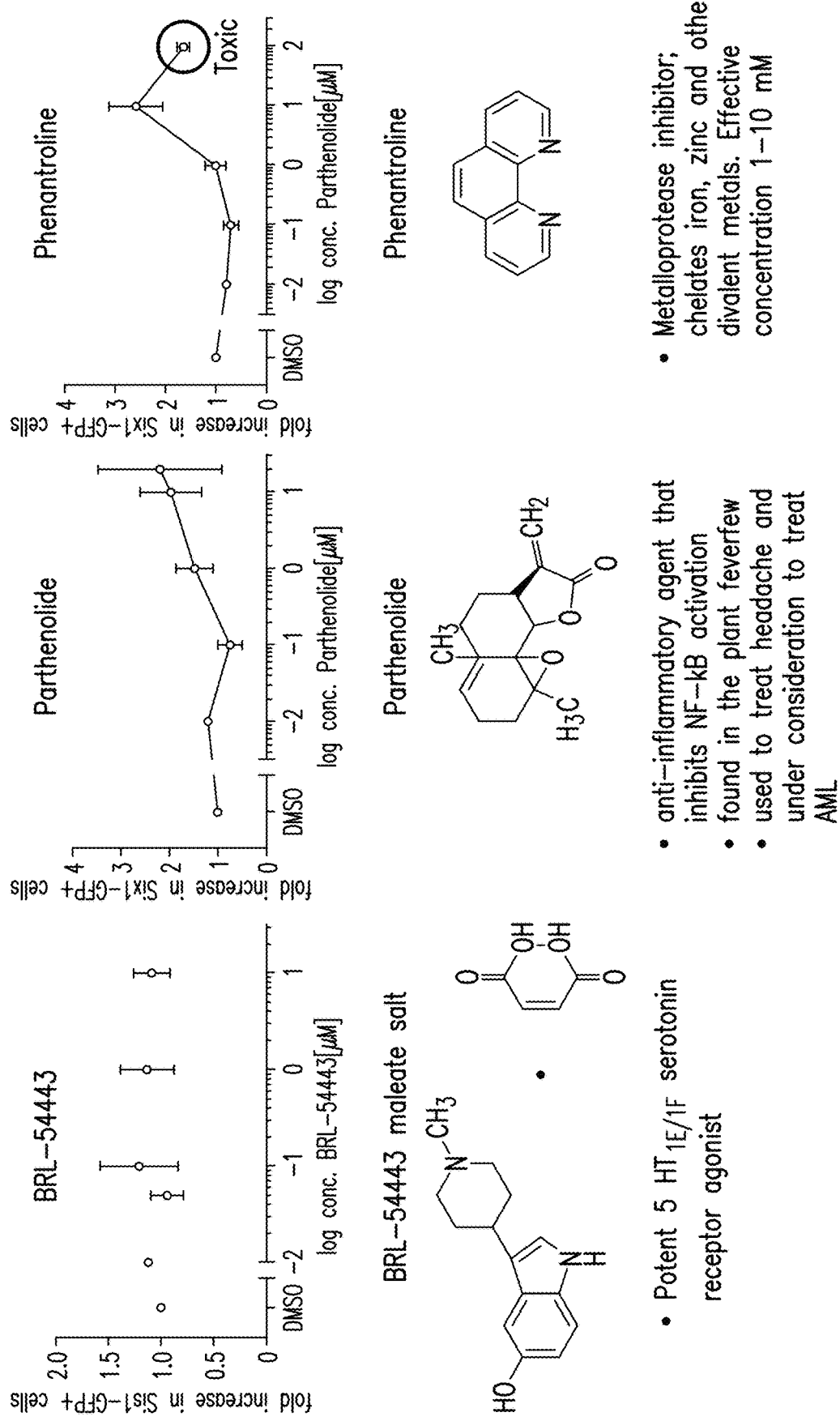

FIG. 62 shows the structures of the candidate placode induction enhancers BRL-54443, Phenanthroline monohydrate, and Parthenolide.

Figure 63A:
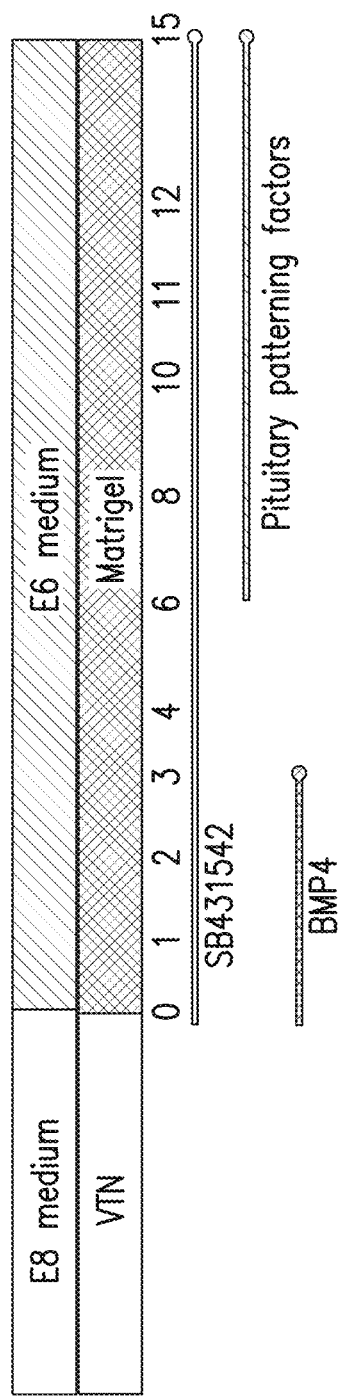
Figure 63B:
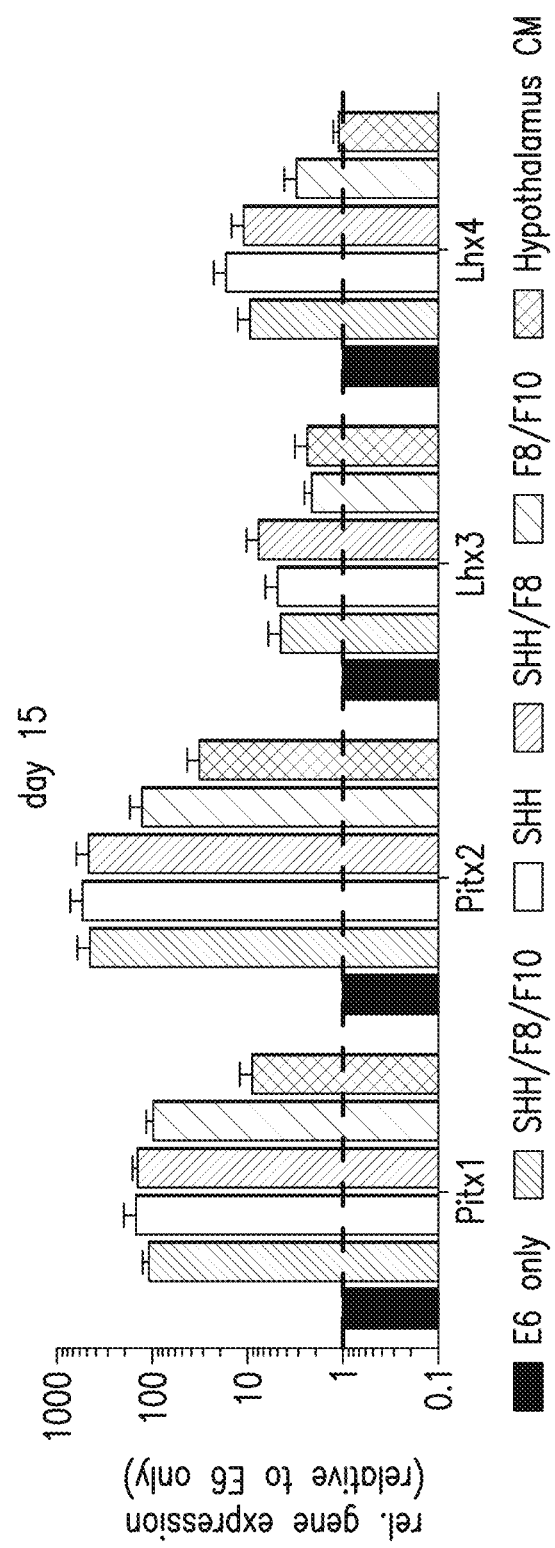

FIGS. 63A-63B show (A) the PIP-E-6 protocol used to induce pituitary placode cells wherein pituitary patterning factors were supplemented to the PIP-E6 media at days 6-15 of the culture; and (B) pituitary placode was induced as evidenced by expression of the pituitary placode markers Pitx1, Pitx2, Lhx3 and Lhx4.

Figure 64:
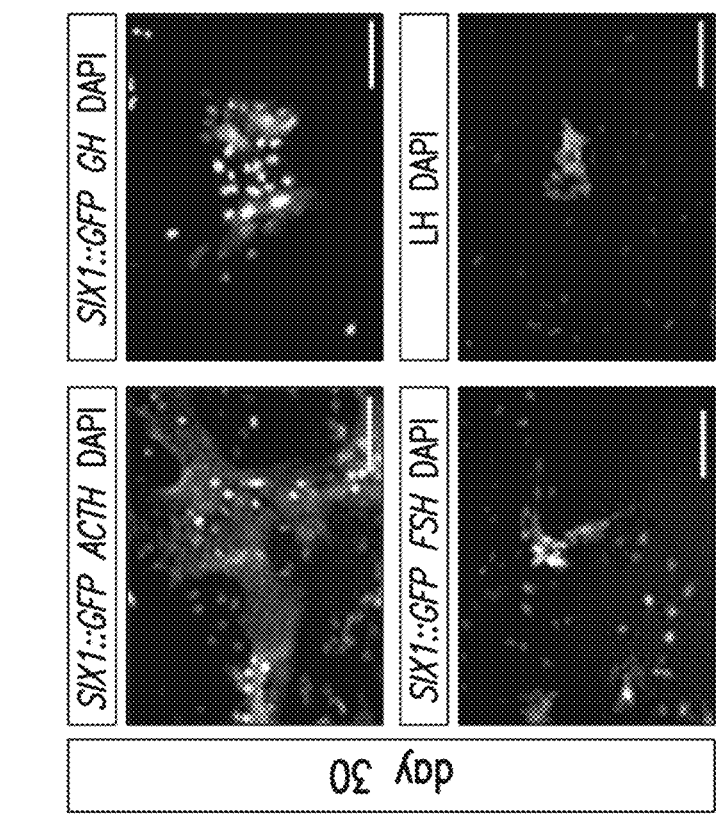
Figure 64:
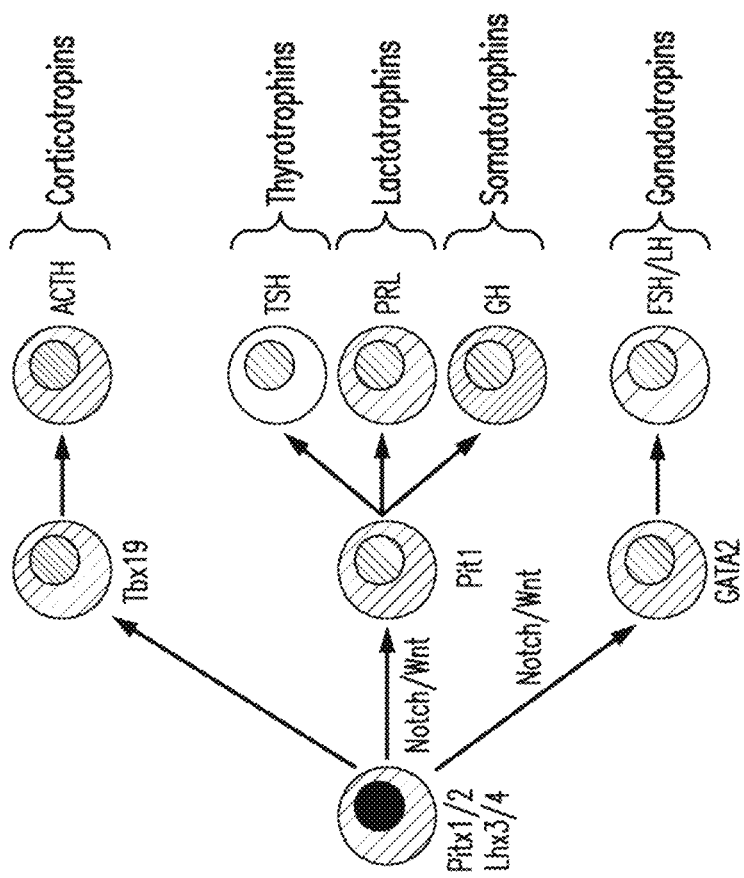

FIG. 64 shows that after differentiation to day 30 using the modified PIP-E6 protocol, pituitary placode cells differentiated into hormone expressing cells corresponding to derivatives of all three pituitary precursor lineages.

Figure 65:
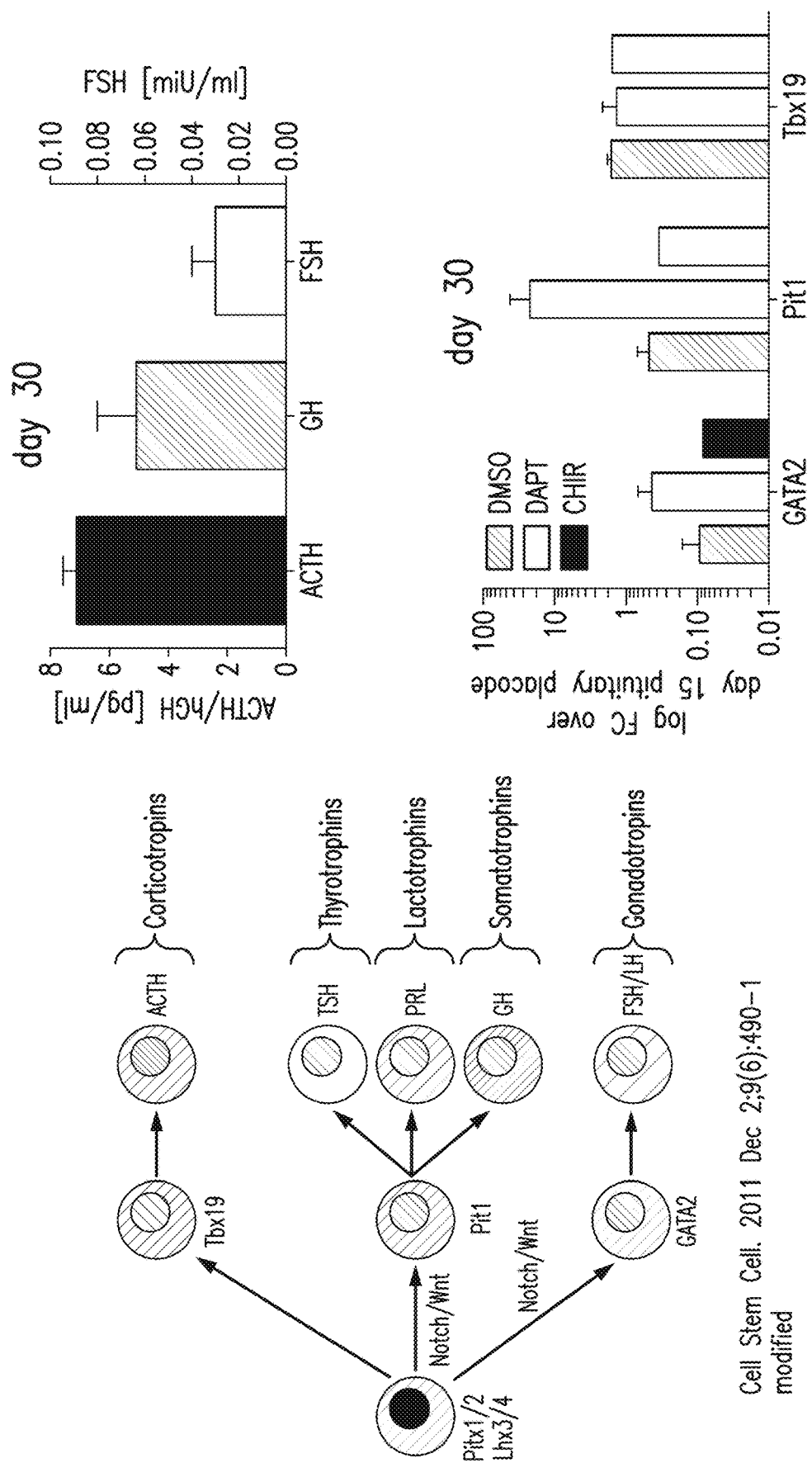

FIG. 65 shows that the proportion of each of the three pituitary precursor lineages was modulated by treating the cells with an inhibitor of Notch signaling (DAPT), and to a lesser extent by CHIR (activator of Wnt).

Figure 66:
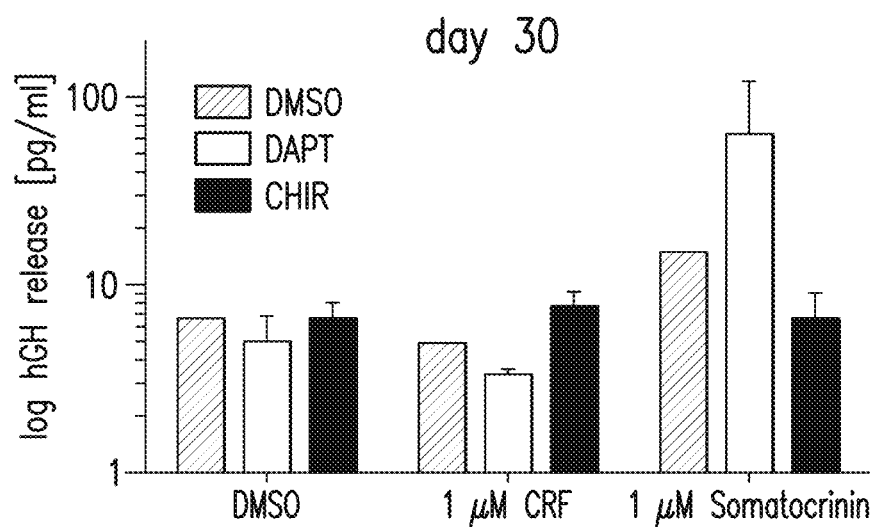
Figure 66:
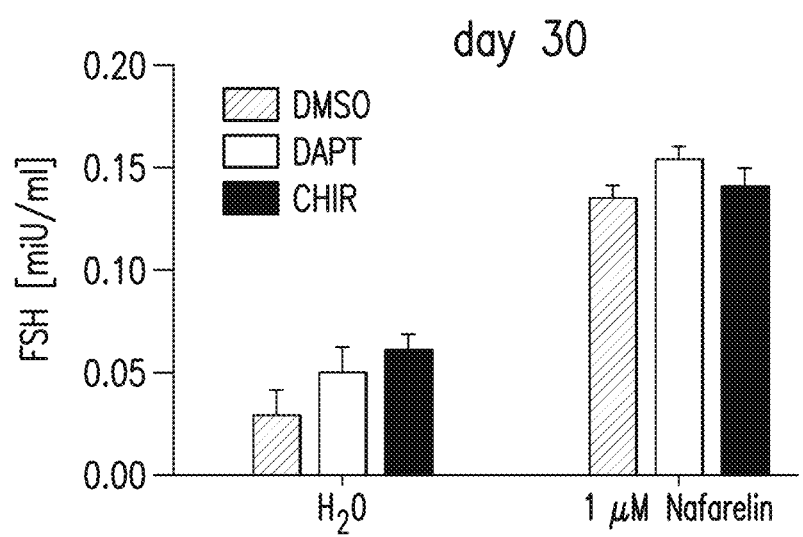

FIG. 66 shows that pituitary hormone expressing cells induced according to the PIP-E6 protocol modified with the addition of pituitary patterning factors at culture day 6 were responsive to external stimuli. In response to somatocrinin the cells release growth hormone (GH). In response to nafarelin the cells released follicle stimulating hormone (FSH).

Figure 67:
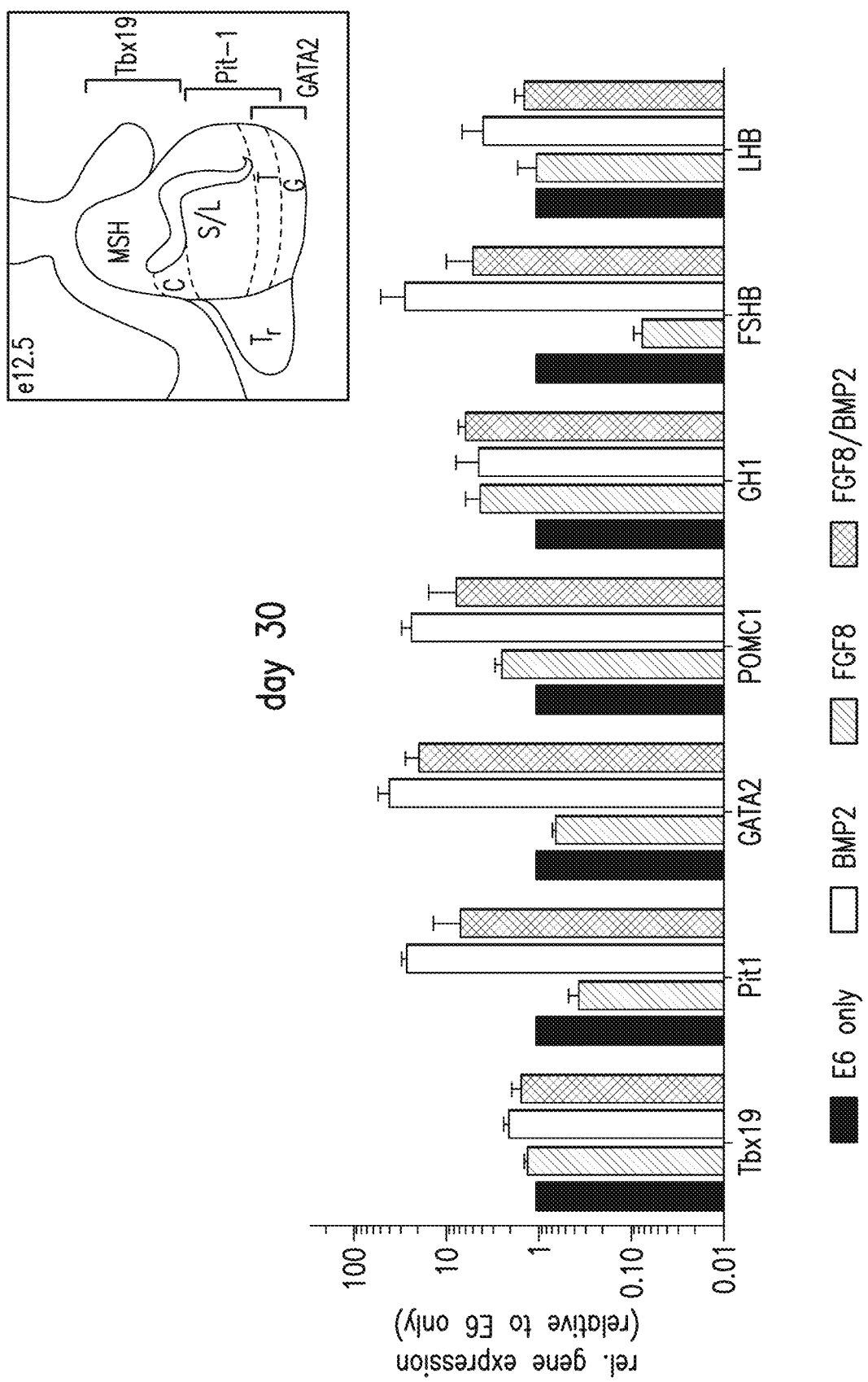

FIG. 67 shows that culturing cells according to the PIP-E6 protocol supplemented with BMP2 was able to increase the yield of several pituitary subtype specific markers.

Figure 68:
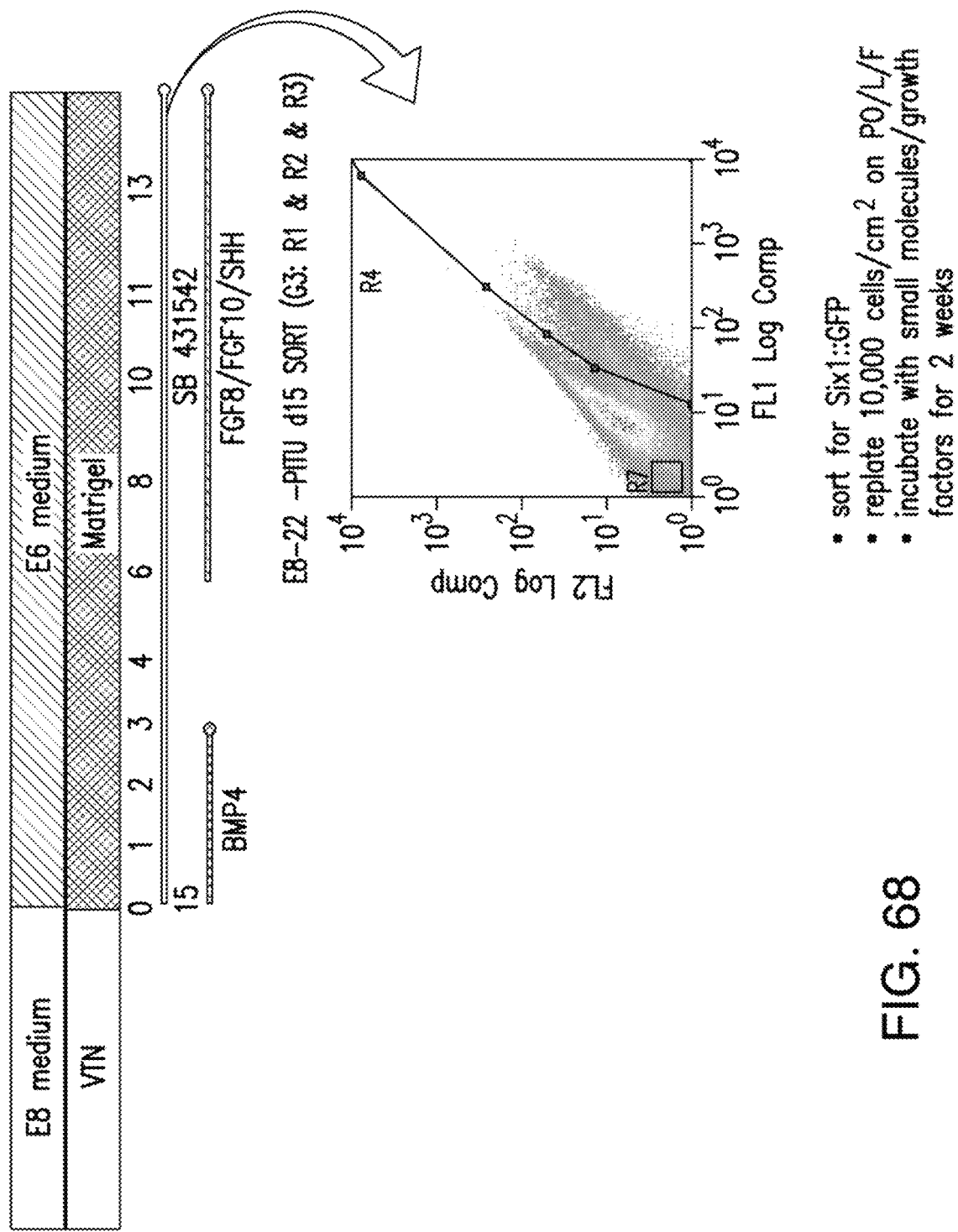

FIG. 68 shows a modified PIP-E6 protocol for the induction of anterior pituitary gland cells wherein SIX1::GFP hPSCs were cultured according to the PIP-E6 protocol, wherein pituitary patterning factors such as FGF8, FGF10 or SHH, etc., were included in the culture media from days 6-14.

Figure 69:
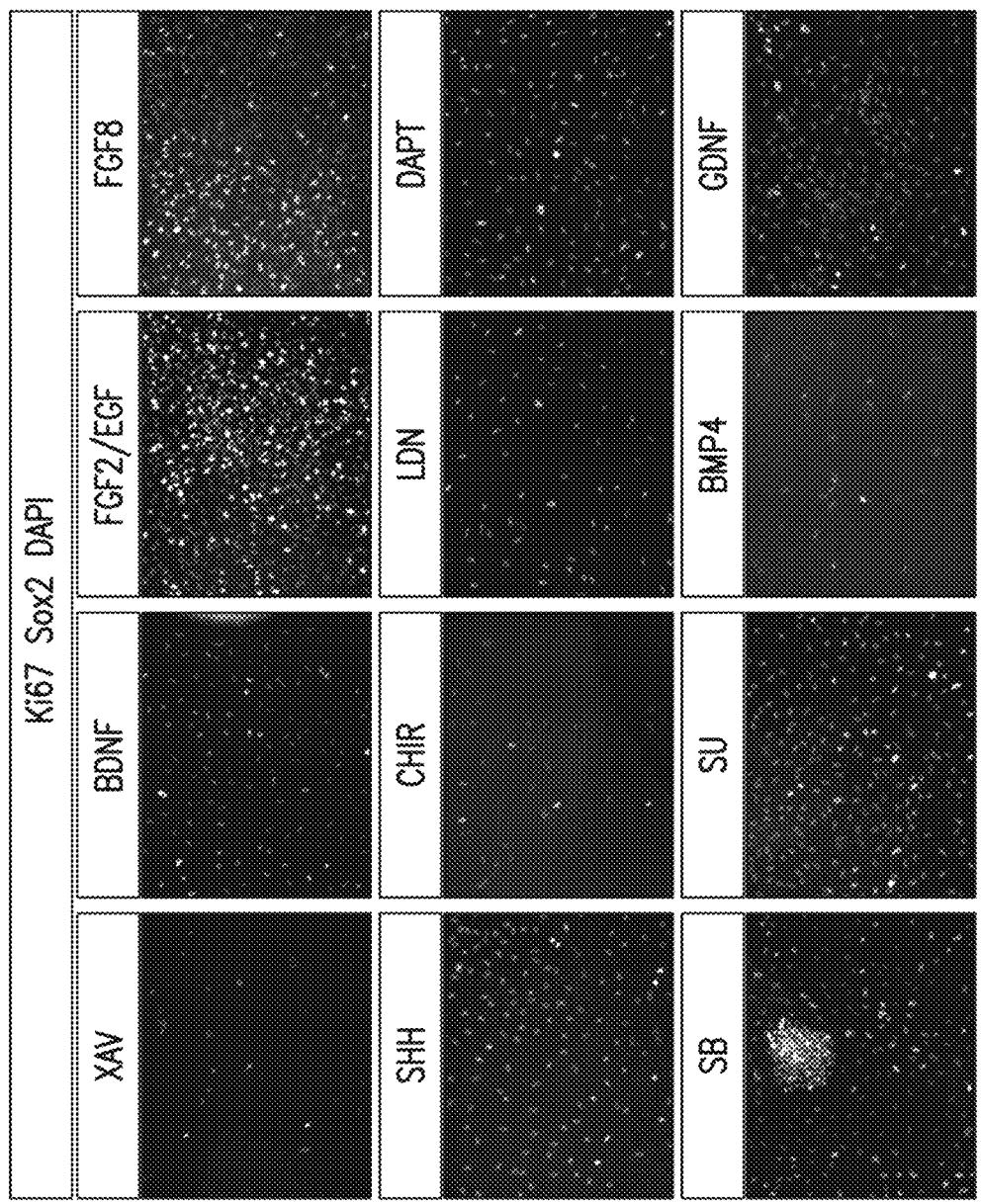

FIG. 69 shows that culturing SIX1::GFP hPSCs according to PIP-E6 supplemented with FGF2 or FGF8 at culture days 6-14 may increase the number of putative pituitary stem cells, as evidenced by expression of Ki67 and Sox2.

Figure 70:
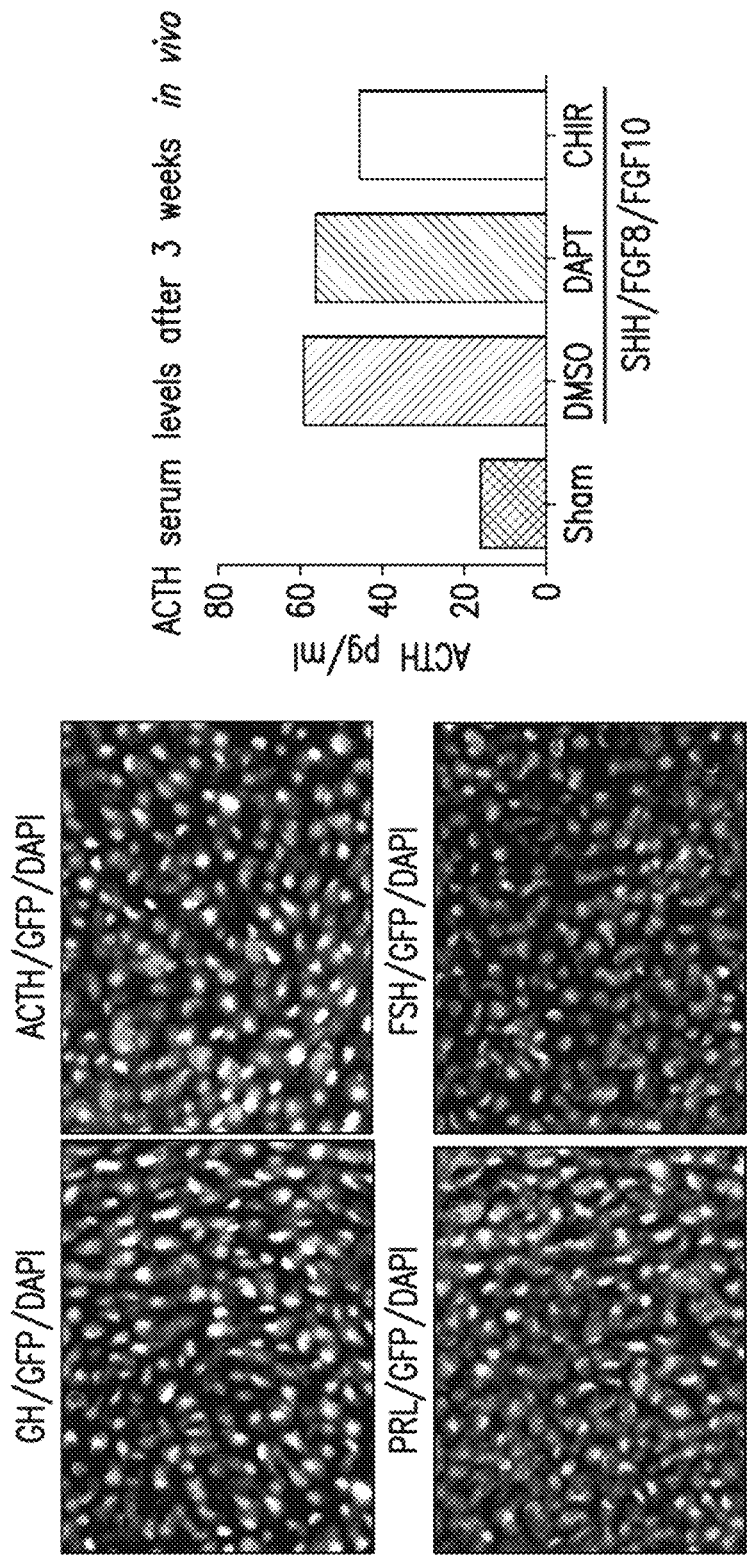

FIG. 70 shows that cells induced to pituitary hormone expressing fates through use of the modified PIP-E6 (supplemented with pituitary patterning factors) protocol survived when grafted into non-lesioned adult rat brain (adjacent to pituitary/hypothalamus), and increased the level of detectable ACTH in the grafted animals compared to control.

Figure 71:
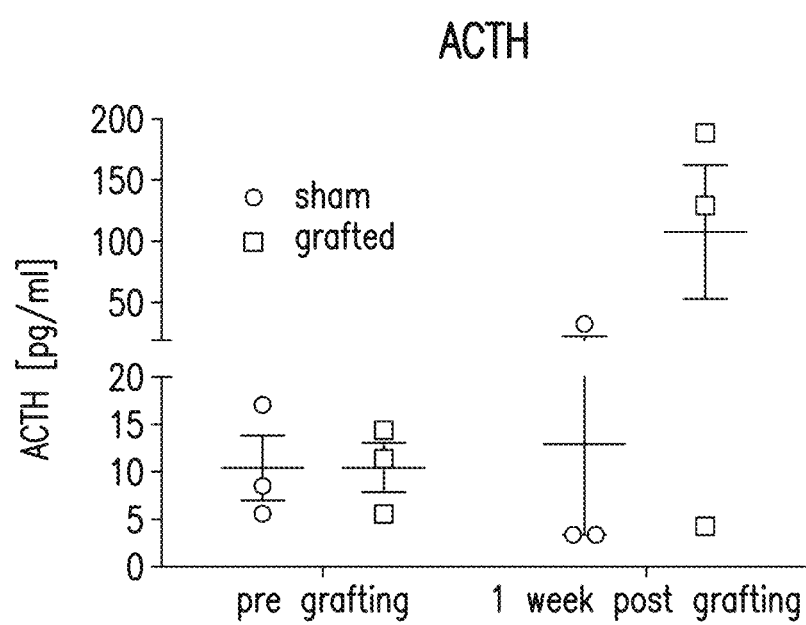

FIG. 71 shows that when a mixture of induced pituitary hormone releasing cells was grafted into hypophysectomized rats, ACTH levels appeared to increase in 2 out of 3 grafted animals.

DEFINITIONS

As used herein, the term "inhibitor" in reference to inhibiting a signaling target or a signaling target pathway refers to a compound that interferes with (i.e. reduces or eliminates or suppresses) a resulting target molecule or target compound or target process, such as a particular differentiation outcome, (for example, suppresses an active signaling pathway promoting a default cell type differentiation, thereby inducing differentiation into a non-default cell type) when compared to an untreated cell or a cell treated with a compound that does not inhibit a treated cell or tissue.

As used herein, the term "Small Mothers Against Decapentaplegic" or "SMAD" refers to a signaling molecule.

As used herein, the term "neural cell" or "neuronal cell" refers to a cell that in vivo would become part of the nervous system and in culture is obtained by methods of the present inventions, for example, CNS progenitor cells, patternable (i.e. a cell capable of undergoing further differentiation) neuronal populations of motorneurons and dopaminergic neurons, placodal precursor cells, high efficiency motor neuron cells, etc.

As used herein, the term "high efficiency motor neuron cell" refers to a neuronal cell capable of conducting an electric current.

As used herein, the term "fate" in reference to a cell, such as "cell fate determination" in general refers to a cell with a genetically determined lineage whose progeny cells are capable of becoming a variety of cell types or a few specific cell types depending upon in vivo or in vitro culture conditions. In other words, a cell's predetermined fate is determined by it's environment to be destined for a particular differentiation pathway such that a cell becomes one cell type instead of another cell type, for example, a stem cell's progeny cells whose "neural fate" is to become a nerve cell instead of a muscle cell or a skin cell. Typically, a cell's "fate" is irreversible except under highly specific conditions. In another example, a "CNS fate" refers to a cell capable of becoming a cell associated with the central nervous system. Conversely, a cell fated to become a neural cell can be called a "neural progenitor cell."

As used herein, the term "neural progenitor cell" refers to a cell capable of forming a part of the nervous system, such as a nerve cell, a glial cell, etc.

As used herein, the term "neuronal subtype" refers to any cell of the neuronal system, such as a dopamine expression neuron, a peripherin neuron, a motor neuron cell, etc.

As used herein, the term "cell of a neural lineage" refers to a cell that differentiated along a neural precursor pathway.

As used herein, the term "placode" in reference to a cell refers to a cell capable of becoming a cell associated with the sensory nervous system. In one embodiment, a placode cell is positive for Six1+, positive for p75 while negative for HNK1. In one embodiment, a placode cell obtained using methods of the present inventions is capable of forming a lens cell.

As used herein, the term "adenohypophyseal precursor" in reference to a cell refers to a cell whose in vivo progeny cells would be or become a part of the pituitary gland. An adenohypophyseal precursor cell of the present inventions refers to a cell capable of expressing Lhx3 and CGA.

As used herein, the term "expressing" in relation to a gene or protein refers to making an mRNA or protein which can be observed using assays such as microarray assays, antibody staining assays, and the like.

As used herein, the term "SMAD inhibitor" in reference to inhibiting a signaling molecule or a signaling molecule's pathway, such as an inhibitor of SMAD signaling, refers to a compound that interferes with (i.e. reduces or eliminates or suppresses) the signaling function of the molecule or pathway. In one embodiment, an inhibitor of the present inventions induces (changes) or alters differentiation from a default to a non-default cell type, for example, one of the methods of the present inventions comprising two inhibitors of SMAD signaling produces a non-default neural progenitor cell.

As used herein, the term "Small Mothers Against Decapentaplegic" or "SMAD" refers to a signaling molecule.

As used herein, the term "cell differentiation" refers to a pathway by which a less specialized cell (i.e. stem cell) develops or matures to possess a more distinct form and function (i.e. neural plate).

As used herein, the term "differentiation" as used with respect to cells in a differentiating cell system refers to the process by which cells differentiate from one cell type (e.g., a multipotent, totipotent or pluripotent differentiable cell) to another cell type such as a target differentiated cell.

As used herein, the term "cell differentiation" in reference to a pathway refers to a process by which a less specialized cell (i.e. stem cell) develops or matures or differentiates to possess a more distinct form and/or function into a more specialized cell or differentiated cell, (i.e. neural cell, neural plate cell, pituitary cell, adrenal cell, etc.).

As used herein, the term "neural stem cell" or "NSC" refers to a cell that is capable of becoming neurons, astrocytes, oligodendrocytes, glial cells, etc., in vivo, and neuronal cell progeny and glial progeny in culture however their in vitro differentiation potential toward multiple region-specific neuron types is low.

As used herein, the term "default" or "passive" in reference to a cell differentiation pathway refers to a pathway where a less specialized cell becomes a certain differentiated cell type in culture, when not treating with certain compounds, i.e., normal cell cultures conditions. In other words, a default cell results when a cell is not contacted by a molecule capable of changing the differentiated cell type (i.e. a morphogen). In contrast, "non-default" in reference to a cell refers to a differentiated cell type that results that is different from a default cell, i.e., a non-default cell is a differentiated cell type resulting from a non-default conditions, such as cell of the present inventions, including a dopamine positive nerve cell, a floor plate cell, posterior FP tissue, etc. A default cell may also be a default cell after a cell has contact with a morphogen to become a non-default cell without a subsequent morphogenic compound, such as a non-default floor plate cell that subsequently becomes a default posterior FP cell of the non-default cell of the present inventions.

As used herein, the term "homodimer" in reference to a SMAD molecule refers to at least two molecules of SMAD linked together, such as by disulfide linkages.

As used herein, the term "Noggin" refers a secreted homodimeric glycoprotein that binds to and inactivates members of the transforming growth factor-beta (TGF-β) superfamily of signaling proteins, such as bone morphogenetic protein-4 (BMP4). Noggin is typically a 65 kDa protein expressed in human cells as a glycosylated, disulfide-linked dimer. (Groppe, et al., (2002). Nature 420, 636-

642; Xu, et al., (2005) Nat Methods 2, 185-190; Wang, et al., (2005) Biochem Biophys Res Commun 330, 934-942). One example of a Noggin amino acid sequence is: Accession #U79163 single amino acid mouse Noggin (SEQ ID NO:1):

MERCPSLGVTLYALVVVLGLRAAPAGGQHYLHIRPAPSDNLPLVDFTLIE

HPDPIFDPKEKDLNETLLRSLLGGHYDPGFMATSPPEDRPGGGGPAGGA

EDLAELFTDQLLRQRPSGAMPSEIKGLEFSEGLAQGKKQRLSKKLRRKLQ

MWLWSQTFCPVLYAWNDFTLGSRFWPRYVKVGSCFSKRSCSVPEGMVCKP

SKSVHLTVLRWRCQRRGGQRCGWIPIQYFTPIISECKCSC.

As used herein, the term "SB431542" refers to a molecule with a number CAS 301836-41-9, a molecular formula of $C_{22}K_8N_4O_3$, and a name of 4-[4-(1,3-benzodioxol-5-yl)-5-(2-pyridinyl)-1H-imidazol-2-yl]-benzamide, for example, see structure below:

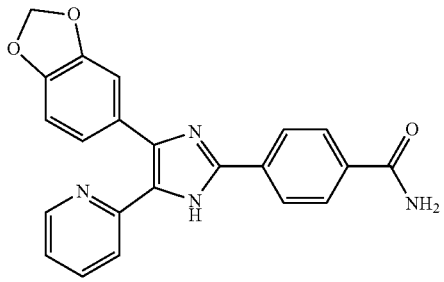 [SMILES: NC(=O)c1ccc(-c2nc(-c3ccc4c(c3)OCO4)c(-c3ccccn3)[nH]2)cc1]

As used herein, the term "Dorsomorphin" refers to a molecule with a number CAS 866405-64-3, a molecular formula $C_{24}H_{25}N_5O$ and a name of 6-[4-[2-(1-Piperidinyl) ethoxy]phenyl]-3-(4-pyridinyl)-pyrazolo[1,5-a]pyrimidine dihydrochloride, for example see structure below.

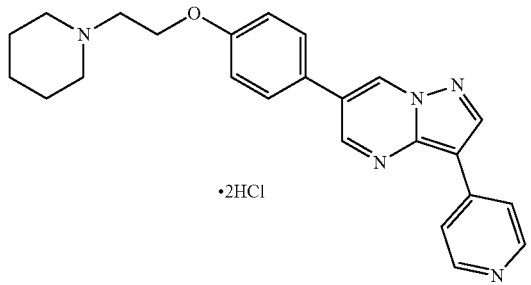 [SMILES: c1cc(-c2cnn3cc(-c4ccc(OCCN5CCCCC5)cc4)cnc23)ccn1]

As used herein, the term "Lefty" refers to a novel member of the transforming growth factor beta superfamily that inhibits TGF-beta, including but not limited to LEFTY1, LEFTY2, LEFTYA, etc., also known as "EBAF" or "endometrial bleeding associated factor" or "left-right determination, factor A" transforming growth factor beta superfamily)). A Lefty protein is required for left-right asymmetry determination of organ systems in mammals.

As used herein, the term "Activin" refers to a member of the transforming growth factor-beta (TGF-β) superfamily, such as Activin A, Activin B, etc.

As used herein, the term "transforming growth factor beta" or "TGF-β" refers to a cytokine that regulates growth and differentiation of diverse types of cells.

As used herein, the term "nodal" refers to a member of the TGF-β family of signaling molecules. Nodal signaling inhibits differentiation of human embryonic stem cells along the neuroectodermal default pathway (Vallier, et al., Dev. Biol. 275, 403-421).

As used herein, the term "ALK" or "anaplastic lymphoma kinase" or "anaplastic lymphoma receptor tyrosine kinase" or "Ki-1" refers to a membrane associated tyrosine kinase receptor.

As used herein, the term "ALK4" in reference to a type I serine/threonine kinase receptor refers to an anaplastic lymphoma receptor tyrosine kinase 4 receptor that binds to activin to function as an activin receptor.

As used herein, the term "ALK5" in reference to a type I serine/threonine kinase receptor refers to an anaplastic lymphoma receptor tyrosine kinase 5 receptor that binds to TGF-β1 to function as a TGF-β1 receptor.

As used herein, the term "ALK7" in reference to a type I serine/threonine kinase receptor refers to an anaplastic lymphoma receptor tyrosine kinase 7 receptor that binds to Nodal and Nodal-related proteins to function as a Nodal and Nodal-related protein receptor.

As used herein, the term "paired box gene 6" or "PAX6" refers to a marker of a nondefault neuroprogenitor cell.

As used herein, the term "kit" refers to any delivery system for delivering materials. In the context of cell differentiation, a kit may refer to a combination of materials for contacting stem cells, such delivery systems include systems that allow for the storage, transport, or delivery of reaction reagents (e.g., compounds, proteins, detection agents (such as PAX6 antibodies), etc. in the appropriate containers (such as tubes, etc.) and/or supporting materials (e.g., buffers, written instructions for performing cell differentiation, etc.) from one location to another. For example, kits include one or more enclosures (e.g., boxes, or bags, and the like) containing the relevant reaction reagents (such as Noggin (or a Noggin substitute) and SB431542 (or a SB431542 replacement), etc.) and/or supporting materials.

As used herein, the term "inducing differentiation" in reference to a cell refers to changing the default cell type (genotype and/or phenotype) to a non-default cell type (genotype and/or phenotype). Thus "inducing differentiation in a stem cell" refers to inducing the cell to divide into progeny cells with characteristics that are different from the stem cell, such as genotype (i.e. change in gene expression as determined by genetic analysis such as a microarray) and/or phenotype (i.e. change in expression of a protein, such as PAX6 or a set of proteins, such as HMB45 positive (+) while negative (−) for SOX10.

As used herein, the term "contacting" cells with a compound of the present inventions refers to placing the compound in a location that will allow it to touch the cell in order to produce "contacted" cells. The contacting may be accomplished using any suitable method. For example, in one embodiment, contacting is by adding the compound to a tube of cells. Contacting may also be accomplished by adding the compound to a culture of the cells.

As used herein, the term "stem cell" refers to a cell that is totipotent or pluripotent or multipotent and are capable of differentiating into one or more different cell types, such as embryonic stems cells, stem cells isolated from organs, for example, skin stem cells.

As used herein, the term "embryonic stem cell" refers to a cell of a stem cell line, such as WA-09, or a cell isolated from an embryo or placenta or umbilical cord.

As used herein, the term "adult stem cell" refers to a stem cell derived from an organism after birth.

As used herein, the term "neural stem cell" or "NSC" refers to a cell that is capable of becoming neurons, astrocytes, oligodendrocytes, and glial cells in vivo, and neuronal cell progeny and glial progeny in culture however their in vitro differentiation potential toward multiple region-specific neuron types is low.

As used herein, the term "mesodermal cell line" refers to a cell line displaying characteristics associated with mesodermal cells.

As used herein, the term "endodermal cell line" refers to a cell line displaying characteristics normally associated with endodermal cells.

As used herein, the term "neural cell line" refers to a cell line displaying characteristics normally associated with a neural cell. Examples of such characteristics include, but are not limited to, expression of FOXA2, SHH, Netrin-1, F-Spondin, and the like.

As used herein, the term "totipotent" refers to an ability of a cell to differentiate into any type of cell in a differentiated organism, as well as a cell of extra embryonic materials, such as placenta, etc.

As used herein, the term "pluripotent" refers to a cell line capable of differentiating into any differentiated cell type.

As used herein, the term "multipotent" refers to a cell line capable of differentiating into at least two differentiated cell types.

As used herein, the term "differentiation" as used with respect to cells in a differentiating cell system refers to the process by which cells differentiate from one cell type (e.g., a multipotent, totipotent or pluripotent differentiable cell) to another cell type such as a target differentiated cell.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reaction that occur within a natural environment.

Figure 27A:
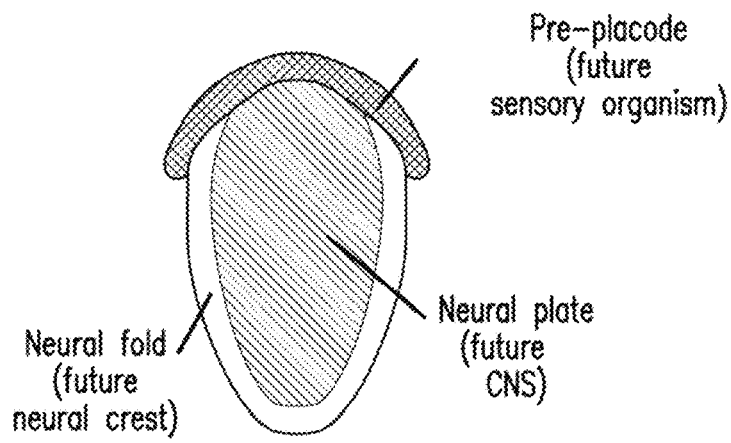
Figure 27B:
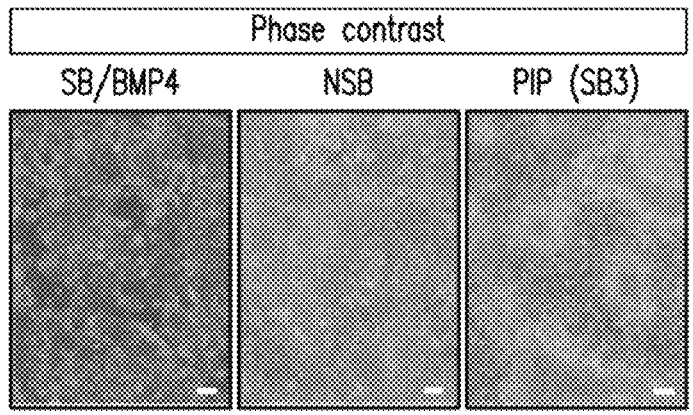
Figure 27C:
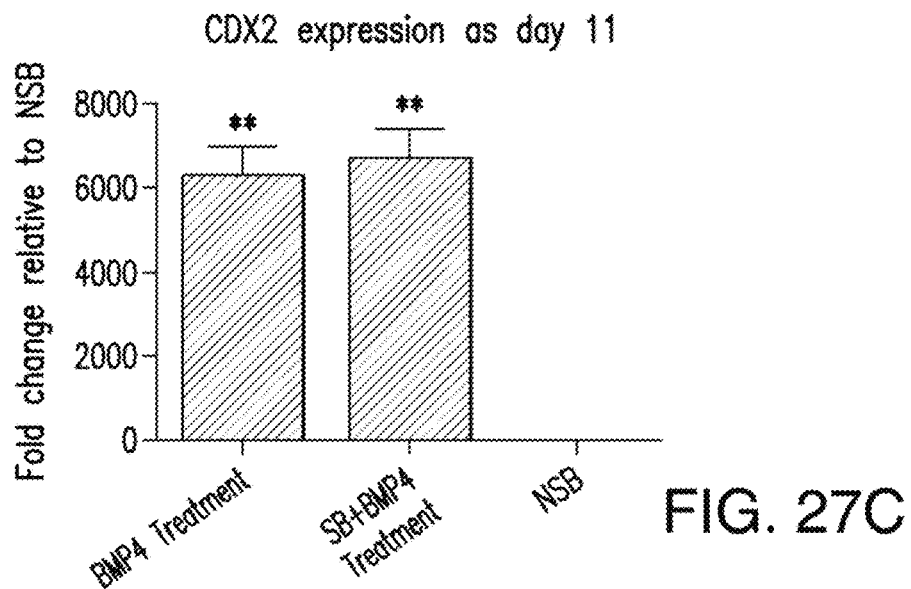

As used herein, the term "neural plate" or "medullary plate" refers to a thickened band of ectoderm (an unpaired ventral longitudinal zone of the neural tube) in the midbody region of the developing embryo, which develops (differentiates) into the neural tube and neural crest; see, FIGS. 26 and 27A. During embryonic development neural plate cells undergo a series of developmental stages and subsequently develop into cells forming a brain, spinal cord, and other tissues of the central nervous system.

As used herein, the term "floor plate" or "FP" or "ventral plate" or "basal plate" or "neural floor plate" refers to an area of cells that develops at the midline of the neural plate and is located at the ventral midline of the neural tube, see, FIGS. 26 and 27A.

As used herein, the term "neural floor plate cell" "or "FP cell" or "floor plate cell" in reference to a cell refers to a cell group also called "specialized neuroepithelial cells" found in a developing embryo in the neural floor plate. FP cell in vitro are cells expressing certain cell markers also found in FP cells in vivo that are not found in other cells.

As used herein, the term "roof plate" or "alar plate" or "dorsal roof plate" refers to a cell group located in at the dorsal region of the forming and formed neural tube areas the unpaired dorsal longitudinal zone of the neural tube.

As used herein, the term "neural tube" refers to a hollow cylindrical structure of neuroepithelial cells formed from the neuroectoderm cells of an early embryo by the closure of the neural groove such that neuroectoderm cells can differentiate into brain cells and spinal cord cells.

As used herein, the term "presumptive" or "progenitor" in reference to a cell or an area of cells refers to the type of cell or area of cells that would develop (differentiate into) under the appropriate conditions, i.e. when contacted with a proper growth factor, compound, extracellular signal, intracellular signal, etc. For example, "progenitor neuron" refers to a cell that has the capability to develop into a neuron.

As used herein, the term "dopamine neuron" or "dopaminergic neuron" in general refers to a cell capable of expressing dopamine. "Midbrain dopamine neurons" or "mDA" refer to presumptive dopamine expressing cells in forebrain structures and dopamine expressing cells in forebrain structures.

As used herein, the term "default" in reference to a cell differentiation pathway refers to a pathway where a less specialized cell becomes a certain differentiated cell type when not contacted by a molecule which changes the differentiated cell type.

As used herein, the term "cell differentiation" refers to a pathway by which a less specialized cell (i.e. stem cell) develops or matures to possess a more distinct form and function (i.e. neural plate).

As used herein, the term "neurite outgrowth refers to observation of elongated, membrane-enclosed protrusions of cytoplasm from cells.

As used herein, the term "attached cell" refers to a cell growing in vitro wherein the cell contacts the bottom or side of the culture dish, an attached cell may contact the dish via extracellular matrix molecules and the like. As opposed to a cell in a suspension culture.

As used herein, the term "marker" or "cell marker" refers to gene or protein that identifies a particular cell or cell type. A marker for a cell may not be limited to one marker, markers may refer to a "pattern" of markers such that a designated group of markers may identity a cell or cell type from another cell or cell type. For example, FP cells of the present inventions express one or more markers that distinguish a FP cell, i.e. FOXA2 positive and BF1 negative, from a non-FP cell, i.e. FOXA2 negative and BF1 positive.

As used herein, the term "test compound" refers to any chemical entity, pharmaceutical, drug, and the like that were used to provide cells of the present inventions.

As used herein, the term "rosette-stage neural cell" or "R-NSC" refers to a neural stem cell type in vitro with broad differentiation potential capable of forming central nervous system (CNS) and peripheral nervous system (PNS) cells (fates) and capable of in vivo engraftment. In other words, a rosette-stage neural cell is capable of forming a rosette structure and rosette-stage neural cell populations have characteristics of neuronal differentiation.

As used herein, the term "rosette structure" or "rosette" in reference to a cell refers to a halo or spoke-wheel arrangement of cells.

As used herein, the term "increasing" in reference to a characteristic refers to a larger amount of a characteristic when compared to said characteristic in a control, such as when comparing an amount of a marker in human embryonic stems cells cultured with and without a test compound.

As used herein, the term "decreasing" in reference to a characteristic refers to a smaller amount of a characteristic when compared to said characteristic in a control, such as when comparing an amount of a marker in human embryonic stems cells cultured with and without a test compound.

As used herein, the term "reducing protein function" or "loss of function" refers to interfering with or blocking a function in order to lower that function, for example, lowering the function of DKK-1 by blocking antibodies.

As used herein, the term "neuron inducing compound" refers to a substance for causing differentiation along a cellular pathway leading to neuronal cell.

As used herein, the term "agent for blocking phosphorylation of a receptor" refers to a substance for reducing receptor function, i.e. by reducing phosphorylation.

As used herein, the term "response," when used in reference to an assay, refers to the generation of a detectable signal (e.g., accumulation of reporter protein, increase in ion concentration, accumulation of a detectable chemical product).

The term "sample" is used in its broadest sense. In one sense it can refer to a cell or tissue. In another sense, it is meant to include a specimen or culture obtained from any source and encompasses fluids, solids and tissues. Environmental samples include environmental material such as surface matter, soil, water, and industrial samples. These examples are not to be construed as limiting the sample types applicable to the present invention.

The terms "purified," "to purify," "purification," "isolated," "to isolate," "isolation," and grammatical equivalents thereof as used herein, refer to the reduction in the amount of at least one contaminant from a sample. For example, a cell type is purified by at least a 10%, preferably by at least 30%, more preferably by at least 50%, yet more preferably by at least 75%, and most preferably by at least 90%, reduction in the amount of undesirable cell types, such as isolated differentiated FP cells from nonFP cells, such as cells present in a mixed cell culture. Thus purification of a cell type results in an "enrichment," i.e., an increase in the amount, of the nucleotide sequence in the sample.

The term "naturally occurring" as used herein when applied to an object (such as cell, tissue, etc.) and/or chemical (such as a protein, amino acid sequence, nucleic acid sequence, codon, etc.) means that the object and/or compound are/were found in nature. For example, a naturally occurring cell refers to a cell that is present in an organism that can be isolated from a source in nature, such as an embryonic cell, wherein the cell has not been intentionally modified by man in the laboratory.

As used herein the term, "in vitro" refers to an artificial environment and to processes or reactions that occur within an artificial environment. In vitro environments exemplified, but are not limited to, test tubes and cell cultures.

As used herein the term, "in vivo" refers to the natural environment (e.g., an animal or a cell) and to processes or reactions that occur within a natural environment, such as embryonic development, cell differentiation, neural tube formation, etc.

As used herein, the term "proliferation" refers to an increase in cell number.

As used herein, the term "ligand" refers to a molecule that binds to a second molecule. A particular molecule may be referred to as either, or both, a ligand and second molecule. Examples of second molecules include a receptor of the ligand, and an antibody that binds to the ligand.

The term "derived from" or "established from" or "differentiated from" when made in reference to any cell disclosed herein refers to a cell that was obtained from (e.g., isolated, purified, etc.) a parent cell in a cell line, tissue (such as a dissociated embryo, or fluids using any manipulation, such as, without limitation, single cell isolation, cultured in vivo, treatment and/or mutagenesis using for example proteins, chemicals, radiation, infection with virus, transfection with DNA sequences, such as with a morphogen, etc., selection (such as by serial culture) of any cell that is contained in cultured parent cells. A derived cell can be selected from a mixed population by virtue of response to a growth factor, cytokine, selected progression of cytokine treatments, adhesiveness, lack of adhesiveness, sorting procedure, and the like.

As used herein, the term "biologically active," refers to a molecule (e.g. peptide, nucleic acid sequence, carbohydrate molecule, organic or inorganic molecule, and the like) having structured, regulatory, and/or biochemical functions.

As used herein, the term "primary cell" is a cell that is directly obtained from a tissue (e.g. blood) or organ of an animal in the absence of culture. Typically, though not necessarily, a primary cell is capable of undergoing ten or fewer passages in vitro before senescence and/or cessation of proliferation. In contrast, a "cultured cell" is a cell that has been maintained and/or propagated in vitro for ten or more passages.

As used herein, the term "cultured cells" refer to cells that are capable of a greater number of passages in vitro before cessation of proliferation and/or senescence when compared to primary cells from the same source. Cultured cells include "cell lines" and "primary cultured cells."

As used herein, the term "cell culture" refers to any in vitro culture of cells. Included within this term are continuous cell lines (e.g. with an immortal phenotype), primary cell cultures, finite cell lines (e.g., non-transformed cells), and any other cell population maintained in vitro, including embryos and embryonic cells.

As used herein, the term "cell line," refers to cells that are cultured in vitro, including primary cell lines, finite cell lines, continuous cell lines, and transformed cell lines, but does not require, that the cells be capable of an infinite number of passages in culture. Cell lines may be generated spontaneously or by transformation.

As used herein, the terms "primary cell culture," and "primary culture," refer to cell cultures that have been directly obtained from cells in vivo, such as from animal tissue. These cultures may be derived from adults as well as fetal tissue.

As used herein, the terms "monolayer," "monolayer culture," and "monolayer cell culture," refers to a cell that has adhered to a substrate and grow as a layer that is one cell in thickness, in other words, an "attached cell." Monolayers may be grown in any format, including but not limited to flasks, tubes, coverslips (e.g., shell vials), roller bottles, et cetera.

As used herein, the terms "feeder cell layer" or "feeder cell population" refers to a monolayer of cells used to provide attachment molecules and/or growth factors for an adjacent cell, for example, used in co-culture to maintain pluripotent stem cells.

As used herein, the terms "suspension" and "suspension culture" refer to cells that survive and proliferate without being attached to a substrate. Suspension cultures are typically produced using hematopoietic cells, transformed cell lines, and cells from malignant tumors.

As used herein, the terms "culture media," and "cell culture media," refer to media that are suitable to support the growth of cells in vitro (i.e., cell cultures, cell lines, etc.). It is not intended that the term be limited to any particular culture medium. For example, it is intended that the definition encompass outgrowth as well as maintenance media.

Indeed, it is intended that the term encompass any culture medium suitable for the growth of the cell cultures and cells of interest.

The term, "cell biology" or "cellular biology" refers to the study of a live cell, such as anatomy and function of a cell, for example, a cell's physiological properties, structure, organelles, interactions with their environment, their life cycle, division and death.

As used herein, the term "cell" refers to a single cell as well as to a population of (i.e., more than one) cells. The population may be a pure population comprising one cell type, such as a population of neuronal cells or a population of undifferentiated embryonic cells. Alternatively, the population may comprise more than one cell type, for example a mixed cell population. It is not meant to limit the number of cells in a population, for example, a mixed population of cells may comprise at least one differentiated cell. In one embodiment a mixed population may comprise at least one differentiated. In the present inventions, there is no limit on the number of cell types that a cell population may comprise.

As used herein, the term "positive cell" in relation to a stain refers to a cell that expresses a marker and thus "stains" for that marker in a detectable quantitative and/or qualitative amount above a control or comparative cell. A positive cell may also refer to a cell that stains for a molecule such as FOXA2, et cetera.

As used herein, the term "negative cell," refers to a cell absent detectable signal for a marker, such as a cell failing to stain following contacting with a FOXA2 antibody detection method, et cetera.

As used herein, the term "caudalization" refers to initiation of posterior pathways of neural development in the dorsalized ectoderm during embronic development, for example, dorsalized ectorderm develops various levels of posterior neural tissues, depending on the extent of caudalization.

As used herein, the term "caudalizing agent" or "caudalizing factor" refers to a compound that induces caudalization, such as Wnt-1 and Retinoic Acid (RA)

As used herein, the terms "reporter gene" or "reporter construct" refer to genetic constructs comprising a nucleic acid encoding a protein that is easily detectable or easily assayable, such as a colored protein, fluorescent protein or enzyme such as beta-galactosidase (lacZ gene).

As used herein, the term "gene targeting" refers the integration of exogenous DNA into the genome of a cell at sites where its expression can be suitably controlled. This integration occurs as a result of homologous recombination.

A "knock-in" approach as used herein refers to the procedure of inserting a desired nucleic acid sequence, such as a sequence encoding a reporter gene, into a specific locus in a host cell via homologous recombination.

As used herein, the term "genome" refers to the genetic material (e.g., chromosomes) of an organism.

The term "nucleotide sequence of interest" refers to any nucleotide sequence (e.g., RNA or DNA), the manipulation of which may be deemed desirable for any reason (e.g., treat disease, confer improved qualities, expression of a protein of interest in a host cell, expression of a ribozyme, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

As used herein, the term "protein of interest" refers to a protein encoded by a nucleic acid of interest.

As used herein, the term "exogenous gene" refers to a gene that is not naturally present in a host organism or cell, or is artificially introduced into a host organism or cell.

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain. The DNA or RNA sequence thus codes for the amino acid sequence.

The term "suspected of having", as used herein, refers a medical condition or set of medical conditions (e.g., preliminary symptoms) exhibited by a patient that is insufficent to provide a differential diagnosis. Nonetheless, the exhibited condition(s) would justify further testing (e.g., autoantibody testing) to obtain further information on which to base a diagnosis.

The term "at risk for" as used herein, refers to a medical condition or set of medical conditions exhibited by a patient which may predispose the patient to a particular disease or affliction. For example, these conditions may result from influences that include, but are not limited to, behavioral, emotional, chemical, biochemical, or environmental influences.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index, and it can be expressed as the ratio LD50/ED50. Compounds that exhibit large therapeutic indices are preferred. The data obtained from these cell culture assays and additional animal studies can be used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The term "disease" or "medical condition", as used herein, refers to any impairment of the normal state of the living animal or plant body or one of its parts that interrupts or modifies the performance of the vital functions. Typically manifested by distinguishing signs and symptoms, it is usually a response to: i) environmental factors (as malnutrition, industrial hazards, or climate); ii) specific infective agents (as worms, bacteria, or viruses); iii) inherent defects of the organism (as genetic anomalies); and/or iv) combinations of these factors.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "graft", "engraft", "engraftment", or "transplant" refers to any method that places a donor living tissue onto a recipient living tissue. For example, a plurality of living placode cells may be placed onto a recipient living tissue under conditions such that the donor cells become viably attached and develop normally.

DETAILED DESCRIPTION OF THE INVENTION

The present invention relates generally to the field of cell biology of stem cells, more specifically the directed differentiation of pluripotent or multipotent stem cells, including human embryonic stem cells (hESC), somatic stem cells, and induced human pluripotent stem cells (hiPSC) using novel culture conditions. In particular, cranial placodes are derived from human pluripotent stem cells by a dual-SMAD inhibition strategy of neural induction coupled with further fate specification at the pre-placode stage. The method generates placode-derived trigeminal ganglia, mature lens fibers and anterior pituitary hormone-producing cells. Applications of these cells include, but are not limited to, human cell-based therapies in sensory and endocrine disease.

I. Neuronal Differentiation Pathways

Transforming growth factor (TGF-beta) and their family members including, but not limited to, bone morphogenetic proteins (BMPs), Nodal, and activins, may be involved in the development and maintenance of various organs, in which stem cells play useful roles. The ectoderm germ layer of the embryo is believed to give rise to the neuroectoderm (the central and peripheral nervous system, neural crest cells, and derivatives). Several lines of evidence suggest a role for Smad signaling during neural induction. Generally, Smad proteins are downstream of TGF-beta superfamily ligands, and when their specific receptors are activated they stimulate the phosphorylation of the receptor-regulated Smads (R-Smads: Smad1, Smad2, Smad3, Smad5 and Smad 8, with Smads 2 and 3 specifically activated by activin/nodal and TGF-beta type I receptors and Smads 1, 5, and 8 activated by BMP type I receptors). Two distinct pathways converse on Smad 4.

Studies in frog identified bone morphogenic protein (BMP) inhibitors including chordin (Sasai, et al., *Cell* 79(5): 779 (1994)), follistatin (Hemmati-Brivanlou, et al., *Cell* 77(2):283 (1994)), and noggin (Smith, et al., *Cell* 70(5):829 (1992)) as the critical neural inducing factors in the Spearman organizer. Mammalian noggin (Valenzuela, et al., *J Neurosci* 15(9):6077 (1995)) has comparable neural inducing properties, and treatment with recombinant Noggin has been used in several hESC neural induction protocols (Lee, et al., *Stem Cells* 25(8):1931 (2007); Elkabetz, et al., *Genes Dev* 22(2):152 (2008)). More recently, the drug SB431542 was shown to enhance neural induction in an embryoid body (EB) based hESC neural induction protocol (Smith, et al., *Dev Biol* 313(1):107 (2008)). SB431542 inhibits the Lefty/Activin/TGFβ pathways by blocking phosphorylation of ALK4, ALK5, ALK7 receptors. While Noggin or SB431542 treatment improve the efficiency of neural induction, neither treatment alone is sufficient to neurally convert hESCs under defined or adherent conditions.

II. Stem Cell Culture Techniques

Efforts to culture stem cells under conditions that are robust and highly repeatable, and minimize opportunities of cross contamination have not been completely successful. Efforts towards establishing well-defined media and methods may allow for repeatability and accuracy for use of stem cells as a therapeutic agent, and there has been a move to establish media and culture conditions that are free of non-human additives and undefined factors. Modifications of the cell culture system have been the focus of a number of recent patents. U.S. Pat. No. 7,005,252, herein incorporated by reference, discusses the growth of primate embryonic stem cells in the present of Fibroblast Growth Factor (FGF) and a feeder cell layer, but in the absence of any animal serum. U.S. Pat. No. 7,297,539, herein incorporated by reference, discusses the growth of pluripotent stem cells utilizing a system containing an extracellular matrix in a Fibroblast Growth Factor containing medium, but without a feeder layer. U.S. Pat. No. 7,211,434, herein incorporated by reference, describes a method for culturing mammalian embryonic stem cells in a serum for free and feeder-layer free media containing leukemia inhibitory factor, another cytokine used to maintain pluripotency. Identification of specific and defined compounds as additives to media to control the fate of embryonic stem cells are the focus of a number of used patents, including U.S. Pat. Nos. 7,332,336, 7,294,510 and 7,252,995, each of which are herein incorporated by reference.

Human stem cells have been suggested for use in cell-replacement therapies, and recent advances in somatic cell reprogramming to induced pluripotent stem cells (hiPSCs) has opened the door to generating patient-specific cells for regenerative medicine and disease modeling (Takahasi et al, 2007; Kim, et al., Cell, 136(3):411-419 (2009)). However, to realize the full potential of these approaches improved differentiation protocols are required that eliminate the use of undefined factors such as neural-inducing stoma (PAX6 or MS5 cells (Kawasaki et al., 2000; Lee et al 2007)), the heterogeneous nature of EB differentiation of the poor yield of protocols based on selective survival of neural progeny. Understanding and selectively triggering the signaling pathways necessary and sufficient for neural indication in hESCs is a goal in this effort.

Neural stem cell progenitors and neural subtypes as derived from stem cells have been the focus of numerous scientific publications and patent applications, but these disclosures lack the most desirable conditions for controlling stem cell fate including the ability to start with a large number of cells, achieve highly homogenous desired cell fates, and use a feeder-free protocol and under adherent conditions. Shang et al., and Reubinoff, et al., *Nature Biotechnology* 19, 1134-1140 (2001) allow for passive development of neural cell types, but cannot control the neural differentiation.

III. Stem Cell Differentiation

United States Patent Application Publication No. 2009/0035285, herein incorporated by reference, teaches methods of producing neural cells, relying on EB and rosette formation. U.S. Pat. No. 6,833,269, herein incorporated by reference, provides differentiation of cells rely on the use of feeder cells and EB formation. U.S. Pat. No. 7,011,828, herein incorporated by reference, and Application Publication No. 2005026747, herein incorporated by reference, teaches and 20060078543, herein incorporated by reference, teach the proliferation of an enrich population of hESCs, which are differentiated to neural progenitor cells, neurons, or glial cells. U.S. Pat. No. 6,887,706, herein incorporated by reference, teaches a method of differentiating heESCs intor neural precursor cells using FGF2, whereby in vitro differentiation was induced by withdrawal of FGF2 and plating on ornithine and laminin substrate. U.S. Pat. No. 7,368,115 teaches differentiation of neural stem cells or neural stem cell progeny with pituitary adenylate cyclase-activating polypeptide.

In a review by Erceg et al., Stem Cells. Jan.; 27(1): 78-87 (2009), herein incorporated by reference, the author noted that the most important concern of the recently published protocols of stem cell differentiation towards neural lineages is (i) the risk of non-neural cell contamination; (ii) that the use of stem cell lines, Matrigel or conditioned media, including procedures relying on EB formation bears the risk of pathogen cross-transfer. None of the foregoing patents or patent applications teaches the derivatization of homogenous population of neural cell lineage from stem cells under the conditions present in this invention.

The present invention further relates to methods of obtaining populations of neural progenitor cells derived from human embryonic stem cells (hESCs), in particular for obtaining neural plate floor tissue. Specifically, some methods of the present invention induce neural plate floor development in hESCs for obtaining dopamine (DA) nerve cells. Further, neural plate floor tissue obtained using some methods of the present invention are contemplated for use in co-cultures with other tissues as inducers for shifting differentiation pathways, i.e. patterning.

Current neural induction protocols in human ES cells (hESs) rely embryoid body formation, stromal feeder co-culture, or selective survival conditions; each strategy displaying significant drawbacks such as poorly defined culture conditions, protracted differentiation and low yield.

In one embodiment, the present invention contemplates a method comprising a synergistic action of two inhibitors of SMAD signaling. For example, Noggin and SB431542 were discovered to be sufficient for inducing rapid and completed neural conversion of hESCs under adherent culture conditions (dual SMAD inhibition protocol). Temporal fate analysis reveals a transient FGF5+ epiblast-like stage followed by PAX6+ neural cells competent of rosette formation. Initial cell density determines the ratio of CNS versus neural crest progeny. Directed differentiation of hiPSC into midbrain dopamine and spinal motor neurons confirm robustness and general applicability of the novel induction protocol. Noggin/SB4315242 based neural induction should greatly facilitate the use of hESC and hiPSCs in regenerative medicine and disease modeling and obviate the need for stromal feeder or EB-based protocols. Further, this method was adapted to culture systems which may enhance the ease, yield efficiency, speed at which neural cells are derived. This should not be considered limiting and culture with additional molecules or growth factors, or incorporating other methods in the art were considered.

Several lines of evidence demonstrate a role for SMAD signaling during neural induction. While Noggin or SB431542 co-treatment improve the efficiency of neural induction, neither treatment alone is sufficient to neurally convert hESCs under defined or adherent conditions. The data presented herein tests whether combined blockade of SMAD signaling using Noggin and SB431542 is sufficient to achieve full neural conversion and to obviate the need for EB- or stromal-feeder based protocols.

Figure 2:
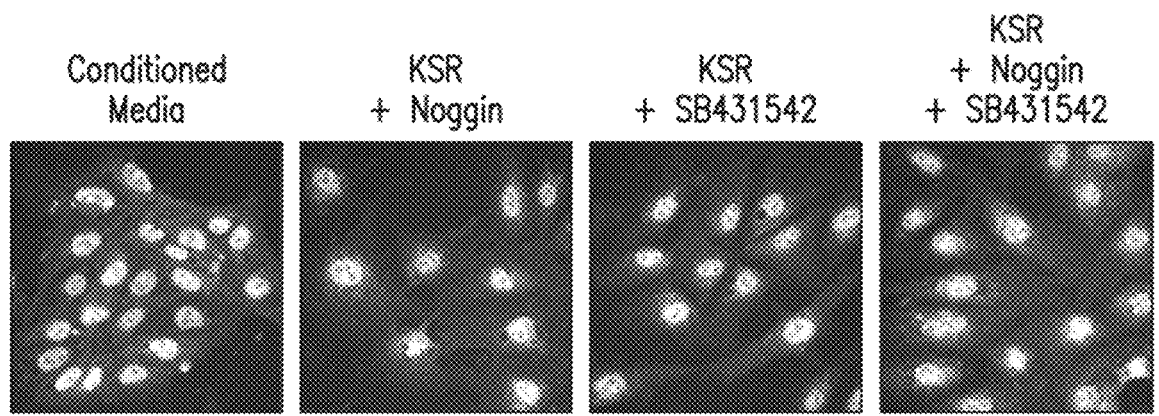
FIG. 2 shows exemplary nuclear localization of SMAD4 that diminishes when hESC cells are treated with Noggin and SB43152 for 24 hours. A proportion of SMAD4 redistributes to a perinuclear localization resulting in a less defined cytoplasmic-to-nuclear border.
Figure 3A:
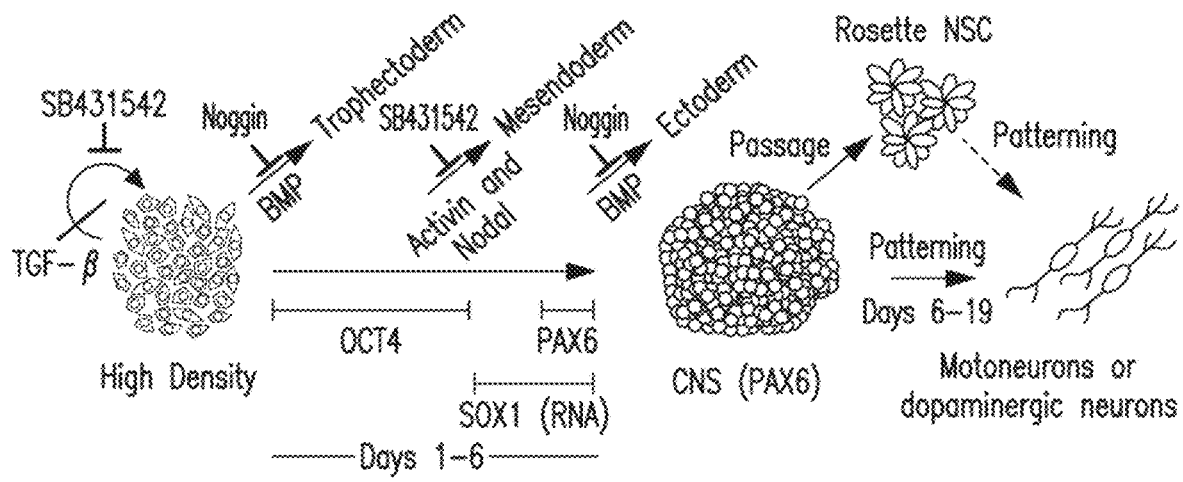
FIGS. 3A-3B show an exemplary model of proposed mechanisms that contribute to the action of Noggin and SB431542. These include, but are not limited to, destabilizing the TGF/activin- and Nanog-mediated pluripotency network, suppression of mesendodermal fates by inhibiting endogenous activin and nodal signals, and/or promoting neuralization of primitive ectoderm through BMP inhibition. (A) At high density, primarily CNS cells that are PAX6+ are formed, which are capable of giving rise to R-NS cells and patternable neuronal populations of motoneurons and dopaminergic neurons within 19 d of differentiation. (B) At lower densities, both CNS fates with the properties described in (A) and neural crest fates are observed. Neural crest lineages include melanocytes and neural crest precursor cells amenable to patterning and subtype specification responses. In addition to cell density, it is likely that further manipulation of signaling pathways, including BMP pathways, may skew that ratio of CNS versus neural crest fates. Solid arrows indicate demonstrated cell fate potential; dashed arrows indicate proposed cell fates on the basis of current literature.
Figure 3B:
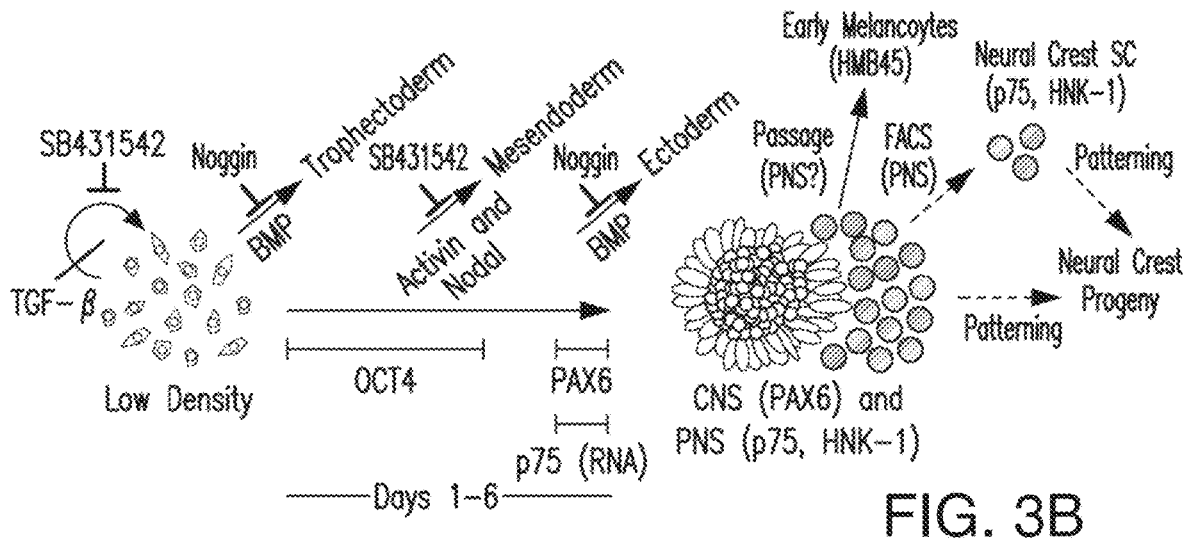

In one embodiment, the present invention contemplates a method establishing an even cell distribution for inducing homogenous neural differentiation of hESCs. To this end, undifferentiated hESC were dissociated into single cells and re-plated onto Matrigel coated dishes in conditioned medium supplement with ROCK inhibitor, Y-27632 (Wananabe et al., 2007). After 72 hours, cells were switched from hESC conditions to knock-out serum replacement medium (KSR) containing either Noggin, SB4315242, or both factors and allowed to differentiate for a total of 11 days (FIG. 1A.). The reduction in nuclear localization of the oblige co-Smad, Smad 4, was observed after 24 hours when both Noggin and SB431542 were present (FIG. 2). Neural induction was monitored by expression of PAX6, an early marker of neuroectodermal differentiation (Callaerts, et al., *Annu Rev Neurosci* 20:483 (1997).

Figure 1B:
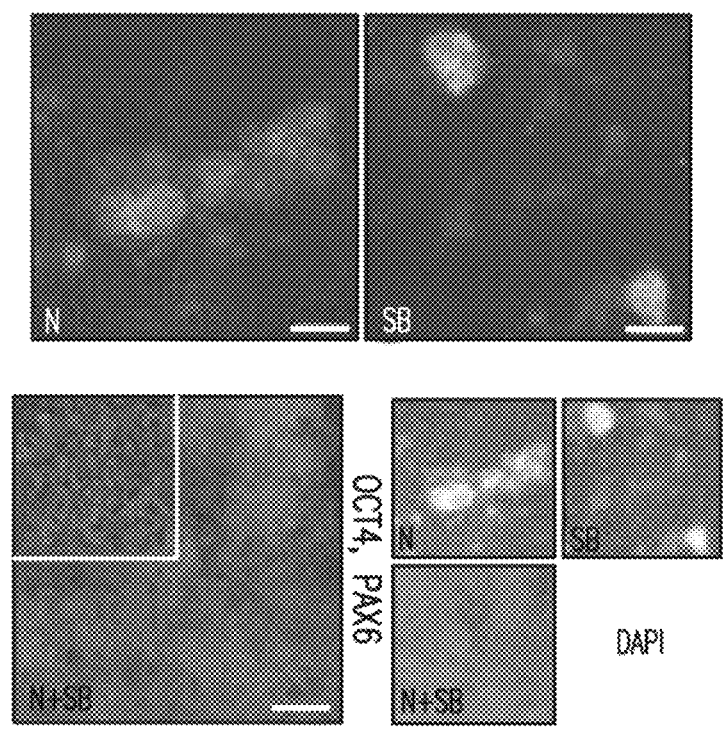

Combined treatment with Noggin and SB431542 dramatically increased the efficiency of neural induction to greater than 80% of total cells, compared with less than 10% PAX6 cells when Noggin or SB431542 were used alone (FIG. 1B). The synergistic action is unexpected, and there are several potential mechanisms that could contribute to the synergistic action of noggin and SB431542. These include, but are not limited to, destabilizing the activin- and Nanog-mediated pluripotency network (Xu, et al., *Cell Stem Cell* 3(2):196 (2008)), suppression of BMP induced differentiation towards trophoblast lineage (Xu, et al., *Nat Biotechnol* 20(12):1261 (2002)), suppression of mes-/endodermal fates by inhibiting endogenous activin and BMP signals (D'Amou, et al., *Nat Biotechnol* 23(12):1534 (2005)) and promoting neuralization of primitive ectoderm by BMP inhibition (Laflamme, et al., *Nat Biotechnol* 25(9):1015 (2007)).

Figure 1C:
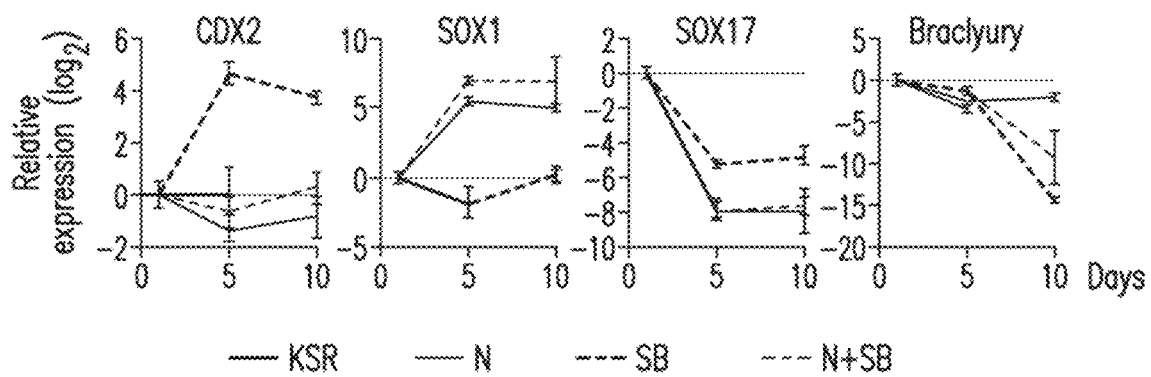

Temporal analysis of gene expression revealed that treatment with SB431542 induced a rapid loss of Nanog expression (FIG. 4) and a dramatic increase in the expression of CDX2 (FIG. 1C). These data suggested SB431542-mediated loss of pluripotency is associated with differentiation towards trophoblast lineage. Suppression of CDX2 in the presence of Noggin or Noggin/SB431542 demonstrates that one role of Noggin is the repression of endogenous BMP signals that drive trophoblast fates upon differentiation. The pronounced induction of SOX1 in Noggin/SB431542 treated cultures confirmed a strong bias towards neurectodermal lineage in the dual SMAD inhibition protocol. There is also evidence for suppression of alternative embryonic germ layers such as Noggin-mediated suppression of SOX17 (endodermal lineage) and SB431542-mediated suppression of Brachyury (mesodermal lineage) (FIG. 1C). Taken together, these results indicate that SB431542 and Noggin work synergistically at multiple stages of differentiation to achieve efficient neural conversion of hESCs.

Figure 1D:
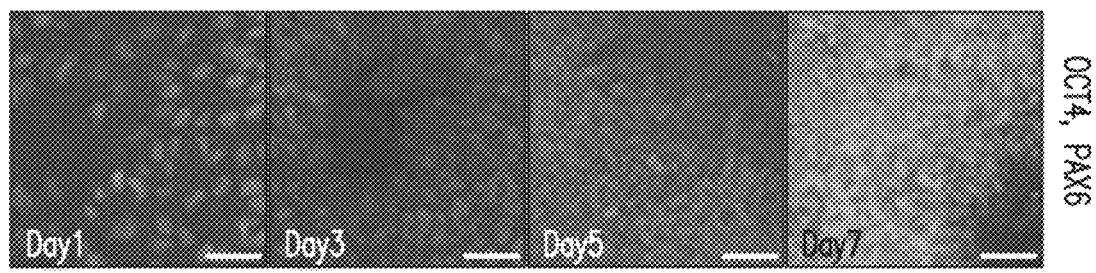
Figure 1E:
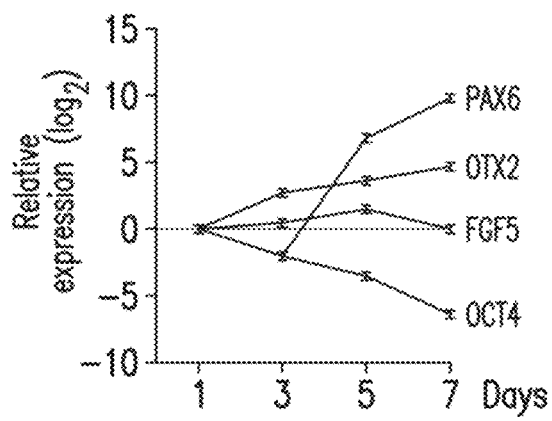

Lineage progression of hESC progeny after the addition of the two inhibitors was characterized. Immunocytochemical analysis showed loss of OCT4 expression by day 5 and strong expression of PAX 6 by day 7 (FIG. 1D). These data pointed to the presence of an intermediate cell type at day 5 of differentiation that was negative for both OCT4 and PAX6. Gene expression analysis revealed peak expression of the epiblast marker FGF5 at day 5 of differentiation concomitant with high expression of Otx2, another epiblast marker whose expression is maintained during neural fate commitment (FIG. 1E). The earliest neural marker expressed was SOX1 (FIG. 1F), preceding induction of other neurepithelial markers such as ZIC1 or PAX6, and preceding expression of anterior CNS (FOXG1) and neural crest (p'75) markers. Early induction of SOX1 is distinct from previous studies that had suggested PAX6 expression preceding SOX1 induction (Munoz-Sanjuan, et al., *Nat Rev Neurosci* 3(4):271 (2002)). One possibility to explain this discrepancy could be a direct modulation of SOX1 transcription by SMAD signaling.

Recently, methods for were described for establishing stable mouse (Munoz-Sanjuan, et al., *Nat Rev Neurosci* 3(4):271 (2002)) and hESC (Placantonakis, et al., *Stem Cells* 27(3):521-532 (2009)) transgenic reporter lines carrying bacterial artificial chromosomes (BACs) engineered to express GFP under control of cell type specific promoters. The data presented herein used the HES5::eGFP BAC transgenic hESC reporter line, marking neural stem and precursor cell progeny to measure the efficiency of neural induction (Tesar, *Nature* 448:196-199 (2007); (Placantonakis, et al., *Stem Cells* 27(3):521-532 (2009)).

Figure 1F:
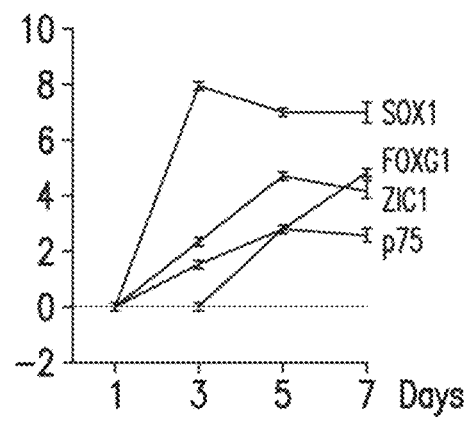
Figure 1G:
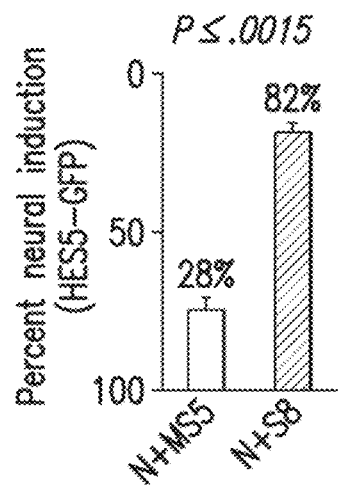
Figure 4:
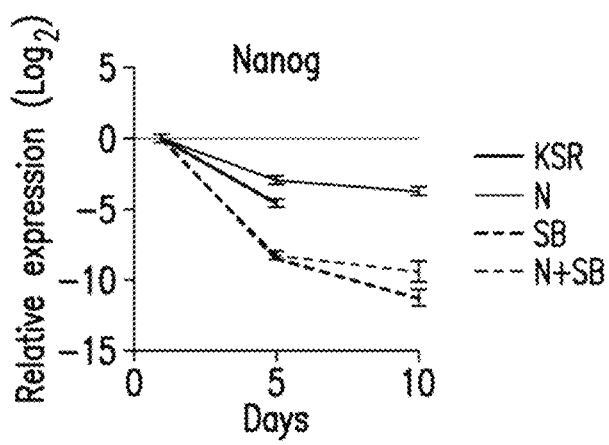
FIG. 4 shows exemplary nanog Real-Time gene expression. hESC treated with knock-out serum (KSR), Noggin (N), SB431542 (SB), or Noggin and SB431542 (N+SM) in KSR were examined for Nanog expression. The most dramatic downregulation was observed with the addition of SB431542. The error bars represent S.E.M.
Figure 5:
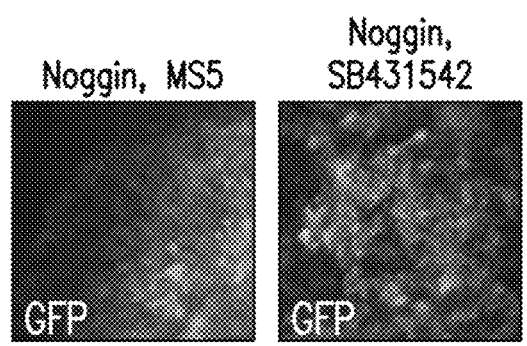
FIG. 5 shows exemplary GFP expression of HES5-GFP BAC reporter hESC line. GFP were observed under both conditions for neural induction (Noggin on MS5s or Noggin with SB431542 at day 13 of differentiation.
Figure 6:
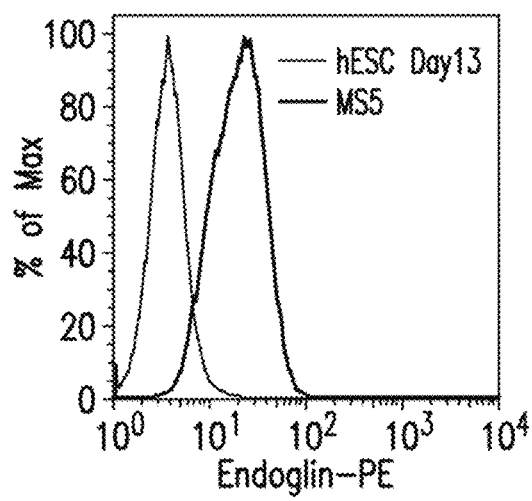
FIG. 6 shows exemplary endoglin (CD105) expression on MS5 feeder cells. MS5 cells used to differentiate hESC are uniformly positive for Endoglin (CD105) expression based on FACS analysis compared to hESC differentiated on day 13 using combined SMAD suppression. Endoglin expression was used to discriminate and remove MS5 cells from HES5-BAC hESC.

The dual SMAD inhibition protocol was compared to the standard MS5 protocol in the presence of Noggin (Perrier, et al., *Proc Natl Acad Sci USA* 101(34):12543 (2004)). To this end HES5::eGFP cells were plated in media supplemented with Noggin either in the presence of MS5 feeder cells or SB431542 and allowed to differentiate for 13 days, a stage when the GFP$^+$ cells were readily observed under both conditions (FIG. 4). GFP expression was quantified by flow cytometry. Non-modified H9 cells were used as negative controls. MS5 cells were excluded from the analysis based on negative selection for the cell surface molecule CD105 (FIG. 5). Dual SMAD inhibition yielded 82% GFP$^+$ cells at day 13, a more than 3 fold increase compared with the MS5/Noggin protocol (FIG. 1F).

In contrast to the MS5 protocol which requires plating of hESC colonies at low density (Li, et al., *Nat Biotechnol* 23(2):215 (2005)), the Noggin/SB431542 condition allowed for high plating densities. Therefore, in addition to higher percentages, the dual SMAD inhibition protocol also resulted in larger absolute numbers of Hes5::eGFP$^+$ cells per each culture plate.

Figure 7A:
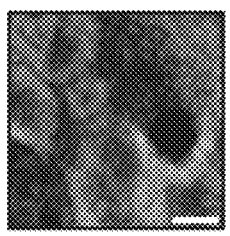
FIGS. 7A-7R show exemplary neuralization of hESC by dual SMAD inhibition that permits a pre-rosette, neural stem cell with dopaminergic and motor neuronal potential. The PAX6 positive neural tissue (green) expressed rosette markers (red) (A) Nestin, (B) PLZF, (C) ZO1. (D) Rosettes are formed when PAX6$^+$ tissue is passaged to conditions promoting rosettes (BASF) confirmed by KI67 (green) and luminal phospho-Histone H3 (red) expression, evidence of interkinetic nuclear migration. In the absence of factors that confer regional neuronal specificity, the PAX6$^+$ neural tissue (green) expressed (E) OTX2, and (F) FOXG1, indicating that the tissue defaults to forebrain specification. Neural crest could be identified on the periphery of the PAX6 positive tissue (green) based on (G) AP2, (H) HNK1, (I) PAX7, and (J) p75 expression (red). Upon passage, the neural crest cells gave rise to (K) pigmented cells (L) that expressed HMB45 (green), indicating melanosome synthesis. (M) Dopaminergic neuronal patterning was initiated with the addition of super sonic on day 5-9, followed by the addition of brain-derived neurotrophic factor (BDNF), ascorbic acid, sonic hedgehog, and FGF8 on day 9-12. Dopaminergic cells were matured on days 12-19 with BDNF, ascorbic acid, GDNF, TGFb3, and cAMP. Motor neuronal patterning was initiated at day 5 with the addition of BDNF, ascorbic acid, sonic hedgehog, and retinoic acid. Cells were passaged on day 11. (N-P) Without passage, tyrosine hydroxylase (TH) positive cells could be observed by day 19. (P) When passaged en bloc on day 12, more mature processes from TH positive cells were observed. For motoneuron induction, nuclear expression of the motor neuron markers (Q) ISL1 and (R) HB9 were observed within a total of 19 days of differentiation from hESC. Scale bars: (A, B, C, E, F, G, H, I, J, O, P, Q, and R)—100 μm; (C, D)—50 μm; (K, L, N)—200 μm.
Figure 7B:
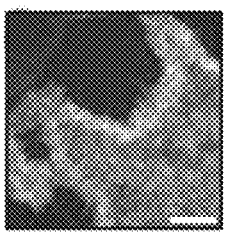

Isolation of rosette neural stem cells was reported (Elkabetz, et al., *Genes Dev.* 22, 152-165 (2008)) (R-NSCs) in addition to development of neural crest stem cells (Lee, et al., *Stem Cells* 25 (8), 1931 (2007)) (NCSCs) from hESCs. The presently disclosed data determines a lineage relationship of the early PAX6$^+$ neuroectodermal cells observed in the dual SMAD inhibition protocol to the R-NSCs and NCSCs populations as described previously. Immunocytochemical analysis showed that, similar to R-NSCs, PAX6$^+$ neuroectodermal cells express general NSC markers such as Nestin and R-NSC markers including PLZF (FIGS. 7A and 7B; day 11 of differentiation).

Figure 7C:
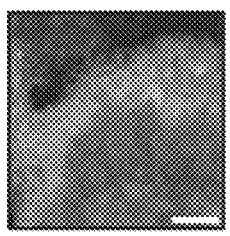
Figure 7D:
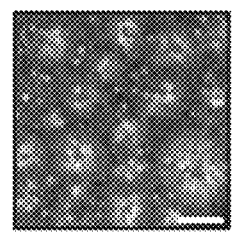
Figure 7E:
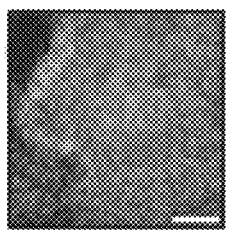
Figure 7F:
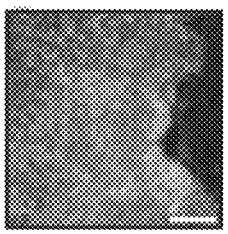
Figure 7G:
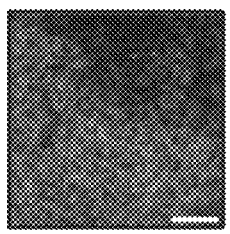
Figure 7H:
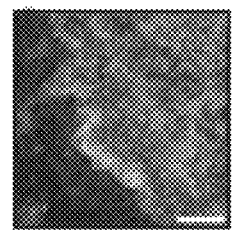
Figure 7I:
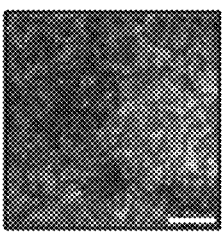
Figure 7J:
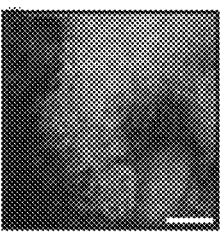
Figure 7K:
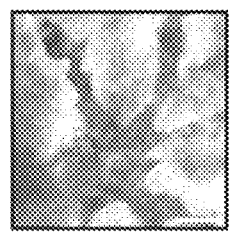
Figure 7L:
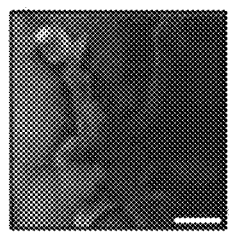
Figure 8:
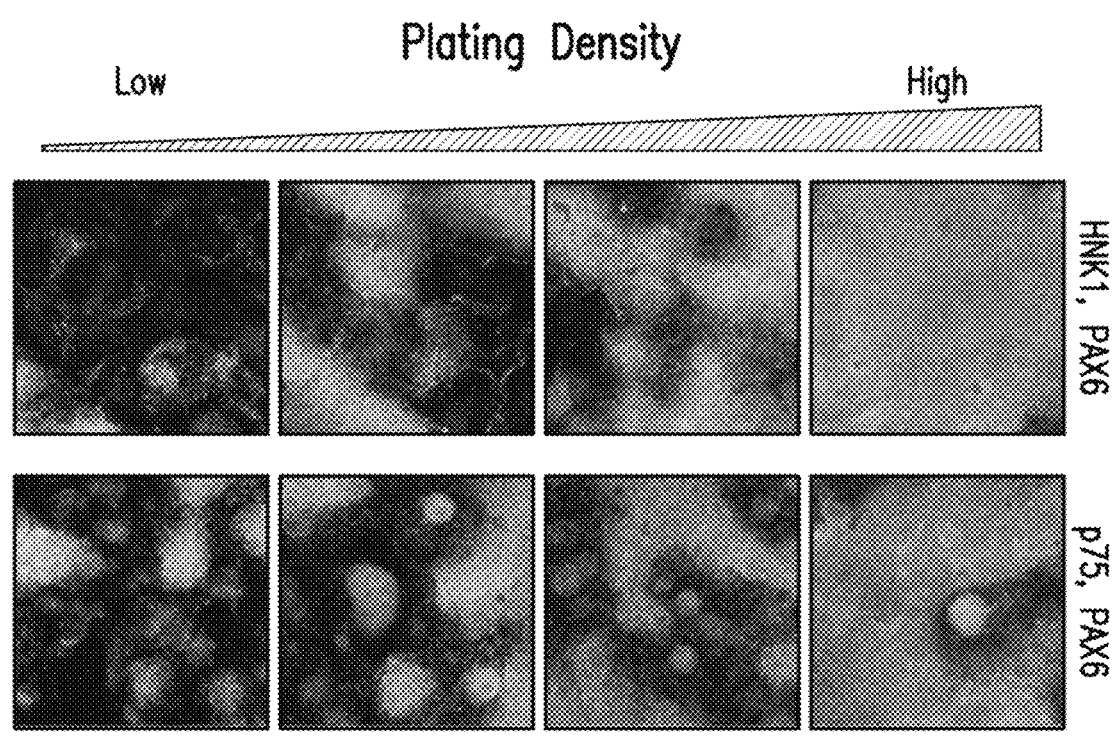
FIG. 8 shows exemplary plating density that influences PNS vs. CNS cell generation. Initial hESC plating density determines the ratio of neural-crest (HNK1, p75; red) to neural tissue (PAX6; green) present at day 11 of differentiation, with higher densities favoring neural differentiation.

However, cytoarchitecture and ZO1 expression indicated that neuroepithelial cells, under these conditions, were non-polarized and exhibited an ESC-like cytoarchitecture. These non-polarized areas were interspersed with R-NSC like areas composed of polarized columnar epithelial cells (FIG. 7C). The developmental hierarchy of these two cell populations was further explored upon subsequent passage. Under these conditions early neuroepithelial cells spontaneously converted into rosette structures with apical ZO1 expression and evidence of interkinetic nuclear migration (FIGS. 7C and 7D). These data suggested that the Noggin/SB431542 protocol yields an early PAX6$^+$ neuroepithelial population capable of rosette formation. The early PAX6$^+$ cells may therefore represent the most primitive hESC derived neural precursor stage isolated to date. R-NSCs have been shown to acquire anterior CNS marker by default (Elkabetz, et al., *Genes Dev.* 22:152-165 (2008)). PAX6$^+$ neuroepithelial cells generated via the dual SMAD inhibition protocol exhibited an anterior CNS character as evidenced by expression of Otx2 and FoxG1B (FIGS. 7E and 7F) similar to R-NSCs (Elkabetz, et al., *Genes Dev.* 22:152-165 (2008)). PAX6 negative cells under these conditions coexpressed markers of neural crest including AP2, HNK1, PAX7, and p75 (NGFR) (FIGS. 7G-7J). Manipulations of the initial hESC plating density skewed the ratio of PAX6$^+$ CNS versus PAX6$^-$ neural crest-like cells. High plating densities resulted in a biased differentiation towards PAX6$^+$ cells, while low densities promoted neural crest-like differentiation (FIG. 8). The presence of large numbers of neural crest-like cells prior to rosette formation suggested that dual SMAD inhibition yields an early neural crest population distinct from R-NSC derived NCSCs (Lee, et al., *Stem Cells* 25(8):1931 (2007)). Supporting the notion of an early neural crest population with distinct lineage potential cells could be readily enriched for pigmented cells co-expressing the melanosome marker, HMB45 (FIGS. 7K and 7L, see Examples for details). In contrast, R-NSC derived NCSCs typically do not yield pigmented cells under comparable conditions (Lee, et al., *Stem Cells* 25(8):1931 (2007)). However, some HMB45+ cells did not coexpress the neural crest marker SOX10 suggesting the presence of other pigmented cell populations including PAX6+ retinal pigment epithelial cells.

Figure 7M:
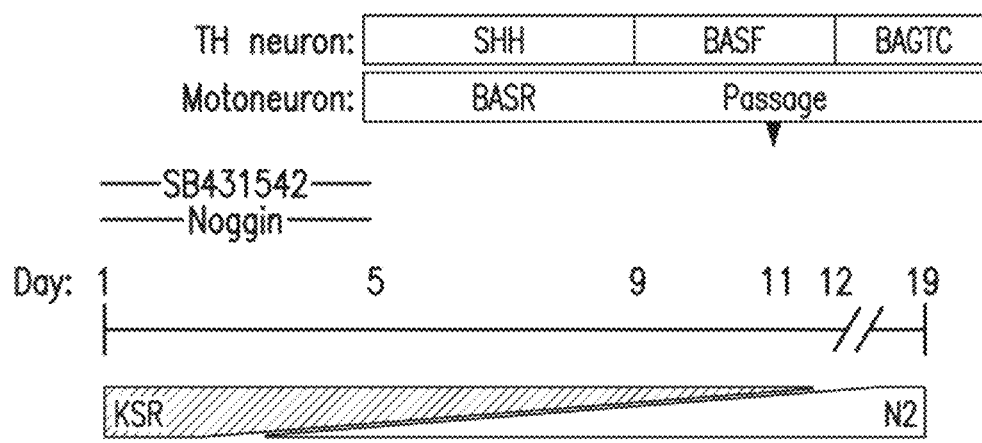
Figures 7N, 7O, 7P:
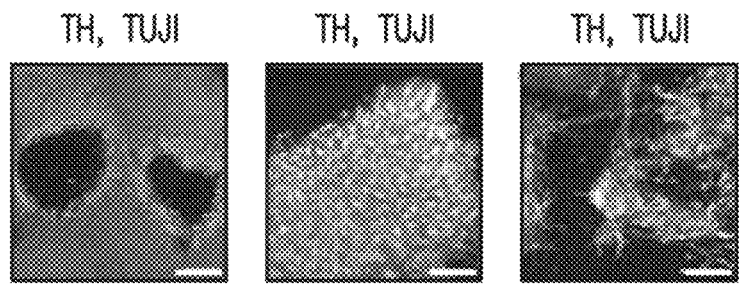

Anterior-posterior (AP) and dorso-ventral (DV) identity and neuronal subtype potential is dependent on early exposure to morphogenic factors such as retinoic acid, FGF8, and SHH. The patterning potential of cells generated via the dual SMAD inhibition protocol was also assessed. For example, day 5 of differentiation may present an appropriate developmental window for neural patterning since Oct4 expression is silenced between day 3 and 5 and the neural marker PAX6 is activated in the majority of cells between day 5 and 7 (FIGS. 1D and 1E). Derivation of cells expressing markers of dopamine neurons was observed following exposure to SHH and FGF8 (Tomishima, et al., *Stem Cells* 25 (1), 39 (2007)) starting at day 5 and day 9 of differentiation respectively (FIG. 7M). One week after SHH exposure, both FGF8 and SHH were withdrawn and further differentiated in medium containing BDNF, ascorbic acid, GDNF, TGF-β3, and cyclic-AMP (BAGTC (Tomishima, et al., *Stem Cells* 25 (1), 39 (2007)), see FIG. 7M). At day 19 of differentiation neurons a large proportion of Tujr neurons coexpressed tyrosine hydroxylase (TH) (FIGS. 7N and 7O), the rate-limiting enzyme in the synthesis of dopamine. TH+ neurons emerged under these conditions spontaneously even in the absence of cell passaging. However, derivation of more mature TH+ cells with long neural processes was promoted following mechanical isolation and en bloc passage at day 12 of differentiation.

Figures 7Q, 7R:
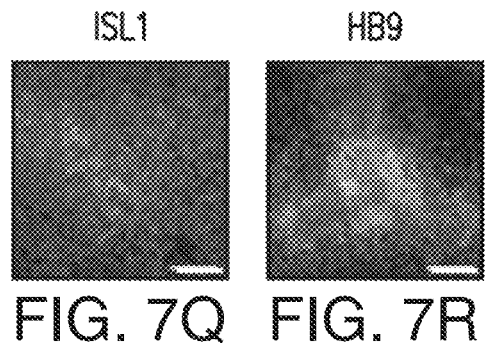

Nuclear expression of the motor neuron markers ISL1 and HB9 was observed two weeks upon exposure to BDNF, ascorbic acid, SHH, and retinoic acid (BASR; day 19 of differentiation) confirming the derivation of somatic type motor neurons (FIGS. 7Q and 7R). Motor neuron derivation was limited to cultures passaged at about day 11 of differentiation suggesting reduced patterning response at very high cell densities as observed for hESC derived R-NSCs (Elkabetz, et al., *Genes Dev* 22 (2), 152 (2008)). These data demonstrate robust patterning response in Noggin/SB431542 treated neural progeny and derivation of relevant neuron subtypes after short differentiation periods (approximately 19 days) compared to 30-50 days when using stromal feeder mediated induction protocols (Lee, et al., *Stem Cells* 25 (8), 1931 (2007); Tomishima, et al., *Stem Cells* 25 (1), 39 (2007)).

As an alternative to the specific Smad inhibitors used here, it is possible to block both distinct Smad pathways using alternative inhibitors or mechanisms. Dorsomorphin is a small molecule alternative to Noggin, targeting the same pathway. Concentrations ranged from 10 uM to 30 nM, each individual amount added to 10 uM of SB431542. The efficiency was not as high as used with Noggin/SB431542 based on the percentage of PAX6+ cells, but combinations of dorsomorphin with SB431542 allowed for a 15 fold reduction in the concentration of Noggin necessary to obtain equivalent efficiency and cell viability. It is possible to utilize other molecules as well, although there is currently no known alternative small molecule to SB431542 that blocks the entire range of targets, but this example demonstrates that total Smad cloaked the two known pathways and can result in robust and synergistic effects that yield a highly homogenous population of neural cells. These alternative methods could also include Smad blockade through mechanism including, but not limited to, interfering DNA (to include antisense, siRNA, shRNA, and standard methods known to the art), or overexpression of a protein that can block, compete or otherwise present Smad 4 function (such as overexpression of Smad 7).

Specific cell fates were tested for their ability to survive, migrate, and function as desired in mammals. Transplantation of neurogenic tissue from hiPSCs that are differentiated using Noggin and SB431542 protocol followed by a dopamine neuron induction protocol can be made into the brains of recipient mice (specifically, Nod/SCID) and assessment of the engraftment potential of the cells is assessed.

Further, it is possible to observe pigmented cells when the cells are further differentiated from the Noggin and SB431542 protocol towards more mature neurons (both motor neurons and dopamine neurons). This data suggests that both melanocytes and retinal-pigmented epithelium are being produced. Additionally, PAX6+ central nervous system progenitor cells and a PAX6-HNK1+ peripheral nervous system progenitor cell were observed. Recent publications have reported the reprogramming of human somatic cells into induced pluripotency stem cells (hiPSCs) (Takahashi, et al., *Cell* 131 (5), 861 (2007); Suter, et al., Stem Cells 27, 49-58 (2008)).

Next it was determined if dual SMAD inhibition could be used to reliably generate a broad repertoire of hiPSC derived neural cell types. Given the expected intrinsic variability among hiPSC clones, reproducible differentiation results would confirm the robustness of the presently disclosed differentiation protocol. For example, two hiPS clones (IPS$^{C14}$, IPS$^{C17}$; FIGS. 9A and 9B) were generated using lentiviral transduction of human fetal lung fibroblasts with cMYC, KLF4, OCT4, and SOX2. Both clones express the pluripotency markers including Nanog, Tra-1-60, and SSEA-3 at the undifferentiated state and are capable of differentiating into derivatives of the three germ layers. Upon neural induction via the noggin/SB431542 protocol, both clones yielded nearly homogenous populations of PAX6+ cells by day 11 of differentiation (FIGS. 9C and 9D). Using the strategies described above manipulating, cell density, passage, and patterning factors both hiPSC clones could be readily biased towards generating HNK1+ putative neural crest progeny (FIGS. 9E and 9F), hiPSC derived R-NSCs (FIGS. 9G and 9H), and specific hiPSC derived neuron subtypes including somatic motor neurons (FIGS. 9I and 9J) and dopamine neurons (FIGS. 9K and 9L). These data demonstrate robustness and modularity of the dual SMAD inhibition strategy beyond hESC differentiation. In one embodiment, the presently disclosed method offers an efficient, defined, and robust platform for the rapid generation of hiPSC derived neural cell types.

Thus a novel method of neural differentiation was discovered by combining at least two signaling inhibitors, i.e. SB431542 and Noggin. While for most of the studies presented herein used a 11-day treatment period, subsequent studies showed that comparable levels of neural induction were achieved when the treatment is shortened to the first 5 days of differentiation (FIG. 10). This reduced time of treatment should further reduce complexity and cost, particularly in the case of recombinant Noggin. In some embodiments, an inhibitor of SMAD signaling is replaced by an inhibitor of a Bone morphogenetic protein (BMP signaling) pathway. Small molecule inhibitors of the BMP pathway are also available that could potentially substitute for noggin function and further reduce costs. Thus, in some embodiments, noggin is replaced by Dorshomophin. In other embodiments, noggin is replaced by LDN-193189, for an exemplary structure see

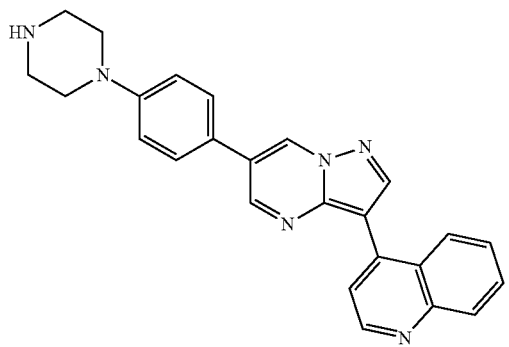 [SMILES: c1ccc2c(-c3cnn4cc(-c5ccc(N6CCNCC6)cc5)cnc34)ccnc2c1]

(another example, 'Stemolecule™ BMP Inhibitor LDN-193189' StemGent, Cambridge, Mass.).

Cranial placodes are transient developmental structures critical for the formation of the lens, nasal epithelium, otic structures, cells of the adenohypophysis, and multiple cranial nerves including the trigeminal ganglion. Little is known about human placode biology due to the inaccessibility of the tissue during development and the lack of validated markers. The art is limited to extrapolating from other species such as *xenopus*, zebrafish, chick, and to lesser extent mouse development.

In one embodiment, the present invention contemplates a derivation of cranial placodes and placode derived sensory neurons from human embryonic stem cells (hESCs). Six1+ hESC derived placode precursors are obtained at high yield (71% of total cells) within 11 days of differentiation using a modified dual SMAD inhibitor protocol. Six1+ cells co-express other putative placode markers such as eyes absent homolog 1 (*Drosophila*) (Eya1), Dachshund homolog 1 (Dach1), eyes absent homolog 4 (*Drosophila*) (Eya4), and SIX homeobox 3 (Six3; sine oculus homeobox homolog 3 (*Drosophila*)) and temporal transcriptome analysis identifies additional placode and sub-placode specific markers. Prospective pan-placode precursor cells were isolated based on the expression of p75 in the absence of HNK1 expression. Specific enhancer GFP constructs enable marking placodal cells with putative specificity to a subset of placodal regions. Human ESC derived placodal cells were highly efficiently converted into pure populations of sensory neurons expressing insulin gene enhancer protein ISL-1 (Isl1), brain-specific homeobox/POU domain protein 3A (Brn3a), β-III-tubulin (Tuj1) and peripherin. The isolation of hESC-derived placodal represents a novel model system to study human placode development and enable the derivation of unlimited numbers of previously inaccessible sensory neuron population for the study of sensory function and pain.

Cranial placodes are transient developmental structures that give rise to the peripheral olfactory system, the lens, the anterior pituitary, otic structures, and sensory ganglia including trigeminal neurons. Defects in placode development are involved in a range of human congenital malformations, including blindness, deafness and loss of the sense of smell (Baker, et al., Dev Biol, 232(1):1-61 (2001); Bailey, et al., Curr Top Dev Biol, 72:167-204 (2001), herein incorporated by reference). Cranial placode development has been well characterized in various model organisms including *Xenopus*, chick and zebrafish (Baker, et al., Dev Biol, 232(1):1-61 (2001); Bailey, et al., Curr Top Dev Biol, 72:167-204 (2006); Bhattacharyya, et al., Curr Opin Genet Dev. 14(5): 520-6 (2004); and Baker, et al., Development, 2000. 127 (14): p. 3045-56, all of which are herein incorporated by reference). Despite the importance of placode biology in development and disease, however, human placode development has remained unexplored. This is largely due to inaccessibility of early human placode tissue and the associated lack of appropriate markers and techniques.

Embryonic stem cells have the unique ability to self-renew in a nearly unlimited fashion while retaining the ability to differentiate into all the various cell types that make up an adult organism. During human development, pluripotent cells of the inner cell mass (ICM) and epiblast from which human ES cells are derived gives rise to the three germ layers and all subsequent derivatives, including placode cells. One question is whether the in vivo differentiation potential of the human ICM were harnessed using human ES cell-based culture systems in vitro.

Over the last few years a number of protocols have been developed for the directed differentiation of human ES cells into various tissue specific cell types, such as midbrain dopamine neurons, Perrier, et al., Proc Natl Acad Sci USA, 101(34):12543-8 (2004), herein incorporated by reference, spinal motoneurons Li, et al., Nat Biotechnol, 23(2): 215-21 (2005), herein incorporated by reference, multipotent mesenchymal precursors, Barberi, et al., PLoS Med, 2(6):e161 (2005); Barberi, et al., Nat Med, 2007. 13(5):642-8, herein incorporated by reference, cardiac cells, Laflamme, et al., Nat Biotechnol, 25(9):1015-24 (2007), herein incorporated by reference, and hepatocyte-like cells Agarwal, et al., Stem Cells, 26(5):1117-27 (2008), herein incorporated by reference. Directed differentiation into cells of peripheral neuron identity has been achieved via a neural crest precursor intermediate. The initial protocols on generating human ES cell-derived neural crest cells, Lee, et al., Nat Biotechnol, 25(12):1468-75 (2007), herein incorporated by reference were based on a MS5 co-culture system promoting neural induction, Perrier, et al., Proc Natl Acad Sci USA, 101(34): 12543-8 (2004); Barberi, et al., Nat Biotechnol, 21(10): 1200-7 (2003), herein incorporated by reference. The MS5 culture system was used successfully for deriving and isolating various neural crest fates from human ES cells and human IPS cells, and for modeling a familial dysautonomia (FD), a rare human genetic disorder affecting neural crest-derived neurons, Lee, et al., Nature, 461(7262):402-6 (Epub 2009 Aug. 19) herein incorporated by reference.

Recently, a defined neural induction strategy that is based on the concomitant inhibition of the BMP and TGFb/Activin/Nodal signaling pathways was reported. Chambers, et al., Nat Biotechnol, 27(3):275-80 (2009), herein incorporated by reference. Exposure to Noggin (N) and SB431542 (SB) leads to a synchronized and rapid differentiation of human ES cells or IPS cells towards neural fates under adherent culture conditions and therefore obviates the need for both co-culture and embryoid body formation during the induction process. The more rapid and synchronized differentiation response using the N-SB protocol enables testing of the precise relationship of specific morphogens in biasing developmental fate in vitro.

In some embodiments, a modified N-SB protocol allow the efficient derivation of highly enriched populations of placodal precursors. Placodal fate is induced at the expense of neuroectodermal cells upon withdrawal of noggin treatment 48 hours after N-SB induction. These data illustrated the use of the N-SB induction system to optimize the generation of non-CNS derivatives, demonstrate the importance of endogenous BMP signaling during hESC differentiation and enable the derivation of unlimited numbers of placode derivates such as cranial sensory neurons for the study of sensory function and pain.

Several observations from the studies described herein are presented as follows for use in some of the methods of the present invention.

A. BMP Dependent Specification of Placodal Fates During HESC Differentiation

BMPs exert wide-ranging effects on early embryonic fate specification in vivo and are involved in the specification of various extra-embryonic structures, determination of definitive mesodermal cells, specification of non-neural ectoderm, placode and neural crest tissues. The use of the N-SB culture system enables a highly synchronized and efficient differentiation of human ES cells. The data herein studies the N-SB system reveals both BMP dose and timing of application can modulate the specification of placodal fates. Important questions remain as to whether the system was used similarly to optimize differentiation towards non-neural ectoderm fates and the generation of primitive skin precursor cells. Data indicated that a subset of Six1 negative cells under the modified N-SB culture conditions express p63, a known marker of early epidermal precursors during development.

Figure 12A:
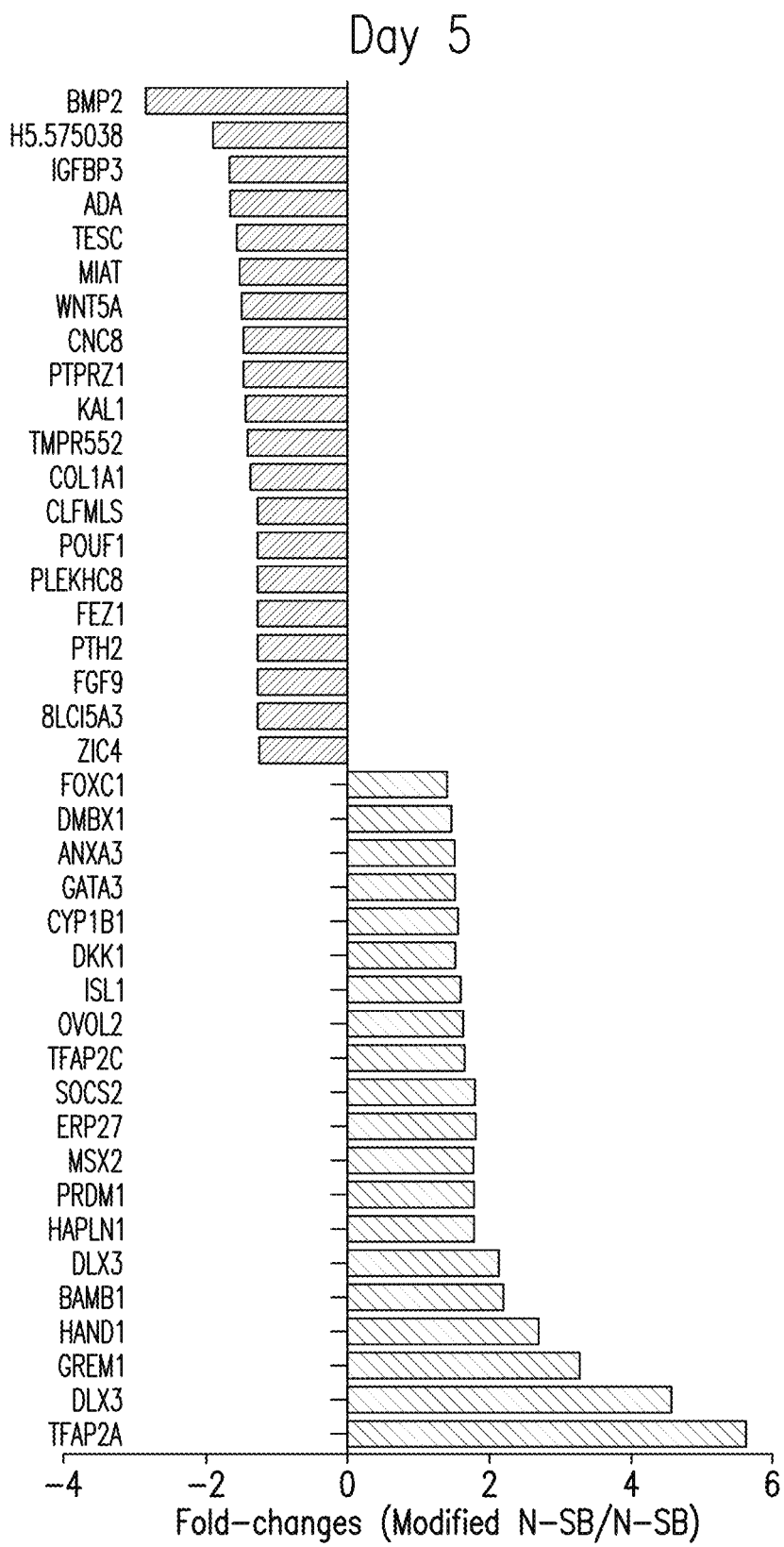
Figure 12B:
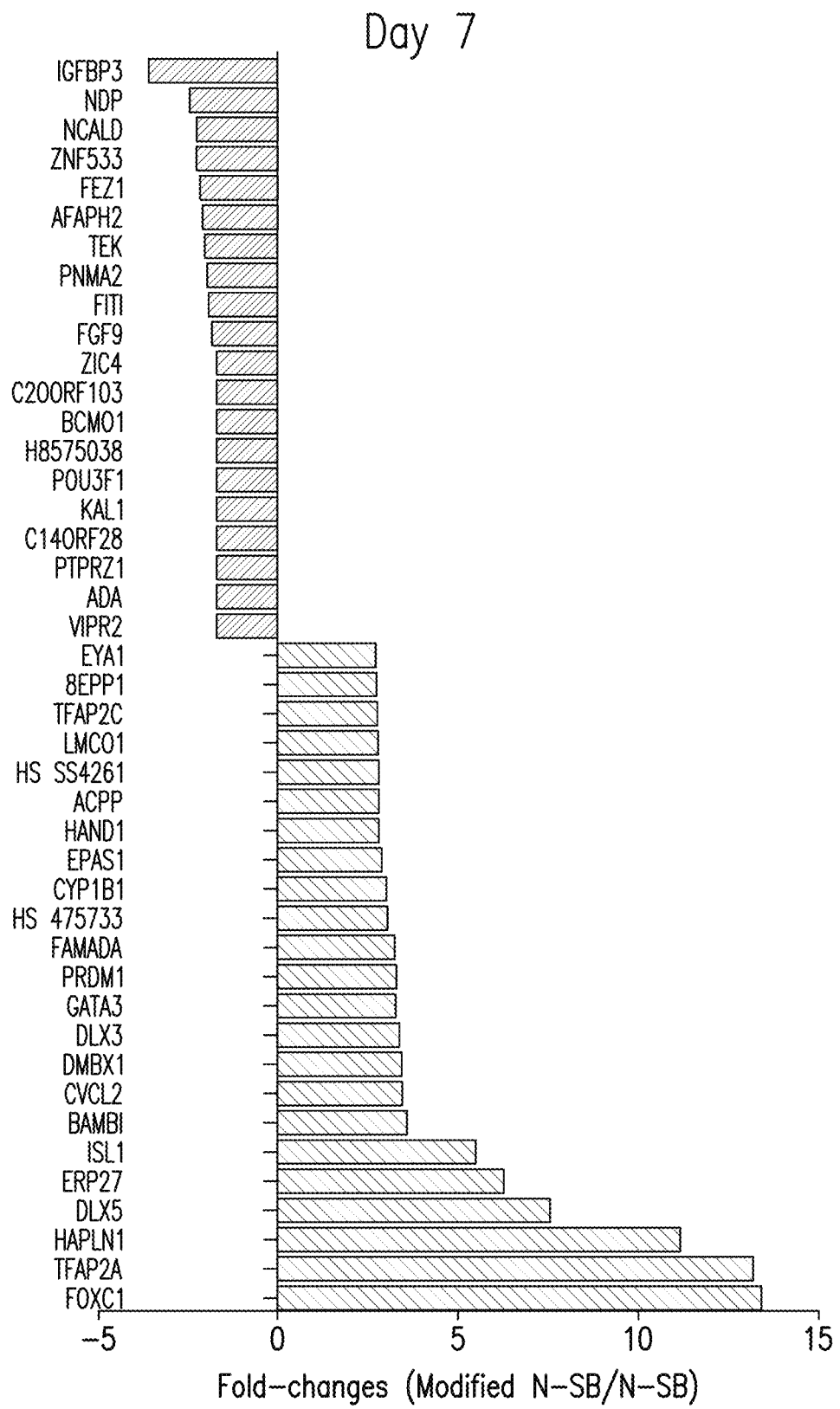
Figure 12C:
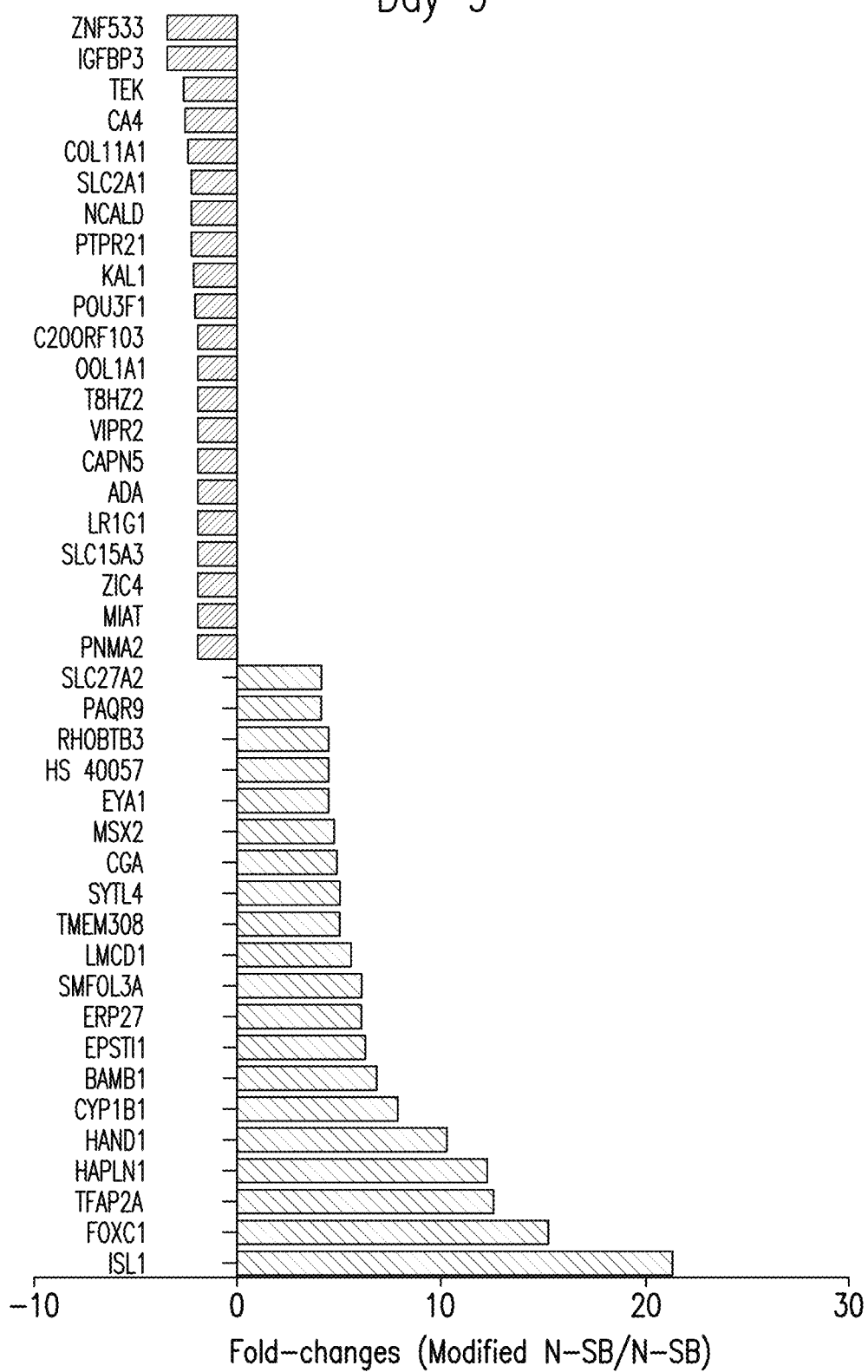
Figure 12D:
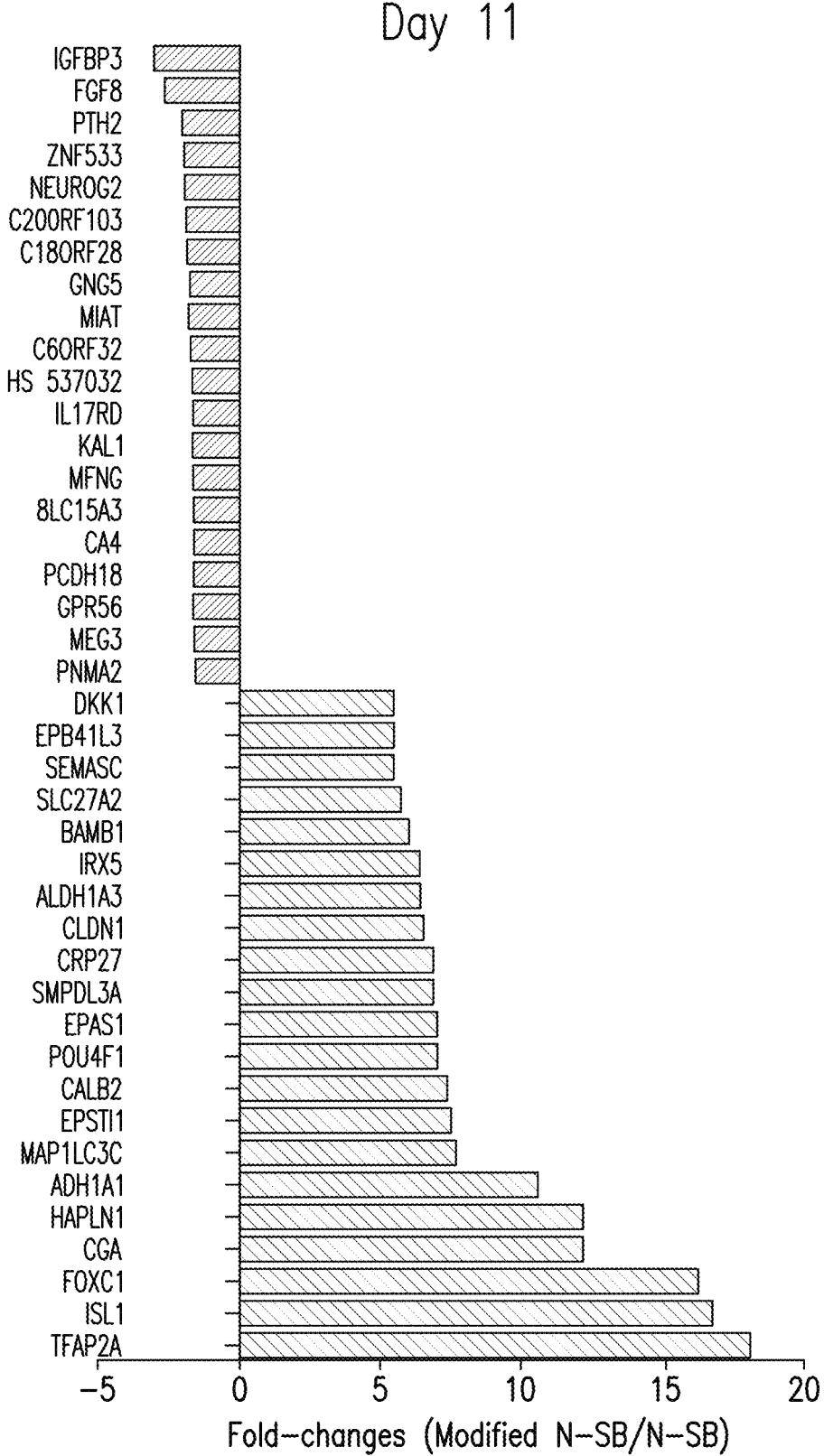
Figure 12E:
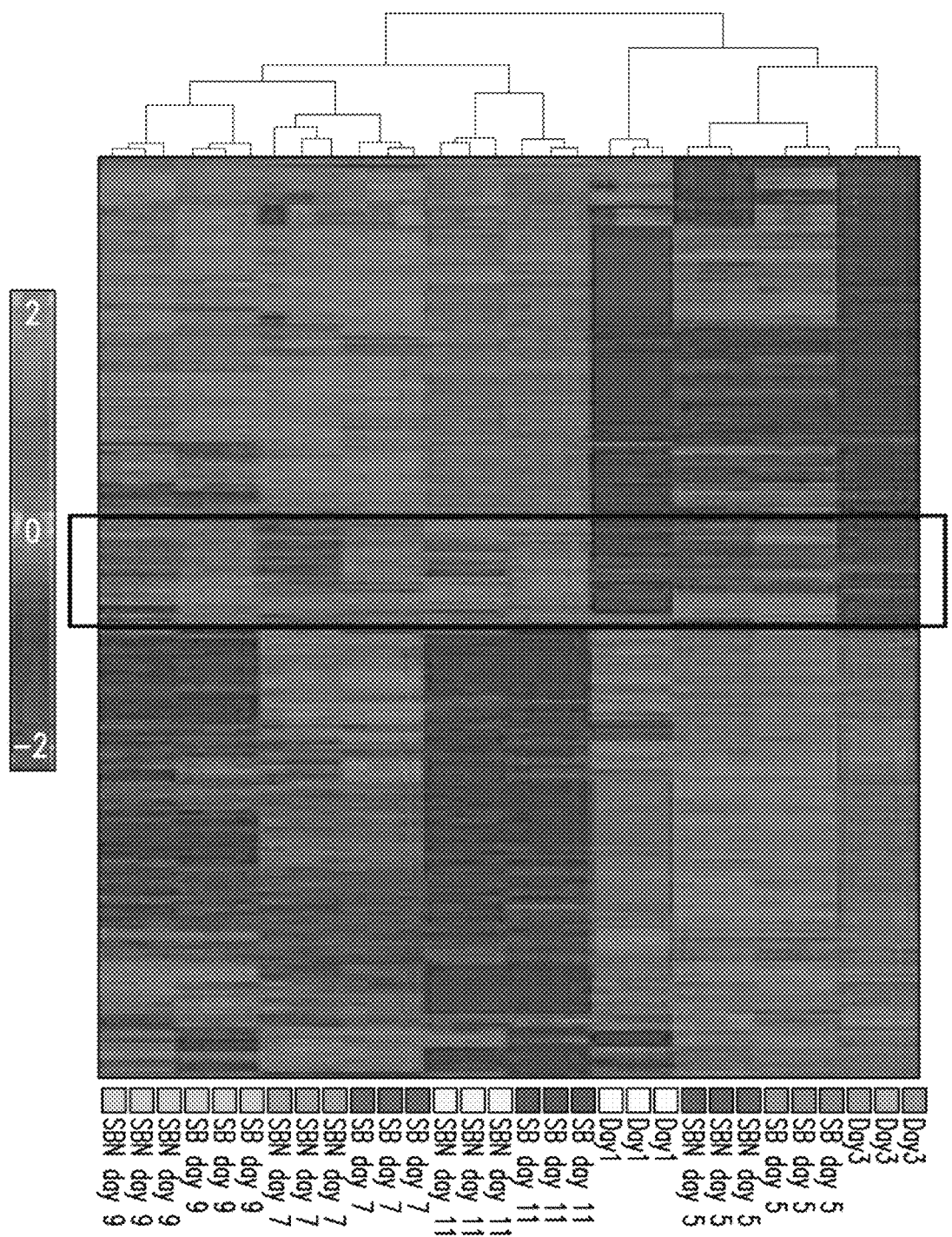

B. The Emergence of Putative Pan-Placodal Fates During Human Embryonic Stem (ES) Cell Differentiation Highly efficient differentiation towards Six1+ fates and the rapid emergence of insulin gene enhancer protein ISL-1, also known as ISL LIM homeobox 1, (Isl1)+ cells during human ES cell differentiation suggest that hESC derived cells may initially adopt a pre-placodal precursor fate. The emergence of a pre-placodal region has been described during *xenopus* and zebrafish development marking a horseshoe shaped area in the most anterior region of the embryo surrounding the anterior neuroectodermal cells. The data presented herein reports on the generation of sensory neuron precursors from the Six1+ placodal regions. However, future studies may address the plasticity of these placodal cells upon exposure to alternative differentiation regimens. Of particular interest may be the derivation of adenohypophyseal cells to study specification of various hormone producing cell types. Such cells are of interest for developmental studies and for studies aimed at defining pharmacological control of hormone release. Approximately, 15% of the cells at the Six1+ stage express Lhx3, a marker of adenohypophyseal precursor cells. Expression of CGA, the precursor protein in the production of adenohypophyseal hormones, was observed during human ES cell differentiation in the modified N-SB protocol at day 11 of differentiation (FIG. 12D). The presence of Lhx3+ putative adenohypophyseal precursor cells and the expression of CGA showed that cells of adenohypophyseal lineage were readily induced using the modified N-SB protocol.

C. Sensory Neuron Specification from Six1+ Placodal Precursors

The presently disclosed findings indicate a placodal origin of the sensory neuron populations generated in the modified N-SB protocol. This is based on the expression of Six1 in the precursor clusters isolated for subsequent sensory neuron generation and the co-expression of Six-1 in early stage sensory neurons. Placode derived sensory neurons share various markers with sensory neurons derived from neural crest lineages such as Brn3A, Isl1 and Peripherin. However, the modified N-SB protocol shows highly efficient induction of FoxG1B and other anterior markers expressed in placodal precursor and not expressed in early neural crest lineages. Initial cell density (Chambers et al., Nature Biotechnology 27(3) 275-280, 2009, Corrigendum: in Nature Biotechnology 27(4):1) and modulation of Wnt signaling (reference) may enable specification of placodal versus neural crest derived sensory neuron populations. Access to highly purified populations of cranial sensory neurons represent a novel tool for the future development high throughput drug discovery assays. For example, compounds modulating placode derived trigeminal neurons may be of particular interest given the well known clinical syndromes associated with trigeminal nerve dysfunction.

D. Specification of Functional Floor Plate Tissue from Human Embryonic Stem Cells Occurs at the Expense of Anterior Neurectoderm The floor plate (FP) is a critical signaling center during neural development located along the ventral midline of the embryo. Little is known about FP development in humans, due the lack of tissue accessibility. This disclosure describes the derivation of human embryonic stem cells (hESC-) and subsequently derived FP tissue capable of secreting Netrin-1 and SHH and influencing patterning of primary and hESC derived tissues. Induction of FP in hESCs is dependent on early SHH exposure and occurs at the expense of anterior neurectoderm (AN). Global gene expression and functional studies identify SHH-mediated inhibition of DKK-1 as key factor in AN repression. hESC derived FP tissue is shown to be of anterior SIX6+ character but responsive to caudalizing factors suppressing SIX6 expression and inducing a shift in expression of region-specific SHH enhancers. These data established hESC derived FP as an experimental model system and define early signaling events that modulate FP versus AN specification.

Neural development is dictated in time and space by a complex set of signals that instruct neural precursor identity. While significant progress has been made in animal models, human neural development remains much less understood. Human embryonic stem cells (hESCs) offer an accessible and manipulatable cell platform to model the early stages of human development.

Previous studies have reported the directed differentiation of mouse (Wichterle et al., 2002; Barberi et al., 2003; Watanabe et al., 2005) and human (Perrier et al., 2004; Li et al., 2008; Eiraku et al., 2008) ESCs into specific neuron types in response to patterning factors defining anterior/posterior (A/P) and dorso-/ventral (D/V) CNS identity. These studies demonstrate evolutionary conservation of signaling systems that specify the major CNS regions. In mammals, sonic hedgehog (SHH) is a ventralizing factor acting in a dose-dependent manner to specify the various ventral cell types including cells expressing floor plate (FP) in primary neural explants (Briscoe and Ericson, 1999) and in mouse ES cells (Mizuseki et al., 2003). While application of SHH to hESC-derived neural cells has been shown to induce various ventral neuron types, the derivation of floor plate (FP) tissue itself has not yet been reported. As FP is one signaling center, the ability to produce FP from human ES cells will be a step forward in furthering an understanding of early human neural development.

The FP runs along the most medial aspect of the ventral neural tube extending most caudally from the spinal cord, through the midbrain, up to the diencephalon with its anterior limit being just below the zona limitans intrathalamica (Jessell et al., 1989). At the most anterior aspect the FP stops where the anterior neurectoderm (AN) begins studies have shown that AN commitment renders cells incapable of responding to FP inductive signals (Placzek et al., 2003). Classic studies have shown FP cells to exhibit a unique, flat morphology, and to express FP specific markers including SHH, FOXA2, F-Spondin, and Netrin-1 (Placzek, 1995). Studies in mouse and chick embryos have identified two major organizer functions for the FP: the secretion of the morphogen SHH patterning the ventral neural tube (Placzek and Briscoe, 2005), and the expression of Netrin-1 guiding commissural axons across the midline (Charron et al., 2003). The FP is generally considered a non-neurogenic region. However, genetic lineage mapping studies in the mouse have recently reported that the midbrain FP selectively exhibits neurogenic potential and is the source of ventral midbrain dopamine neurons (Kittappa et al, 2007; Ono et al., 2007; Joksimovic et al., 2009).

To date, little is known about FP development in humans, due to lack of accessibility to tissue. In animals, the FP is a major site of SHH production and several human developmental disorders are related to alterations in midline SHH signaling (Mullor et al., 2002) including certain forms of holoprosencephaly and microphthalmia, skeletal disorders including various cleft plate syndromes, and tumor conditions such as Gorlin's syndrome; a rare genetic disorder caused by a mutation in the SHH receptor Patched 1. Thus, understanding how human FP is generated will assist comparative developmental studies of human neural patterning and axonal pathfinding and the resulting cells could potentially serve as a source of specific neuron types that have a FP origin.

The data provided herein demonstrate exemplary directed differentiation of hESCs into FP tissue, as the first example of generating a human developmental organizer structure in vitro. For example, human FP specification may be dependent on early high-dose SHH signaling that represses DKK1-mediated specification of AN. Functionality of the FP is demonstrated by secretion of Netrin-1 and SHH and the ability to induce ectopic FP tissue and neurite outgrowth in primary mouse and rat explants.

Human ESC-derived FP adopts anterior identity by default but were specified to posterior fates in response to caudalizing cues providing access to region-specific FP tissue. The experimental system presented here, and in combination with compositions and methods described for highly efficient neural conversion of human ES and iPS cells by dual inhibition of SMAD signaling, Nat. Biotechnol. 26, 275-280 (2009); published online 1 Mar. 2009; corrected after print 16 Mar. 2009, Corrigendum: Chambers, et al., should facilitate studies on FP-mediated signaling events critical during early human neural development.

IV. Stem Cell Lines

The present invention is not limited to the use of any particular type of human stem cells. Indeed, the use of a variety of types of human stem cells is contemplated. Methods for obtaining totipotent or pluripotent cells from humans, monkeys, mice, rats, pigs, cattle and sheep have been previously described. See, e.g., U.S. Pat. Nos. 5,453,357; 5,523,226; 5,589,376; 5,340,740; and 5,166,065 (all of which are specifically incorporated herein by reference); as well as, Evans, et al., Theriogenology 33(1):125-128, 1990; Evans, et al., Theriogenology 33(1):125-128, 1990; Notarianni, et al., J. Reprod. Fertil. 41(Suppl.):51-56, 1990; Giles, et al., Mol. Reprod. Dev. 36:130-138, 1993; Graves, et al., Mol. Reprod. Dev. 36:424-433, 1993; Sukoyan, et al., Mol. Reprod. Dev. 33:418-431, 1992; Sukoyan, et al., Mol. Reprod. Dev. 36:148-158, 1993; Iannaccone, et al., Dev. Biol. 163:288-292, 1994; Evans & Kaufman, Nature 292: 154-156, 1981; Martin, Proc Natl Acad Sci USA 78:7634-7638, 1981; Doetschmanet al. Dev Biol 127:224-227, 1988); Gileset al. Mol Reprod Dev 36:130-138, 1993; Graves & Moreadith, Mol Reprod Dev 36:424-433, 1993 and Bradley, et al., Nature 309:255-256, 1984.

In some embodiments, undifferentiated human embryonic cells lines are contemplated for use, for examples, cell line WA09, and the like.

V. Dual SMAD Differentiation

One finding of the studies described herein, is the "default" nature and anterior bias of the embryonic cell derived FP tissue. The lack of any obvious mesodermal intermediates in both NSB (Chambers et al., 2009; FIG. 18) and the FP (FIG. 18) induction protocol presented here, suggests that the in vitro derivation of neuroectoderm and FP tissue is not dependent on any additional mesoderm derived signals. FP induction occurs readily even in the presence of SB431542, an inhibitor of TGFb/Activin/Nodal signaling in contrast to data in zebrafish where nodal is thought to be essential for FP induction (reviewed Placzek and Briscoe, 2005). The anterior default of the FP tissue reported here is reminiscent of the anterior default observed in hESC derived neuroectodermal cells. Studies in chick development have proposed two distinct origins of anterior versus posterior FP namely progenitors in the epiblast and axial mesoderm (Placzek et al., 2003). This data indicated that human FP precursor cells, similar to neuroectodermal cells, are capable of being respecified towards posterior FP identity in response to caudalizing factors including FGF8 and Wnt-1.

To date, it has not been clearly shown whether expression of AN markers inhibits the ability of cells to yield certain lineages. In hESC derived neural rosette cells, expression of BF1 does not preclude patterning towards posterior CNS fates including HB9+ somatic motoneurons.

However, the efficiency of generating caudal neuron fates is significantly reduced as compared to BF1-negative rosettes (Elkabetz, et al., 2008). Previous studies in primary mouse explants showed that AN cells are not competent to differentiate into FP cells in response to SHH alone (Placzek, et al., 1993). The methods and results described herein during the development of the present inventions showed an AN commitment that was not capable of FP specification.

Figure 19I:
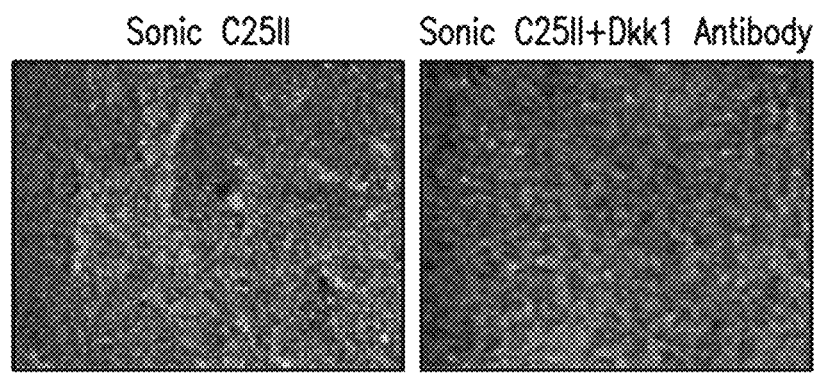
Figure 19J:
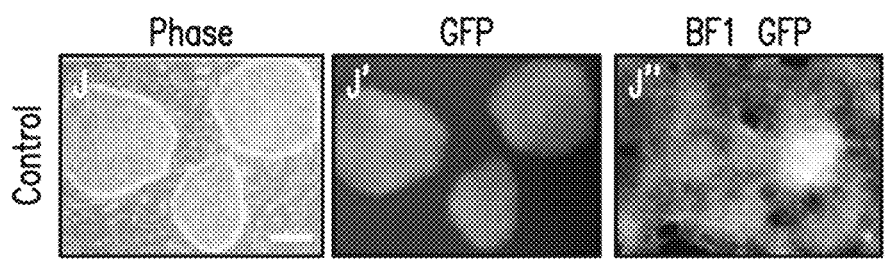
Figure 19K:
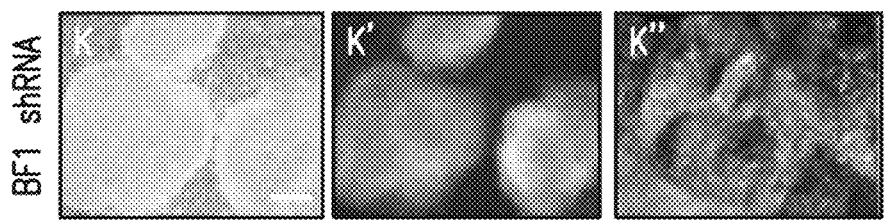

An additional key finding described herein is a dramatic (strong) induction of DKK-1 during NSB-mediated neural differentiation. During neural differentiation of mouse ESCs exposed to extrinsic DKK-1 enhanced AN induction under serum-free embryoid body (SFEB) conditions (Watanabe et al., 2005). Thus, some embodiments of the present invention contemplate that early induction of endogenous DKK-1 during neural differentiation is least in part responsible for the AN default phenotype observed in hESCs. Functional studies demonstrated herein that inhibition of DKK-1 using blocking antibodies significantly improved FP yield. Further, addition of DKK-1 antibodies along with SHH at day 5 or later time-points was not sufficient to extend the temporal window of FP competency (FIGS. 19H and 19I). Similarly, the addition of WNTs (Wnt-1, Wnt3A or GSK inhibitor (BIO)) to neural rosette stage cells was not sufficient to induced FP competency (FIG. 25). These data demonstrated that very early DKK1 mediated AN bias suppresses FP potential of hESC derived precursors.

Additional data in BF1 knockdown hESC lines showed enhanced FP yield with improved yield of posterior CNS cell types such as HB9+ motoneurons. Thus a model system presented herein is contemplated to be suitable to assess the contribution of other molecules with WNT inhibitory function such as Cerberus (Bouwmeester, et al., 1996) to AN specification and repression of FP fate. Finally, the system and methods described herein are contemplated to allow the identification of potential upstream regulators of DKK-1 expression regulating AN default in hESCs.

Suppression of DKK-1 and subsequently AN fates via early exposure to high levels of extrinsic SHH results was a surprising result, as SHH is a classic ventralizing factor and not known to exert effects on AP specification during neural development. Our studies did not address whether regulation of DKK-1 by SHH is direct or caused by inducing an alternative precursor population devoid of DKK-1 expression. While DKK-1 inhibited FP induction, exposure to WNT1 enhanced the derivation of FP tissue from hESCs. These data raised the question whether RA that induce a similar increase in FP yield would affect WNT signaling or whether induction of posterior fates enhances FP yield independently of Wnt signaling.

The availability of an unlimited number of FP cells of defined regional identity provides a valuable tool for studying human neural development. Recent studies in the mouse suggest that some regions of the FP, beyond roles in neural patterning and axonal path finding, may serve as a source of specific neuron types including midbrain dopamine neurons. Re-specification of regional identity of hESC derived FP was demonstrated towards midbrain character based on the expression of midbrain specific markers and the activation of midbrain specific SHH enhancer elements. Evidence was found that hESC derived FP tissue is capable of yielding TH+/FOXA2+ putative midbrain DA neurons (FIG. 25). The results shown herein provided insights into the induction and regional specification of human FP versus AN fates and established hESCs as a powerful model system to create a functional organizer tissue suitable for modeling more complex interactions during human development.

In conclusion, exemplary data shown herein showed that neural differentiation hESCs default towards an AN fate by upregulating DKK-1 and subsequently BF1, while AN commitment actively repressed FP competency in hESC progeny. However, an early high level of SHH reduced DKK-1 levels enabling FP induction at the expense of AN while loss-of-function of DKK-1 or BF1 increased FP production. Thus human ESC derived FP is anterior by default but was posteriorized in response to caudalizing factors. This is summarized in FIG. 20E.

Thus, numerous embodiments of the present inventions are summarized in the following Tables.

TABLE A

Exemplary ranges of amounts of compounds for obtaining neural cells of the present inventions.

| | Noggin Concentration | Dorsomorphin Concentration | SB431542 Concentration | Sonic C25H (SHH) Concentration |
|---|---|---|---|---|
| Noggin with SB431542 | 125-500 ng/ml | NA | 0.001 to 1000 microM | NA |
| Noggin with SB431542 and SHH | 500 ng/ml | NA | 0.001 to 1000 microM | 200-2000 ng/ml |
| Dorsomorphin with SB431542 | NA | 100-5000 nM, best results 600 nM | 0.001 to 1000 microM | NA |
| Noggin with Dorsomorphin with SB431542 | 25-500 ng/ml, high efficiency to 30 ng/ml | 100-5000 nM, best results 600 nM | 0.001 t0 1000 microM | NA |

TABLE B

Exemplary time of addition of compounds of the present inventions for producing neural cell types of the present inventions.

| Start Cell Type and conditions | Stem cells including iPS and hESC. Low density of cells: KSR medium or conditioned medium | Stem cells including iPS and hESC. High density of cells: KSR medium or conditioned medium | Stem cells including iPS and hESC. Low or high density of cells: KSR medium or conditioned medium | Modified N-SB treated hESC or iPS: KSR medium or conditioned medium | N-SB treated hESC or iPS in non-adherent embryoid bodies |
|---|---|---|---|---|---|
| N-SB: Noggin and/or Dorsomornhin with SB431542 | Add both day 0 of culture of culture and continue adding fresh aliquots when feeding cells | Add both day 0 of culture and continue adding fresh aliquots when feeding cells | Add both day 0 of culture and continue adding fresh aliquots when feeding cells | NA | Add both day 0 of culture and continue adding fresh aliquots when feeding cells; SB withdraw at or around Day 7 |

TABLE B-continued

Exemplary time of addition of compounds of the present inventions for producing neural cell types of the present inventions.

| | | | | | |
|---|---|---|---|---|---|
| Modified N-SB Noggin/ Dorsomorphin withdrawal 2 days (1-3) after N-SB induction | NA | NA | NA | Add both day 0 of culture and replace with cell media without Noggin and/or Dorsomornhin day 1 (ranging from 6 hours to 4 days after day 0) | NA |
| SHH or C25I1 | NA | NA | Add day 1 after N-SB additions (ranging 0-5 days) Gradually replacing KSR media with N2 media between Day 5 and 11. | NA | NA |
| Resulting cells | CNS progenitor cells (PAX6+) and PNS progenitor cells (p75+, HNK-1+) | CNS progenitor cells (PAX6+) (R-NS cells and patternable neuronal populations of motoneurons and dopaminergic neurons within 19 d of initiating differentiation) | FOXA2+ (BF1 reduced) SOX17- neural cells i.e. FP differentiation with FP anterior cells as a default type but posterior FP tissue can be induced in the presence of caudalizing factors such as Wnt-1, FGFF8 or RA. | Six1+ placodal precursors leading to Brn3a+ progenitor cells, leading to immature neuronal cells, Tuj1+, peripherin+ and mature neurons. | High efficiency motor neuron cells |

VI. Speciation of Cranial Placode Cells

In one embodiment, the present invention contemplates a method comprising the specification of trigeminal, lens and anterior pituitary placode lineages. In one embodiment, the method further comprises specification of precursor placode cells using a modified PIP condition. Although it is not necessary to understand the mechanism of an invention, it is believed that other placode fates are also accessible as well using modified PIP conditions. For example, exposure of pre-placode cells to FGF8 enriches for ASCL1 expression compatible with olfactory placode fate (Balmer and LaMantia, 2005). Exposure to caudalizing cues such as WNT3A leads to the induction of a population of cells coexpressing SIX1 and SOX10 compatible of otic placode fates. Those conditions, while requiring further optimization, support the notion that PIP represents a universal platform for cranial placode fate specification.

Cranial placodes are embryonic structures essential for sensory and endocrine organ development. Human placode development has remained largely inaccessible despite the serious medical conditions caused by the dysfunction of placode-derived tissues. In some embodiments, the efficient derivation of cranial placodes from human pluripotent stem cells is disclosed. For example, a timed removal of the BMP inhibitor Noggin, a component of the dual-SMAD inhibition strategy of neural induction, triggers placode induction at the expense of other CNS fates. Alternatively, a concomitant inhibition of FGF signaling may disrupt placode derivation and induces surface ectoderm. Further fate specification at the pre-placode stage enables the selective generation of cranial placode cells including, but not limited to, placode-derived trigeminal ganglia capable of in vivo engraftment, mature lens fibers and anterior pituitary hormone-producing cells that upon transplantation produce human GH and ACTH in vivo. The data disclosed herein establish a powerful experimental platform to study human cranial placode development and set the stage for the development of human cell-based therapies in sensory and endocrine disease.

An understanding of human cranial placode development has been challenging due to the lack of a tractable experimental system, the inaccessibility of this transient structure during early human development and the absence of validated human placode markers. The presently disclosed data resolve those major challenges and establish a versatile platform for the study of human placode and ectoderm development (FIG. 40). While previous studies have observed the emergence of certain placode derivatives such as lens (Ooto et al., 2003; Zhang et al., 2010) or otic placode derived cells (Chen et al., 2012; Oshima et al., 2010), the mechanisms of specific placode induction were not addressed, and no general model of placode specification were suggested in those studies.

Very recent studies have reported an ability to direct pluripotent stem cells towards placode fates (Leung et al., 2013; Mengarelli and Barberi, 2013; Shi et al., 2007). However, no functional human placode derivatives have been generated under those conditions. In contrast, studies in mouse ESCs have successfully derived functional otic (Koehler et al., 2013) and pituitary (Suga et al., 2011) placode derivatives.

A developmental question of particular interest is the origin of placode cells. The prevalent hypothesis in the art is that placode tissue originates from non-neural ectoderm upon response to inductive signals from the adjacent neural tissue (Schlosser, 2006). The presently disclosed data indicate that human placode development similarly originates from non-neural ectoderm based on the result that TFAP2A expression precedes the induction of SIX1 while TFAP2A is suppressed during N-SB induction. BMP-based induction of TFAP2A and GATA3 may be useful in establishing non-neural ectoderm lineage competent for placode induction (Kwon et al., 2010).

The ability to block placode induction at the expense of non-neural ectoderm by inhibition of FGF signaling further supports a non-neural ectoderm origin and suggests that endogenous FGF signals may be the neural signal responsible for the placode default in PIP. In one embodiment, a method delineates a time point of developmental commitment to placodal fate by day 7, given that treatment of cells at day 7 of differentiation (pre-placode) induced a switch between various placode fates but did not affect the ratio of cells of placode versus non-neural ectoderm fate.

Previous work described FOXG1 and DACH1 as markers of anterior neuroectoderm and neural rosette stage cells during hPSC differentiation (Chambers et al., 2009; Elkabetz et al., 2008). The data presented herein demonstrates that a small percentage of SIX1+ cells emerge spontaneously under NSB conditions. Therefore, differentiation studies aimed at generating CNS lineages should address whether contaminating placodal tissues are present in hPSC derived neural cultures.

Although it is not necessary to understand the mechanism of an invention, it is believed that those spontaneously emerging placodal cells are likely the source of lentoid bodies and other placode derivatives observed in past neural differentiation studies. The gene expression data presented herein define a broad set of placode markers. For example, OVOL2 has been previously reported to be expressed in the mouse epiblast and surface ectoderm, and loss of OVOL2 leads to early embryonic lethality (Mackay et al., 2006).

In one embodiment, the present invention contemplates that OVOL2 as a human pre-placode marker. In other embodiment, FOXC1 and ISL1 are additional transcription factors specifically expressed at the pre-placode stage. The presently disclosed data provide a framework for defining transcriptional networks that distinguish cranial placode identity from early CNS, neural crest and surface ectoderm identity.

In one embodiment, the present invention contemplates a method comprising a transient pre-placode population competent to adopt various specific placode identities. The emergence of a pre-placodal region has been described during *Xenopus* and zebrafish development (Bailey et al., 2006; Martin and Groves, 2006; Schlosser, 2006). The data described herein show that PIP initially yields a PAX6+/SIX1+ anterior pre-placode population that spontaneously adopts a more posterior, PAX3+ ophthalmic trigeminal fate upon further differentiation, likely due to the caudalizing effects of endogenous FGF and WNT signals.

In other embodiment, exposure to SHH or suppression of FGF signaling at day 7 of differentiation directs the putative pre-placode precursors into anterior pituitary and lens placodes fates. Lens placode has been suggested as the default state during chick placode development with FGF8 being necessary and sufficient to specify olfactory placode fate (Bailey et al., 2006). Other studies in mouse ESCs (Koehler et al., 2013; Suga et al., 2011) have shown the feasibility of generating hormone-producing pituitary cells and otic sensory neurons respectively using sophisticated 3D culture systems.

The presently disclosed data demonstrate that modified PIP conditions yield human pituitary precursors efficiently without the need for complex 3D culture conditions. While a bias was observed in generating preferentially TBX19-related pituitary lineages including ACTH producing cells, all three major precursor lineages (GATA-2, TBX19, and PIT1 lineages, FIG. 38A) could be derived. Therefore it is likely that further optimization of the protocol will provide selective access to individual pituitary hormone lineages.

In one embodiment, the present invention contemplates a method comprising engrafting cranial placode cells in vivo. In one embodiment, the cranial placode cells comprise anterior pituitary cells. In one embodiment, the engraftment is on a leg muscle. In one embodiment, the engraftment is on the hypothalamic-pituitary axis. In one embodiment, the engraftment is on the hypothalamus. In one embodiment, the engraftment is on the sella. In one embodiment, the engrafted pituitary placode cells produce and secrete pituitary hormones.

In one embodiment, the present invention contemplated a method comprising a PIP-based differentiation capable of deriving trigeminal sensory neurons. It has been reported that trigeminal neurons are involved in several pain syndromes such as trigeminal nerve palsy, trigeminal neuralgia and migraine pain (Love and Coakham, 2001). Therefore, an ability to generate large numbers of trigeminal neurons will be particularly useful for modeling human nociception and for the development of cell-based drug screens in pain research. Another important application will be modeling Herpes simplex encephalitis using human iPSCs (Lafaille et al., 2012). HSV-1 is a virus that specifically persists in a latent form within the trigeminal ganglia (Barnett et al., 1994).

The ability to derive trigeminal neurons from patient-specific iPSCs should address whether defects in the control of viral latency contributes to Herpes simplex encephalitis. The robust in vivo survival of trigeminal placode precursors raises the possibility for developing future regenerative approaches with the goal of nerve repair following mechanical, radiation or chemotherapy-induced damage.

Although it is not necessary to understand the mechanism of an invention it is believed that a potential large impact on regenerative medicine may come from deriving functional hormone producing cells. For example, hypopituitarism is a common consequence of congenital defects, head injury or therapeutic intervention in patients with pituitary tumors or patients receiving radiation therapy (Tabar, 2011). While replacement hormones can be given to normalize resting serum levels in patients, the financial, logistic and medical costs for such life-long treatments are considerable. Furthermore, hormone replacement therapy does not allow for dynamic release in response to circadian rhythms, or rapid adjustments to physiological changes in the environment or stressful challenges. Therefore, an ability to generate large numbers of functional ACTH and GH producing cells launches the possibility of long-term therapeutic cell replacement strategies in pediatric and adult patients for restoring endocrine function.

A. Cranial Placode Development

Cranial placodes are believed to give rise to cells of the sensory organs, including, but not limited to, the optic lens, the nasal epithelium, otic structures, the adenohypophysis, and a subset of cranial nerves such as the trigeminal ganglia. During development, sensory placodes are formed at the interface of the non-neural ectoderm and neural plate, surrounding the anterior portion of the future central nervous system (CNS) (FIG. 27A).

Defects in placode development may cause a wide spectrum of human congenital malformations ranging from blindness and deafness to hormone imbalance or loss of smell (Abdelhak et al., 1997; Baker and Bronner-Fraser, 2001; Ruf et al., 2004). To date, cranial placode development has been characterized in model organisms, including the frog, zebrafish, chicken and to a lesser extent, the mouse (Baker and Bronner-Fraser, 2001; Bhattacharyya and Bronner-Fraser, 2004; Schlosser, 2006). However, human placode development has remained largely unexplored due to lack of access to early human tissue and specific placode markers. Human pluripotent stem cells (hPSCs), including human embryonic (hESCs) and human induced pluripotent stem cells (hiPSCs) have the potential to self-renew, while retaining a very broad differentiation potential. Over the last few years, protocols have been developed for directing the fate of hESCs into specific cell lineages. For example, the derivation of CNS cells was among the first hESC differentiation protocols developed in the field (Reubinoff et al., 2001; Zhang et al., 2001). The differentiation of hESCs into cells of the peripheral nervous system has also been achieved (Lee et al., 2007; Menendez et al., 2011).

In contrast to the successful derivation and application of defined CNS and NC derived cell types, there has been limited success on modeling cranial placode development in hPSCs. Recently, a neural induction strategy based on the concomitant inhibition of the Bone Morphogenetic Protein (BMP) and TGFβ/Activin/Nodal signaling pathways (dual-SMAD inhibition (dSMADi)) was reported (Chambers et al., 2009)). This strategy exposes hPSCs to Noggin (N) and SB431542 (SB) that leads to a synchronized, rapid and efficient differentiation of hPSCs into a variety of CNS cell fates.

In one embodiment, the present invention contemplates a method comprising a de-repression of endogenous BMP signaling during dSMADi induced differentiation that is sufficient for the selective induction of human cranial placodes. In one embodiment, a novel placode induction protocol (PIP) induces >70% of all cells to adopt a SIX1+ cranial placode precursor fate by day 11 of differentiation.

In one embodiment, the present invention contemplates a method to identify a pre-placodal lineage competent to differentiate into selective placode fates including, but not limited to, trigeminal sensory neurons, mature lens fibers and/or hormone-producing anterior pituitary cells. In one embodiment, trigeminal sensory neurons are characterized by techniques including, but not limited to, marker expression, electrophysiology and transplantation into the developing chick embryo and/or the adult mouse CNS. In other embodiments, the method is capable of deriving human pituitary cells producing growth hormone (GH) and/or adrenocorticotropic hormone (ACTH) either in vitro and/or in vivo.

B. De-Repression of Endogenous BMP Signaling Induces Placode at the Expense of Neuroectoderm To address whether the previously reported dSMADi protocol (supra) is suitable for derivation of placodal cells, a set of appropriate placode markers was defined. Based on studies in model organisms, members of the SIX, EYA, and DLX family of transcription factors have been reported to mark human placode fate (Baker and Bronner-Fraser, 2001; Schlosser, 2006). Within the ectodermal lineage, SIX1 is placode-specific, marking both the early pre-placodal region and the various specific placodes (Schlosser, 2006). Based on studies in the chick embryo, placode induction relies on a complex interplay of FGF, BMP and WNT signals during early ectodermal patterning in vivo (Litsiou et al., 2005). Activity of BMPs within the ectoderm is also thought to be particularly useful in allocating fates. For example, a model has been proposed initially whereby high levels of signaling promote an epidermal fate, moderate levels induce placodes, intermediate levels specify NC and a complete absence of BMP activity is required for neural plate formation (Wilson et al., 1997). More recent studies have revised the above model by confirming an early role for BMP signaling in establishing placode competence (Kwon et al., 2010) while the subsequent stage was shown to require BMP-inhibition rather than BMP activation (Ahrens and Schlosser, 2005; Kwon et al., 2010; Litsiou et al., 2005).

To test whether early BMP exposure promotes the derivation of SIX1+ placodal cells, SB (the TGFβ inhibitor) treated hESCs were exposed to various concentrations of BMP4. However, addition of BMP4 in the presence of SB caused a dramatic morphological change and triggered induction of CDX2 (FIGS. 27B, 27C), similar to the BMP-mediated induction of trophectoderm-like lineages reported previously (Xu et al., 2002).

Figure 28A:
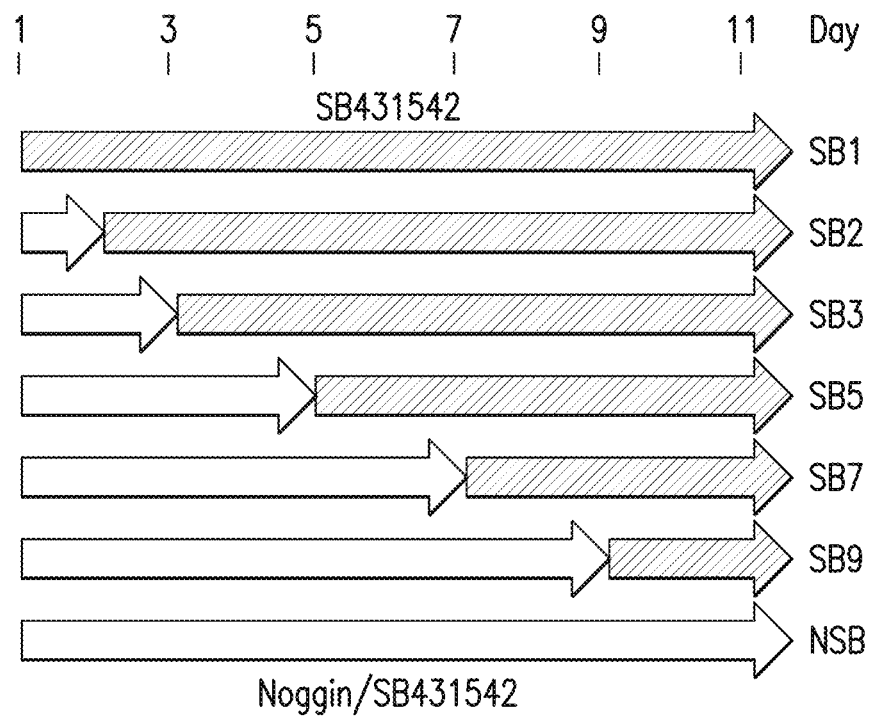
Figure 28B:
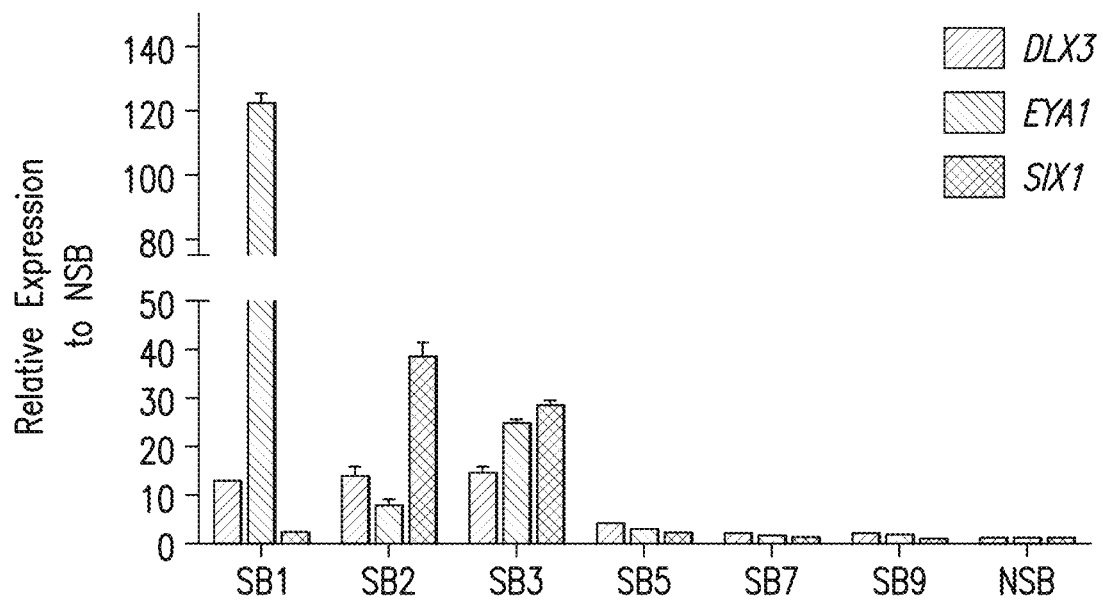

A timed withdrawal of the BMP inhibitor Noggin during N-SB differentiation was also tested to determine if placodal fates could be induced via derepressing endogenous BMP signaling. A time course analysis was performed during which Noggin was removed at different time points of the N-SB protocol (FIG. 28A). Gene expression analysis at day 11 revealed a robust induction of DLX3, SIX1 and EYA1 (FIG. 28B) upon withdrawal of Noggin at day 2 or 3 of differentiation. In contrast, Noggin withdrawal at day 1 of differentiation led to the induction of EYA1 in the absence of SIX1 expression and triggered morphological changes as well as CDX2 expression, suggesting trophectodermal differentiation (though CDX2 and EYA1 can also be expressed in hESC-derived mesodermal lineages (Bernardo et al., 2011)).

Figure 27D:
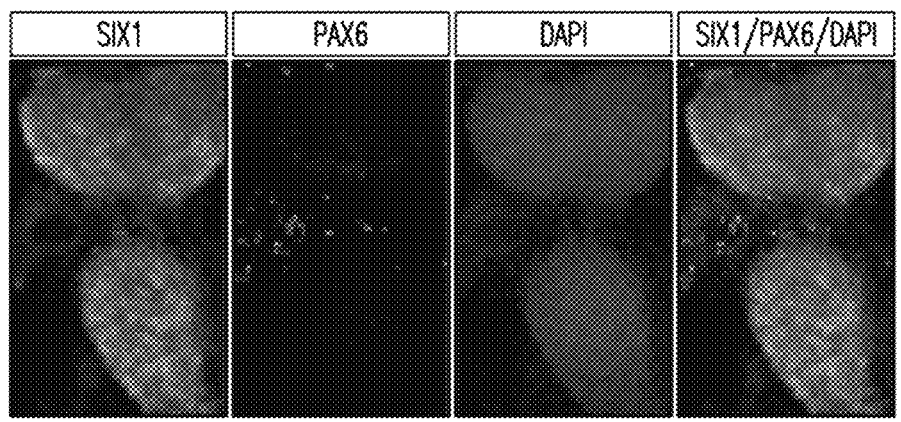
Figure 28C:
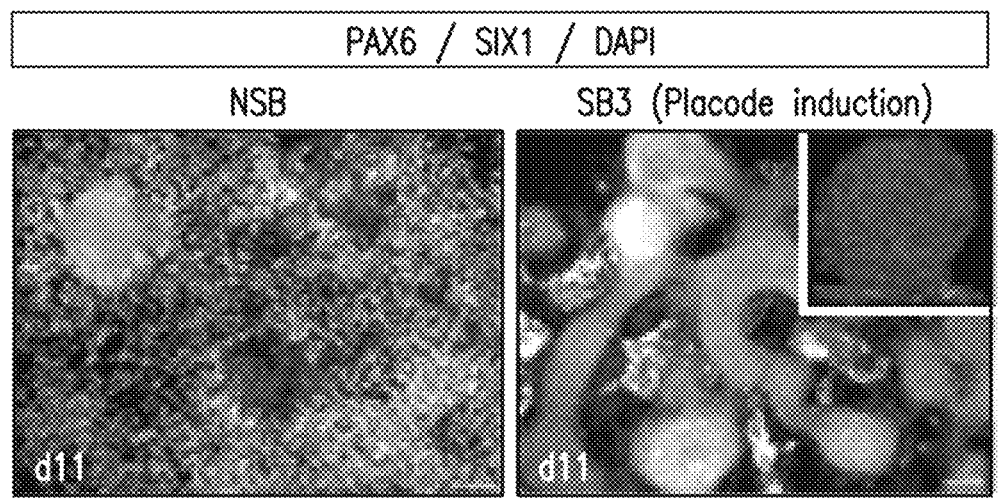
Figure 28D:
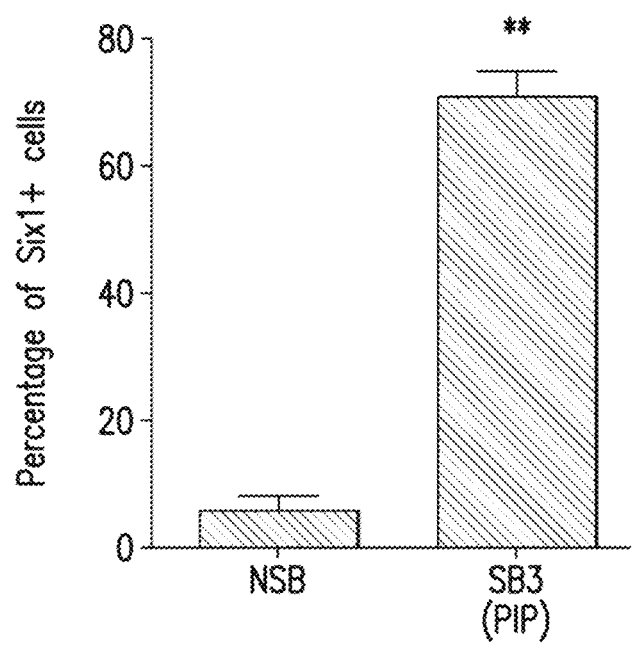
Figure 28E:
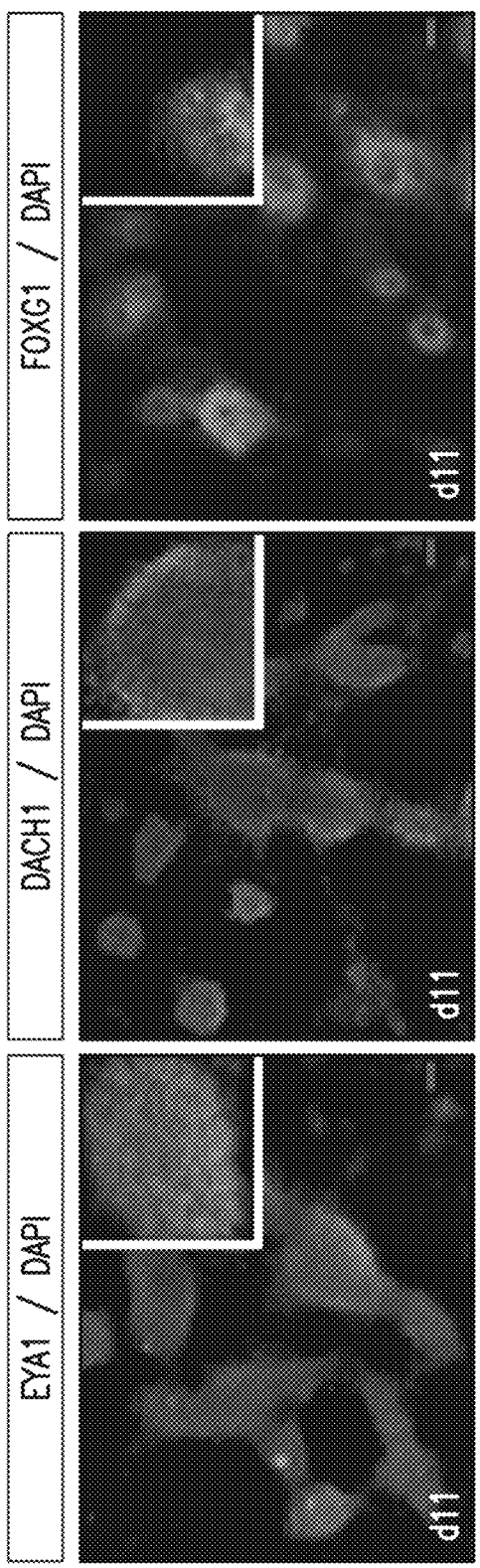
Figure 28F:
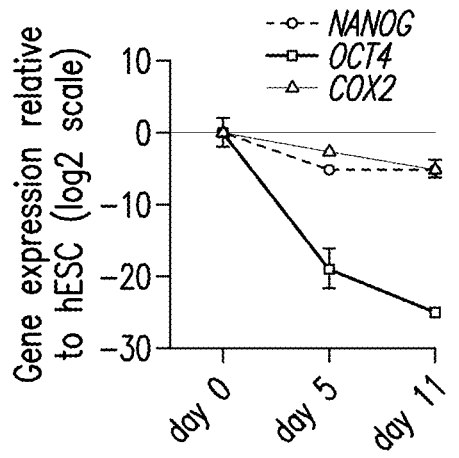

These data indicate that EYA1 is expressed in both trophectodermal and placodal lineages, and that co-expression with SIX1 can define a placodal lineage. Immunocytochemical analysis of hESC progeny at day 11 of differentiation demonstrated that Noggin withdrawal at day 3 (PIP conditions) induced a switch from 82% PAX6+ neuroectodermal cells under N-SB conditions to 71% SIX1+ putative placode precursor cells under PIP (FIGS. 28C, 28D, 27D). SIX1+ clusters expressed other placodal markers such as EYA1, DACH1 and FOXG1 (BF1) (FIG. 28E).

Figure 27E:
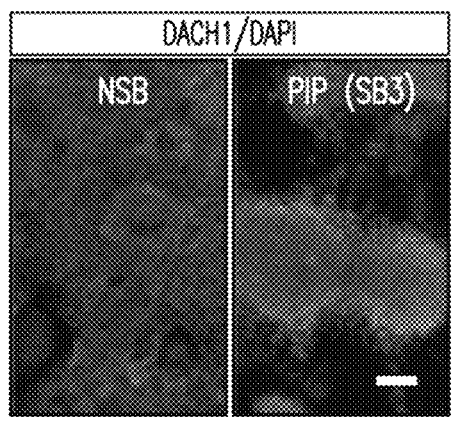
Figure 28G:
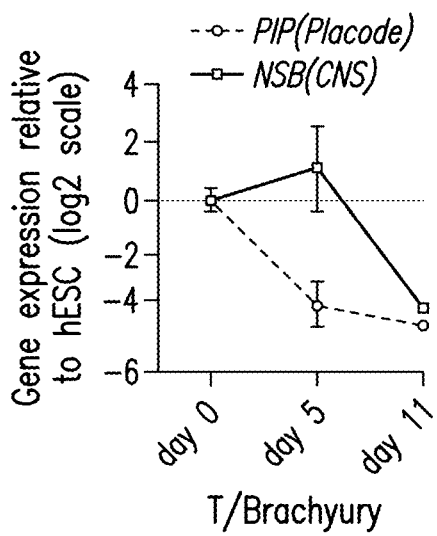
Figure 28G:
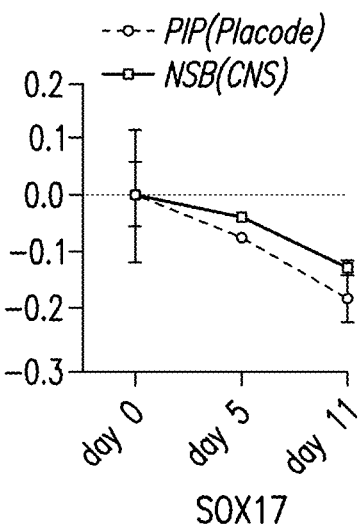

DACH1 is also expressed in anterior neuroectodermal cells (Elkabetz et al., 2008) marking neural rosettes while in PIP treated cultures DACH1 marks placodal clusters (FIG. 27E). Temporal analysis of gene expression under PIP conditions revealed rapid downregulation of pluripotency markers (OCT4, NANOG), as well as markers of trophectoderm (CDX2) (FIG. 28F), mesoderm (T) and endoderm (SOX17) (FIG. 28G). SIX1 expression in placode was confirmed in human primary tissue (Carnegie Stage 15, ~5.5 weeks p.c.; data not shown). SIX1 is also expressed in precursors of skeletal muscle, thymus and kidney cells.

Figure 27F:
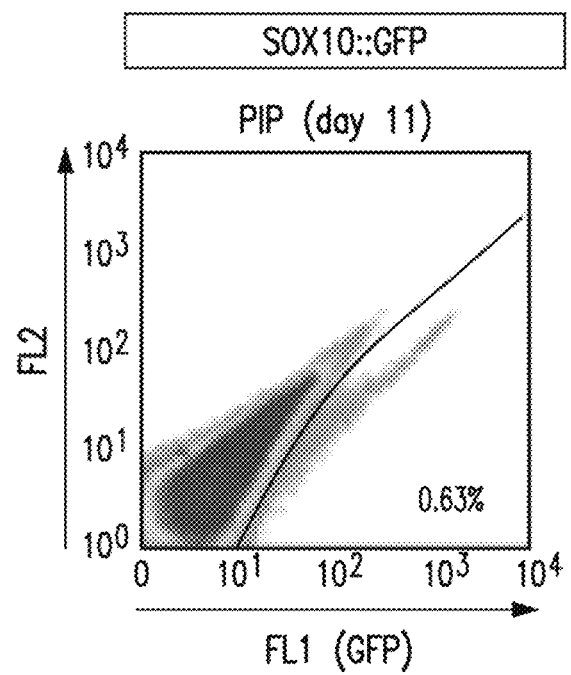

However, expression of skeletal muscle (MYOD), endoderm (SOX17), or mesoderm (Brachyury (T)) markers were not detected during PIP confirming that the hESC-derived SIX1+ cells are of placode identity. Very few (<1%) NC lineage cells were observed under PIP conditions based on SOX10 expression by immunocytochemistry and SOX10::GFP (Chambers et al., 2012; Mica et al., 2013) reporter line expression (FIG. 27F).

Figure 27G:
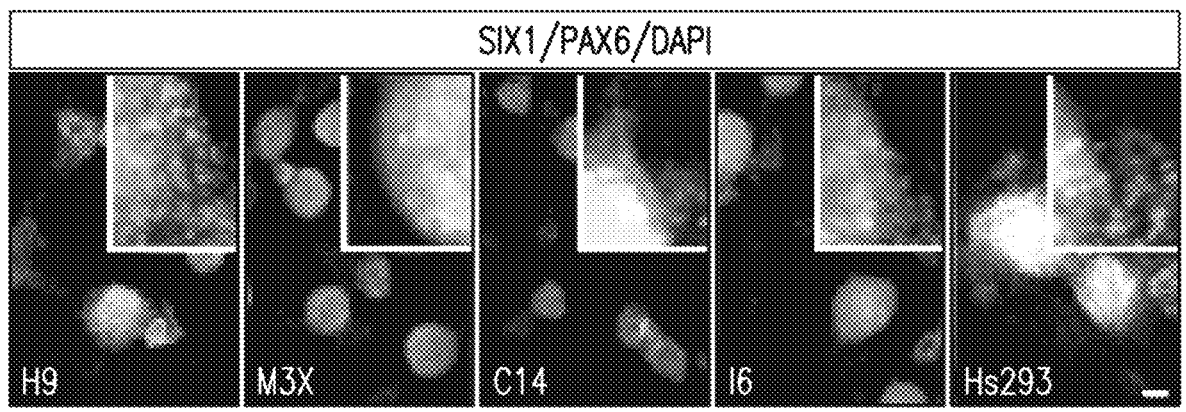
Figure 27H:
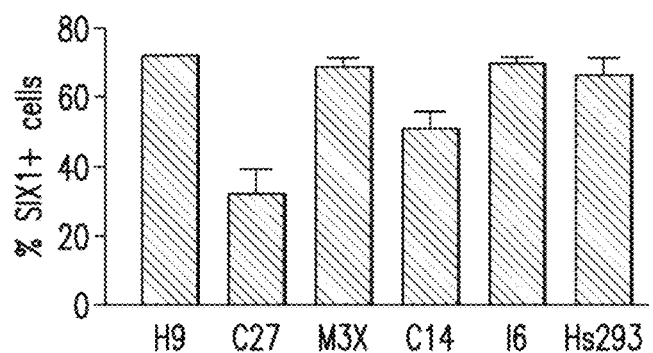
Figure 27I:
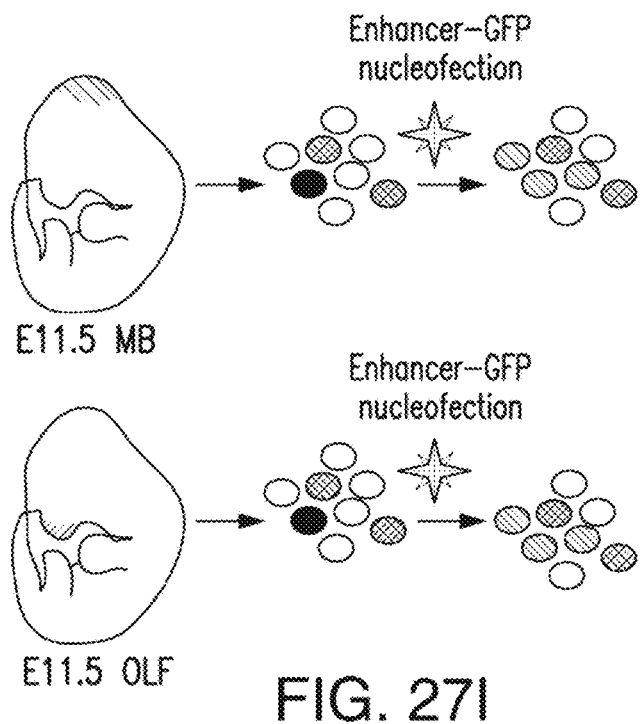
Figure 27J:
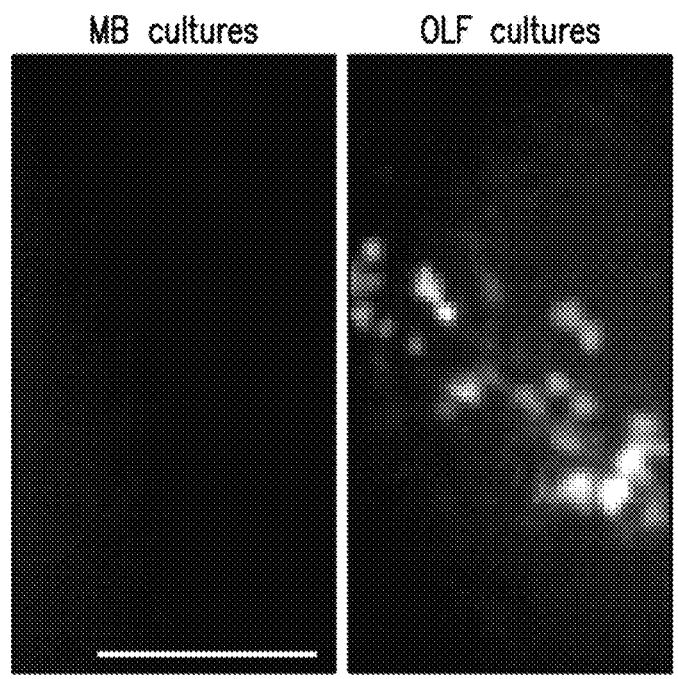
Figure 27K:
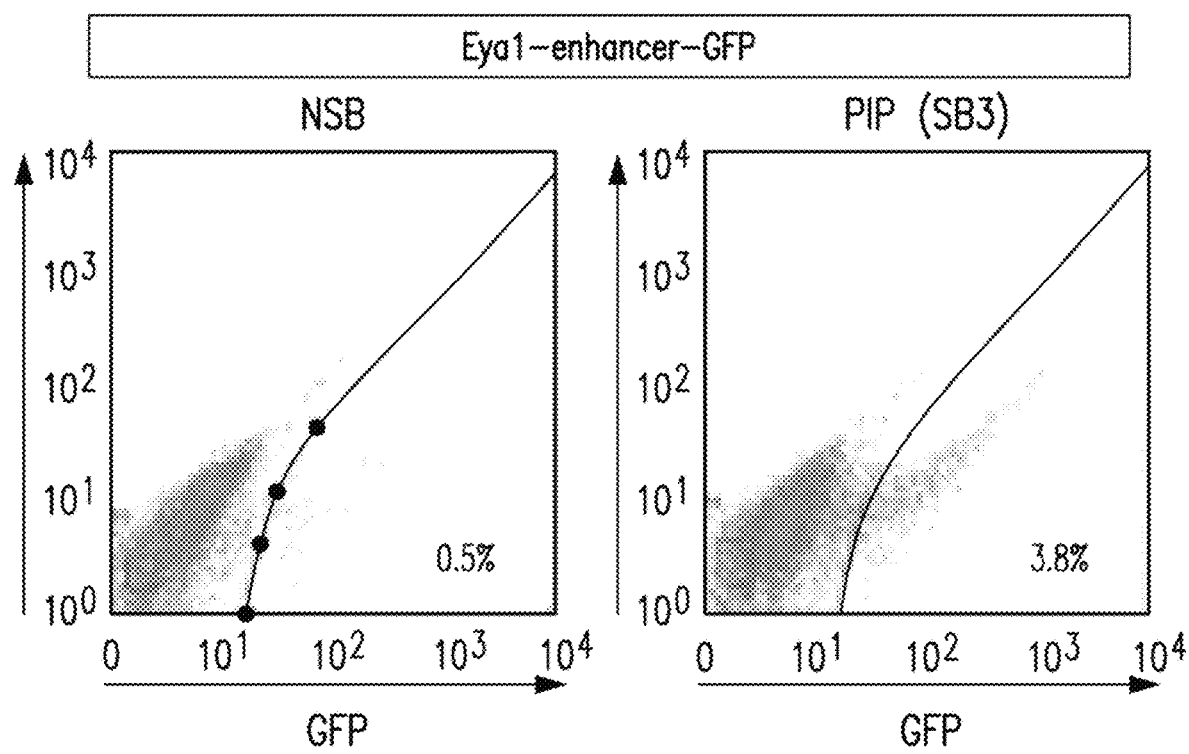
Figure 28H:
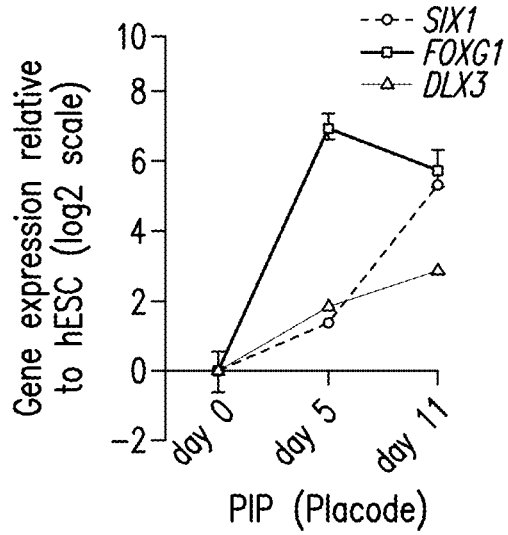

Induction of cranial placode markers was observed by day 5 with FOXG1 preceding expression of SIX1 and DLX3 (FIG. 28H). The PIP protocol was validated in multiple hESC and hiPSC lines (FIGS. 27G, 27H). A conserved Eya1 enhancer element (Ishihara et al., 2008) was used to further validate the identity of hESC-derived placodal precursors. GFP expression was readily observed following nucleofection of the enhancer in olfactory placode but not in age-matched midbrain cultures (FIGS. 27I, 27J) confirming specificity. In hESC-derived placode an 8-fold increase was observed in the percentage of cells with enhancer activity in PIP versus N-SB (FIG. 27K).

C. Microarray Analysis Reveals Novel Human Placode Progenitor Gene Expression

A temporal transcriptome analysis was performed to establish an unbiased molecular assessment of the in vitro placode induction process. RNA was collected at five time points in triplicate (day 1, 3, 5, 7, and 11) in control N-SB versus PIP treated cultures (FIGS. 30A-30E; all raw data are available on GEO: (ncbi.nlm.nih.gov/geo/: Accession #pending). Prior to microarray analysis, the quality of each sample was verified for expression of a panel of placode markers (SIX1, DLX3, EYA1) and the absence of other lineage markers (FOXA2, (endoderm), SOX17 (endoderm), MYOD (skeletal muscle), CDX2 (trophoblast), and T (mesoderm).

Figure 29A:
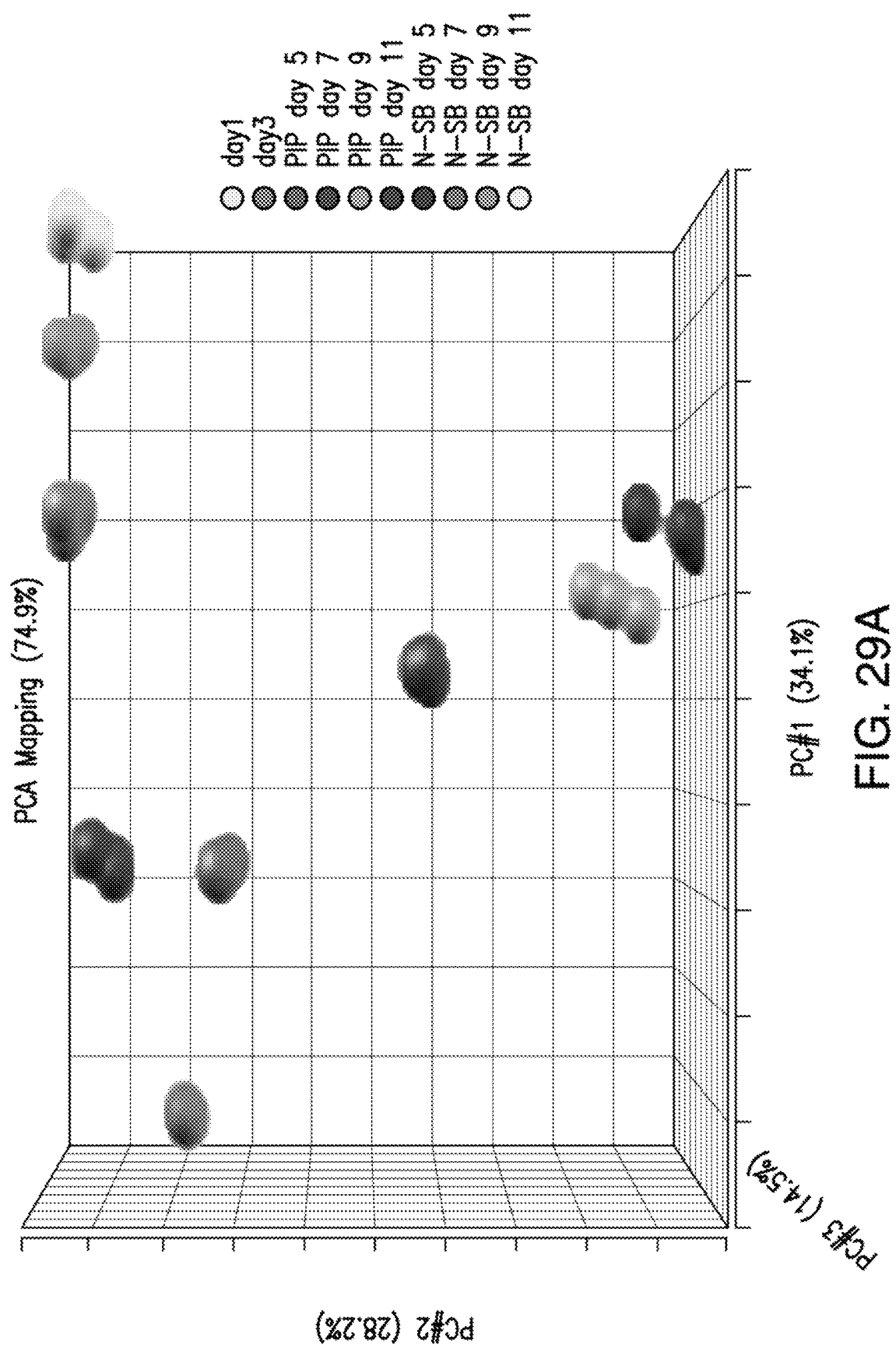
Figure 29B:
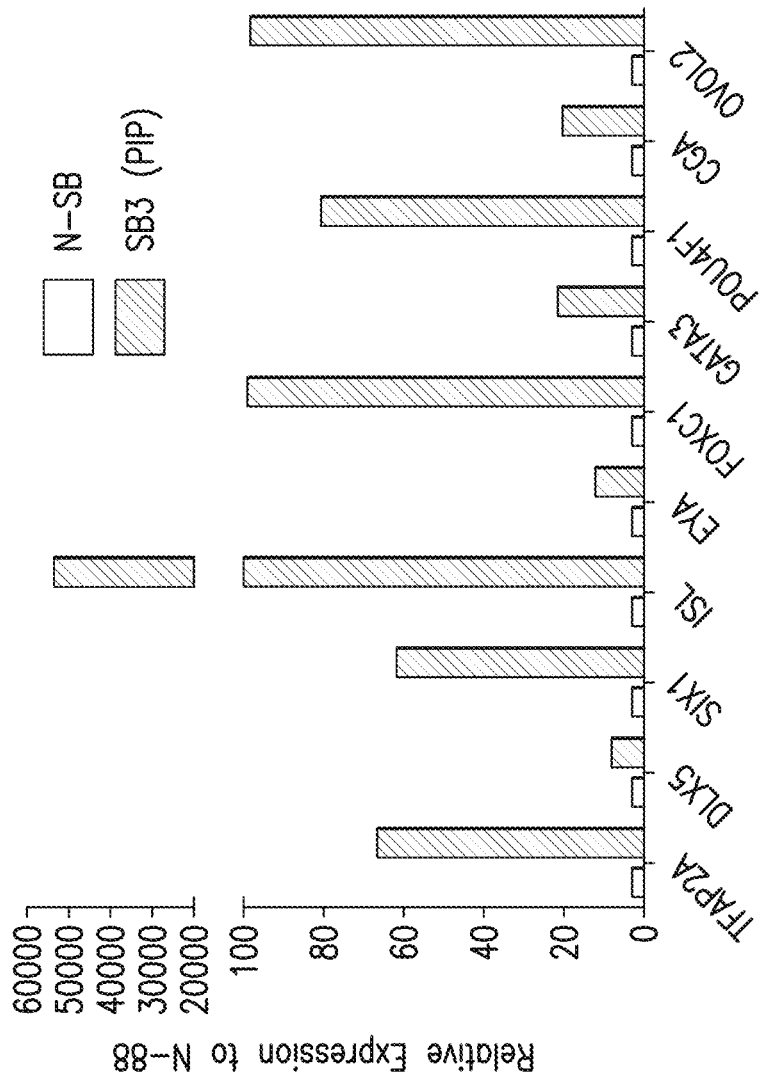
Figure 30A:
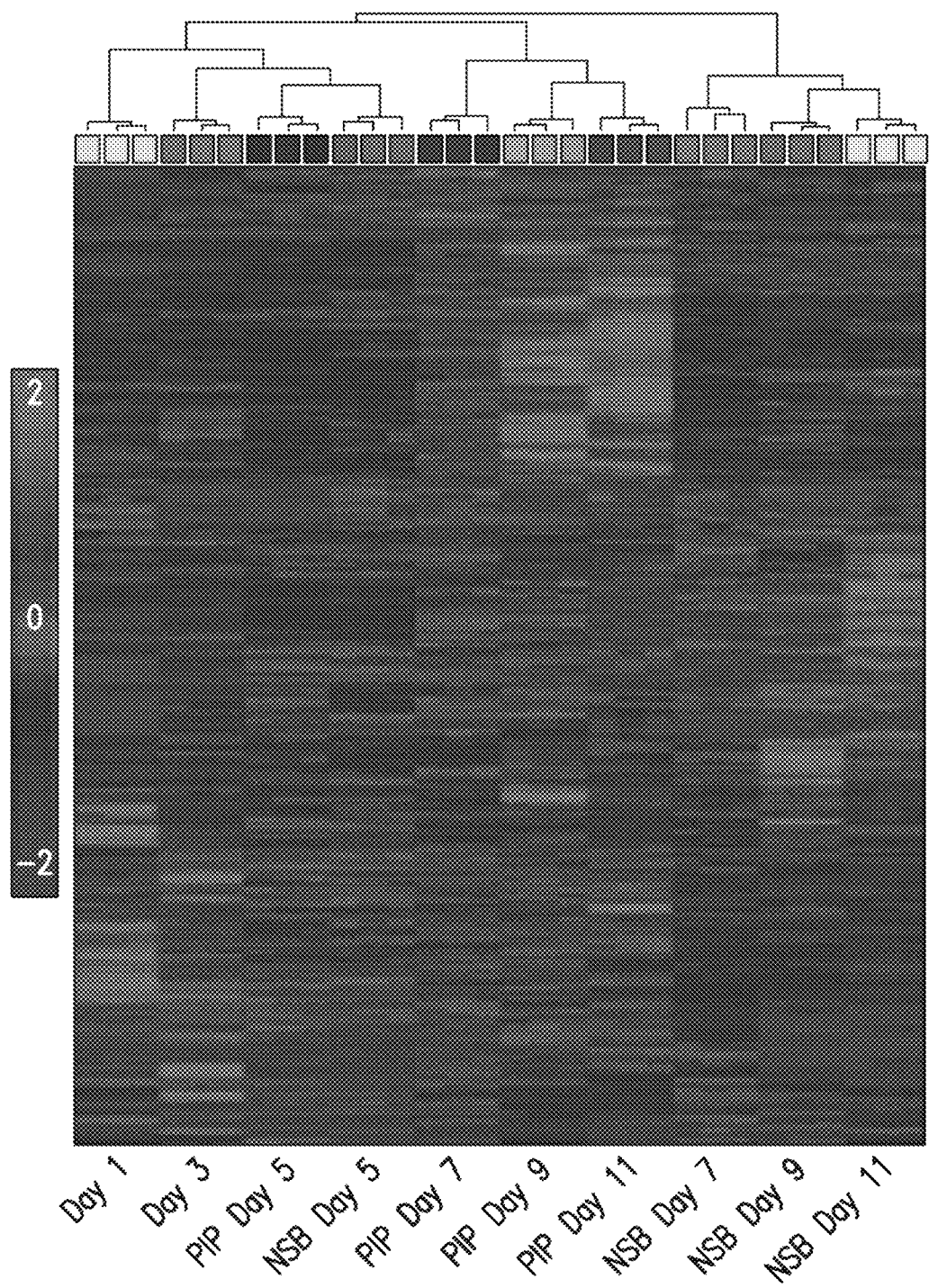
Figure 30B:
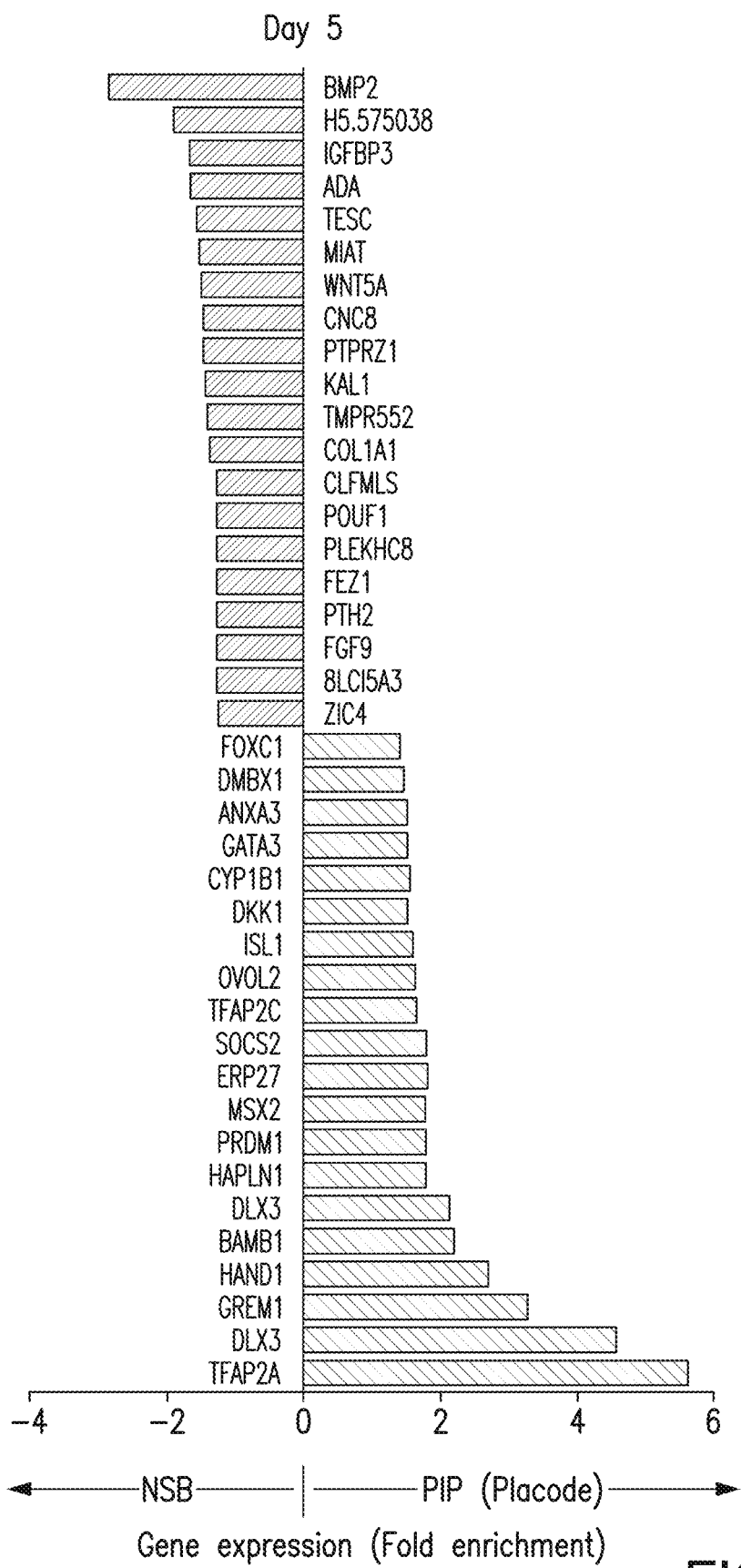
Figure 30C:
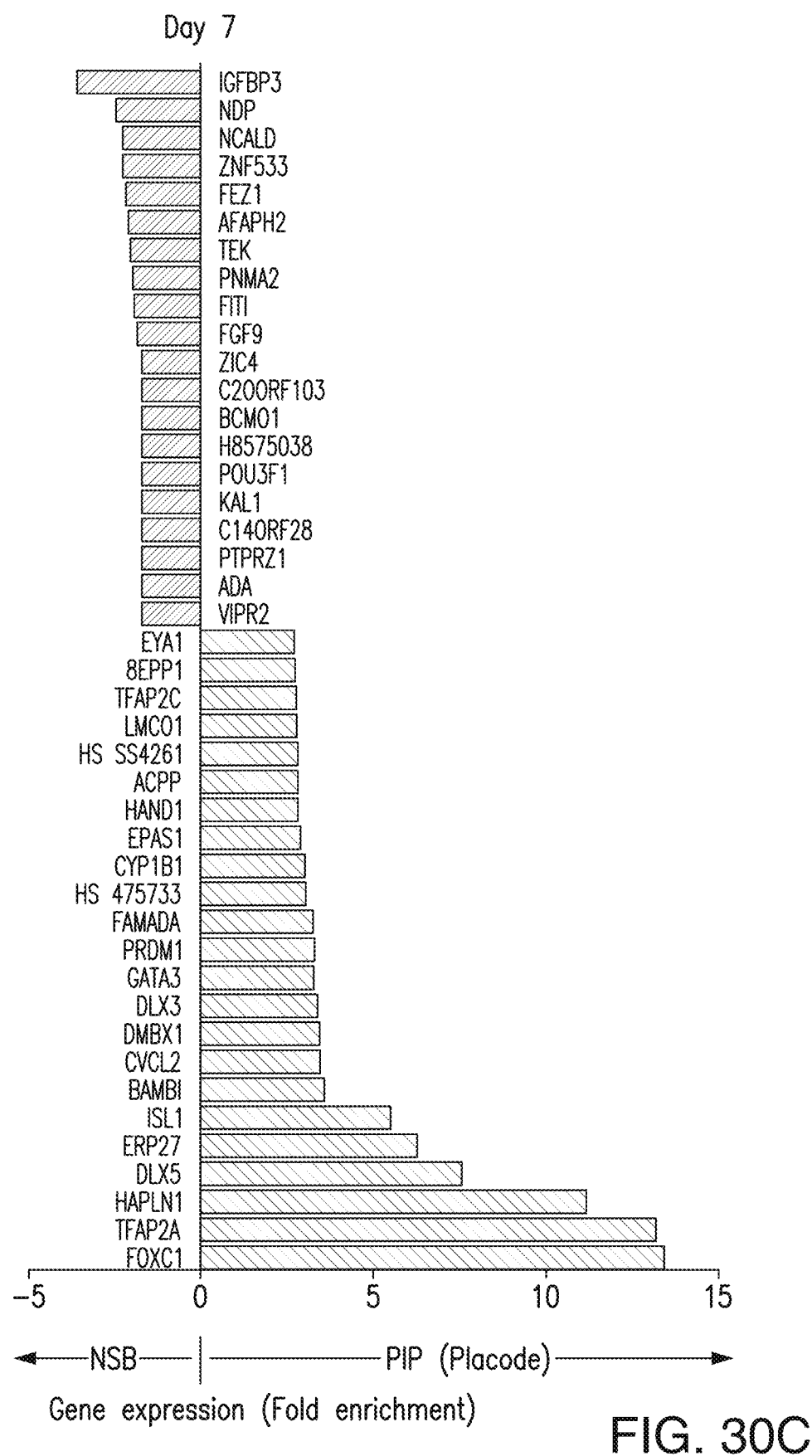
Figure 30D:
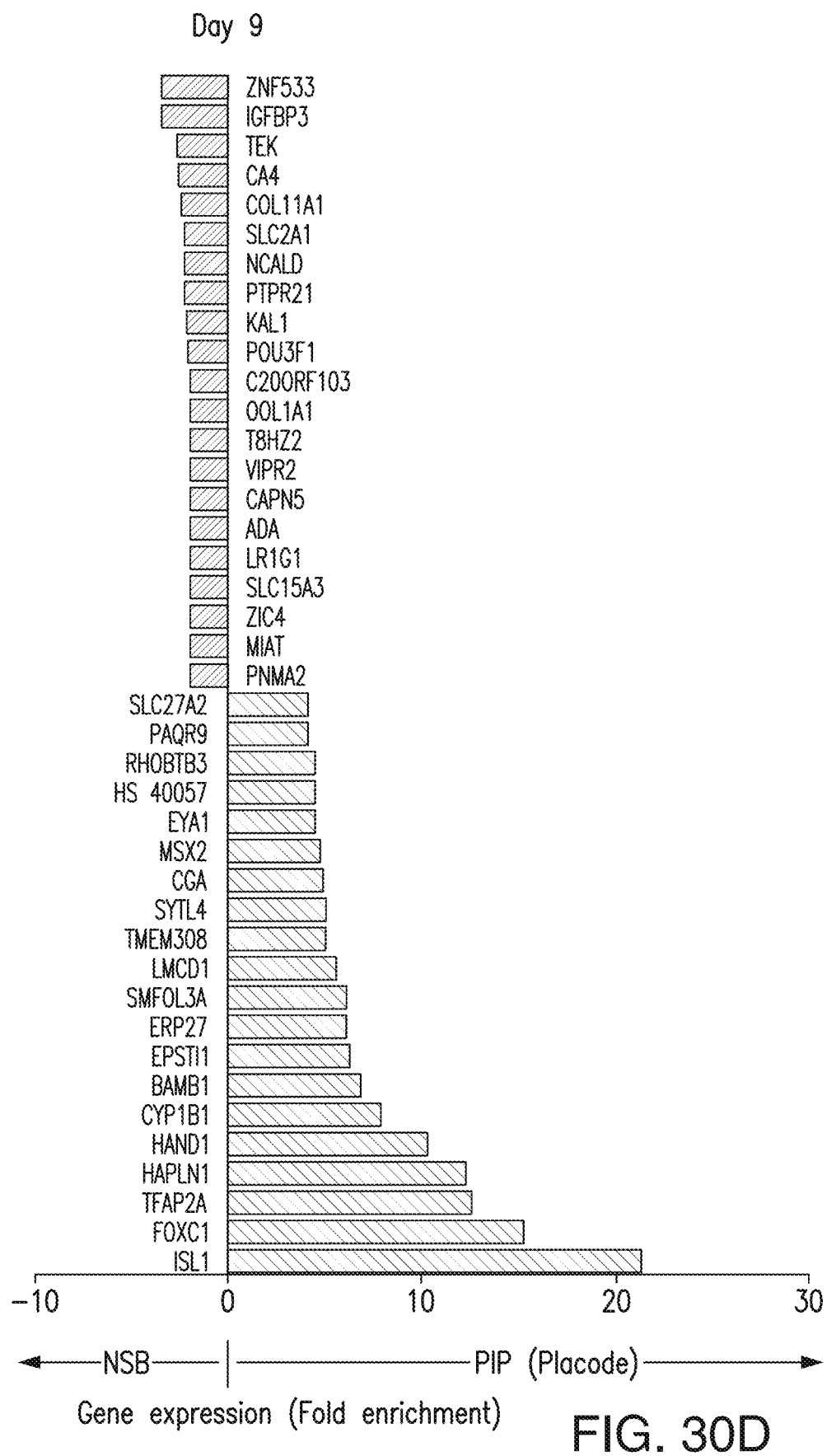
Figure 30E:
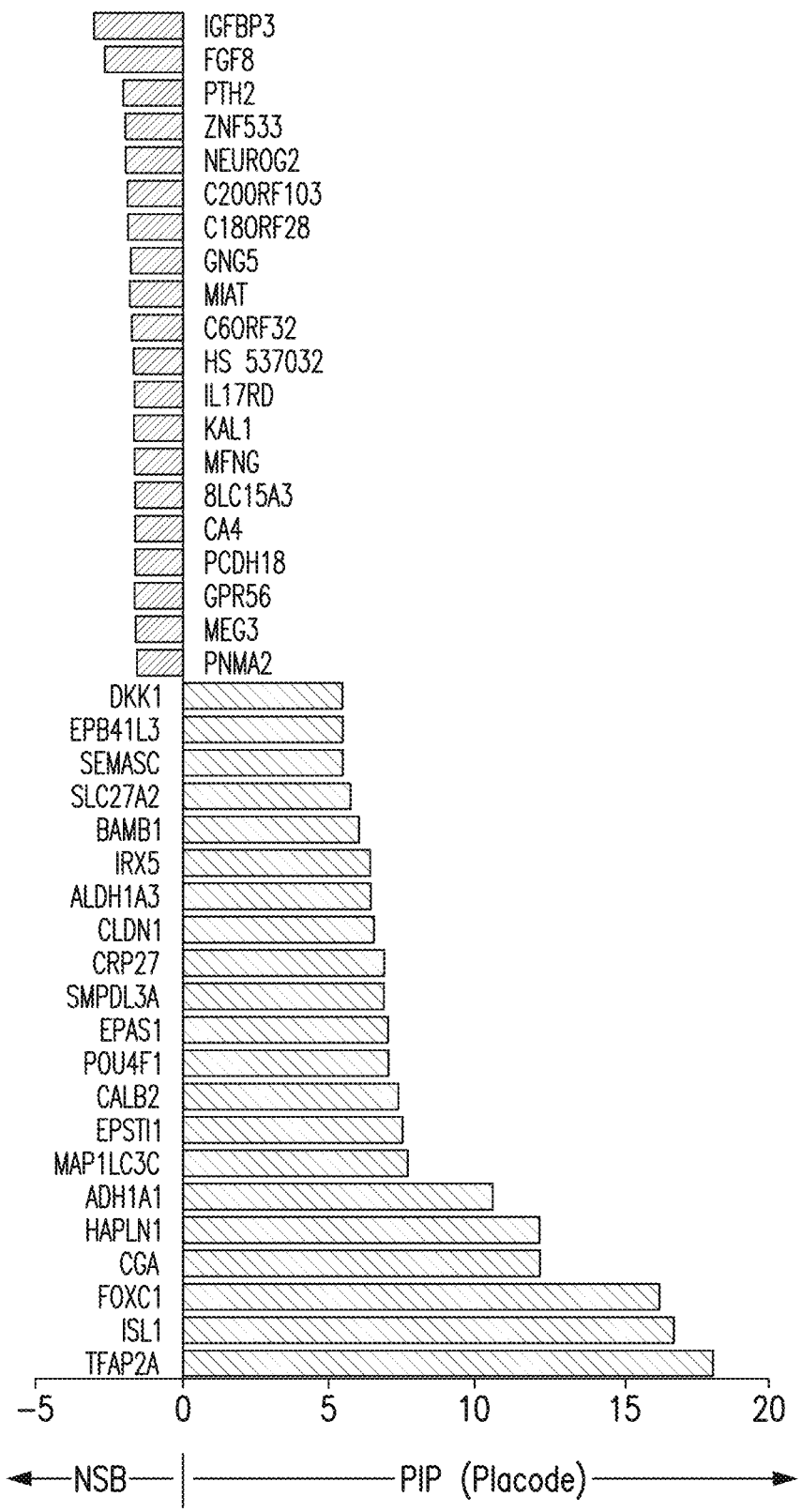
Figure 30F:
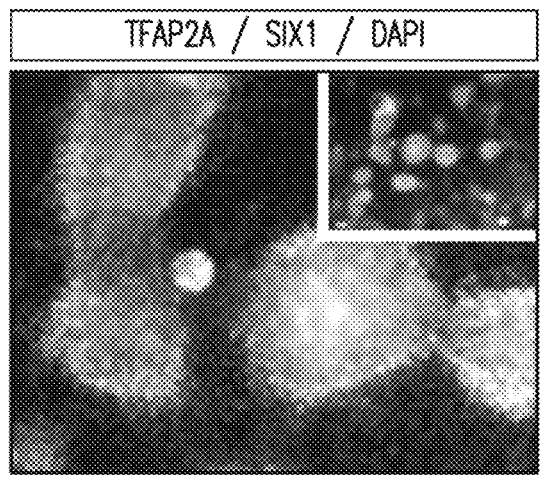

Cluster and principal component analyses showed a temporal segregation of the transcriptome data in PIP versus N-SB treated cells by day 7 of differentiation (FIGS. 30A and 29A). Transcriptome data also defined a set of genes that distinguish placodal fate from neuroectodermal fate. To gain insight into specific genes differentially expressed during placode induction, pairwise comparisons were performed for each differentiation time point (FIGS. 30B-30E). Among the most highly enriched transcripts under PIP condition were known placode markers such as GATA3, DLX5, DLX3, TFAP2A, and TFAP2C. SIX1 was significantly upregulated in the microarray analysis by day 9 of differentiation, though it was not among the most differentially regulated genes. Differential expression for these and additional genes was verified by qRT-PCR (FIG. 29B).

Figure 30G:
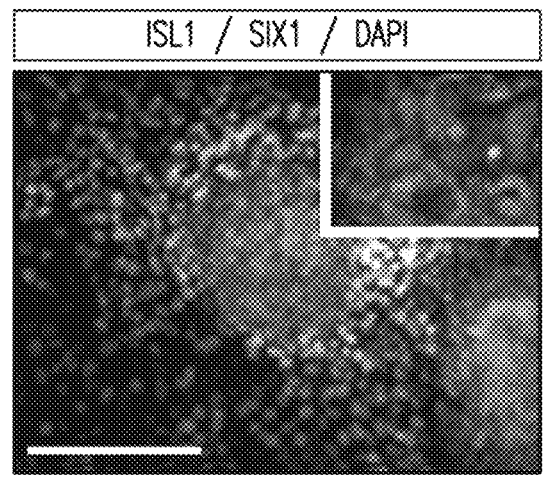

A significant transcriptional change was observed in WNT and BMP pathway components such as an increase in the WNT pathway inhibitor DKK-1 and BMP antagonists, such as GREMLIN-1 and BAMBI (FIGS. 30B-30D), which are known transcriptional targets of BMP signaling (Grotewold et al., 2001). Interestingly, ISL1, a reported marker for sensory neurons, motoneurons, heart progenitors and pancreatic islet cells was also induced (Hunter and Rhodes, 2005). Based on the early onset of ISL1 expression and the absence of mesodermal fates, it was surmised that, under PIP conditions, ISL1 represents an early human placode marker. ISL1 was one of the first makers induced during PIP differentiation. Similar to TFAP2A and SIX1 (FIG. 30F), ISL1 protein remained expressed in the majority of cells by day 11 of differentiation partially co-localizing with SIX1 (FIG. 30G).

Figure 30H:
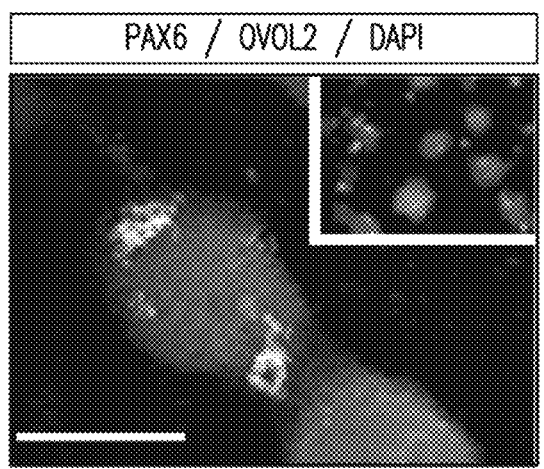
Figure 30I:
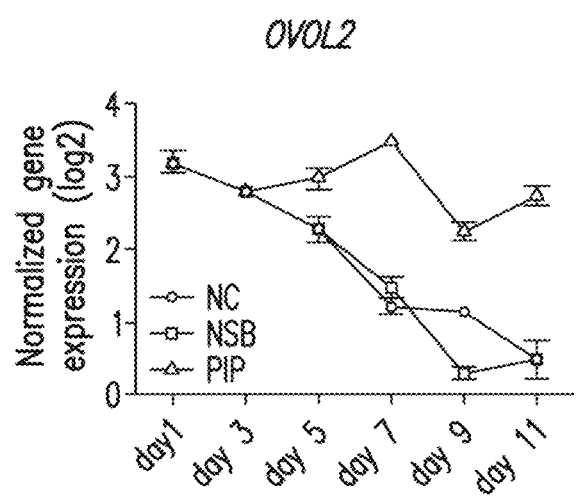

Another novel placode marker identified in the presently disclosed microarray expression data is OVOL2, a member of the Ovo family of zinc-finger transcription factors. OVOL2 was enriched during PIP by day 5 of differentiation and placode clusters showed strong immunoreactivity for OVOL2 (FIG. 30H). In contrast, OVOL2 was downregulated under conditions promoting CNS (N-SB) or neural crest (N-SB/CHIR (Chambers et al., 2012; Mica et al., 2013)) fates (FIG. 30I).

Figure 29C:
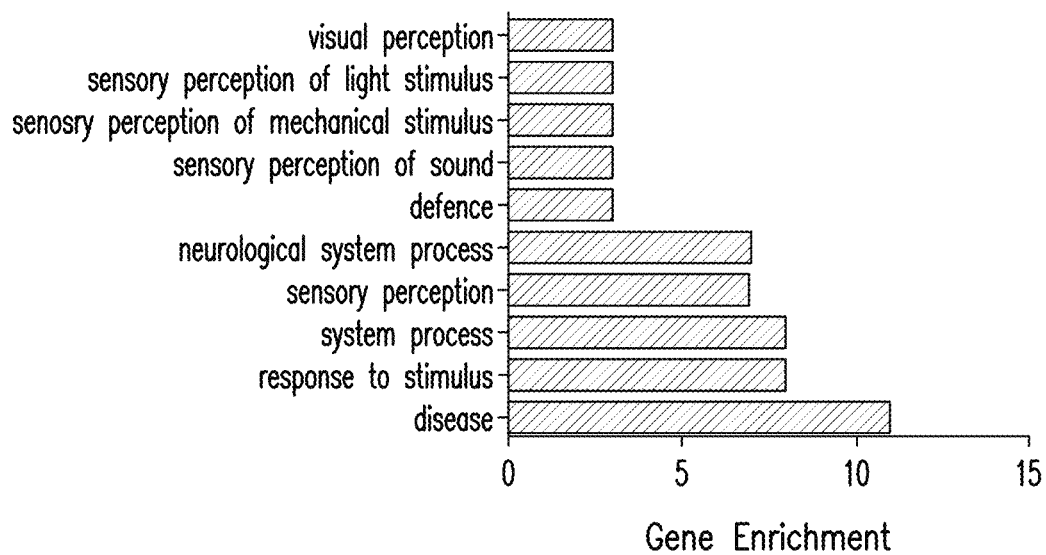
Figures 29D, 29E:
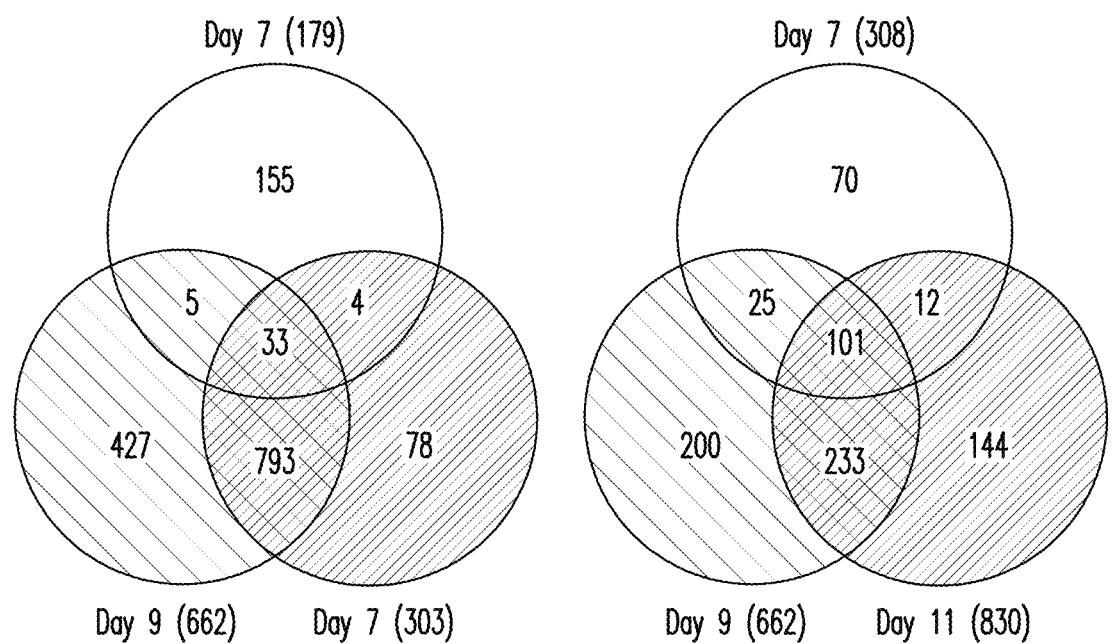

Also identified were additional differentially expressed genes during anterior placode specification, including FOXC1 and HAPNL1 (also known as CRTL1). FOXC1 marks the lens placode during chick development (Bailey et al., 2006) but may also be expressed at the pre-placode stage (Sasaki and Hogan, 1993). HAPNL1 was one of the most differentially expressed genes in PIP and was previously shown to be expressed in the surface ectoderm and chick neural plate border (Colas and Schoenwolf, 2003). Gene ontology (GO) analysis, using DAVID (david.abcc.ncifcrf.gov/; (Dennis et al., 2003)) indicated that BMP and WNT pathways transcripts are highly enriched in PIP versus N-SB conditions at day 7 and day 9 of differentiation that are associated with sensory organ, ectoderm and epidermis development (FIG. 29C). The total number of differentially expressed genes increased by day 7 of differentiation (FIGS. 29D, 29E) matching the proposed time frame for placode commitment. In summary, the presently performed molecular analyses provide a preliminary roadmap of human placode development and an important resource for future functional studies.

D. Early Treatment with FGF-Inhibitor Suppresses Placode and Induces Surface Ectoderm Fate Lineage studies in several vertebrate species indicate that cranial placode precursors originate from the surface ectoderm and are induced by signals emanating from the adjacent neuroectoderm (Pieper et al., 2012), rather than being of neural origin. However, no such data are available for human development.

The putative timing of human placode induction (~day 20 p.c.) (O'Rahilly, 1987)) makes this a stage largely inaccessible to experimental manipulations. Gene expression data during PIP indicate that TFAP2A is one of the earliest upregulated and differentially expressed genes (FIGS. 30B-30E). During mouse development early expression of the orthologous gene, Tcfap2a (E7.5) is restricted to the future surface ectoderm (Arkell and Beddington, 1997).

Figure 32A:
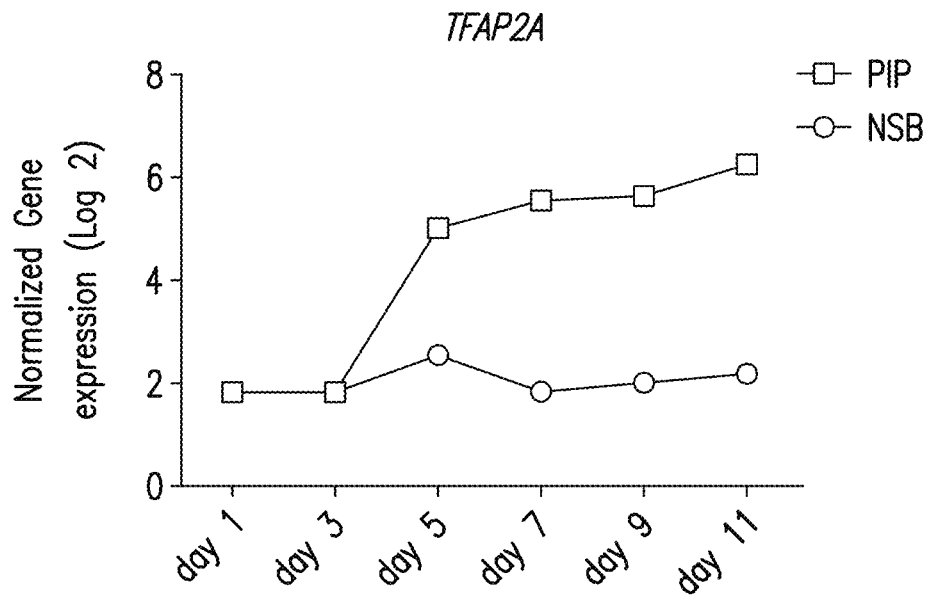

The data presented herein demonstrates an initial detection of TFAP2A induction at day 5 of PIP while absent in N-SB protocol (FIG. 32A). This observation suggests that the period between day 3 and 5 of PIP corresponds to a commitment towards surface ectoderm development. SIX1 was induced two days later than TFAP2A (FIGS. 32A, 32B) further pointing to a surface ectoderm intermediate.

Figure 32B:
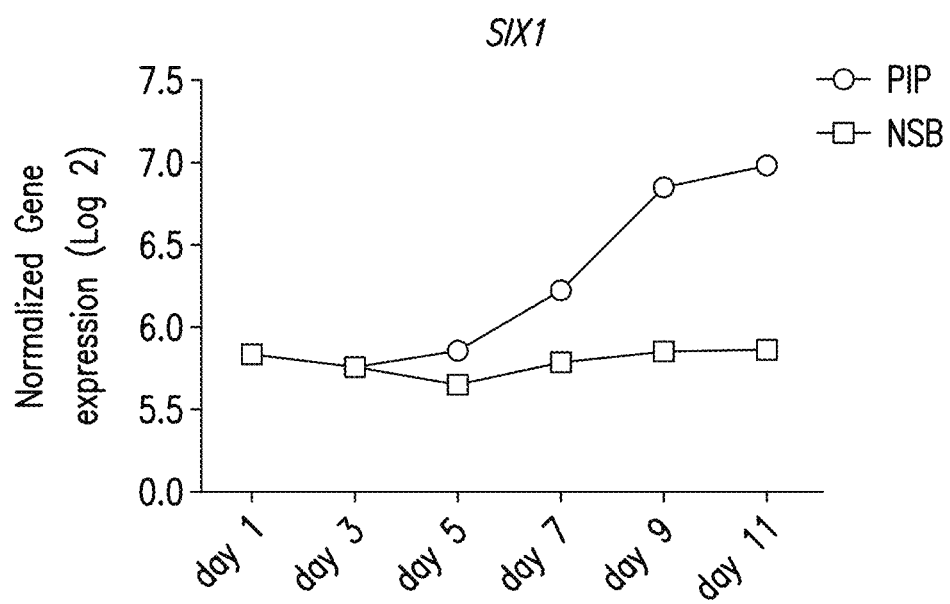
Figure 32C:
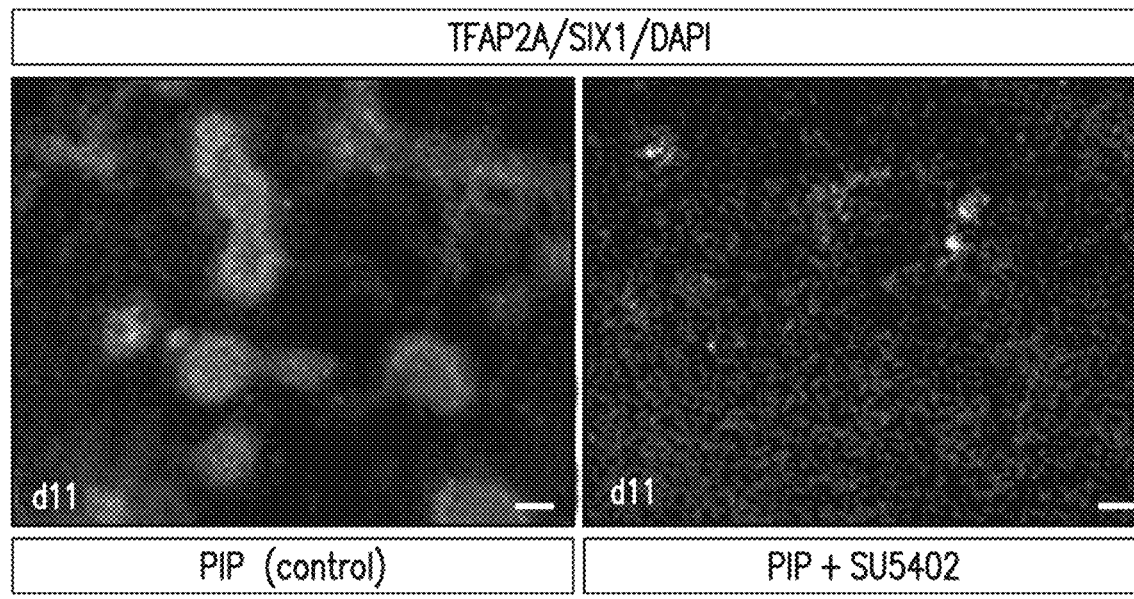
Figure 32D:
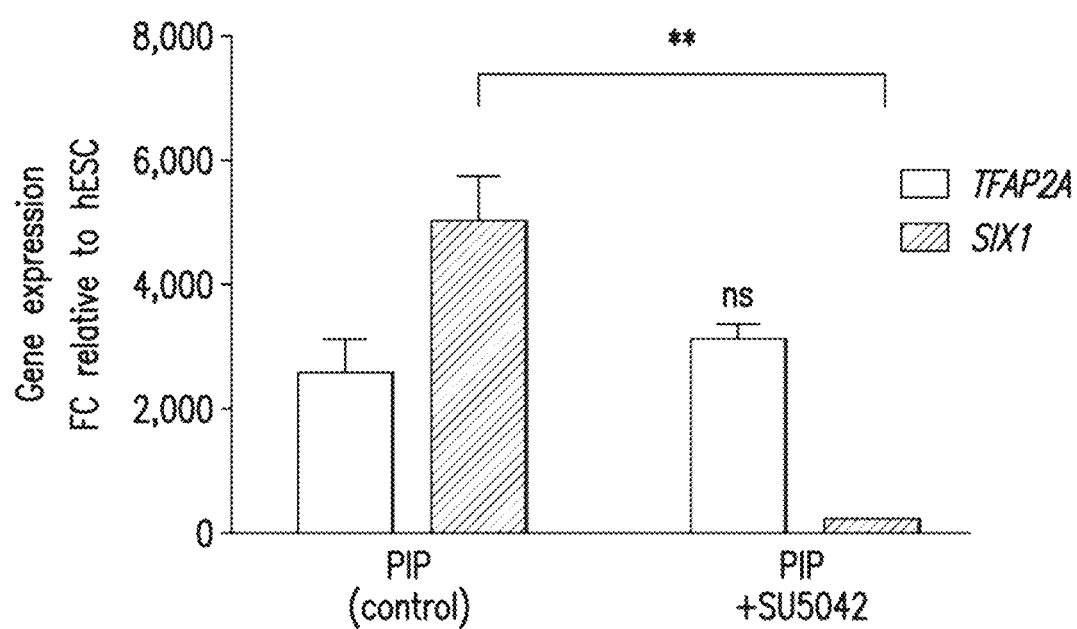

In vivo genetic studies indicate that high levels of BMPs, in the absence of FGF signaling, promote epidermal fate whereas placodal cells are established at reduced levels of BMPs upon activation of FGFs (Kudoh et al., 2004; Litsiou et al., 2005). Although it is not necessary to understand the mechanism of an invention, it is believed that blocking endogenous FGF signaling under PIP conditions may disrupt placode induction and trigger epidermal fate. For example, the present data show that SU5402, a small molecule inhibiting FGF signaling, from day 3-11 of differentiation (FIG. 32A) suppressed the emergence of SIX1+ clusters while maintaining TFAP2A expression (FIG. 32C).

Figure 31A:
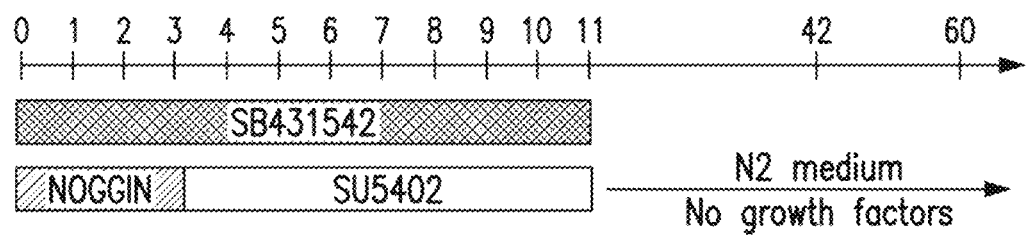
Figure 31B:
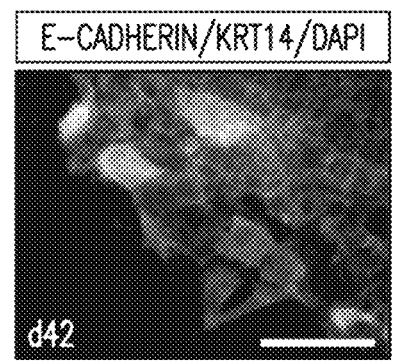
Figure 31C:
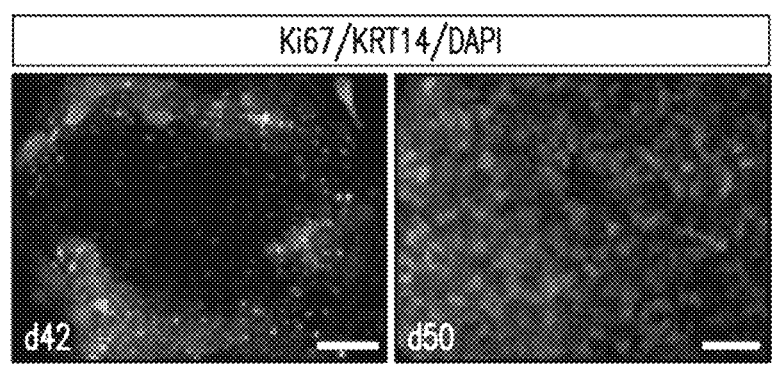
Figure 31D:
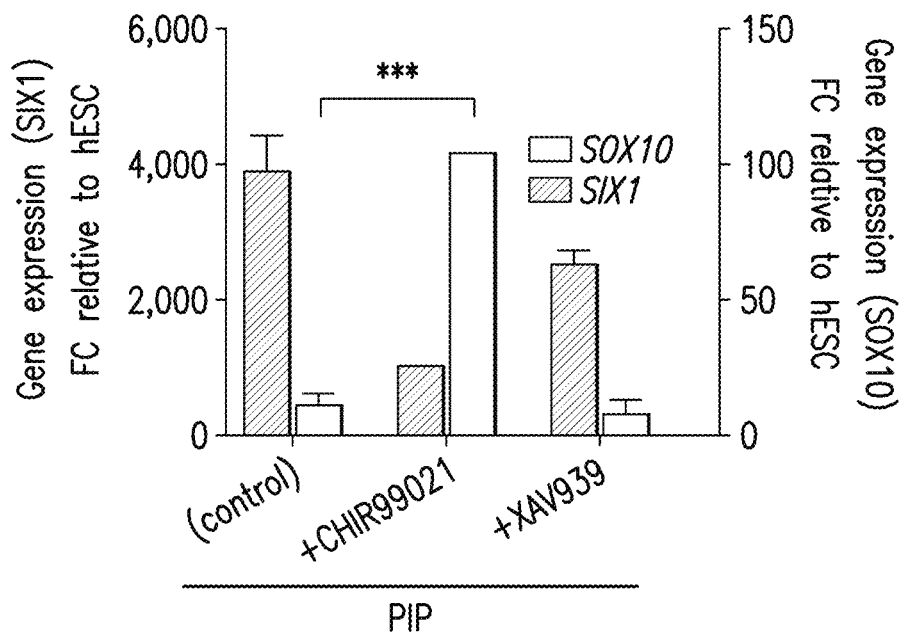
Figure 31E:
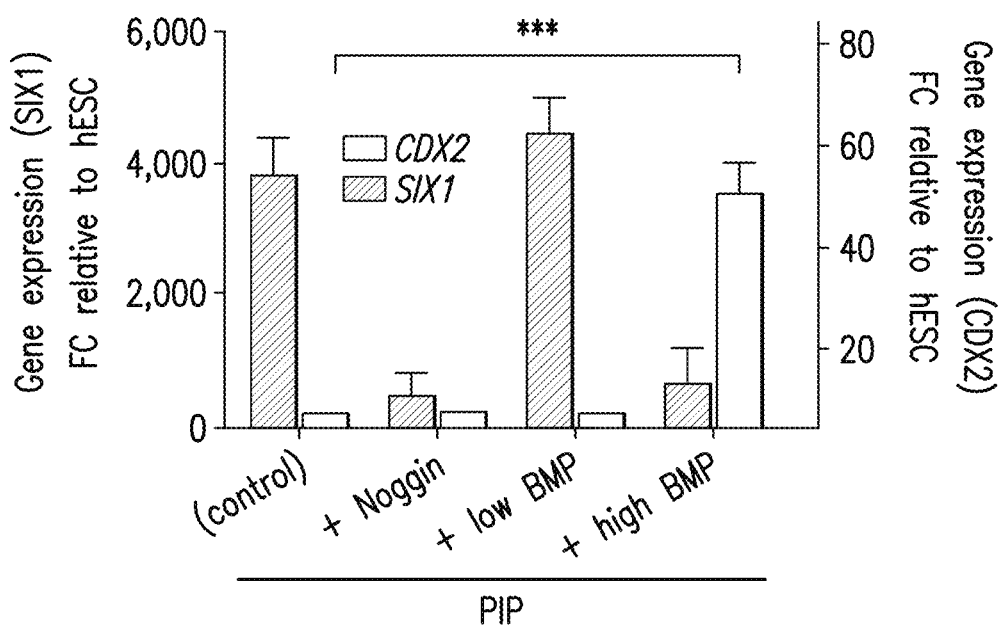
Figure 32E:
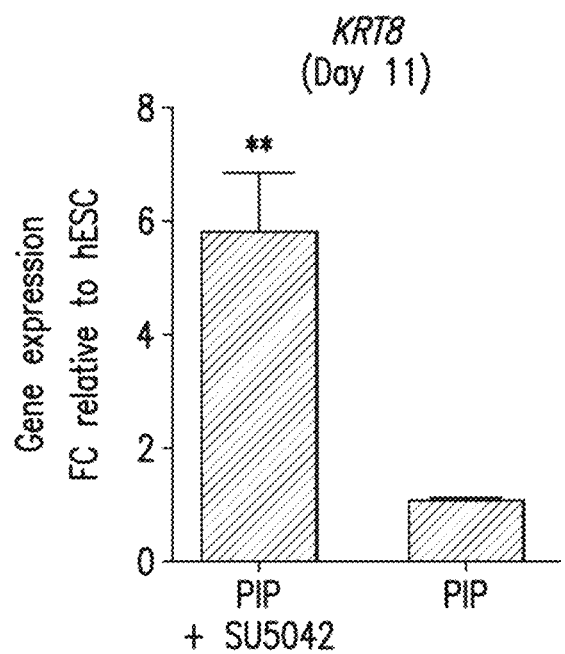
Figure 32F:
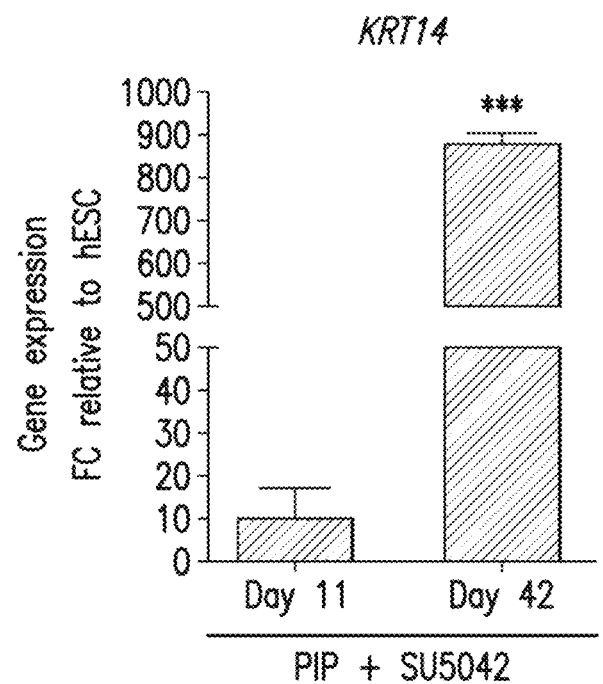
Figure 32G:
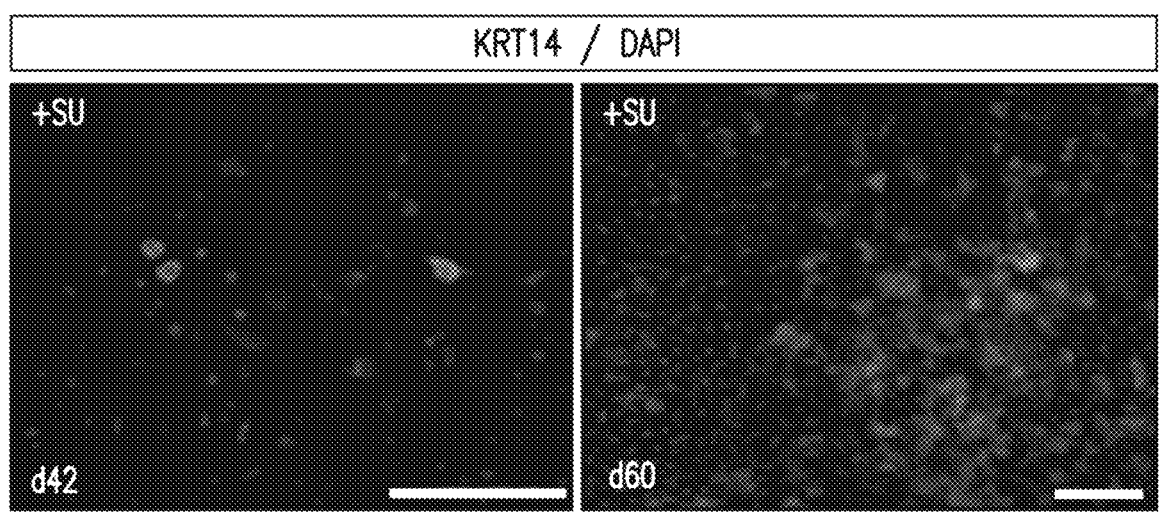

Quantification of SIX1 and TFAP2A gene expression at day 11 confirmed a complete loss of placode marker expression (FIG. 32D), while TFAP2A expression was maintained. The ectodermal precursor identity of TFAP2A+ cells was supported by the expression of the epidermal precursor marker KRT8 in PIP+SU5402 treated cultures (FIG. 32E). Furthermore, long-term cultures (day 42-60) showed robust induction of the mature keratinocyte marker KRT14 (FIG. 32F) and formed E-CADHERIN positive patches with KRT14-immunoreactive cells at the periphery (FIG. 31B). Analysis of the proliferative capacity of the epidermal precursors showed KI67 expression primarily in E-CADHERIN+/KRT14-cells. Cell proliferation decreased by day 60 concomitant with an increased percentage of cells expressing KRT14 (FIGS. 32G, 31C). In addition to the requirement for endogenous FGF signaling, low WNT and BMP levels were observed as other useful parameters for the transition from surface ectoderm (day 3) to early placode fate. Exposure to high concentrations of CHIR or BMP4 suppressed placode at the expense of NC or putative trophectoderm, respectively (FIGS. 31D, 31E).

Figure 33A:
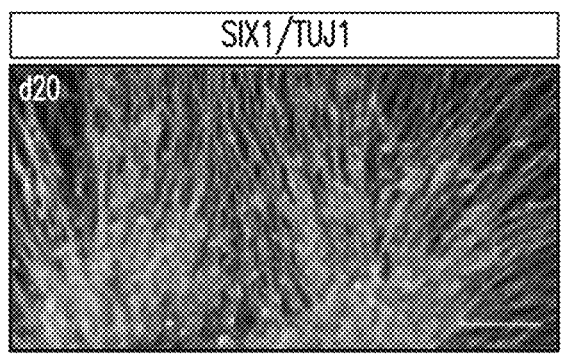
Figure 33B:
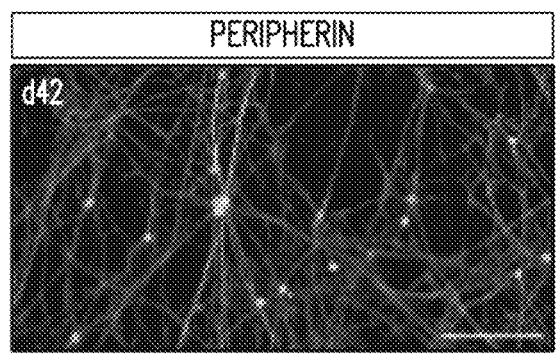
Figure 33C:
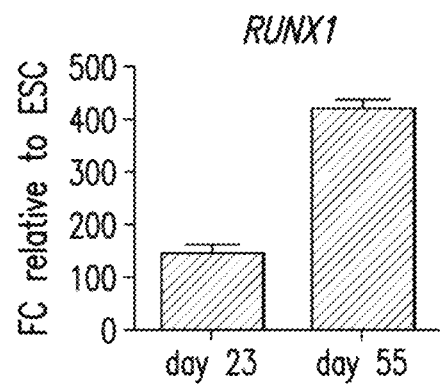
Figure 33D:
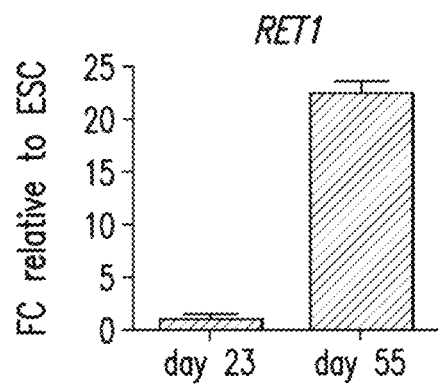
Figure 33E:
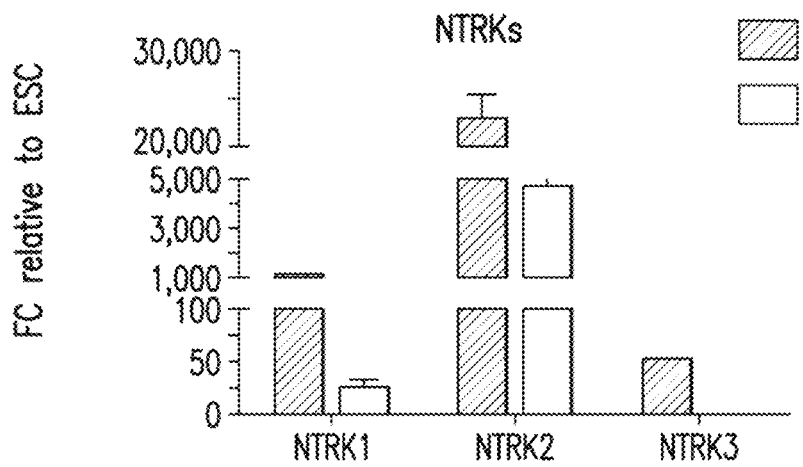

E. Placode Precursors Efficiently Differentiate into Trigeminal-Type Sensory Neurons Cranial placodes are believed give rise to a broad range of specialized cell types including, but not limited to, hormone producing cells of the anterior pituitary gland, structural cells such as lens fibers in the eye and sensory neurons including, but not limited to, trigeminal neurons (FIG. 34A). Placodes can be characterized by the expression of specific PAX genes (McCauley and Bronner-Fraser, 2002). The data presented herein show that under standard PIP conditions most SIX1+ clusters coexpressed PAX3 (FIG. 34B) suggesting an ophthalmic trigeminal placode identity (McCabe et al., 2004; Stark et al., 1997). The spontaneous generation of HNK1+(Metcalfe et al., 1990) cells with neuronal morphologies and co-expression of ISL1 confirmed peripheral sensory neuron identity (FIG. 34C). To further ascertain a placode origin of the sensory neurons under PIP conditions, coexpression of neuronal markers with SIX1 was assessed (FIGS. 34D, 33A). A lack of SOX10 expression during PIP-based sensory neuron differentiation ruled out a neural crest origin. By day 20 of differentiation (7 days after replating), the cells formed ganglia-like structures with neurons extending long, radial processes and with nuclear expression of BRN3A (FIGS. 34D, 34E), a sensory neuron marker. Most neurons retained ISL1 expression by day 42 of differentiation and acquired expression of the peripheral neuron marker peripherin (FIGS. 34F, 33B). Immunocytochemical analysis for neurotransmitter phenotypes revealed expression of glutamate (FIG. 34G) but lack of expression of TH and GABA (data not shown). These data are compatible with the generation of glutamatergic trigeminal sensory neurons. Gene expression analysis showed induction of RUNX1 (FIGS. 34H, 33C) and RET (FIG. 33D) indicating sensory/nociceptive lineage. Expression of TRK receptors (FIGS. 34I, 33E) including NTRK1 and NTRK2 points to the presence of both nociceptive and non-nociceptive sensory neurons (FIGS. 33E-33G).

Diagnostic markers of nociceptive neuron identity include expression of specific sodium channels (SCN9A, SCN10A, SCN11A; FIG. 34J) as well as classic pain receptors such as the capsaicin receptor (TRPV1), the receptor for cold sensation (TRPM8) and the P2X3 receptor critical for sensation of inflammatory pain mediated by ATP (FIG. 34K). Gene expression analysis in long-term trigeminal neuronal cultures (day 55) showed sustained expression of RET1 and RUNX1 (FIGS. 33C, 33D).

Figure 33G:
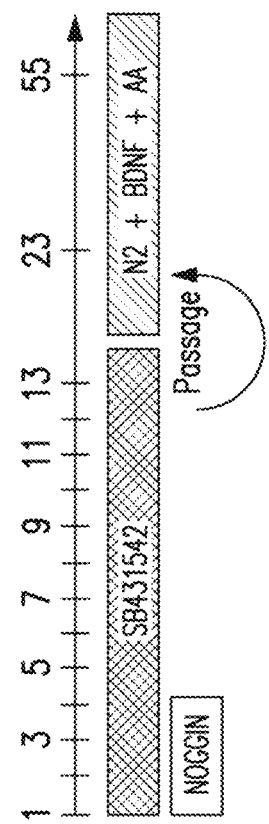
Figure 33F:
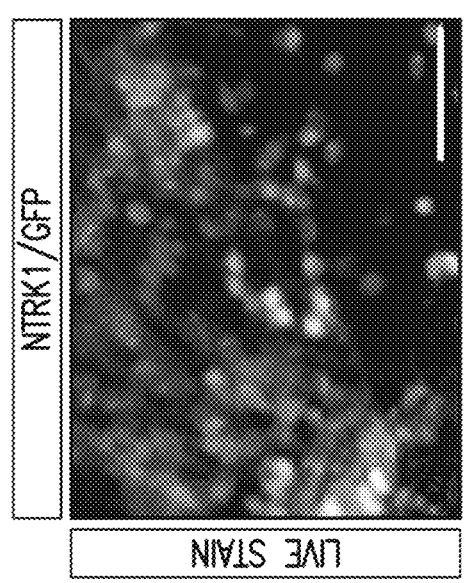
Figure 33H:
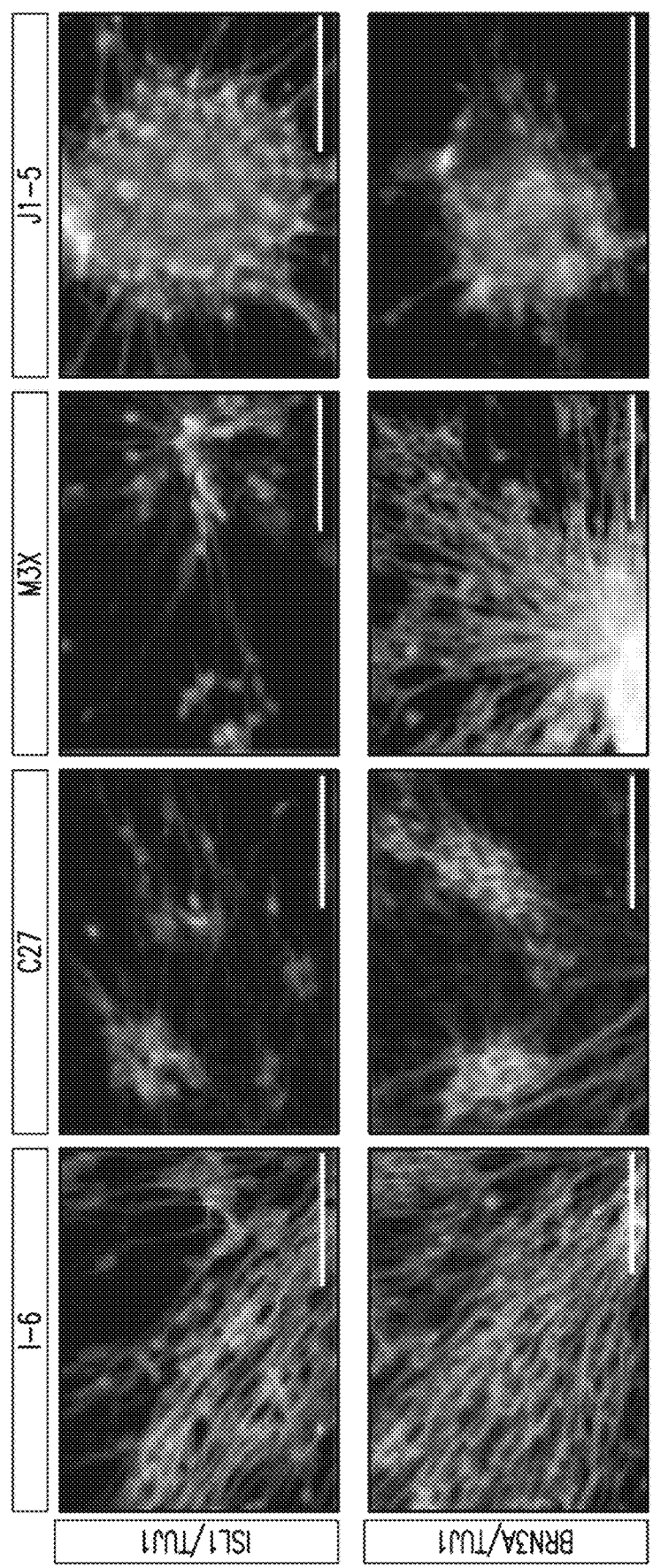

A functional analysis of placode-derived sensory neurons was performed by whole-cell patch-clamp recordings (FIG. 33G). Neurons were filled with Lucifer yellow from the recording pipette exhibiting either bipolar or tripolar morphologies (FIGS. 34L, 34M). Responses were measured to a series of hyperpolarizing and depolarizing pulses (FIG. 34N). The hESC-derived neurons produced single action potentials at a threshold depolarization matching the functional properties reported for primary embryonic trigeminal neurons (Grigaliunas et al., 2002). The average resting membrane potential (RMP) was −65.6±6.7 (FIGS. 34L, 34M). Passive membrane and action potential properties were comparable between bipolar and tripolar sensory neurons as summarized in (FIG. 34O) suggesting that two morphologically distinct populations do not reflect functionally distinct subgroups. The robustness of the trigeminal sensory neuron induction protocol was further assessed across multiple hESC and hiPSC lines where comparable percentages of ISL1 and BRN3A expressing neurons were observed (FIG. 33H).

Figure 35A:
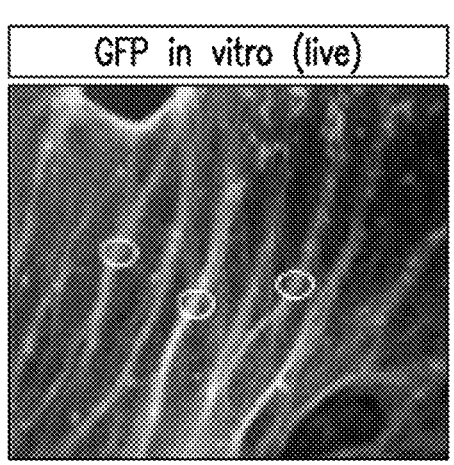
Figure 35B:
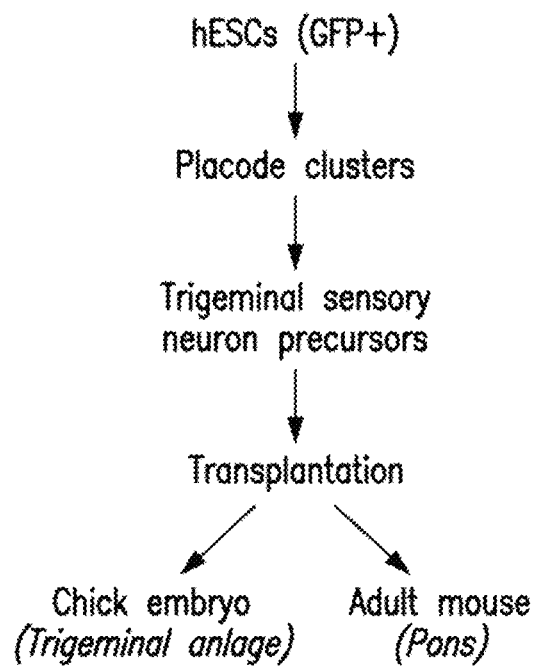
Figure 35C:
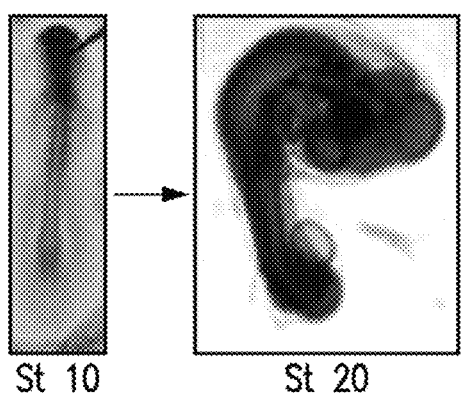
Figure 35D:
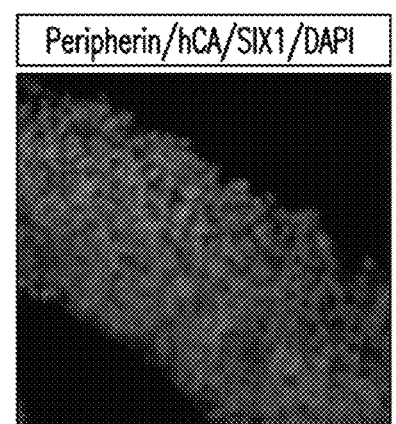

F. In Vivo Analysis of hESC-Derived Trigeminal Neurons in the Developing Chick Embryo and Adult Mouse CNS To assess the in vivo properties of hESC-derived trigeminal placode precursors, PIP-induced neuronal clusters, derived from a constitutively GFP expressing hESC line (FIGS. 35A, 35B), were injected into the developing chick embryo targeting the early trigeminal anlage at H&H stage 10-12 (FIG. 35C). Human cells were identified based on GFP expression and use of human specific antibodies against cytoplasmic antigen (hCA). Two days after in ovo transplantation surviving GFP+ cells were found dispersed in the area of the endogenous chick trigeminal ganglion (FIG. 34P). Extensive GFP+ human fiber bundles coexpressing hCA and peripherin were observed (FIGS. 34Q, 34R). In contrast, no hCA or peripherin expression was detected in the neural tube of the embryo (FIG. 35D). The in vivo fiber outgrowth 2 days after transplantation was reminiscent of the extensive in vitro fiber outgrowth of replated trigeminal neuron clusters (FIG. 35A). Peripherin expression in vivo (FIG. 34S) confirmed the peripheral neuron identity of the grafted cells.

hESC-derived trigeminal neurons were assessed as to whether they can engraft in the adult mouse CNS and project towards a physiological target. The trigeminal nuclei in the brainstem receive afferent innervation from the trigeminal sensory ganglion that is relayed to the contralateral thalamus. The pons was selected as site for transplantation, as it is surgically accessible and located within proximity of the trigeminal brain stem nuclei that receive afferent input from the trigeminal ganglia. Hence, GFP+ human trigeminal neuron clusters were injected into adult NOD/SCID mice via stereotactic surgery. Histological analysis 4 weeks after transplantation showed survival of GFP+ human cell graft in the ventral pons. While GFP+ cell bodies remained tightly clustered at injection site, GFP+ fibers showed extensive projections into the host brain (N=6) including the endogenous trigeminal nuclei. Expression of BRN3A confirmed the sensory neuron identity of the cells. Graft-derived human fiber bundles (hNCAM+ and GFP+) were observed emanating from the graft core.

These data demonstrate in vivo survival of trigeminal placode derivatives, differentiation along sensory neuron lineage and the establishment of axonal projections towards relevant endogenous targets in the embryonic chick and adult mouse brain. The data suggests that trigeminal sensory neurons may be useful for drug screening for pain syndromes and migraines. For example, a read out could be done by in vitro electrophysiology on trigeminal neurons generated from trigeminal placode cells. The data presented herein shows that placodal-trigeminal sensory neurons has single action potentials matching the functional properties recorded for primary trigeminal sensory neurons. Moreover, these cells express diagnostic markers of nociceptive neuron identity include expression of specific sodium channels.

G. Identification of a Putative Pre-Placode Stage

The data presented herein indicate that PIP conditions efficiently induce ophthalmic trigeminal placode fates. To investigate whether other placodal fates can be generated using modified PIP conditions, the presence of putative pre-placode cells in the culture system was addressed.

During vertebrate development, the pre-placode is characterized as the developmental anlage containing precursor cells competent to respond to signals determining placode identity (Martin and Groves, 2006). Pre-placodal cells in various model organisms have been shown to express Six1 and to co-express markers of both ectodermal and neural fate. However, the development of a human pre-placode remains unexplored.

A time-course co-expression analysis was performed for TFAP2A (early ectodermal marker) and PAX6 (early neuroectoderm marker (Zhang et al., 2010)). During the first three days of differentiation only a few sparse patches of PAX6 or TFAP2A expressing cells were observed without evidence of co-expression (FIG. 36A). At day 5, two days following Noggin withdrawal (PIP), there was an increase in the number of TFAP2A+ cells (FIG. 36B) under PIP conditions and a concomitant loss of TFAP2A+ cells in N-SB (FIG. 36C). At day 7, N-SB conditions yielded PAX6+ cells devoid of TFAP2A expression (FIG. 36C) while PIP treated cultures showed extensive co-expression of TFAP2A and PAX6, indicating pre-placode identity (FIG. 36B). The emergence of TFAP2A/PAX6 double positive cells coincided with the onset of SIX1 gene expression and the emergence of SIX1+ clusters around day 7 of differentiation (FIGS. 32B, 37A). By day 11, placode clusters were negative for PAX6 but retained expression of TFAP2A (FIG. 36B) suggesting that early anterior PAX6+ pre-placode cells give rise to PAX6-negative posterior placode populations enriched for PAX3+. This differentiation model was further supported by gene expression data showing a robust PAX3 increase from day 7-11 of PIP (FIG. 36D). Treatment with inhibitors of WNT or FGF signaling from day 7-11 of PIP suppressed PAX3 induction (FIG. 36E) while maintaining PAX6 (FIG. 36F).

These results indicate that endogenous signals contribute to the transition from an anterior PAX6+ pre-placode to a posterior PAX3+ placode lineage. The small number of TFAP2A cells in day 11 N-SB cultures (FIG. 36C) likely represents neural crest precursors (Chambers et al., 2009) that lack PAX6 expression. Under PIP conditions the percentage of contaminating SOX10+NC cells at day 11 was <1% (FIG. 27F).

H. Treatment with FGF-Inhibitor SU5402 at Pre-Placode Stage Induces Lens Fates

Putative pre-placode cells were tested as to whether they can be differentiated into specific placode fates other then trigeminal neurons. The spontaneous appearance of lens precursors (lentoid bodies) from primate and hESCs has been previously reported (Ooto et al., 2003; Zhang et al., 2010), although the lineage origin and inducing signals remained unexplored in those studies.

The impact of four developmental signaling pathways on lens placode specification was tested by using activators and inhibitors of BMP, FGF, WNT, and Hedgehog signaling. To quantify the induction of lens placode fate, the lens precursor marker PITX3 expression was monitored at day 16 of differentiation (FIG. 37B). PITX3 expression was significantly induced in the presence of recombinant BMP4 or upon exposure to the FGF-inhibitory molecule, SU5402 (FIG. 36G). A role for BMPs and FGFs has been previously proposed in developmental studies in the chick (Sjödal et al., 2007). Further differentiation revealed strong induction of αβ-crystalline and the formation of mature lens fiber structures by day 57 (FIG. 36H, left panel). The characteristic layering of lens fibers (FIG. 36H, right panel) mimicked the structural properties of developing lens in vivo.

I. Treatment with SHH at Pre-Placode Stage Induces Anterior Pituitary Cells

Figure 38B:
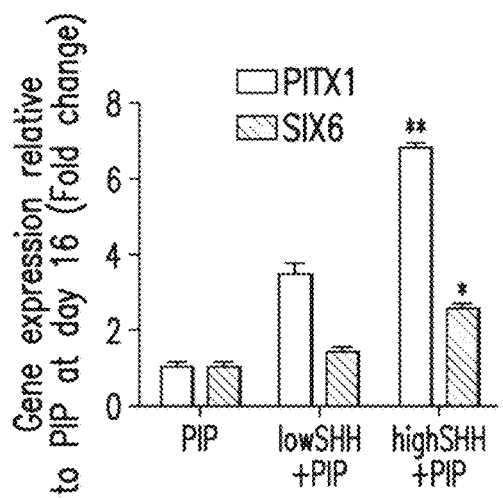
Figures 38C, 38D:
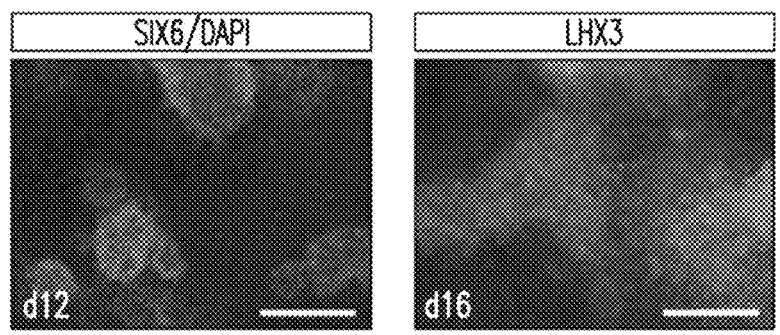

The data presented herein show that pre-placodal cells can be differentiated into anterior pituitary placode and recreate the various pituitary precursors and hormone producing cell types (FIG. 38A). Further treatment with agonists for SHH signaling (FIG. 39A) at the pre-placode stage (day 7-11) induced expression of the oral ectoderm marker SIX6 and PITX1 (FIG. 38B), master regulators of pituitary gland development (Tremblay et al., 1998). Induction of PITX1 and SIX6 at transcript and protein levels was dependent on SHH dose (FIGS. 38B, 38C). Furthermore, SHH treatment triggered the expression of the definitive pituitary precursor marker LHX3 (FIG. 38D).

Figure 38G:
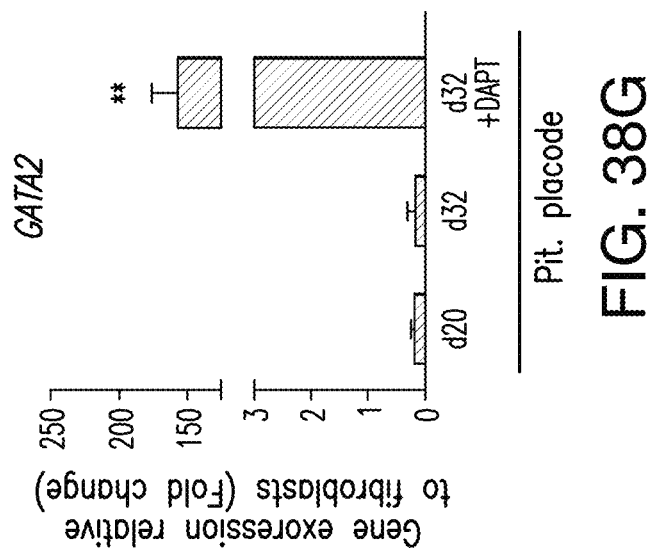
Figure 38F:
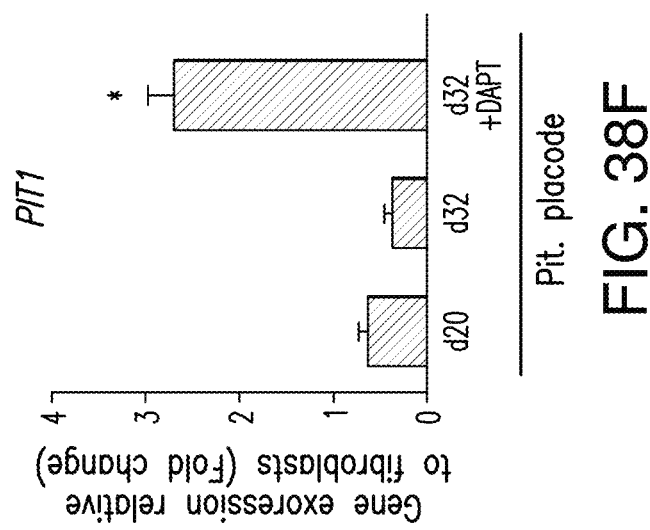
Figure 38E:
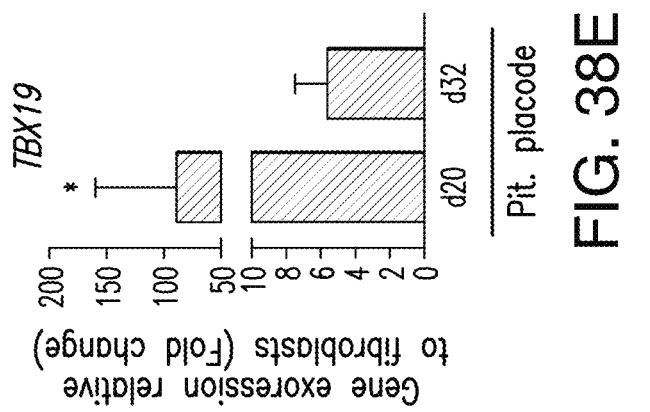
Figure 38H:
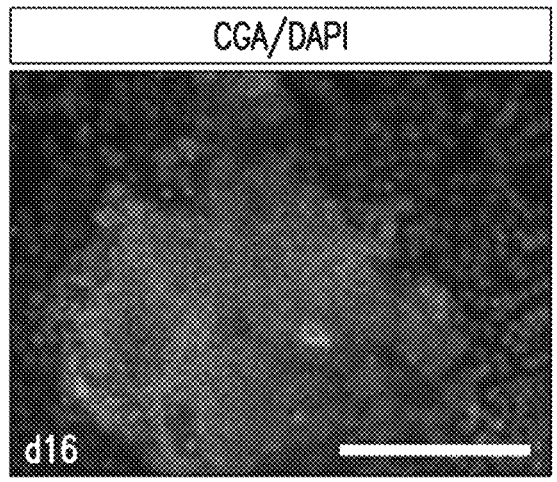
Figure 38I:
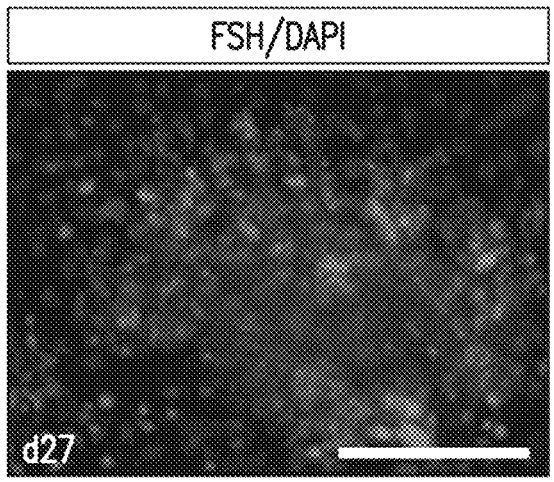
Figure 38J:
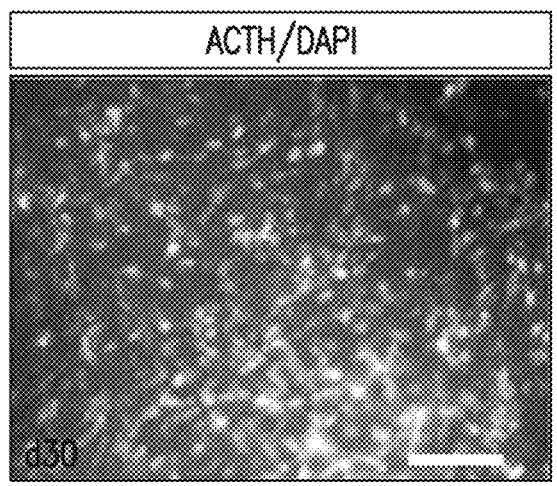
Figure 38K:
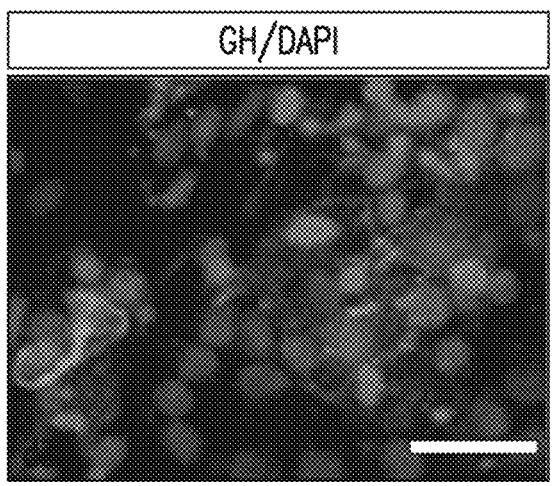

Endocrine cells of the anterior pituitary gland are derived from three main precursors lineages (Scully and Rosenfeld, 2002). Following PIP+SHH treatment, a robust induction of TBX19 was observed (FIG. 38E), that was specific to precursors giving rise to ACTH and MSH producing cells. Induction of PIT1 and GATA2 precursor lineages was less efficient but was increased following treatment with the γ-secretase inhibitor DAPT (FIGS. 38F, 38G).

Immunocytochemistry for pituitary hormones showed expression of CGA by 16 days while protein expression of FSH, ACTH and GH was first observed by day 25-30 of differentiation (FIGS. 38H-38K). The induction of ACTH+ cells was particularly efficient (FIG. 38J) and in vitro release of ACTH hormone could readily be detected by ELISA (FIG. 38L).

Furthermore, these hESC-derived pituitary cells are capable of in vivo survival and function in mouse and rat xenograft models (FIGS. 38M, 39B, 39C). Subcutaneous injection of GFP-marked, hESC-derived pituitary precursors (day 16 of differentiation) into adult male NOD/SCID mice demonstrated survival of GSU and FSH cells in vivo (FIGS. 39D, 39E).

Longer-term survival studies in nude male rats (n=8; 4-6 weeks post grafting) showed significant increases in serum ACTH levels (FIG. 38N) as measured during early morning hours (low point of endogenous ACTH expression during diurnal cycle). Human GH levels were measured in vivo using an ELISA assay that selectively detects human but not mouse GH (FIG. 38O).

Transplantation into rat hosts allowed for repeated blood draws and showed a consistent increase of ACTH and GH levels in grafted as compared to sham injected (matrigel-only) animals. Finally, histological analysis demonstrated an average 0.46±0.015 million surviving hNCAM+ cells (FIG. 38P) at 6 weeks after transplantation. About 10% of the surviving human cells expressed ACTH (FIG. 38Q) and 6% of the cells were immunoreactive for GH (FIG. 38R).

The ability to derive functional hormone producing pituitary cells from hESCs via modified PIP conditions is particularly intriguing given previous work in mouse ESCs suggesting the need for complex co-culture systems to induce pituitary lineages (Suga et al., 2011). In vivo survival and production of graft-derived ACTH and GH suggest translational potential for patients suffering from genetic, surgical or radiation induced hypopituitarism (Tabar, 2011).

ACTH producing in vitro pituitary cells derived from pituitary placode cells could be used to generate ACTH in vitro. ACTH is very important for treating the infantile spasms. Furthermore, one commercially available composition (Acthar Gel) is a long lasting animal product used to treat infantile spasms. Acthar Gel has an disadvantage in that it is currently an extremely expensive pharmaceutical product. Prices per vial have been as high as $36,000. Growth hormone could be also used for metabolic disorders such as growth hormone insufficiency.

VII. Induction of Placode Cells from Non-Placode Cells

In certain embodiments, the present invention provides for compositions, kits and methods for inducing placode precursor cells from non-placode cells, such as, for example, embryonic stem cells (ESCs) including human embryonic stem cells (hESCs), or induced pluripotent stem cells (iPSCs), including human iPSCs. In certain embodiments, the placode precursor cells are induced by culturing the non-placode cells with an inhibitor of SMAD, as described herein. In certain embodiments, the SMAD inhibitor is an ALK inhibitor. In certain embodiments, the ALK inhibitor inhibits the Lefty/Activin/TGFbeta pathways by blocking phosphorylation of the ALK4, ALK5 and/or ALK7 receptors. In certain embodiments, the SMAD inhibitor is SB431542. In certain embodiments, the compositions, kits and methods further include a BMP active agent, for example, BMP4. In certain embodiments, the non-placode cells are cultured in media comprising the SMAD inhibitor and the BMP active agent, wherein the BMP active agent is withdrawn from the media after 1, or 2, or 3, or 4, or 5, or 6, or 7, or 8, or 9, or 10 days of culture. In certain embodiments, the BMP active agent is withdrawn from the media after 3 days of culture. In certain embodiments, the BMP active agent is present in the culture media at a concentration of between about 0.5 and about 20 ng/mL, or between about 1 and about 15 ng/ml, or between about 2 and about 10 ng/ml, or between about 3 and about 5 ng/ml. In certain embodiments the BMP active agent is present in the culture media at a concentration of about 5 ng/ml.

In certain embodiments, culturing the non-placode cells according to the methods described herein induces differentiation of cells expressing detectable levels of SIX1 and PAX6. In certain embodiments the cells also express a detectable level of TFAP2A. In certain embodiments, the cells expressing detectable levels of SIX1 and PAX6 are placode precursor cells.

In certain embodiments, culturing the non-placode cells according to the methods described herein induces cells expressing detectable levels of SIX1 and PAX3. In certain embodiments, the cells expressing detectable levels of SIX1 and PAX3 are trigeminal placode cells. in certain embodiments, the cells expressing detectable levels of SIX1 and PAX3 are induced by culturing cells expressing detectable levels of SIX1 and PAX6 (for example, placode precursor cells) with a trigeminal placode inducing agent such as brain-derived neurotrophic factor (BDNF) and/or a Wnt. In certain embodiments, the BDNF and Wnt are human BDNF and Wnt. In certain embodiments, the trigeminal placode inducing agents are added to the culture media at day 3, or day 4, or day 5, or day 6, or day 7, or day 8, or day 9, or day 10 of the placode inducing cell culture protocol described herein.

In certain embodiments, the induced cells expressing SIX1 and PAX3 also express detectable levels of GD2. In certain embodiments, the cells expressing SIX1, PAX3 and GD2 are trigeminal placode cells. In certain embodiments, the present invention provides for methods of isolating or sorting cells expressing detectable levels of GD2 from a mixture of cells not expressing detectable levels of GD2. In certain embodiments, said methods include FACS sorting or any other cell sorting method known in the art.

In certain embodiments, the induced cells expressing SIX1 and PAX3 also express detectable levels of CD57 (HNK1). In certain embodiments, the cells expressing SIX1, PAX3 and CD57 (HNK1) are trigeminal placode cells. In certain embodiments, the present invention provides for methods of isolating or sorting cells expressing detectable levels of CD57 (HNK1) from a mixture of cells not expressing detectable levels of CD57 (HNK1). In certain embodiments, said methods include FACS sorting or any other cell sorting method known in the art.

In certain embodiments, culturing the non-placode cells according to the methods described herein induces cells expressing detectable levels of SIX1 and PITX3. In certain embodiments, the cells expressing detectable levels of SIX1 and PITX3 are lens placode cells. In certain embodiments, the cells expressing detectable levels of SIX1 and PITX3 are induced by culturing cells expressing detectable levels of SIX1 and PAX6 (for example, placode precursor cells) with a lens placode inducing agent such as sonic hedgehog (SHH), purmorphamine, a γ-secretase inhibitor and/or an FGF inhibitor. In certain embodiments, the SHH is human SHH. In certain embodiments, the lens placode inducing agents are added to the culture media at day 3, or day 4, or day 5, or day 6, or day 7, or day 8, or day 9, or day 10 of the placode inducing cell culture protocol described herein.

In certain embodiments, culturing the non-placode cells according to the methods described herein induces cells expressing detectable levels of SIX1 and PITX1. In certain embodiments, the cells expressing detectable levels of SIX1 and PITX1 are pituitary placode cells. In certain embodiments, the cells expressing detectable levels of SIX1 and PITX1 are induced by culturing cells expressing detectable levels of SIX1 and PAX6 (for example, placode precursor cells) with a pituitary patterning factor, for example, sonic hedgehog (SHH), purmorphamine, a γ-secretase inhibitor, FGF8, FGF10, BMP2, and/or hypothalamus CM. In certain embodiments, the SHH, FGF8, FGF10, BMP2 and hypothalamus CM are human SHH, FGF8, FGF10, BMP2, and hypothalamus CM. In certain embodiments, the pituitary patterning factors are added to the culture media at day 3, or day 4, or day 5, or day 6, or day 7, or day 8, or day 9, or day 10 of the placode inducing culture protocol described herein. In certain embodiments, the pituitary placodes cultured under the conditions described herein further differentiate into pituitary hormone expressing cells.

In certain embodiments, the present invention provides for methods of grafting pituitary placode cells and/or pituitary hormone expressing cells induced according to the methods described herein into a subject in need thereof, for example, in a subject diagnosed or at risk for hypopituitarism. In certain embodiments, the cells are grafted into the brain or pituitary gland of the subject.

In certain embodiments, the invention provides for cells prepared according to the methods described herein.

In certain embodiments, "detectable" levels of proteins means that the proteins are detectable by immunocytochemical techniques known in the art.

In certain embodiments, an "induced pluripotent stem cell" refers to a pluripotent stem cell that is generated from a non-pluripotent cell, such as from an adult cell, for example, and adult somatic cell, or from any other differentiated or mature cell.

In certain embodiments, the cells prepared according to the methods described herein, and administered or grafted to a recipient subject for therapeutic purposes, as described herein, are heterologous, autologous, allogenic, xenogeneic, or syngeneic to the recipient of the cells.

VIII. Screen for Placode Inducing Agents

In certain embodiments, the present invention provides for methods of screening for compounds that enhance the induction of placode and placode precursor cells induced from non-placode cells cultured according to the methods described herein.

In certain embodiments the screening method comprises culturing non-placode cells according to the methods described herein, wherein a test compound is added to the culture media at day 1, or day 2, or day 3, or day 4, or day 5, or day 6, or day 7. In certain embodiments, the test compound is added to the culture media at day 3. In certain embodiments, the screening method comprises determining the level of detectable expression of placode precursor markers, such as SIX1 and/or PAX6 and/or TFAP2A, in cells cultured with the test compound and comparing said levels to the level of expression of the same markers in cells cultured in media without the test compound, wherein an increase in the level of marker expression in the cells cultured with the test compound indicates that the test compound enhances placode precursor induction.

In certain embodiments, the present invention provides for compounds that enhance placode precursor induction as described herein. In certain embodiments, the compound is BRL-54443, or a salt thereof, such as BRL-54443 maleate.

In certain embodiments, the compound is parthenolide.

In certain embodiments, the compound is phenantroline.

In certain embodiments, the invention provides for methods of enhancing the induction of placode precursor cells, wherein non-placode cells are cultured according to the methods described herein, and wherein the cell culture media is supplemented with a compound that enhances placode precursor induction at a concentration of between about 0.001 and about 20 mM, or between about 0.01 and about 15 mm, or between about 0.1 and about 10 mM, or between about 1 and about 10 mM, or between about 2 and 5 mM.

REFERENCES

Reference List 1

The following references are herein incorporated in their entirety. Barberi, et al., (2003). *Nat Biotechnol.* 10:1200-1207; Bouwmeester, et al., (1996). *Nature* 382:595-601; Briscoe, J., and Ericson, J. (1999). *Semin Cell Dev Biol.* 3:353-62; Chambers, et al., (2009). *Nat Biotechnol* 27, 275-280; Charrier, et al., (2002). *Development* 129:4785-4796; Charron, et al., (2003). *Cell* 113:11-23; D'Amour, et al., (2005). *Nat Biotechnol* 23, 1534-1541; Dennis, et al., (2003). DAVID: Database for Annotation, Visualization, and Integrated Discovery. *Genome Biol* 4, P3; Eiraku, et al., (2008). *Cell Stem Cell* 3, 519-53; Elkabetz, et al., (2008). *Genes Dev* 22:152-165; Ericson, et al., (1996). *Cell* 87, 661-673.; Fasano, et al., (2007). *Cell Stem Cell* 1, 87-99; Fasano, et al., (2009). *Genes Dev* 23, 561-574; Glinka, et al., (1998). *Nature* 391, 357-362; Haung, et al., (2009). *Nat Protoc* 4, 44-57; Hunter, et al., (1991). *Proc Natl Acad Sci USA* 88, 3666-3670; Ivanova, et al., (2006). *Nature* 442, 533-538; Jeong, et al., (2003). *Development* 130, 3891-3902; Jeong, et al., (2005). *Development.* 133, 7761-7772; Jeong, et al., (2008) *Nat Genet* 40, 1348-1353; Jessell, (2000). *Nat Rev Genet* 1, 20-29; Jessell, et al., (1989). *Ciba Found Symp* 144, 255-276; discussion 276-280, 290-255; Joksimovic, et al., (2009). *Nat Neurosci* 12, 125-131; Kimura-Yoshida, et al., (2006). *PNAS* 104, 5919-59249; Kittappa, et al., (2007). *PLoS Biol* 5, e325; Li, et al., (2008). *Stem Cells* 4, 886-89399; Lois, et al., (2002). *Science* 295, 868-872; Lyuksyutova, et al., (2003). *Science* 302, 1903-1904; Matise, et al., (1998). *Development* 125, 2759-2770; Mizuseki, et al., (2003). *Proc Natl Acad Sci USA* 100, 5828-5833; Mukhopadhyay, et al., (2001). *Dev Cell* 3, 423-434; Mullor, et al., (2002).*Trends Cell Biol* 12, 562-569; Ono, et al., (2007). *Development* 134, 3213-3225; Perrier, et al., (2004). *Proc Natl Acad Sci USA* 101, 12543-12548; Placzek, et al., (1993). *Development* 117, 205-218; Placzek, M. (1995). *Curr Opin Genet Dev* 5, 499-506; Placzek, et al., (2003). *Development* 130, 4809-4821; Placzek, et al., (2005). *Nat Rev Neurosci* 6, 230-240; Roelink, et al., (1994). *Cell* 76, 761-775; Shen, et al., (2006). *Nat Neurosci* 9, 743-751; Shirasaki, et al., (1995). *Neuron* 14, 961-972; Suter, et al., *Stem Cells,* 27(1):49-58 (2009); Venezia, et al., (2003). *PLoS Biol* 10, e301; Watanabe, et al., (2005). *Nat Neuro* 3, 288-296; Weinstein, et al., (1999). *Annu Rev Cell Dev Biol* 15, 411-433; Wichterle, et al., (2002). *Cell* 110, 385-397; Zhang, et al., *Nature Biotechnology* 19, 1129-1133 (2001); and Zoltewicz, et al., (1999). *Development* 126, 5085-5095.

Reference List 2

Abdelhak, S., Kalatzis, V., Heilig, R., Compain, S., Samson, D., Vincent, C., Weil, D., Cruaud, C., Sahly, I., Leibovici, M., et al. (1997). A human homologue of the Drosophila eyes absent gene underlies branchio-oto-renal (BOR) syndrome and identifies a novel gene family. *Nature genetics* 15, 157-164.

Ahrens, K., and Schlosser, G. (2005). Tissues and signals involved in the induction of placodal Six1 expression in *Xenopus laevis*. Developmental biology 288, 40-59.

Arkell, R., and Beddington, R. S. (1997). BMP-7 influences pattern and growth of the developing hindbrain of mouse embryos. *Development* 124, 1-12.

Bailey, A. P., Bhattacharyya, S., Bronner-Fraser, M., and Streit, A. (2006). Lens specification is the ground state of all sensory placodes, from which FGF promotes olfactory identity. *Dev Cell* 11, 505-517.

Baker, C. V., and Bronner-Fraser, M. (2001). Vertebrate cranial placodes I. *Embryonic induction. Dev Biol* 232, 1-61.

Balmer, C. W., and LaMantia, A. S. (2005). *Noses and neurons: induction, morphogenesis, and neuronal differentiation in the peripheral olfactory pathway. Developmental dynamics: an official publication of the American Association of Anatomists* 234, 464-481.

Barnett, E. M., Jacobsen, G., Evans, G., Cassell, M., and Perlman, S. (1994). Herpes simplex encephalitis in the temporal cortex and limbic system after trigeminal nerve inoculation. *J Infect Dis* 169, 782-786.

Bernardo, A. S., Faial, T., Gardner, L., Niakan, K. K., Ortmann, D., Senner, C. E., Callery, E. M., Trotter, M. W., Hemberger, M., Smith, J. C., et al. (2011). BRACHYURY and CDX2 mediate BMP-induced differentiation of human and mouse pluripotent stem cells into embryonic and extraembryonic lineages. *Cell Stem Cell* 9, 144-155.

Bhattacharyya, S., and Bronner-Fraser, M. (2004). Hierarchy of regulatory events in sensory placode development. *Curr Opin Genet Dev* 14, 520-526.

Chambers, S. M., Fasano, C. A., Papapetrou, E. P., Tomishima, M., Sadelain, M., and Studer, L. (2009). Highly efficient neural conversion of human ES and iPS cells by dual inhibition of SMAD signaling. *Nat Biotechnol* 27, 275-280.

Chambers, S. M., Qi, Y., Mica, Y., Lee, G., Zhang, X. J., Niu, L., Bilsland, J., Cao, L., Stevens, E., Whiting, P., et al. (2012). Combined small-molecule inhibition accelerates developmental timing and converts human pluripotent stem cells into nociceptors. *Nat Biotechnol* 30, 715-720.

Chen, W., Jongkamonwiwat, N., Abbas, L., Eshtan, S. J., Johnson, S. L., Kuhn, S., Milo, M., Thurlow, J. K., Andrews, P. W., Marcotti, W., et al. (2012). Restoration of auditory evoked responses by human EScell-derived otic progenitors. *Nature* 490, 278-282.

Colas, J. F., and Schoenwolf, G. C. (2003). Localization of cartilage linking protein 1 during primary neurulation in the chick embryo. *Brain Res Dev Brain Res* 141, 141-148.

Dennis, G., Sherman, B. T., Hosack, D. A., Yang, J., Gao, W., Lane, H. C., and Lempicki, R. A. (2003). DAVID: Database for Annotation, Visualization, and Integrated Discovery. *Genome Biology* 2003 4:P3 4, P3.

Elkabetz, Y., Panagiotakos, G., Al Shamy, G., Socci, N. D., Tabar, V., and Studer, L. (2008). Human ES cell-derived neural rosettes reveal a functionally distinct early neural stem cell stage. *Genes Dev* 22, 152-165.

Grigaliunas, A., Bradley, R. M., MacCallum, D. K., and Mistretta, C. M. (2002). Distinctive neurophysiological properties of embryonic trigeminal and geniculate neurons in culture. *Journal of Neurophysiology* 88, 2058-2074.

Grotewold, L., Plum, M., Dildrop, R., Peters, T., and Rüther, U. (2001). Bambi is coexpressed with Bmp-4 during mouse embryogenesis. *Mech Dev* 100, 327-330.

Hunter, C. S., and Rhodes, S. J. (2005). LIM-homeodomain genes in mammalian development and human disease. *Mol Biol Rep* 32, 67-77.

Ishihara, T., Sato, S., Ikeda, K., Yajima, H., and Kawakami, K. (2008). Multiple evolutionarily conserved enhancers control expression of Eya1. *Dev Dyn* 237, 3142-3156.

Koehler, K. R., Mikosz, A. M., Molosh, A. I., Patel, D., and Hashino, E. (2013). Generation of inner ear sensory epithelia from pluripotent stem cells in 3D culture. *Nature* doi: 10. 1038/nature12298.

Kudoh, T., Concha, M. L., Houart, C., Dawid, I. B., and Wilson, S. W. (2004). Combinatorial Fgf and Bmp signalling patterns the gastrula ectoderm into prospective neural and epidermal domains. *Development* 131, 3581-3592.

Kwon, H. J., Bhat, N., Sweet, E. M., Cornell, R. A., and Riley, B. B. (2010). Identification of early requirements for preplacodal ectoderm and sensory organ development. *PLoS Genet* 6, e1001133.

Lafaille, F. G., Pessach, I. M., Zhang, S.-Y., Ciancanelli, M. J., Herman, M., Abhyankar, A., Ying, S.-Y., Keros, S., Goldstein, P. A., Mostoslaysky, G., et al. (2012). Impaired intrinsic immunity to HSV-1 in human iPSC-derived TLR3-deficient CNS cells. *Nature* 491, 769-773.

Lee, G., Kim, H., Elkabetz, Y., Al Shamy, G., Panagiotakos, G., Barberi, T., Tabar, V., and Studer, L. (2007). Isolation and directed differentiation of neural crest stem cells derived from human embryonic stem cells. *Nat Biotechnol* 25, 1468-1475.

Leung, A. W., Kent Morest, D., and Li, J. Y. (2013). Differential BMP signaling controls formation and differentiation of multipotent preplacodal ectoderm progenitors from human embryonic stem cells. *Dev Biol* 379, 208-220.

Litsiou, A., Hanson, S., and Streit, A. (2005). A balance of FGF, BMP and WNT signalling positions the future placode territory in the head. *Development* 132, 4051-4062.

Love, S., and Coakham, H. B. (2001). Trigeminal neuralgia: pathology and pathogenesis. *Brain* 124, 2347-2360.

Mackay, D. R., Hu, M., Li, B., Rhéaume, C., and Dai, X. (2006). The mouse Ovol2 gene is required for cranial neural tube development. *Dev Biol* 291, 38-52.

Martin, K., and Groves, A. K. (2006). Competence of cranial ectoderm to respond to Fgf signaling suggests a two-step model of otic placode induction. *Development* 133, 877-887.

McCabe, K. L., Manzo, A., Gammill, L. S., and Bronner-Fraser, M. (2004). Discovery of genes implicated in placode formation. *Dev Biol* 274, 462-477.

McCauley, D. W., and Bronner-Fraser, M. (2002). Conservation of Pax gene expression in ectodermal mplacodes of the lamprey. *Gene* 287, 129-139.

Menendez, L., Yatskievych, T. A., Antin, P. B., and Dalton, S. (2011). Wnt signaling and a Smad pathway blockade direct the differentiation of human pluripotent stem cells to multipotent neural crest cells. *Proceedings of the National Academy of Sciences of the United States of America* 108, 19240-19245.

Mengarelli, I., and Barberi, T. (2013). Derivation of multiple cranial tissues and isolation of lens epithelium-like cells from human embryonic stem cells. *Stem Cells Transl Med* 2, 94-106.

Metcalfe, W. K., Myers, P. Z., Trevarrow, B., Bass, M. B., and Kimmel, C. B. (1990). Primary neurons that express the L2/HNK-1 carbohydrate during early development in the zebrafish. *Development* 110, 491-504.

Mica, Y., Lee, G., Chambers, S. M., Tomishima, M. J., and Studer, L. (2013). Modeling neural crest induction, melanocyte specification, and disease-related pigmentation defects in hESCs and patient specific iPSCs. *Cell Rep* 3, 1140-1152.

O'Rahilly, R. M., F. (1987). *Developmental stages in human embryos*, Vol 637, (Washington, D.C.: Carnegie Institution of Washington).

Ooto, S., Haruta, M., Honda, Y., Kawasaki, H., Sasai, Y., and Takahashi, M. (2003). Induction of the differentiation of lentoids from primate embryonic stem cells. *Invest Ophthalmol Vis Sci* 44, 2689-2693.

Oshima, K., Shin, K., Diensthuber, M., Peng, A. W., Ricci, A. J., and Heller, S. (2010). Mechanosensitive hair cell-like cells from embryonic and induced pluripotent stem cells. *Cell* 141, 704-716.

Pieper, M., Ahrens, K., Rink, E., Peter, A., and Schlosser, G. (2012). Differential distribution of competence for panplacodal and neural crest induction to non-neural and neural ectoderm. *Development* 139, 1175-1187.

Reubinoff, B. E., Itsykson, P., Turetsky, T., Pera, M. F., Reinhartz, E., Itzik, A., and Ben-Hur, T. (2001). Neural progenitors from human embryonic stem cells. *Nature biotechnology* 19, 1134-1140.

Ruf, R. G., Xu, P. X., Silvius, D., Otto, E. A., Beekmann, F., Muerb, U. T., Kumar, S., Neuhaus, T. J., Kemper, M. J., Raymond, R. M., Jr., et al. (2004). *SIX1 mutations cause branchio-oto-renal syndrome by disruption of EYA1-SIX1-DNA complexes. Proceedings of the National Academy of Sciences of the United States of America* 101, 8090-8095.

Sasaki, H., and Hogan, B. L. (1993). Differential expression of multiple fork head related genes during gastrulation and axial pattern formation in the mouse embryo. *Development* 118, 47-59.

Schlosser, G. (2006). Induction and specification of cranial placodes. *Dev Biol* 294, 303-351. Scully, K. M., and Rosenfeld, M. G. (2002). Pituitary development: regulatory codes in mammalian organogenesis. *Science* 295, 2231-2235.

Shi, F., Corrales, C. E., Liberman, M. C., and Edge, A. S. (2007). BMP4 induction of sensory neurons from human embryonic stem cells and reinnervation of sensory epithelium. *Eur J Neurosci* 26, 3016-3023.

Sjödal, M., Edlund, T., and Gunhaga, L. (2007). Time of exposure to BMP signals plays a key role in the specification of the olfactory and lens placodes ex vivo. *Dev Cell* 13, 141-149.

Stark, M. R., Sechrist, J., Bronner-Fraser, M., and Marcelle, C. (1997). Neural tube-ectoderm interactions are required for trigeminal placode formation. *Development* 124, 4287-4295.

Suga, H., Kadoshima, T., Minaguchi, M., Ohgushi, M., Soen, M., Nakano, T., Takata, N., Wataya, T., Muguruma, K., Miyoshi, H., et al. (2011). Self-formation of functional adenohypophysis in three-dimensional culture. *Nature* 480, 57-62.

Tabar, V. (2011). Making a pituitary gland in a dish. *Cell Stem Cell* 9, 490-491. Tremblay, J. J., Lanctot, C., and Drouin, J. (1998). The pan-pituitary activator of transcription, Ptx1 (pituitary homeobox 1), acts in synergy with SF-1 and Pit1 and is an upstream regulator of the Lim-homeodomain gene Lim3/Lhx3. *Mol Endocrinol* 12, 428-441.

Wilson, P. A., Lagna, G., Suzuki, A., and Hemmati-Brivanlou, A. (1997). Concentration-dependent patterning of the Xenopus ectoderm by BMP4 and its signal transducer Smad1. Development 124, 3177-3184.

Xu, R. H., Chen, X., Li, D. S., Li, R., Addicks, G. C., Glennon, C., Zwaka, T. P., and Thomson, J. A. (2002). BMP4 initiates human embryonic stem cell differentiation to trophoblast. *Nat Biotechnol* 20, 1261-1264.

Zhang, S. C., Wernig, M., Duncan, I. D., Brustle, O., and Thomson, J. A. (2001). In vitro differentiation of transplantable neural precursors from human embryonic stem cells. *Nat Biotechnol* 19, 1129-1133.

Zhang, X., Huang, C. T., Chen, J., Pankratz, M. T., Xi, J., Li, J., Yang, Y., Lavaute, T. M., Li, X., Ayala, M., et al. (2010). Pax6 is a human neuroectoderm cell fate determinant. *Cell Stem Cell* 7, 90-100.

Reference List 3

Amit, M., and Itskovitz-Eldor, J. (2002). Derivation and spontaneous differentiation of human embryonic stem cells. *Journal of Anatomy* 200, 225-232.

Chambers, S. M., Fasano, C. A., Papapetrou, E. P., Tomishima, M., Sadelain, M., and Studer, L. (2009). Highly efficient neural conversion of human ES and iPS cells by dual inhibition of SMAD signaling. *Nat Biotechnol* 27, 275-280.

Chen, G., Gulbranson, D. R., Hou, Z., Bolin, J. M., Ruotti, V., Probasco, M. D., Smuga-Otto, K., Howden, S. E., Diol, N. R., Propson, N. E., et al. (2011). Chemically defined conditions for human iPSC derivation and culture. *Nat Methods* 8, 424-429.

Dennis, G., Sherman, B. T., Hosack, D. A., Yang, J., Gao, W., Lane, H. C., and Lempicki, R. A. (2003). DAVID: Database for Annotation, Visualization, and Integrated Discovery. *Genome Biology* 2003 4:P3 4, P3.

Downey, T. (2006). Analysis of a multifactor microarray study using Partek genomics solution. *Methods Enzymol* 411, 256-270.

Huang, D. W., Sherman, B. T., and Lempicki, R. A. (2009). Systematic and integrative analysis of large gene lists using DAVID bioinformatics resources. *Nature Protocols* 4, 44-57.

O'Rahilly, R. M., F. (1987). *Developmental stages in human embryos*, Vol 637, (Washington, D.C.: Carnegie Institution of Washington).

EXPERIMENTAL

The following examples serve to illustrate certain embodiments and aspects of the present invention and are not to be construed as limiting the scope thereof. In the experimental disclosures which follow, the following abbreviations apply: N (normal); M (molar); mM (millimolar); µM (micromolar); mol (moles); mmol (millimoles); (micromoles); nmol (nanomoles); pmol (picomoles); g (grams); mg (milligrams); µg (micrograms); ng (nanograms); pg (picograms); L and (liters); ml (milliliters); µl (microliters); cm (centimeters); mm (millimeters); µm (micrometers); nm (nanometers); U (units); min (minute); s and sec (second); deg (degree); and ° C. (degrees Centigrade/Celsius).

The following are general cell culture formulations:

hESC Medium for Maintenance (1 Liter):
  800 mL DMEM/F12, 200 mL of Knockout Serum Replacement, 5 mL of 200 mM L-Glutamine, 5 mL of Pen/Strep, 10 mL of 10 mM MEM minimum non-essential amino acids solution, 1000 µL of β-mercaptoethanol, bFGF (final concentration is 4 ng/mL)

KSR Medium for hESC Differentiation (1 Liter):
  820 mL of Knock out DMEM, 150 mL of Knock out Serum Replacement, 10 mL of 200 mM L-Glutamine, 10 mL of Pen/Strep, 10 mL of 10 mM MEM, 1 mL of β-mercaptoethanol N2 Medium for hESC Differentiation (1 Liter):
  985 ml dist. $H_2O$ with DMEM/F12 powder, 1.55 g Glucose, 2.00 g $NaHCO_3$, 25 mg insulin, 0.1 g apotransferrin, 30 nM sodium selenite, 100 µM putrescine, 20 nM progesterone DMEM with 10% FBS for Preparing PMEF (1 Liter):
  885 mL of DMEM, 100 mL of FBS, 10 mL of Pen/Strep, 5 mL of L-Glutamine Alpha MEM with 10% FBS for preparing MS-5 feeder (1 liter):
  890 mL of Alpha MEM, 100 mL of FBS, 10 mL of Pen/Strep Gelatin Solution (500 ml):
  Dissolve 0.5 g of gelatin in 500 ml of warm (50-60° C.) Milli-Q water. Cool to room temperature.

Noggin was purchased from R&D system as Catalog Number:719-NG, Recombinant Mouse Noggin Fc Chimera.

Example I

Bone morphogenetic protein (BMP) Levels Determine Placode Fate Identity: Sensory placodes are developmental structures formed at the interface of early neuroectodermal and non-neural ectoderm tissue. To address whether the N-SB culture system is suitable for the derivation of placodal cells, a set of markers was established to identify placode identity in human embryonic stem cells (hESCs)-derived cultures. From studies in other model organisms, a number of candidate markers to identify human placodal precursor during hESC differentiation include, but are not limited to, members of the Six, Eya, and Dlx family of transcription factors. Six1 marks a pre-placodal region and placodal cells in model organisms but is also expressed in skeletal muscle precursors.

Immunocytochemical analyses revealed 6%±4% Six1+ cells at day 11 of N-SB differentiation. The absence of the expression of skeletal muscle markers in Six1+ cells suggested placodal precursor cell identity.

A large number of developmental studies have demonstrated a role for BMP signaling during early ectodermal patterning in vivo. One model suggests that a gradient of BMP activity within the ectoderm allocates different cell fates, with high levels of signaling promoting epidermis, moderate levels inducing placodes, intermediate levels specifying neural crest and complete absence of BMP activity being required for neural plate formation in vivo Streit, et al., Dev Biol, 2004. 276(1): p. 1-15, herein incorporated by reference. To test whether addition of exogenous BMPs enhances the derivation of Six1+ cells, SB431542 (1 µM) treated hESCs were exposed to various concentration of BMP4. However, early addition of BMP4 caused a dramatic morphological chance of the cells and induction of cdx2 suggesting differentiation towards trophoectodermal fates. The absence of SB431542 has demonstrated that early exposure to BMPs can drive trophoectodermal fates during hESC differentiation. Chambers, et al., Nat Biotechnol, 2009. 27(3): p. 275-80; Xu, et al., Nat Biotechnol, 2002. 20(12): p. 1261-4, herein incorporated by reference.

Figure 11A:
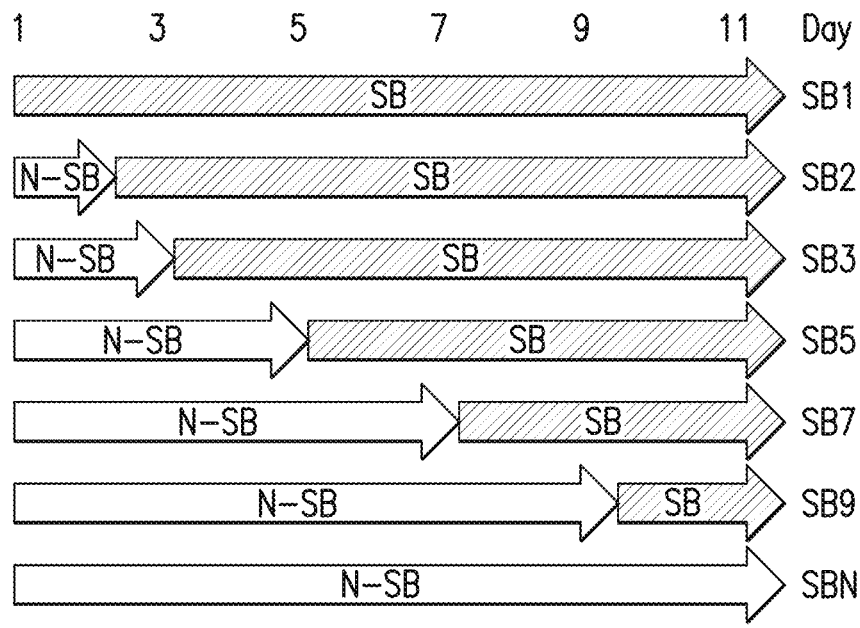
FIGS. 11A-11D show exemplary derivation of Six1+ placodal precursors using a modified N-SB protocol.
Figure 11B:
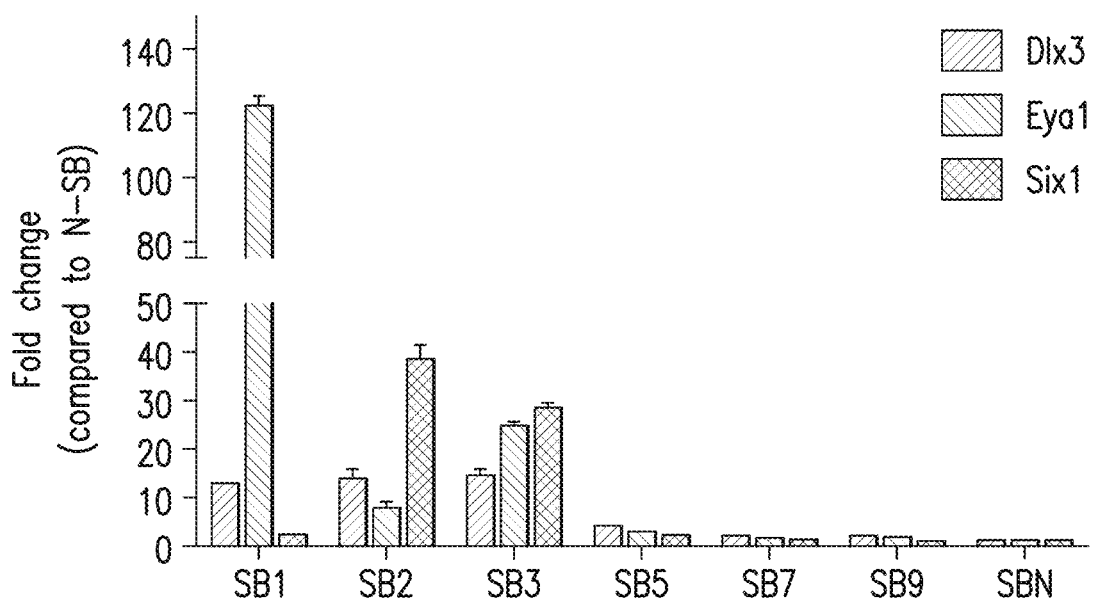
Figure 11C:
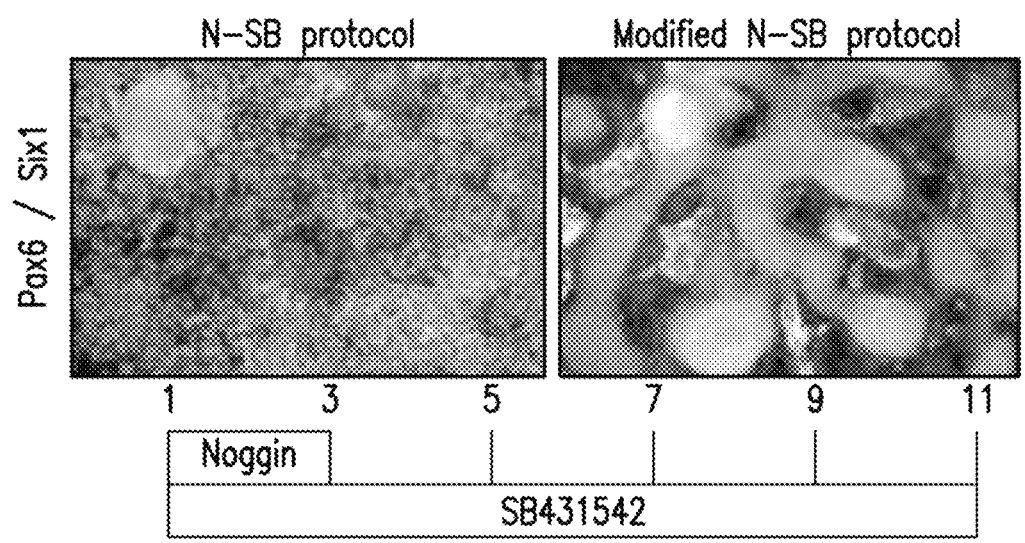
Figure 11D:
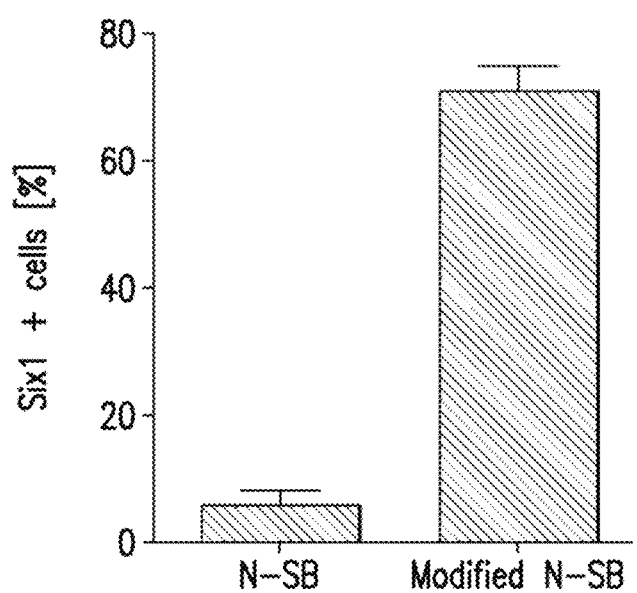

Withdrawal of the BMP inhibitor noggin during N-SB differentiation may enhance the emergence of placodal fates by de-repressing endogenous BMP signaling. To this end, a time course study was performed by removing noggin at different time points of the NSB protocol (FIG. 11A) while monitoring the induction of placodal marker (—FIG. 11B) trophoectodermal, neurectodermal by qRT-PCR analysis at day 11 of differentiation. Withdrawal of noggin at day 2 or 3 of differentiation yielded efficient induction of Six1 while noggin withdrawal at day 1 of differentiation lead to the induction of Eya1 in the absence of Six1 expression. The induction of morphological changes and expression of Cdx2 in cultures subjected to day 1 noggin withdrawal indicated differentiation towards trophoectodermal fates and suggested that Eya1 is expressed in trophoectodermal precursors in addition to placodal cells. Immunocytochemical analysis demonstrated that that noggin withdrawal at day 3 of differentiation induced a switch from primarily Pax6+ neurectodermal cells obtained under standard N-SB conditions to populations composed of 71% Six1+ putative placode precursor cells (FIG. 11C, D). Co-labeling studies demonstrated co-expression of other placodal markers in Six1+ cells such as Eya1 in the absence of markers of skeletal muscle fates.

Microarray analysis reveals novel human placode progenitor gene expression: To obtain an unbiased measure of placode induction of placode precursor cell identity, the inventors performed a time course analysis of global gene expression using the Illumina bead array platform. RNA was collected at five time points during differentiation (Day 1, 3, 5, 7, and 11) in control N-SB cultures (yielding anterior neural plate cells; noggin/SB431542 treatment for day 1-11) and under conditions promoting placodal fates (anterior placode cells; SB431542 treatment for 11 days; Noggin treatment from day 1-3). Prior to a microarray analysis the quality of each sample was verified for expression of a panel of placode markers (Six1, Dlx3, Eya1) and the absence of other lineages such as Foxa2 (endoderm), Sox17 (endoderm), MyoD (skeletal muscle), cdx2 (trophoblast), and T (Brachyury)(mesoderm). Global gene expression studies were carried out in three independent samples for each time point and culture condition. Data were converted into log 2 ratios comparing levels of gene expression in placode versus N-SB protocol during differentiation (FIG. 12A-D).

The time course data were subjected to gene ontology (GO) enrichment analysis using DAVID (http://david-.abcc.ncifcrf.gov/; Dennis, et al., Genome Biology 2003 4:P3, 2003. 4(5): p. P3, herein incorporated by reference) as unbiased assessment of placode transcription profile. Among the transcripts highly enriched in placode conditions versus NSB control cultures at day 5 and day 7 of differentiation were genes associated with the sensory organ development, BMP and Wnt pathways, inner ear development and neural patterning. Enrichment for sensory organ development and neural patterning factors further confirm anterior placode identity of cultures derived using the modified N-SB protocol. Neural plate markers and neuronal markers were also down-regulated in the modified N-SB (noggin withdrawal after 2 days of differentiation) versus NSB (i.e. treatment of cells with at least 2 SMAD or BMP signaling compounds) protocol.

To gain insight into specific genes differentially expressed during placode specification, the inventors performed pair-wise comparisons at for each differentiation stage. While the majority of genes significantly regulated at day 5 and day 7 of differentiation (as compared to day 1) were shared in NSB and modified N-SB protocol, a subset of transcripts was differentially regulated. In particular, an increase in Islet-1, a very well known marker for sensory neuron development was observed in the modified N-SB protocol. Isl1 is also expressed in other lineages such as motoneuron, heart progenitors and pancreatic islet cells. The early expression onset of expression during hESC differentiation suggests that Islet-1 marks early placode precursor cells similar to its expression during zebrafish development where it marks the horseshoe shaped at the anterior pre-placodal region. Thus, Islet-1 is one of the first placode markers expressed during differentiation of human pluripotent stem cells. The modified N-SB protocol induced highly enriched expression for Islet-1 at day 5, day 7, day 9 and day 11 when compared to NSB conditions. In microarray data, placode genes, GATA3, Dlx5, TFAP2a, and TFAP2c are enriched. Significant changes in Wnt pathway and BMP pathway components were also observed. For example, as early as Day 5, there was a significant increase of the Wnt pathway inhibitor DKK-1 and this increase was sustained over the course of the protocol. A significant down-regulation of several Wnt receptors was observed in response to removal of Noggin. Induction of BMP antagonists such as gremlin-l and BAMBI that are activated in response to BMP signaling confirm that noggin withdrawal causes changes in endogenous BMP signaling during hESC differentiation with a corresponding increase of downstream genes.

Furthermore, a number of additional genes were identified that were differentially expressed during anterior placode specification including Shisa2, Ovol2 and Foxc1. Differential expression for these and additional genes was verified by qRT-PCR. Ovol2 is a known marker of surface ectoderm and placodal fates in various model organisms. In mice, the Ovol2 knockout is lethal and Ovol2−/− mouse embryos do not develop placode-derived tissues such as optic cup, and otic vesicle.

A gene cluster analysis showed when genes were expressed the highest; time of maximum (TOM) and the lowest; time of minimum expression (TIM). GO ontology terms were mapped into this analysis and were able to identify precise developmental windows during placode precursor cell specification. These data additionally confirmed the identity of hESC derived placodal tissue and revealed markers and pathways involved in placode versus anterior neural plate (AN) specification.

Figure 12F:
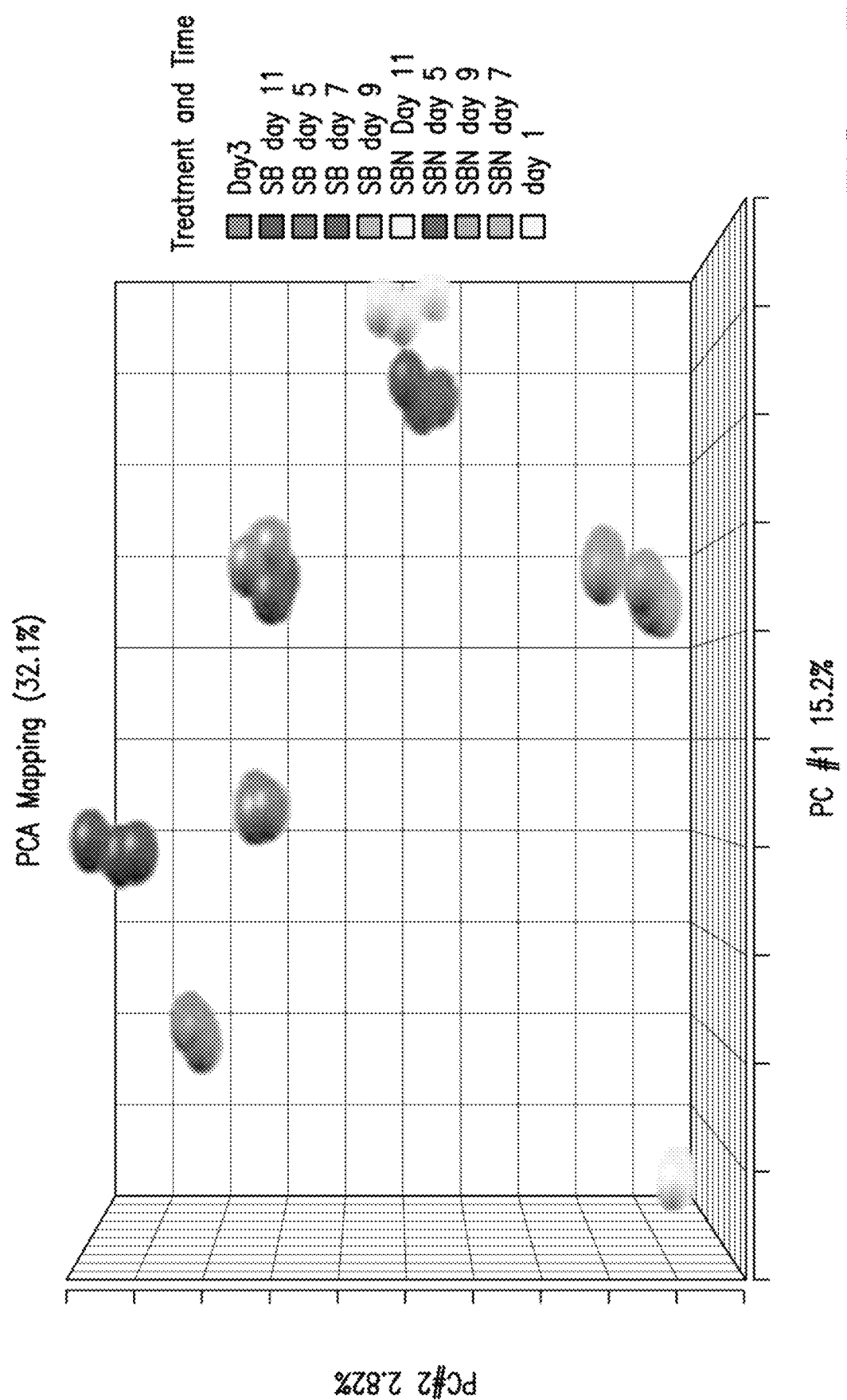

Clustering of differentially expressed transcripts (FIG. 12E) revealed correct matching of all replicate samples. These data also revealed a close temporal matching of samples independent of treatment while pinpointing to a subset of genes that distinguish neuroectodermal from placodal precursors (boxed area in FIG. 12E). Principle component analysis confirmed high temporal correlation of samples with increasing divergence between neuroectodermal and placodal precursor cells at later differentiation stages (FIG. 12F).

Placode progenitors are believed give rise to sensory neurons. Isolation of Six1+ placodal precursors followed by culture under serum free conditions revealed efficient differentiation into neurons that retain Six1 expression (FIGS. 13A-13C). The sensory neuron identity of these cells was confirmed by the expression of Brn3A, Isl-1 measured at day 20 of differentiation (FIG. 13D, E). Longer-term differentiation studies (day 40) resulted in cells with strong expression of the peripheral neuron marker Peripherin (FIG. 13F) and reduced expression of Tuj1 compatible with in vitro maturation of sensory neuron progeny. In vitro developmental progression from placode precursor identity to mature sensory neuron fates is illustrated schematically in FIG. 13G.

Figure 14A:
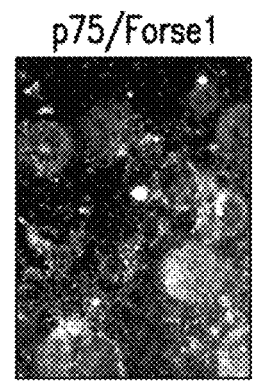
Figure 14B:
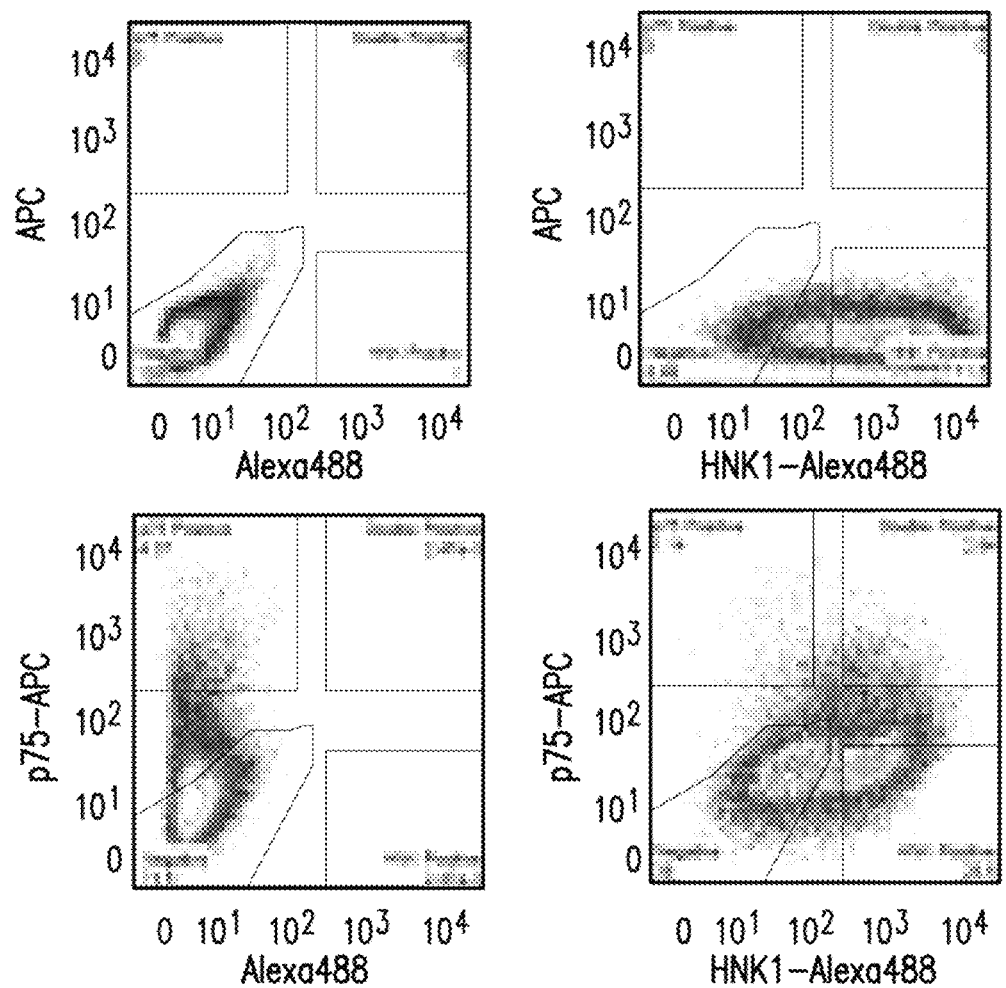
Figure 14C:
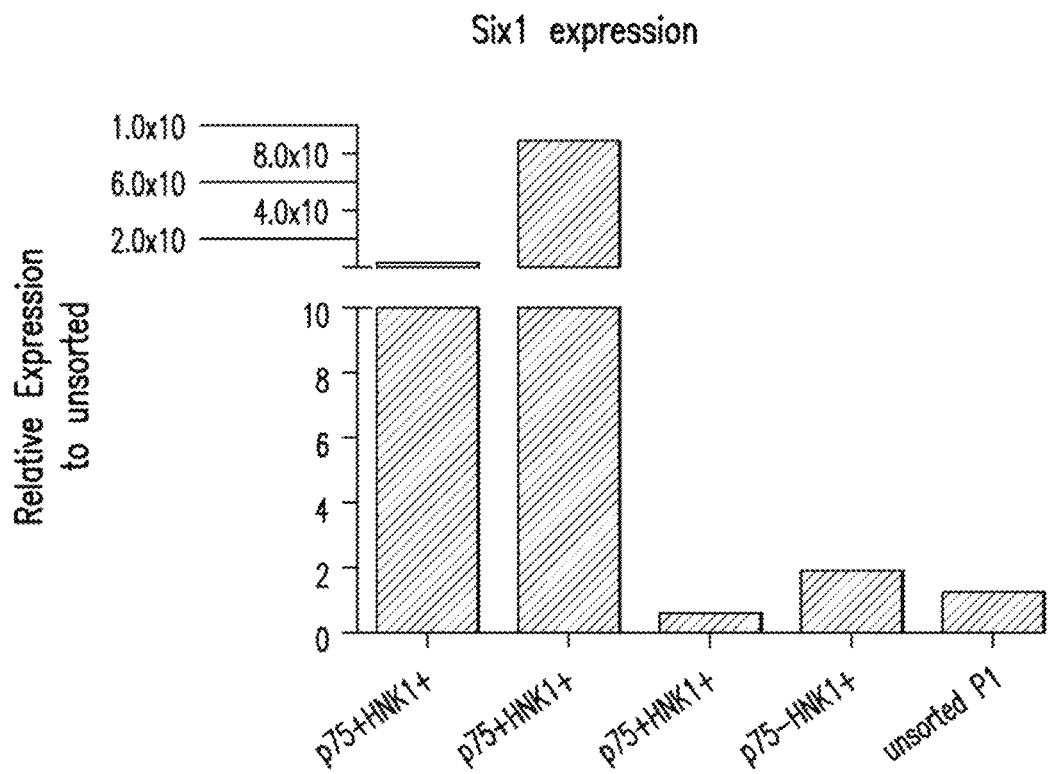
Figure 14D:
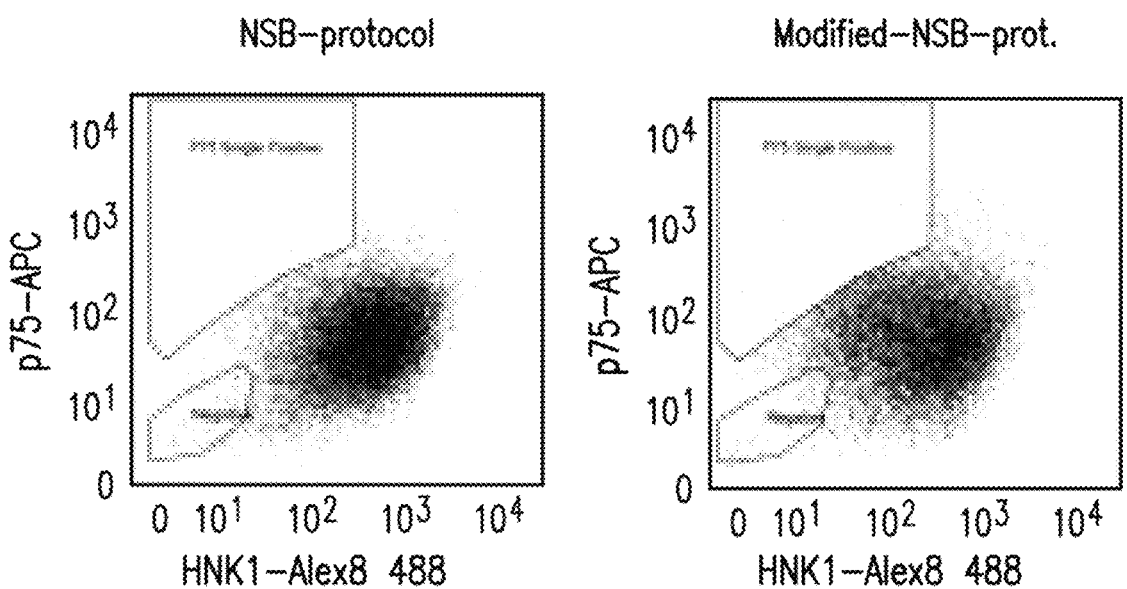

Results showed that simple modifications in the N-SB protocol induce a switch in differentiation from neuroectoderm to placodal precursors. Using timed-noggin withdrawal, the inventors obtained a yield of 71% of total cells expressing Six1. The isolation of pure placodal precursors requires markers that prospectively identify placode fate. The identification of prospective markers is also useful to reliably distinguish placodal cells from other alternative lineages such as CNS precursor, neural crest lineages and non-neural ectoderm. Of particular interest is the separation of placode derived from neural crest derived precursors to reliably separate neural crest from placode derived neuronal populations. Previously, it was demonstrated that isolation of p75+/HNK1+ cells during neural early neural differentiation marks a population of cells fated towards neural crest identity (Lee et al., Nature Biotechnology, 25(12):1468-75 (2007), herein incorporated by reference). Here, a relationship of those markers within the placodal lineages was tested. It was observed that NGFR efficiently marks placodal cultures in a modified N-SB protocol (FIG. 14A) separated by populations of precursors expressing Forsel, a marker previously associated with anterior neuroectodermal fates (Elkabetz, G&D, 2008, herein incorporated by reference). Double sorting for p75 and human natural killer-1 (HNK1) epitope (also known as CD57) expression revealed that p75-single positive cells, negative for HNK1, are dramatically enriched in Six1 expression based on qRT-PCR analysis (FIG. 14B, C). The placodal identity of the cells is further supported by the increase in the number of p75+/HNK1- cells in the placode-inducing modified N-SB protocol as compared to the neuroectoderm-inducing classic N-SB protocol (FIG. 14D).

Example II

IPS Cell Generation:

The cDNAs encoding hOct4, hSox2, hKlf4 and c-myc (purchased from Open Biosystems) were subcloned into self-inactivating lentiviral vectors driven by the human phosphoglycerate kinase (PGK) promoter. Lentiviral vector supernatants were produced by triple co-transfection of the plasmid DNA encoding the vector, pCMVΔR8.91 and pUCMD.G into 293T cells. Human fetal lung fibroblasts (MRC-5) purchased from ATCC (CCL-171) were seeded at $1.5 \times 10^4$ cells/cm$^2$ in Eagle's Minimum Essential Medium supplemented with 10% fetal bovine serum (FBS). The following day the fibroblasts were transduced with equal amounts of supernatants of the four lentiviral vectors in the presence of 4 ug/ml polybrene for ~16 hours. Six days after transduction, fibroblasts were harvested by trypsinization and plated at $2 \times 10^4$ cells per 60 mm dish on a feeder layer of mytomycin C-treated mouse embryonic fibroblasts (CF-1). The next day, the medium was switched to hESC medium. The hiPS lines were confirmed positive for Tra-1-81, Tra-1-60, SSEA-4 and Nanog by immunoflouresence and flow cytometry. In both hips clones the 4 vector-encoded transgenes were found to be silenced.

Materials and Methods:

Cells and Culture Conditions (dual SMAD and floor plate). hESCs (WA-09; passages 35-45) were cultured on mouse embryonic fibroblasts plated at 12-15,000 cells/cm2 (MEFs, Global Stem). A medium of DMEM/F12, 20% knockout serum replacement (GIBCO), 0.1 mM b-mercaptoethanol, 6 ng/mL FGF-2 was changed daily. Cells were passaged using 6 U/mL of dispase in hESCs media, washed and re-plated at a dilution of 1:5 to 1:10.

Neural Induction (Dual SMAD).

hESC cultures were disaggregated using accutase for 20 minutes, washed using hESC media and pre-plated on gelatin for 1 hour at 37° C. in the presence of ROCK inhibitor to remove MEFs. The nonadherent hESC were washed and plated on matrigel at a density of 10,000-25,000 cells/cm$^2$ on matrigel (BD) coated dishes in MEF conditioned hESC media (CM) spiked with 10 ng/mL of FGF-2 and ROCK-inhibitor. Ideal cell density was found to be 18,000 cells/cm$^2$. The ROCK inhibitor was withdrawn, and hESC were allowed to expand in CM for 3 days or until they were nearly confluent. The initial differentiation media conditions included knock out serum replacement (KSR) media with 10 nM TGF-beta inhibitor (SB431542, Tocris) and 500 ng/mL of Noggin (R&D). Upon day 5 of differentiation, the TGF-b inhibitor was withdrawn and increasing amounts of N2 media (25%, 50%, 75%) was added to the KSR media every two days while maintaining 500 ng/mL of Noggin. For MS5 induction, established methods previously reported were used.

Quantitative Real-Time (Dual SMAD).

Total RNA was extracted using an RNeasy kit (Qiagen). For each sample, 1 ug of total RNA was treated for DNA contamination and reverse transcribed using the Quantitect RT kit (Qiagen). Amplified material was detected using Quantitect SYBR green probes and PCR kit (Qiagen) on a Mastercycler RealPlex2 (Eppendorf). Results were normalized to a HPRT control and are from 4-6 technical replicates of 2-3 independent biological samples at each data point.

Neuronal Patterning and Differentiation (Dual SMAD).

Dopaminergic patterning was initiated using BDNF, ascorbic acid, sonic hedgehog, and FGF8 in N2 media as previously reported,[18] and maturation was performed in the presence of BDNF, ascorbic acid, GDNF, TGFb-1, and cyclic-AMP. Motor neuron patterning was performed using BDNF, ascorbic acid, sonic hedgehog, and retinoic acid in N2 media as previously reported.[16]

Microscopy, Antibodies, and Flow Cytometry (Dual SMAD).

Tissue was fixed using 4% paraformaldehyde for 20 minutes, washed with PBS, permeablized using 0.5% Triton X in PBS, and blocked using 1% BSA in PBS. Primary antibodies used for microscopy included PAX6 (Covance), Oct4 (Biovision), AP2 (Novus Biologicals), GBX2 (Sigma), HNK1 (Sigma), HOXB4 (Developmental Studies Hybridoma Bank (DSHB)), Nestin (R&D), NKX6.1 (DSHB), OTX2 (gift), p75 (Advanced Target Systems.), PAX7 (DSHB), PLZF (Calbiochem), TUJ1 (Covance), ZO1 (Zymed), BF1 (FOXG1, gift Esseng Lai), TH (Sigma), HB9

(DSHB), ISL1 (DSHB). CD105-PE (eBioscience) was used for excluding MS5 stromal cells for flow cytometry on a FACScan (BD).

Floor Plate: Neural Induction.

For MS5 induction, established methods previously reported were used (Perrier et al., 2004). Feeder free neural induction was carried out as previously described (Chambers et al., 2009). Briefly, hESCs cultures were disaggregated using accutase for 20 minutes, washed using hESCs media and pre-plated on gelatin for 1 hour at 37° C. in the presence of ROCK inhibitor to remove MEFs. The nonadherent hESCs were washed and plated on matrigel at a density of 20,000 cells/cm2 on matrigel (BD) coated dishes in MEF conditioned hESCs media (CM) spiked with 10 ng/mL of FGF-2 and ROCK-inhibitor. The ROCK inhibitor was withdrawn, and hESCs were allowed to expand in CM for 3 days or until they were nearly confluent. The initial differentiation media conditions included knock out serum replacement (KSR) media with 10 nM TGF-b inhibitor (SB431542, Tocris) and 500 ng/mL of Noggin (R&D). Upon day 5 of differentiation, increasing amounts of N2 media (25%, 50%, 75%) was added to the KSR media every two days while maintaining 500 ng/mL of Noggin and TGF-b inhibitor. For FP induction, Sonic C25II was added at 200 ng/ml. In some experiments, DKK-1 (R&D 100 ng/ml) FGF8 (R&D 50 ng/ml), Wnt-1 (Peprotech 50 ng/ml) and Retinoic Acid (R&D 1 uM) were added.

Quantitative Real-Time PCR.

Total RNA was extracted using an RNeasy kit (Qiagen). For each sample, 1 ug of total RNA was treated for DNA contamination and reverse transcribed using the Superscript III (Invitrogen). Amplified material was detected using Taqman probes and PCR mix (ABI) on a Mastercycler RealPlex2 (Eppendorf). All results were normalized to a HPRT control and are from 3 technical replicates of 3 independent biological samples at each data point.

Micorarray Analysis.

Total RNA was isolated at Days 2, 3, 5, 7, and 11 of differentiation from both control (NSB) and FP (NSB+Shh C25II) using Trizol (Invitrogen). Three biological replicates per time point were used. All samples were processed by the MSKCC Genomics Core Facility and hybridized on Illumina human 6 oligonucleotide arrays. Normalization and model-based expression measurements were performed with using the Illumina analysis package (LUMI) available through open-source Bioconductor project (www.bioconductor.org) with in the statistical programming language R (http://cran.r-project.org/). A pairwise comparison between NSB and NSB+Sonic was performed using the Linear Models for Microarray Data package (LIMMA) available through Bioconductor. Genes found to have an adjusted p-value <0.05 and a fold change greater than 2 were considered significant. Expression differences are reported as the log 2 of the fold change. Gene Ontology enrichment was determined by entering gene lists into the Database for Annotation, Visualization, and Integrated Discovery (DAVID; http://www.david.niaid.nih.gov) (Huang et al., 2009 and Dennis et al., 2003). Timing of maximal and minimal expression was calculated as previously reported (Venezia et al., 2004).

Briefly, a regression line was fit to both the NSB+Sonic C25II and NSB conditions. From these trend lines, genes were categorized based on at which time point its maximal and minimal expression occurred.

Microscopy, Antibodies, and Flow Cytometry.

Tissue was fixed using 4% paraformaldehyde and Picric acid for 15 minutes, washed with PBS, permeablized using 0.3% Triton X in PBS, and blocked using 10% Donkey Serum. Primary antibodies used for microscopy included PAX6 (Covance), TUJ1 (Covance), ZO1 (Zymed), BF1 (FOXG1, gift E.Lai), TH (Pelfreez), NKX6.1 (DSHB) and FOXA2 (SantaCruz).

Vector Design and Lentiviral Production.

A third generation lentiviral vector (Lois et al., 2002) was modified to express a BF1 ORF from the Ub-C promoter (Fasano et al., 2009) and a BF1 shRNA from the H1 promoter as described (Fasano et al., 2007; Ivanova et al., 2006). Foxg1 shRNA constructs were used as previously described (Shen et al., 2006). The shRNA expressing lentiviral plasmid was co-transfected with plasmids pVSV-G and pCMVd8.9 into 293FT cells. Viral containing media were collected, filtered, and concentrated by ultracentrifugation. Viral titers were measured by serial dilution on NIH 3T3 cells followed by flow cytometric analysis after 72 hours.

Generation of BF1 shRNA and Over-Expressing Human ES Lines.

hESCs (WA-09; passages 35) were dissociated and plated on Matrigel with the ROCK inhibitor as singles cells. 24 hrs post plating the ES cells were transduced with either control (empty vector), BF1 shRNA, or BF-1 ORF containing vectors. 1 week later, GFP expressing colonies were manually picked and plated on MEFs. Cells were then expanded, tested for mycoplasma, and a normal karyotype.

Dissection of Primary Explants.

E8.5, TP Taconic Swiss Webster females were dissected and embryos were removed. Neurectodermal tissues were dissected and left as chunks plated on top of FP cells. For neurite growth assay E12.5 Sprague-Dawley rat cerebellar plate tissue was dissected and plated on top of hESC derived FP cells or control neuroectodermal cells (NSB protocol). Outgrowth from rat explants tissue was analyzed at day 3 of co-culture.

Conditioned Media and ELISA.

hESCs were differentiated to neural or FP cells, Shh was removed a day 6, and the media was harvested at both day 9 and day 11 of cultures. Using a human Netrin-1 ELISA kit (Axxora) according to the manufactures protocol, Netrin-1 protein levels were detected. For co-culture experiments, the media was filtered and added to cultures straight or a 1:2 dilution in fresh media.

Statistical Analysis.

Results shown are mean+s.e.m. Asterisks and pound signs identify experimental groups that were significantly different from control groups by a t-test, one way ANOVA, or two way ANOVA with a Bonferroni correction for multiple comparisons (p-value, 0.05), where applicable.

Example III

Early High-Dose SHH Exposure Induces FOXA2 and Represses BF1.

hESC derived neural cells at the rosette stage were differentiated into both CNS and PNS progeny and patterned towards multiple cells fates along the A/P and D/V axis (Elkabetz et al., 2008). These results demonstrated that rosette stage cells were highly plastic and responsive to patterning cues including SHH. Specification of progenitor cells into FP tissue and cells during mouse development was thought to depend on SHH signaling within early neural lineages. The inventors tested whether rosette-stage neural cells were competent to undergo FP specification in response to SHH. High concentrations of SHH were needed to induce FP during mouse development (Roelink et al., 1994; Ericson et al., 1996). Recombinant N-terminal SHH has a limited activity range due to the lack of posttranslational modifications required for full SHH action. Recently, a modified version of recombinant SHH became available where SHH was tethered to two Isoleucines (Sonic C25II, R&D Systems), mimicking more closely the potency of mammalian SHH protein. In most functional assays C25II was ~10 times more potent than non-modified N-terminal SHH.

However, dose-response studies done during the development of the present inventions with both conventional SHH and SHH-C25II on established rosette-stage neural cells did not yield cells expressing FP markers such as FOXA2 (FP marker) under any of the conditions tested. The majority of cells retained rosette cytoarchitecture and staining for the AN marker BF1 as described previously (FIG. 15A) (Elkabetz et al., 2008). These results were a surprise, i.e. exposure to high SHH was not sufficient to convert established rosette-stage cells into FP.

Figure 15A:
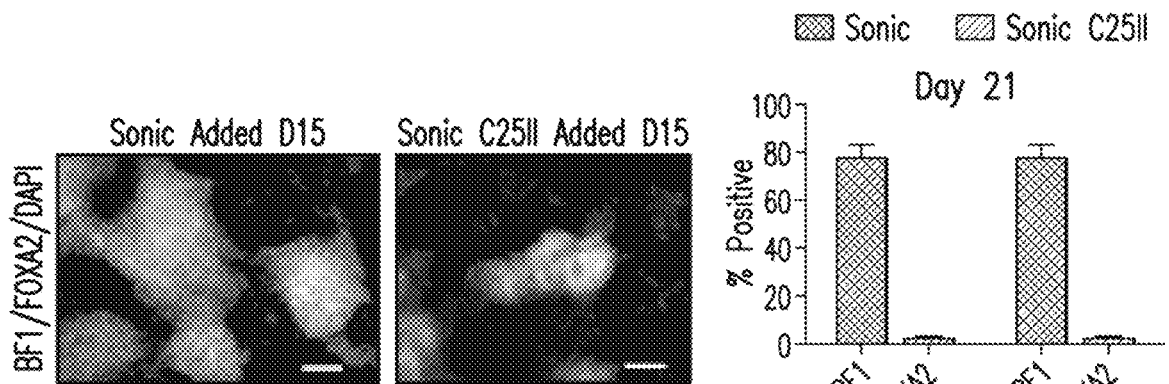
Figure 15B:
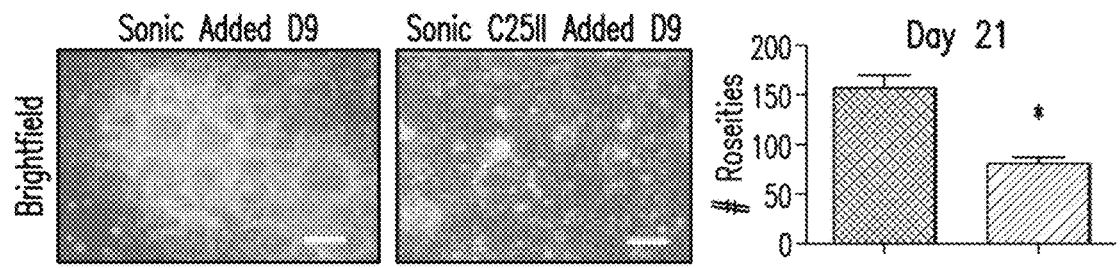
Figure 15C:
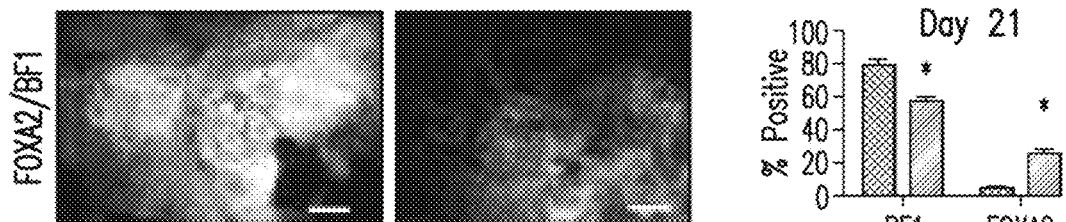
Figure 15D:
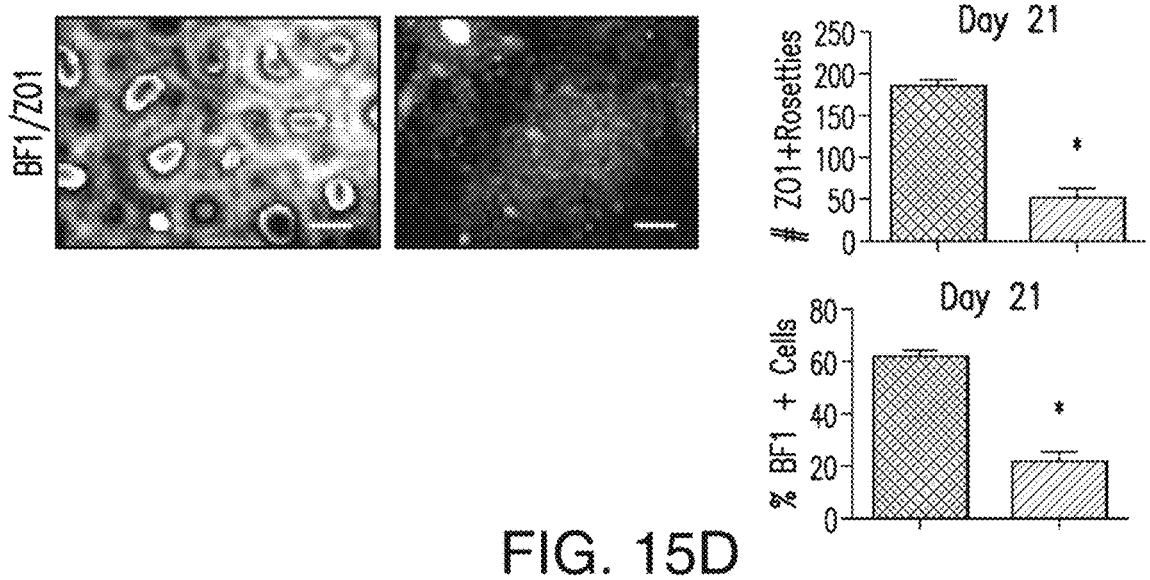
Figure 15E:
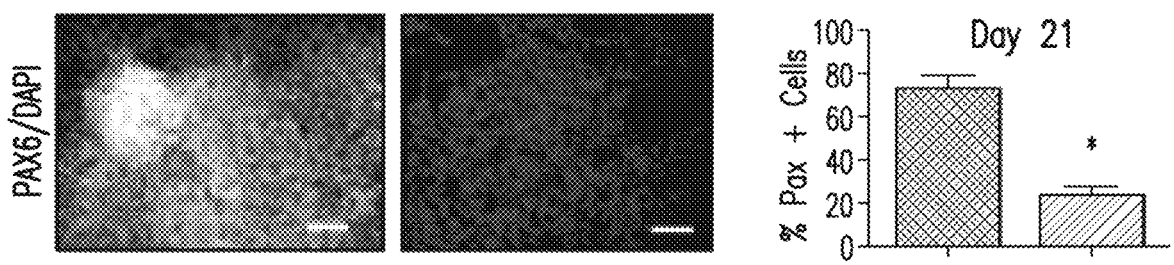
Figure 15F:
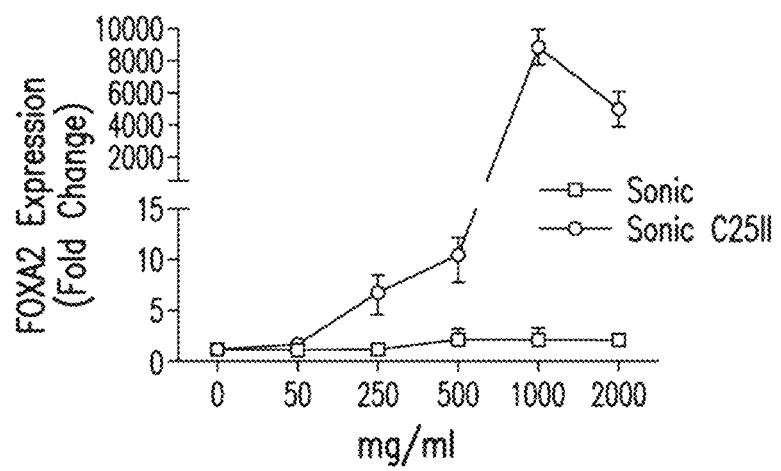
Figure 15G:
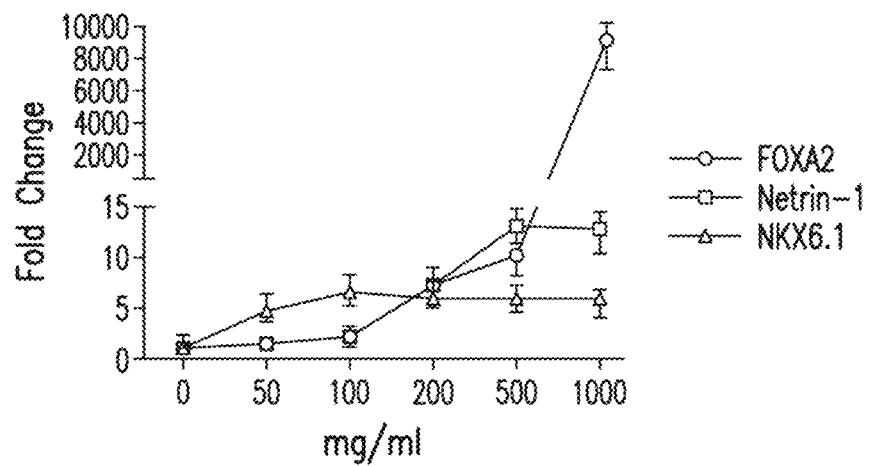

Based on the hypothesis that FP specification in the mouse occurs at early developmental stages, at the time of or prior to neural induction, the inventors repeated SHH induction studies at Day 9, the time of rosette specification, using classic stromal-feeder mediated neural induction protocols (Elkabetz et al., 2008). Under this paradigm the inventors noticed a drastic change in cell morphology restricted to the cells treated with SHH-C25II (FIG. 15B). Cells exhibited a flat morphology devoid of rosette structures. Furthermore, the inventors' observed a robust upregulation of FOXA2+ and a concomitant decrease in BF1+ cells (FIG. 15C) and the decrease in the total number of ZO1+ rosettes (FIG. 15D). In addition to decreased expression of BF1 the inventors also observed decreased expression of PAX6, another maker expressed in the AN (FIG. 1E). Dose-response studies demonstrated that induction of FOXA2+ cells and the concomitant decrease in BF1 and PAX6 expression were achieved at concentrations of 125-500 ng/ml of SHH C25II (FIG. 15F and not shown). No efficient induction of FOXA2+ cells was observed with any of the concentrations tested using non-modified N-terminal SHH. The inventors performed dose response studies to understand how FP marker induction compared to that of NKX6.1 expression; a gene known to respond to lower concentrations of SHH. At low concentrations of Sonic C25II there is no expression of FP markers FOXA2 and Netrin-1 but a robust increase in NKX6.1 expression. At higher concentrations FP markers rapidly rise, while NKX6.1 expression tapers off (FIG. 15G). These data demonstrated that early exposure to high levels of SHH decreases anterior AN markers and induces the FP marker FOXA2.

Example IV

The Competency for FP Induction is Restricted to a Narrow Window of Differentiation.

While a robust (strong observed signal, such as staining) upregulation of FOXA2 was induced with the initial procedures, merely around 30% of the cells were positive after about 21 days of culture using classic stromal-feeder mediated neural induction. Therefore the inventors tested several types of culture compositions and methods for increasing the total number of cultured cells expressing FOXA2.

Figure 16A:
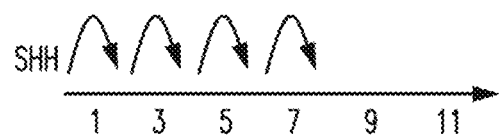
Figure 16B:
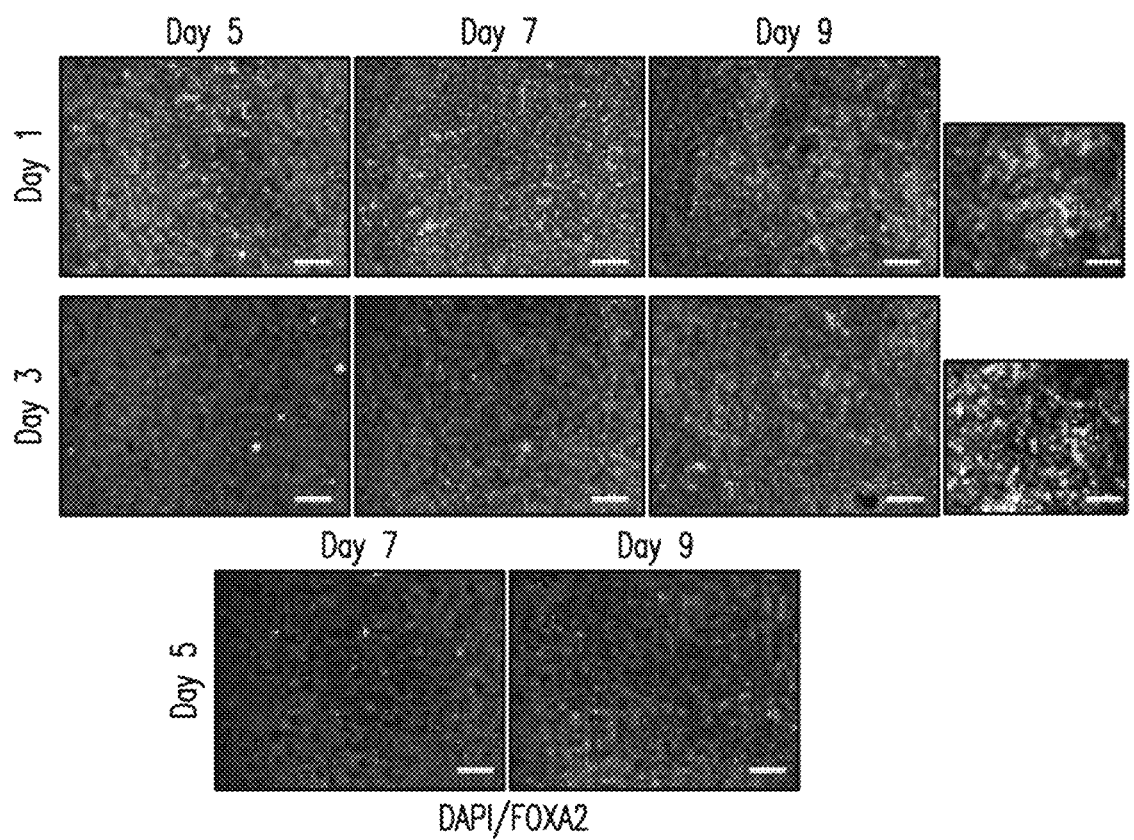
Figure 16C:
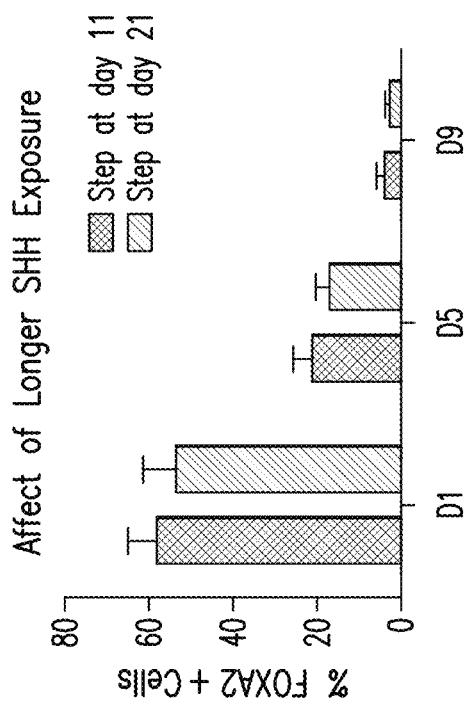
Figure 16D:
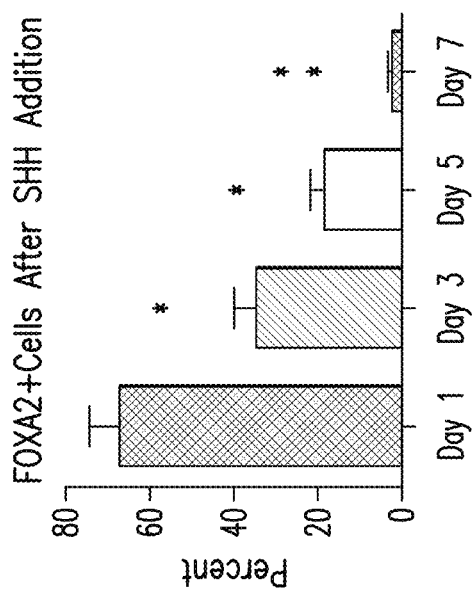
Figure 16E:
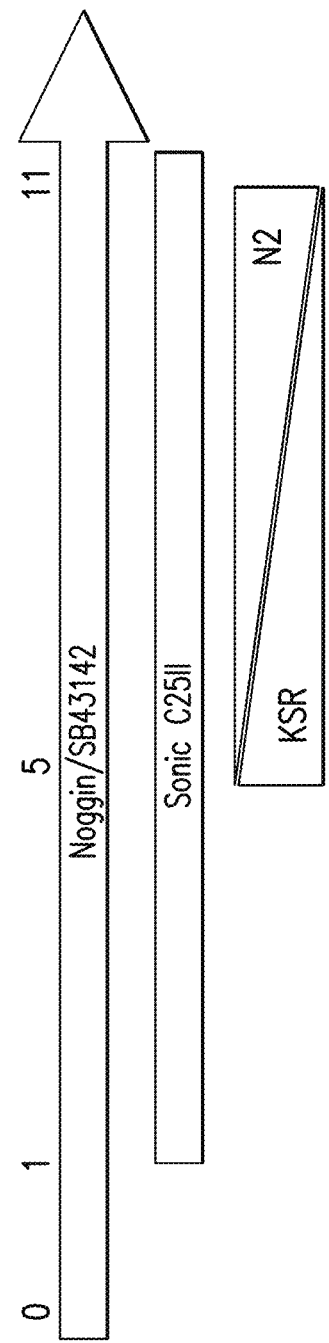

Recently the inventors developed and described a rapid and defined neural induction paradigm yielding significantly higher numbers of neural cells based on inhibiting SMAD signaling via exposure to noggin and SB431542 (NSB protocol; (Chambers et al., 2009)). Using this protocol, in combination with compositions and methods of the present inventions, the inventors aimed to optimize FP differentiation by adding Sonic C25II at different time points during neural induction and assaying for FOXA2 expression. Differentiation was initiated upon NSB exposure, and Sonic C25II was added at Day 1, Day 3, Day 5, or Day 7 (FIG. 16A). The most efficient FOXA2 induction was observed in cultures treated with SHH starting at day 1 of differentiation with FOXA2+ cells representing about 65% of total cells (FIGS. 16B and 16C). Extended SHH treatment beyond Day 11 of differentiation did not increase FOXA2 yield (FIG. 16D). These data demonstrated that an early high SHH signal is needed to establish FP identity and suggest a critical window of competency for FP specification. Furthermore, the differentiation conditions establish a robust platform for inducing human FOXA2+ cells in vitro.

Figures 21A, 21B:
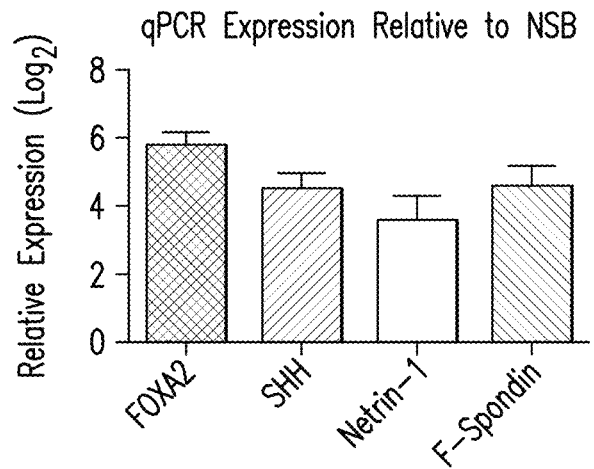
Figure 21C:
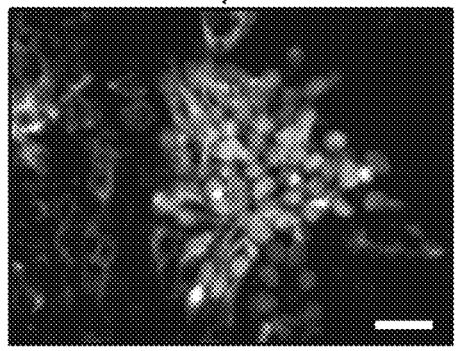
Figure 21D:
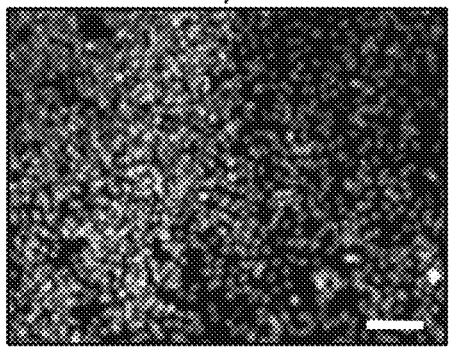
Figure 21E:
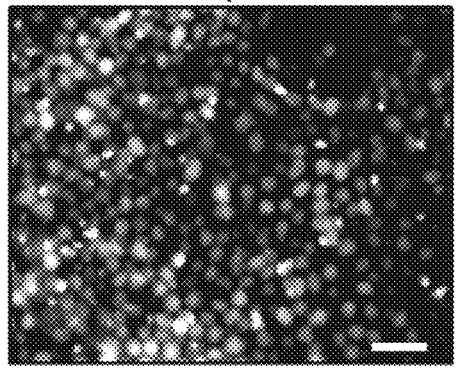
Figure 21F:
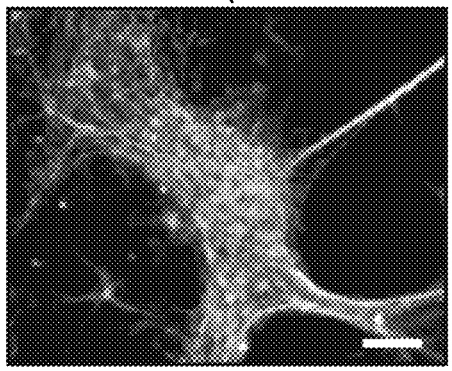
Figure 21G:
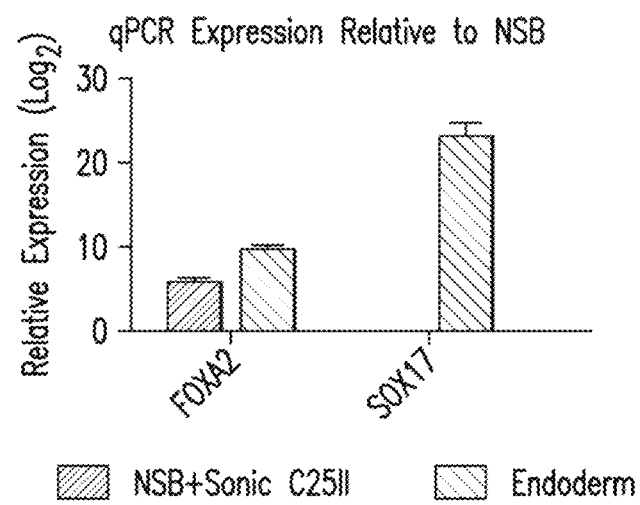
Figure 21H:
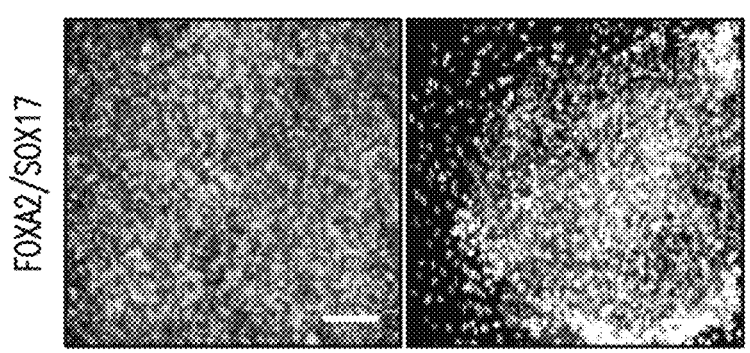

FOXA2 is a key marker of FP development. However, FOXA2 is also highly expressed in the endoderm. To further characterize the hESC derived putative FP tissue, the inventors performed qRT-PCR analyses for candidate markers at Day 11. Using the NSB protocol as a control, the inventors confirmed a dramatic increase in the expression of FOXA2 and other FP markers including SHH, F-Spondin, and Netrin-1 (FIG. 21A). The inventors further characterized the nature of FOXA2+ putative FP cells using a panel of neural precursor, glial, neuronal and non-neural markers (FIG. 21B). FOXA2+ cells co-labelled with only a limited subset of these markers including Nestin (86%) and SOX2 (17%) (FIGS. 21C-21F). To distinguish FOXA2 expression in hESC derived FP versus endoderm tissue, the inventors differentiated hESCs to endoderm (D'Amour et al., 2005) (FIGS. 21G and 21H). As expected, under both FP and endoderm differentiation conditions, the inventors observed an increase in FOXA2 expression compared with NSB treated control cells. However, induction of the endoderm marker SOX17 was limited to the endoderm condition and no SOX17 was present in hESC derived FP cells (FIGS. 21G and 21H). The inventors also did not observe expression of other endodermal markers such as AFP and Albumin expression in hESC derived FP cells. These data demonstrated that hESC derived FOXA2+ cells in the NSB+SHH protocol express FP and early neural precursor markers and lack expression of endodermal markers.

Example V hESCs Derived FP Cells are Functional.

Figure 17A:
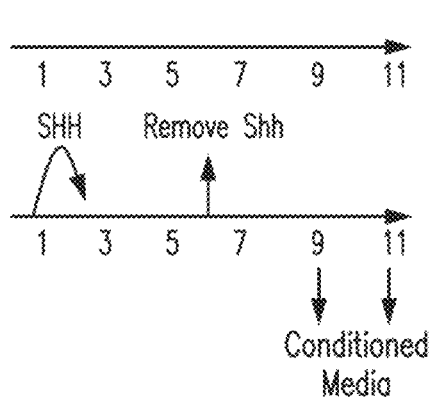
Figure 17B:
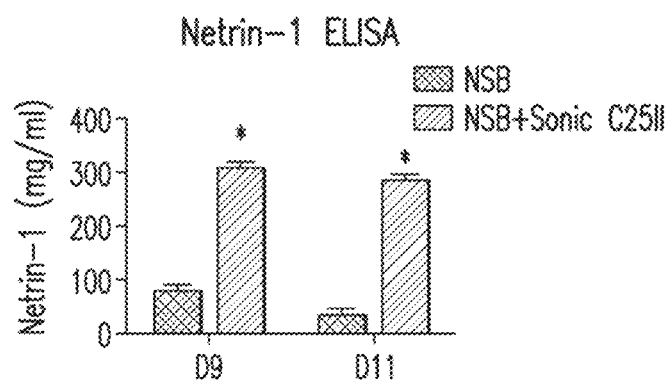
Figure 17C:
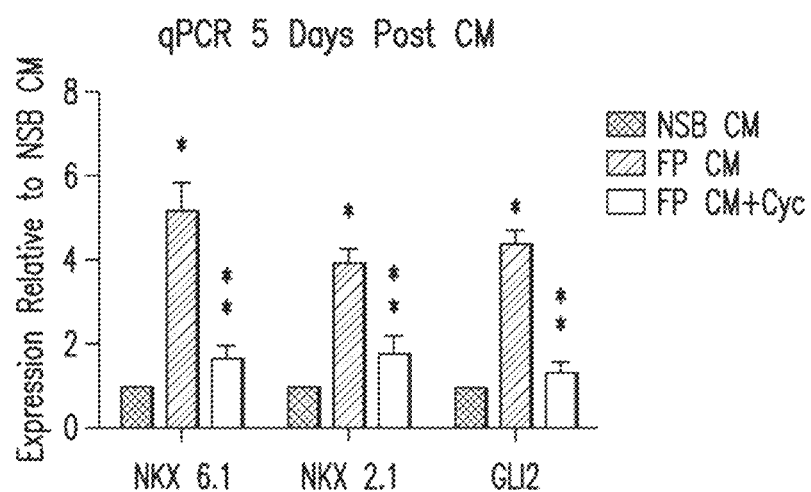
Figure 17D:
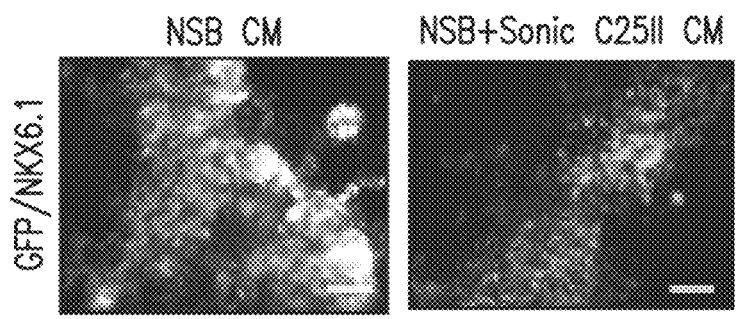
Figure 17:
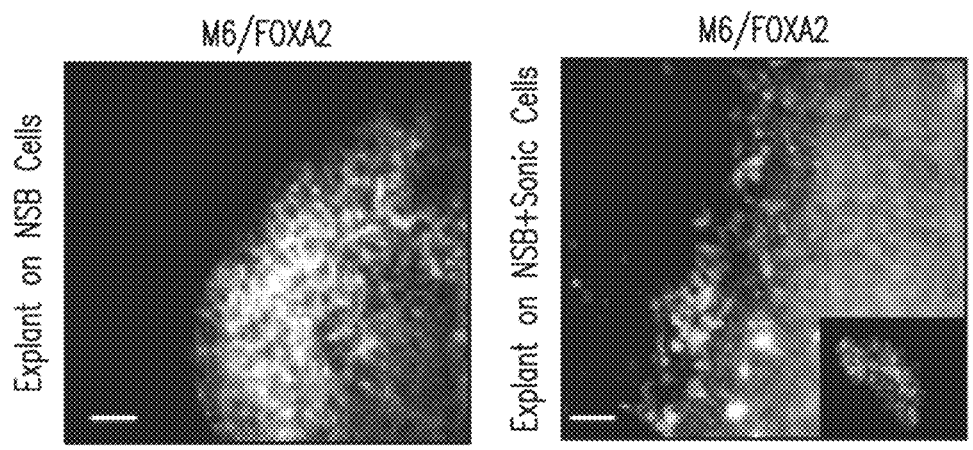
Figure 17:
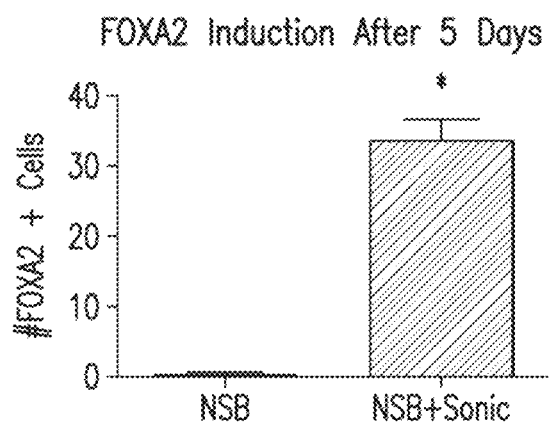

The FP has important functional roles during development in neural patterning and axonal path finding (Jessell, 2000). To assess the functional properties of hESCs derived FP conditioned media was isolated at days 9 and 11 and tested for expression of Netrin-1 in the medium using ELISA (FIG. 17A). Under normal NSB conditions, Netrin-1 is detectable at Day 9 and decreases at Day 11 while in the NSB+SHH condition, there is a 3.5 fold increase in Netrin-1 levels, increasing at Day 11 (FIG. 17B). SHH is a critical patterning factor secreted by FP cells and specifying ventral cell types in a dose-dependent manner. To test if hESCs derived FP secretes factors that can specify ventral precursor domains, conditioned media (CM) was isolated at Days 9 and 11 of the differentiation. At Day 6, exogenous SHH was removed and cultures were washed to eliminate any exogenously added SHH from the medium. Naïve neural progenitor cells were isolated at Day 11 of the control (NSB) protocol and cultured with either NSB CM or FP CM. After Day 5 of culture in the presence of CM, the inventors probed for the expression of ventral precursor markers and expression of the SHH responsive gene GLI2. The inventors found that compared with CM obtained from NSB control cultures, CM from hESC derived FP tissue efficiently induced expression of ventral genes including NKX2.1 and NKX6.1 (FIG. 17C). Increase in the expression of ventral markers was confirmed at the level of protein (FIG. 17D).

To see if this result was SHH-mediated, the inventors demonstrated increased expression of GLI2 upon exposure to CM from hESC derived FP. When this experiment was repeated in the presence of the SHH antagonist cyclopamine, all three genes, NKX2.1, NKX6.1, and GLI2 were significantly reduced (FIG. 17C) demonstrating dependence of patterning response on SHH signaling.

Classical studies demonstrated that FP explants can induce an ectopic FP in early neuroectodermal tissue (Placzek et al., 1993). To test if the hESCs derived FP is capable of inducing FP markers in primary mouse explants, neuroectodermal tissue was isolated from an E8.5 mouse embryo and placed it in direct contact with hESC derived FP cells. After 3 days of co-culture explants were identified based on expression of the mouse specific M6 marker, rinsed and mounted on slides to be stained for FOXA2. As a control condition, mouse explants were co-cultured with hESC derived neural tissue using the NSB protocol. While co-culture with control hESC derived neural tissue did not yield FOXA2+ cells, explants co-cultured with hESC derived FP cells showed robust induction of FOXA2+ cells, particularly at the periphery of the explant (FIGS. 17E and 17F). Neurite growth promoting effects of hESC derived FP cells was observed in primary rat E12.5 rat cerebellar plate explants (FIG. 8), an assay used previously to demonstrate axonal growth promoting effects of primary rodent FP tissue (Shirasaki et al., 1995). These experiments demonstrated that hESCs derived FP can mimic the functional properties of primary FP tissue as an organizer by secreting Netrin-1 and SHH capable of ventralizing naïve hESC derived and primary mouse neural precursor cells.

Example VI

Temporal Transcriptome Analysis Reveals that FP Specification Occurs at the Expense of AN.

To gain further insight into the factors critical for human FP specification, high resolution temporal gene expression profiles of candidate markers were performed at 6 time points during the 11 day protocol. FOXA2 expression was observed as steady increase in transcript levels starting at day 3 of differentiation (compared to NSB) consistent with immunostaining data (FIG. 18A). Interestingly, other FP markers; SHH, Netrin-1, and F-Spondin followed a different expression pattern (FIGS. 18B-18D). All three markers showed a more delayed induction with a dramatic increase in expression (compared to NSB condition) at day 7 of differentiation.

PTCH1 expression is used commonly as a transcriptional readout of SHH activity. Dramatic increase in PTCH1 expression was observed as early as day 3 of differentiation with levels further increasing by a factor of 3 over the next 2 days (FIG. 18E). It has been shown previously that the SHH downstream effector GLI2 is essential for FP induction but decreases at later stages of FP development (Matise et al., 1998) and that GLI2 can directly activate FOXA2 expression (Jeong and Epstein, 2003). An early increase in both GLI2 and FOXA2 expression (FIGS. 18A and 18F) was observed followed by a decrease in GLI2 at Day 11 consistent with a role of GLI2 specifically during FP induction. A similar trend albeit at much lower induction levels is observed for GLI1 (FIG. 18G).

SOX1 is an early neural marker and is not expressed in the medial FP (Charrier et al., 2002). Consistent with a rapid neural induction, SOX1 was rapidly up regulated in NSB conditions and continued to increase with time. Upon addition of SHH a much smaller increase in SOX1 levels is observed at day 3 compared with control NSB conditions (FIG. 18H). NSB conditions yield neural cells with a AN bias expressing BF1 at high levels (Chambers et al., 2009). However, when SHH is added to the culture, there is a drastic reduction in PAX6 and BF1 at day 7 (FIGS. 18I and 18J). FInduction of the endoderm marker SOX17 and mesoderm marker Brachury was not observed (FIGS. 18K and 18L) suggesting that FP induction, similar to AN induction using the NSB protocol, occurs without contribution of an obvious mesodermal or endodermal intermediate. These data demonstrated appropriate marker expression in hESC derived FP, initiated by GLI2 and FOXA2 expression and followed by expression of functional FP markers such as Netrin-1, SHH, and F-Spondin. The drop in PAX6 and BF1 expression at the time of FP specification suggests that induction of FP occurs at the expense of AN.

Example VII

Global Transcriptome Analysis During hESC Derived FP Specification.

Temporal profiles of global gene expression at 5 time points during differentiation was established during the development of the present inventions (Day 1, 3, 5, 7 and 11) in control NSB cultures (yielding AN) and in Sonic C25II treated cultures (yielding FP; see FIGS. 18M18R). Prior to microarray analysis the quality of each sample was verified for expression of a panel of FP markers (FIG. 23). Global gene expression studies were carried out in three independent samples for each time point and culture condition. Data were converted into log 2 ratios comparing levels of gene expression in FP versus NSB protocol during differentiation (FIGS. 18M-18R). Raw data are available in GEO database (http://www.ncbi.nlm.nih.gov/geo/) accession number: GSEXXX (number available at time of publication).

The time course data were subjected to gene ontology (GO) enrichment analysis using DAVID (http://david.abcc.ncifcrf.gov/; Dennis et al., 2003) as unbiased assessment of the FP transcriptional profile. Among the transcripts highly enriched in SHH treated versus NSB control cultures at day 7 and 11 of differentiation were genes associated with the Wnt and hedgehog pathways, axon guidance, and secreted proteins (FIGS. 18M and 18N). Enrichment for patterning and axonal guidance factors further confirm FP identity of SHH treated cultures. Further, SHH-mediated suppression of AN was demonstrated when transcripts that included genes involved in forebrain development showed a larger amount of downregulation in the FP culture methods for producing floor plate cells than when compared to cells cultured with the NSB protocol (FIGS. 18M and 18N).

Pairwise comparisons at for each differentiation stage was done to gain insight into specific genes differentially expressed during FP specification. While the majority of genes significantly regulated at day 3 and day 5 of differentiation (as compared to day 1) were shared in NSB and FP protocol, a subset of transcripts was differentially regulated (FIGS. 18O-18R). In particular, an increase in Patched-1 (PTCH1), a component and known transcriptional downstream target of the SHH signaling was noticed. In this protocol, PTCH1 is highly enriched at all time points, except D11 where it starts to decrease (FIG. 18O-18R).

The inventors observed significant changes in the Wnt pathway components. As early as Day 5 there was a significant decrease of the Wnt pathway inhibitor DKK-1 and this decrease was sustained over the course of the protocol (FIGS. 18O-18R and 19A-19C). Significant upregulation of several Frizzled genes that have been previously shown to be involved in midline axon guidance during mouse development (Lyuksyutova et al., 2003) in the midline (FIGS. 18Q and 18R) was also observed. Additionally, a number of additional genes were identified that were differentially expressed during FP specification including SIX6, CAPN6, IGFBP3 and FIBLN1 (FIGS. 18O-18R). Differential expression for these and additional genes was verified by qRT-PCR (FIG. 29B). While systematic in situ hybridization screens in mouse and human embryonic tissue will be required to validate putative human FP markers, based on the literature and MGI (Mouse gene expression database), many of the genes identified have compatible expression patterns in the anterior midline and floor plate tissue such as HESX1 (Zoltewicz et al., 1999) or RBP1 (CRBP1—Hunter et al., 1991) respectively.

Example VIII

A gene cluster analysis was also done that showed when genes are expressed the highest; time of maximum (TOM) and the lowest; time of minimum (TIM) expression. GO ontology terms were mapped during this analysis and were able to identify precise developmental windows during the FP specification process. These data further confirmed the identity of hESC derived FP tissue and provides insight into genes differentially expressed during FP versus neuroectodermal fate specification.

Example IX

Suppression of DKK-1 Blocks AN Commitment and Enhances FP Generation.

The inventors observation that FP commitment occurs at the expense of AN was strengthened by the global gene expression profiles obtained herein that revealed a rapid down regulation of the Wnt signaling inhibitor DKK-1. DKK-1 was initially identified as a factor expressed in the *xenopus* head organizer that was necessary and sufficient to induce head development (Glinka et al., 1998). DKK-1-mediated inhibition of Wnt signaling during mouse development is essential for anterior brain development (Mukhopadhyay et al., 2001), and FOXA2 knockout embryos show increased expression of DKK-1 in the ectoderm at E7.5 (Kimura-Yoshida et al., 2006). During NSB induction it was observed that DKK-1 transcript levels rise sharply at day 5 from 200 to 5000 fold and then drop back down consistent with the role of DKK-1 as an AN inducer. ELISA assays were done to measure DKK-1 protein levels in the medium and found levels as high as 12 ng/ml (FIGS. 19A and 19B). A drastic reduction of DKK-1 at both mRNA and protein levels was observed as early as 2 days post Sonic C25II treatment (FIGS. 19A-19C). The decrease in DKK-1 expression was sustained and accompanied by decreases in AN markers including PAX6, BF1, OTX1, OTX2, and EMX1.

To test whether DKK-1 is functionally involved during hESC differentiation in FP specification, the inventors added recombinant DKK-1 in combination with Sonic C25II and assessed FP marker expression. While treatment with Sonic C25II alone resulted in a decrease of the AN marker BF1 and an upregulation of FOXA2 (FIGS. 19D and 19F), the addition of DKK-1 caused a decrease in FOXA2 message and protein and a more rapid rise in BF1 transcript (FIGS. 19D and 19F). Conversely, addition of DKK-1 antibody to cells in the NSB protocol caused a significant delay and decrease in the levels of BF1 expression. These data indicated that endogenous DKK-1 levels are critical for AN specification. Next, hESCs were differentiated in the presence of both Sonic C25II and DKK-1 neutralizing antibody. Under these conditions, early transient induction of BF1 transcript at day 5 is suppressed and accompanied by an increase in FOXA2 levels (FIGS. 19E and 19G).

The data obtained during the development of the present inventions revealed a critical window for FP specification during neural induction. With the observation that DKK-1 expression can inhibit FOXA2 expression, the following test was designed to demonstrate whether the addition of DKK-1 blocking antibody extends the window of competency for SHH mediated FP induction. DKK-1 antibody was added at Day 1, Day 5, and Day 9 of differentiation. Exposure to SHH was initiated at the same time points and the expression of FOXA2 was assayed following 9 days of SHH exposure. When DKK-1 was added along with SHH at Day 1 an increase in FOXA2+ cells was observed. However, when added at Day 5 or Day 9, DKK-1 antibody FOXA2+ cells were not observed (FIGS. 19H and 19I). These data indicate that high, early endogenous levels of DKK-1 in the NSB protocol initiated AN commitment and suppressed FP competency. Early treatment with SHH repressed DKK-1 mediated AN specification and enabled differentiation towards FP lineage. However, inhibition of DKK-1 at day 5 of later stages did not extend the temporal window for FP induction.

Example X

Bf1 Expression Represses Fp Commitment.

The inventors discovered that SHH addition to stem cell cultures caused FP differentiation at the expense of AN, mediated at least in part, through inhibition of DKK-1. DKK-1 was shown to specify BF1+ neurectoderm BF1 (Mukhopadhyay et al., 2001), and BF1 is expressed in most neural cells upon NSB induction (FIGS. 4 and 5). To test whether expression of the forkhead factor BF1 directly represses FP competency during neural induction, hESCs were transduced with a BF1 shRNA construct (Fasano et al., 2009; Shen et al., 2006) and clonal lines were derived. BF1 is not highly expressed in hESCs and there was no difference in cell morphology or colony size (FIG. 10)).

Figure 19L:
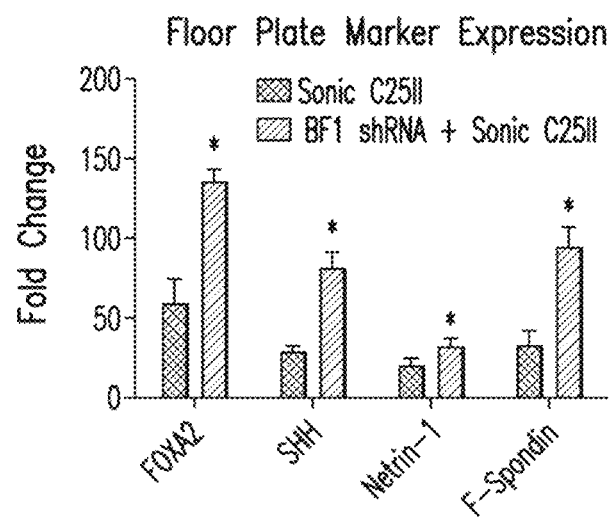
Figure 19M:
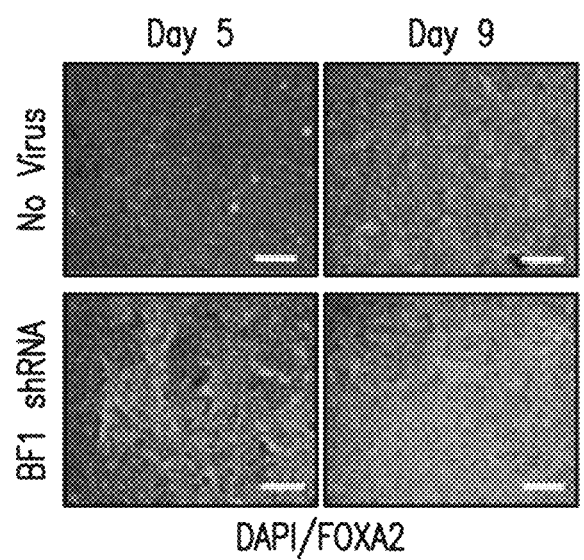
Figure 24E:
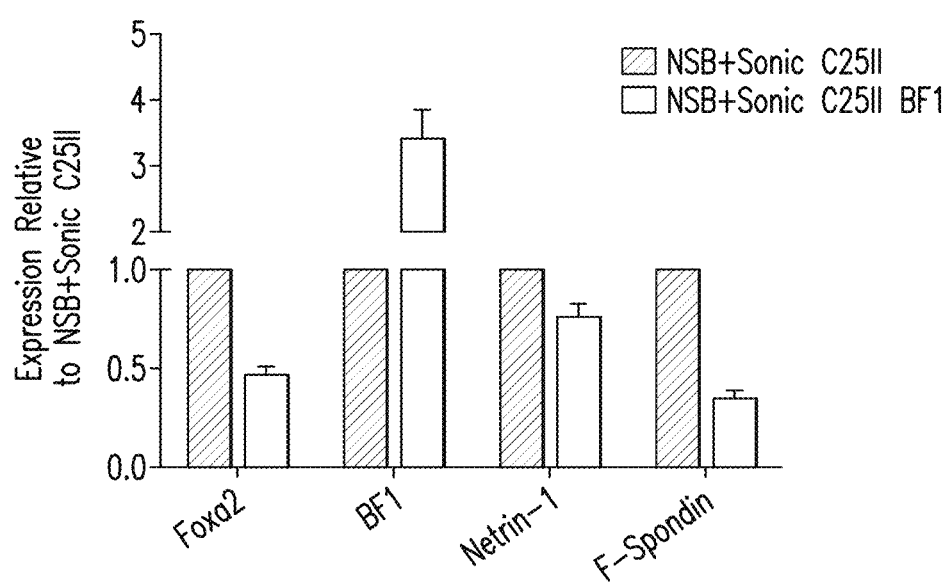

However, upon neural differentiation of hESCs there was a decrease in BF1 protein expression (FIGS. 19J and 19K, right panels) and an 80% decrease in BF1 transcript (FIG. 10). While BF1 loss of function has been associated with deficits in proliferation and cell cycle progression at the neural precursor stage, BF1 knockdown lines at the hESC stage showed cell cycle kinetics comparable to control vector transduced lines (FIG. 24B). BF1 knock-down and control hESCs were then differentiated to FP and subjected to qRT-PCR analysis for a panel of FP markers. After 11 days of differentiation, there was as significant increase in expression of all FP markers in the BF1 shRNA condition (FIG. 19L). Furthermore, immunocytochemical analyses revealed a significant increase in the number of FOXA2+ cells, representing greater than 90% of total cells in the BF1 knockdown hESC line (FIG. 19M).

hESC lines were generated by overexpression of BF1 using a previous described vector (Fasano et al., 2009). These transgenic cells were then cultured under conditions that induced differentiation towards FP lineage. At Day 11, compared to a control GFP expressing clones, there was a reduction of FOXA2+ cells and a decrease in FP marker expression (FIG. 24E). These data demonstrated that BF1 expression inhibited the derivation of hESC derived FP.

Example XI

The A/P Axis of the FP were Altered by Caudalizing Agents.

While certain characteristics are shared among all FP cells, such as FOXA2 and Netrin-1 expression, differences have been reported between different regions of the floor plate along the A/P axis (Placzek and Briscoe, 2005). In particular, recent studies have shown that the midbrain FP expresses markers such as CORIN (Ono et al., 2007) and NOV (Placzek and Briscoe, 2005).

Additionally, the midbrain FP was shown to be neurogenic giving rise to midbrain DA neurons and expressing markers of DA progenitors such as LMX1B and NGN2 (Joksimovic et al., 2009). In contrast both the hindbrain and spinal cord FP appear to be non-neurogenic. To better understand the A/P identity of the FP cells generated from hESCs qRT-PCR analysis for the midbrain FP markers CORIN and NOV was done, as well as analysis of DA progenitor markers LMX1B and EN1. However expression of these markers was not detected. Next gene expression data sets were used to identify differentially regulated transcripts markers that could shed light onto the positional identity of the FP cells.

Elegant studies in the mouse showed that specific enhancer elements direct Shh expression in different regions along the A/P axis of the FP (Jeong et al., 2005). SIX6 were dramatically increased during FP induction compared with NSB control conditions (About 50,000-fold increase in mRNA levels at Day 5 of differentiation; FIG. 23). SIX6 has been shown to bind to the SHH gene at an enhancer region known as SBE2 that directs SHH expression to the most anterior aspect of the ventral brain (Jeong et al., 2008). The inventors contemplated the use of SIX6 as a putative marker of anterior FP identity. Thus SIX6 status of the hESC derived FP was used to mark respecification in response to known caudalizing agents such as FGF8, Wnt-1, and Retinoic Acid. Each of these caudalizing factors was added in combination with SHH and the resulting tissue was assessed for expression of the FP markers FOXA2 and NETRIN-1, the AN marker BF1, and putative anterior FP marker SIX6. FP generation was found not compromised in the presence of caudalizing factors. In fact, the addition of Wnt-1 or RA significantly potentiated FP production based on FOXA2 and Netrin-1 expression (FIGS. 20A and 20B). Enhanced expression of FP markers in the RA and Wnt-1 group was correlated with a dramatic reduction in BF1 expression further supporting the notion that AN commitment counteracts FP induction (FIG. 20B). Strikingly, in all conditions, there was a significant reduction in SIX6 expression, with the Wnt-1 and RA conditions being the most effective at suppressing anterior FP identity.

Example XII

This example shows exemplary experiments designed to determine whether any of the methods (conditions) used herein would lead to an upregulation of midbrain FP and DA progenitor markers. The inventors discovered that different factors had varied effects on marker expression (FIG. 20C). In particular, exposure to Wnt-1 resulted in a significant increase in the midbrain FP markers CORIN and NOV, as well as increases in the DA progenitor markers LMX1B, EN1, and NGN2. Previous studies showed that Wnt signaling was critical in the neurogenic response of the midbrain FP (Joksimovic et al., 2008).

Figure 20D:
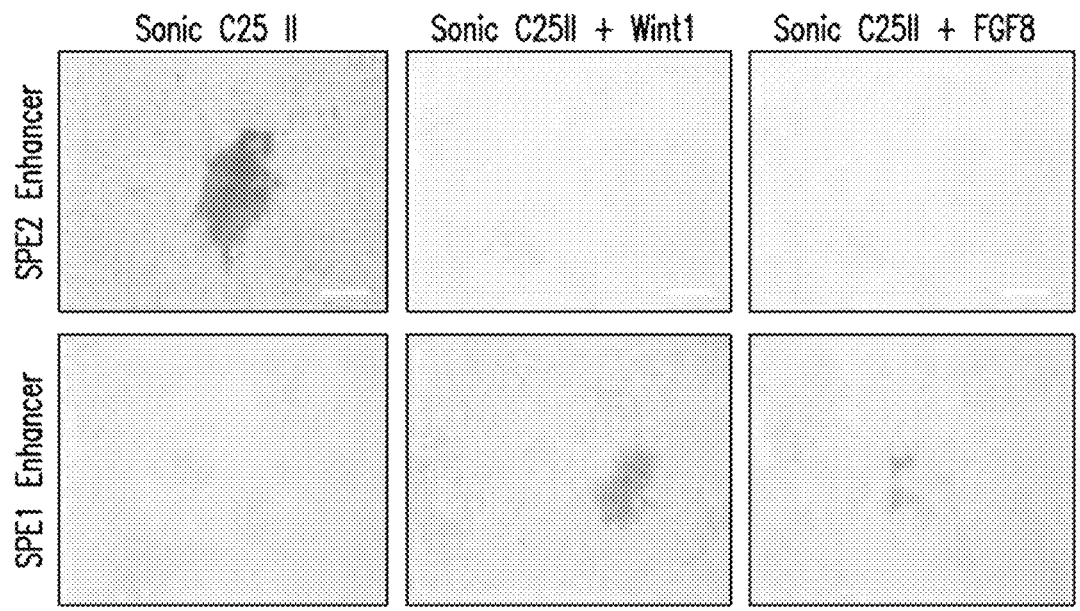
Figure 20E:
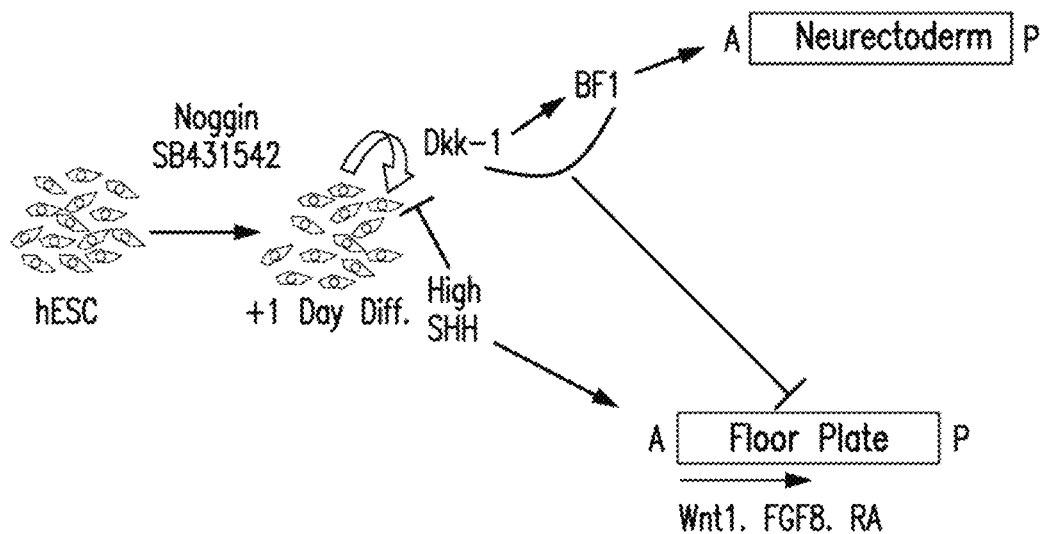

As mentioned above, studies had identified different enhancers that directed SHH expression to different A/P region along ventral axis (Jeong et al., 2008). To further demonstrate that the addition of caudilizing factors respecifies A/P identity of the resulting FP tissue, hESCs derived FP were generated in the presence or absence of Wnt-1 or FGF8, and transfected the resulting tissue with two SHH enhancer constructs driving LacZ expression in different A/P domains of the FP. The SBE1 construct directs SHH expression to the midbrain region of the floor plate while the SBE2 enhancer directs SHH expression to the most anterior region of the FP where Six6 has been shown to bind. In the absence of caudalizing factors (SHH C25II alone), LacZ expression was observed herein following transfection with the SBE2 but not the SBE1 enhancer supporting the hypothesis that hESC derived FP is anterior by default (FIG. 20D). In contrast SBE2 activity was abolished upon treatment with Wnt1 or FGF8 while SBE1 activity was induced under these conditions. These data indicated that FGF8 or Wnt1 treatment induces a shift in FP identity towards a more caudal, midbrain-like identity (FIG. 20D).

In conclusion, our data demonstrated that upon neural differentiation hESCs default towards an AN fate by upregulating DKK-1 and subsequently BF1, and that AN commitment actively represses FP competency in hESC progeny. However, an early high level of SHH reduces DKK-1 levels enabling FP induction at the expense of AN while loss-of-function of DKK-1 or BF1 increases FP production. Human ESC derived FP is anterior by default but were posteriorized in response to caudalizing factors. This is summarized in FIG. 20E.

Example XIII

Cell culture: hESCs (WA-09; passages 35-45), hiPSC lines (iPS-14, iPS-27; passages 20-30), and 16 were maintained at undifferentiated state and differentiated towards CNS lineages using dual-SMAD inhibition protocol described previously. For placode induction protocol (PIP), Noggin was removed at day 3 of differentiation. In some experiments, BMP-4, Noggin, DKK-1, FGF8, SU5402, Wnt-3a, DAPT, CHIR99021, Cyclopamine, Sonic Hedgehog (SHH) and Purmorphamine were added. For differentiation towards trigeminal sensory fate placode clusters were maintained in N2 medium supplemented with ascorbic acid and BDNF. Pituitary fate was induced by exposure to SHH and Purmorphamine from day 7-11 of PIP followed by treatment with DAPT to promote PIT1+ fate.

Example IVX

Cell characterization: qRT-PCR data were normalized to HPRT and are based on 4-6 technical replicates from at least 3 independent experiments. Global gene expression analysis was performed by the MSKCC genomics core according to the specification of the manufacturer (Illumina Human-6 oligonucleotide arrays). Detailed information on the use of primary antibodies for immunocytochemistry and flow analysis and on the electrophysiological analyses is presented in extended supplementary methods.

Example XV

Animal studies: Animal studies were done in accordance with protocols approved by our institutional Animal Care and Use Committee and following NIH guidelines. Hormone producing cells were injected subcutaneously into adult male NOD-SCID IL2Rgc mice and adult 8 male nude rats. Blood was collected at 4-6 weeks after the transplantation followed by ELISA analysis for determining hormone levels. Chick transplantation studies were performed at HH Stage 9-10 and embryos were harvested at HH Stage 20. Injections into pons of adult NOD-SCID IL2Rgc mice were performed by stereotactic surgery.

Example XVI

Statistical analysis: Statistical analysis was performed using GraphPad Prism version 5.0b (GraphPad Software). All data were derived from at least 3 independent experiments. Asterisks mark experimental groups that were significantly different from control groups by a two-tailed Students t-test, or by ANOVA followed by Dunnett test to compare control against multiple independent treatment groups. Data are presented as mean±SEM unless indicated otherwise.

Example XVII

Cells and culture conditions: hESCs (WA-09; XX, passages 35-45), hiPSC lines (iPS-14, iPS-27; passages 20-30) (Chambers et al., 2009), and 16 (Amit and Itskovitz-Eldor, 2002) were cultured on mouse embryonic fibroblasts plated at 12-15,000 cells/cm2 (MEFs, Global Stem) and maintained in medium consisting of DMEM/F12, 20% knockout serum replacement (GIBCO), 0.1 mM b-mercaptoethanol, 6 ng/mL FGF-2 changed daily or in mTeSR™1 (StemCell Technologies, Inc., Vancouver, Canada) on hESC-qualified Matrigel™ (BD Biosciences, San Jose, Calif.) coated plates. Cells were passaged using 6 U/mL of dispase in hESCs media, washed and re-plated at a dilution of 1:10 to 1:15.

Example XVIII

Neural Induction and placode induction: Feeder-free neural induction was carried out as previously described (Chambers et al., 2009). Briefly, hESCs cultures were disaggregated using accutase for 20 minutes, washed using hESCs media and pre-plated on gelatin for 1 hour at 37° C. in the presence of ROCK inhibitor to remove MEFs. The non-adherent hESCs were washed and plated on matrigel at a density of 60,000 cells/cm2 on matrigel (BD) coated dishes in MEF conditioned hESCs media (CM) spiked with 10 ng/mL of FGF-2 and ROCK-inhibitor. The ROCK inhibitor was withdrawn after 24 hours, and hESCs were allowed to expand in CM for 2 days or until they were 95% confluent. The initial differentiation media conditions included knock out serum replacement (KSR) media with 10 μM TGF-β inhibitor (SB431542, Tocris) and 250 ng/mL of Noggin (R&D). Upon day 5 of differentiation, increasing amounts of N2 media (25%, 50%, and 75%) were added to the KSR media every two days while maintaining 500 ng/mL of Noggin and TGF-β inhibitor. Similar results could be obtained when using KSR-free conditions (E6 medium (Chen et al., 2011)) following adjustments in BMP signaling; data not shown). For placode induction, Noggin was removed at day 3 of differentiation. In some experiments, BMP-4 (R&D 50 ng/ml), Noggin (R&D 250 ng/ml), DKK-1 (R&D 100 ng/ml), FGF8 (R&D 50 ng/ml), SU5402 (Tocris 10 μM), Wnt-3a (R&D 50 ng/ml), DAPT (Tocris, 10 μM), CHIR99021 (Stemgent, 3 μM), Cyclopamine (Tocris, 10 μM), Sonic Hedgehog (C25II-R&D 100 ng/ml), and Purmorphamine (Stemgent, 1 μM), were added.

Example IXX

Terminal differentiation of trigeminal sensory neurons: The placode clusters were isolated manually at day 13-17. Clusters were replated onto culture dishes pre-coated with 15 μg/mL polyornithine, 1 μg/mL laminin (Po/Lam) and maintained in N2 medium supplemented with ascorbic acid (AA, 0.2 mM), and BDNF (20 ng/mL). For electrophysiology experiments, NGF and ROCK inhibitor was used in the ACSF, which increases the survival of cells within the chamber.

Example XX

Differentiation of hormone producing cells: During placode induction protocol, Sonic Hedgehog (C25II-R&D 100 ng/ml) and Purmorphamine (Stemgent, 1 μM) were added between days 7-11 of PIP to promote differentiation towards pituitary placode anlage. The cells were maintained without passaging in N2 medium and treated with additional factors such as DAPT (Tocris, 10 μM), between day 13 and day 17 of differentiation to induce PIT1+ and GATA2+ precursor cells (see FIG. 39A).

Example XXI

Quantitative Real-time PCR: Total RNA was extracted using an RNeasy kit (Qiagen) or Trizol. For each sample, 1 μg of total RNA was DNAase treated and reverse transcribed using the Quantitect RT kit (Qiagen). Amplified material was detected using Taqman probes and PCR mix (ABI) on a Mastercycler RealPlex2 (Eppendorf). All results were normalized to a HPRT housekeeping gene control and are based on 4-6 technical replicates from each of at least 3 independent experiments.

Example XXII

Microarray Analysis: Total RNA was isolated at day 1, 3, 5, 7, 9 and 11 of differentiation from both control (NSB) and PIP using Trizol (Invitrogen). Three biological replicates per time point were used. All samples were processed by the MSKCC Genomics Core Facility and hybridized on Illumina Human-6 oligonucleotide arrays. Quantile Normalization and model-based expression measurements were performed by using the Partek Genomic Suite (Partek GS) (Downey, 2006). A pair-wise comparison between NSB and PIP was performed. Genes found to have an adjusted p-value <0.001 and a fold change greater than 2 were considered significant. Expression differences are reported as the log 2 of the fold change. Gene Ontology enrichment was determined by entering gene lists into the Database for Annotation, Visualization, and Integrated Discovery (DAVID; david.niaid.nih.gov) (Dennis et al., 2003; Huang et al., 2009).

Example XXIII

Microscopy, antibodies, and flow cytometry: Cells were fixed using 4% paraformaldehyde for 15 minutes, washed with PBS, permeabilized using 0.3% Triton X in PBS, and blocked using 1% BSA. Primary antibodies used for microscopy included PAX6 (Covance, DSHB), TUJ1 (Covance), BRN3A (Chemicon), AP2a (DSHB), HNK1 (Sigma), PAX3

(DSHB), SIX1 (ABR, Atlas), ISL1 (DSHB), PERIPHERIN (Santa Cruz), GSU (gift A. McNeilly), CRYAB (Chemicon), DACH1 (Proteintech), EYA1 (gift Kawakami), E-CADHERIN (Abcam), FSH (gift A. McNeilly), GATA2 (Abcam), chick GFP (Abcam), hNCAM (Santa Cruz), GLUTAMATE (Sigma), KRT14 (Labvision), SIX6 (Atlas), LHX3 (Abcam), OVOL2 (Aviva), TFAP2A (DSHB), FOXG1 (gift E. Lai), hCA (Stem Cells), and Ki67 (Sigma). Appropriate Alexa 488, Alexa 568, Alexa 647 secondary antibodies (Molecular Probes) and/or DAPI counterstaining was used for visualization. For Flow Cytometry, cells were mechanically dissociated after exposure to accutase for 20 min at 25° C. To eliminate dead cell populations in FACS analysis, we used DAPI or 7-AAD according to manufacturer's recommendation. Cells were analyzed using FACScan (Becton Dickinson) and FlowJo software (Tree Star, Inc.).

Example IVXX

Electrophysiology: The clusters were seeded on glass slides. Slides are recovered in artificial CSF (ACSF) containing the following: 119 mM NaCl, 2.5 mM KCl, 26.2 mM NaHCO$_3$, 2.5 mM CaCl2, 1.3 mM MgCl2, 1 mM NaH2PO4, and 20 mM glucose (pH 7.4, osmolarity 300 mOsm), bubbled with 5% CO2/95% O2 at room temperature for a minimum of 1 h before recording. Slices were constantly perfused with ACSF during recordings. Whole-cell recordings were made from the neurons migrating from the clusters, which tended to be more mature than cells in the center of the clusters. Patch electrodes (5-8 M) were filled with intracellular solution containing the following: 130 mM K-gluconate, 16 mM KCl, 2 mM MgCl2, 10 mM HEPES, 0.2 mM EGTA, 4 mM Na2-ATP, and 0.4 mM Na3-GTP (pH 7.25, osmolarity 290 mOsm). The membrane potential of each cell was identified shortly after rupturing the patch and periodically during the course of the experiment to ensure there was no significant deterioration of the health of the cell. Spontaneous miniature synaptic currents were recorded in voltage-clamp mode held at −60 mV. Depolarizing and hyperpolarizing current steps (0.2 Hz; duration 500 ms) were applied to the cells to help characterize their electrophysiological profile. All parameters were measured for a minimum of three trials for each cell, and the average value was calculated.

Example XXV

In vivo transplantation: All animal experiments were done in accordance with protocols approved by our institutional Animal Care and Use Committee and following NIH guidelines for animal welfare. Murine subcutaneous injections of hormone producing cells: For subcutaneous transplantations, 1×10$^6$ hESC-derived pituitary cells (at day 16 and day 32 of differentiation) in 0.5 ml of matrigel or matrigel alone (as controls) were injected into adult 8-weeks-old male NOD-SCID IL2Rgc null strain mice and adult 8-weeks-old male nude rats (Taconic). The whole blood collections or retrorbital blood collection per RARC guidelines were performed a week, 4 weeks and 6 weeks after the transplantations for hormone measurements from the plasma. Animals were sacrificed at 2 days, 1 week, and 6 weeks after transplantation and processed for histology. Matrigel plugs from adult mice were fixed in 4% paraformaldehyde and cryosectioned for immunohistochemical analysis.

Example XXVI

Transplantation into chick trigeminal ganglion anlage: For in ovo transplantation, fertile eggs (Charles River) were incubated at 37° C. in a humidified incubator. The GFP hESC-placode derived neurons were transplanted into the prospective trigeminal ganglion of HH Stage 9-10 chick embryos. Eggs are incubated until HH Stage 20. The chick embryo was sectioned transverse at the level of the midbrain neural tube to visualize the trigeminal ganglia.

Example XXVII

Transplantation into mouse pons region: The GFP expressing hESC derived trigeminal neuron/progenitor cells at day 22 of differentiation were transplanted into the right pons of nine NOD-SCID IL2Rgc null strain mouse by using stereotactic surgery; the coordinates are Lambda: −0.77, Bregma: −4.16, D/V: 4.65 and M/L: +0.5 (Right). For each animal 200,000 cells were transplanted in a 100K/µl density. Tissues from chick embryos and adult mice were fixed in 4% paraformaldehyde and cryosectioned for immunohistochemical analysis.

Example XXVIII

In vitro and in vivo analysis of ACTH and GH release: Hormone producing hESC-derived cells were analyzed at day 36 of differentiation. The cells were rinsed with HBSS and subsequently exposed to fresh HBSS (500 µl at 37° C. for 10 min). The supernatant was subsequently collected and subjected to ELISA using the ACTH LumELISA kit (Calbiotech). ACTH was also readily detected from conditioned medium subjected to ELISA. For in vivo studies, blood samples from mice and rats engrafted with hESCderived anterior pituitary cells and matrigel-only controls were collected into K2 EDTA-treated BD Microtainer MAP (BD) at 8 a.m. under conditions to minimize stress. Plasma was isolated by centrifugation for 20 min at 2,000 g using a refrigerated centrifuge. The supernatant was collected for ELISA to measure hormone levels. GH levels were measured similarly both in vitro and in vivo after transplantation using the Human Growth Hormone ELISA kit (Calbiotech).

Example XXIX

PIP protocol using E8/E6 cell culture media: E8/E6 cell culture media (Essential8™/Essential6™, Nat Methods. 2011 May; 8(5):424-9) comprises the ingredients DMEM/F12, ascorbic acid, selenium, insulin, NaHCO$_3$, transferrin, FGF2 and TGFβ. The media differs from KSR media described herein in that E8/E6 does not include an active BMP or Wnt ingredient. The present example describes a modified PIP protocol that utilizes the BMP deficient E8/E6 media.

A Six1 knock in GFP reporter cell line (SIX1::H2B-GFP) was developed to monitor when cells have been transformed to a placode fate. (FIGS. 41A-41E). Culturing the reporter cells in E8/E6 media according to the KSR PIP protocol described herein, in which cells were cultured in media comprising the SMAD inhibitors SB431542 and LDN193189, wherein LDN193189 was withdrawn after 2 days of culture, yielded low levels of placode cells after 11 days of culture. (FIGS. 42A-42B). BMP4, which is not present in E8/E6 media, is necessary for cells to differentiate into non-neural ectoderm and placode, as evidenced by expression of the marker AP2. (FIGS. 43A-43C). Culturing the SIX1::H2B-GFP reporter cells in E8/E6 comprising SB431542 and BMP4, wherein BMP4 was withdrawn after 3 days of culture, resulted in placode development when BMP4 was present in the media at a concentration of 5 ng/ml. However, at a concentration of 20 ng/ml, or culture with 5 ng/ml of BMP4 for more than 5 days, resulted in the induction of non-neural ectoderm (skin precursors) instead of placode precursors. (FIGS. 44A-44C). Culturing the SIX1::H2B-GFP cells in E8/E6 with SB431542 and 5 ng/ml BMP4, wherein BMP4 was withdrawn after 3 days of culture (compared to withdrawal after 1 or 2 days of culture), produced the highest yield of placode precursors after 6 total days of culture in the E8/E6 media. (FIGS. 45A-45B). Culturing the cells according to the modified PIP protocol (PIP-E6, wherein BMP4 is present at a concentration of 5 ng/ml and is withdrawn after day 3) resulted in the induction of various placode markers after 11 days of culture. It also resulted in the loss of pluripotency (OCT4), lack of muscle (MyoD) or general mesoderm (Brachyury) induction, and the lack of endoderm (SOX17) or neural crest (SOX10) induction. (FIGS. 46 and 47). Although the yield of induced placode cells was low using the PIP-E6 protocol, the induction was highly consistent compared to the KSR PIP protocol. (FIG. 48).

Example XXX

Modified PIP-E6 to induce trigeminal placode as a default: Unlike KSR, E8/E6 does not include any Wnt active compounds. In order to make the trigeminal placode fate the default fate when culturing using the PIP-E6 protocol, PIP-E6 was modified by adding CHIR (Wnt activator) to the culture protocol. Including CHIR in the media during days 2-4 of the PIP-E6 protocol resulted in the induction of trigeminal placodes as the default placode. (FIGS. 49A-49B). FIG. 50 depicts the pituitary, lens and trigeminal placodes that can be induced using the PIP-E6 culture protocol.

Example XXXI

Identification of trigeminal placode markers GD2 and CD57 (HNK1): Six1::GFP marker cells were cultured according to the PIP-E6 protocol, as described by FIG. 49. After 11 days of culture, the following steps were performed:
 Cells were replated at a concentration of 50,000 cells/96 well
 Cells were allowed to attach to plates during a 4 h attachment phase
 Live cell staining was conducted using BD Lyoplate
 242 human cell surface antigens were detected (mostly CD proteins)
 Cells were fixed after 2nd antibody staining
 Cells were imaged using Operetta the following day
 The % of Six1::GFP+/Marker+ (Alexa647+) and Marker+ (Alexa647+) was quantified
Surface markers that enrich for trigeminal placode are shown in FIG. 51. Marker GD2 was identified as a marker for trigeminal placode and subsequently used for isolation of trigeminal placode from human ESC/ipSC cells cultured under conditions described herein. GD2 is a disialoganglioside expressed on neural tissue including tumors of neuroectodermal origin such as neuroblastoma. The structure of GD2 is shown in FIG. 52. FIGS. 53A-53B show the co-expression of GD2 and the placode marker SIX1::GFP in trigeminal placode cells. FIGS. 54A-54B show positive control cells in which CD24 and SIX1::GFP are expressed in all neural cells, including trigeminal placode.
CD57 (HNK1) was also identified as a marker that may be useful for identifying and isolating trigeminal placode. (FIG. 55). Co-expression of CD57 (HNK1) and SIX1::GFP in placode cells is shown in FIGS. 56A-56B.

FIG. 57 describes a PIP-E6 protocol that can be used to generate trigeminal placode as the default placode fate, wherein placodes are isolated and sorted based on their expression of the GD2 marker. Under these culture conditions, cells are cultured in E8/E6 media supplemented with SB431542, BMP4 and CHIR99021 (Wnt), wherein BMP is withdrawn after 3 days of culture, and CHIR99021 (Wnt) is included in the media from about days 1.5-3.5. After sorting, the cells were cultured in a media to support trigeminal differentiation (in NBM/B27 media supplemented with BDNF, GDNF, NGF, and DAPT (a Notch inhibitor)). FIG. 58 shows the morphology of GD2 positive trigeminal cells after 28 days of differentiation (14 days after GD2 sorting) compared to GD2 negative cells. FIG. 59 shows the trigeminal neurons after 48 days of differentiation (33 days after GD2 sorting).

Example XXXII

High throughput screen for compounds that promote placode induction: SIX1::GFP cells were cultured according to the PIP-E6 protocol. 1280 test compounds were screened for their ability to enhance placode induction. Each test compound was added to the cell culture media at day 3, and cells were imaged to determine the level of placode induction at day 6. (FIG. 60). FIG. 61 shows that results of the screen. Three candidate compounds were identified as promoting placode induction: BRL-54443, Phenanthroline monohydrate, and Parthenolide, (FIG. 61 and FIG. 62).

Example XXXIII

Induction of anterior pituitary gland cells: Pituitary placode cells were induced by culturing SIX1::GFP cells according to the PIP-E6 protocol, wherein pituitary factors SHH, FGF8, FGF10 and/or hypothalamus CM were supplemented in the culture media from days 6-15. (FIG. 63A), As shown in FIG. 63B, pituitary placode was induced as evidenced by expression of the markers Pitx1, Pitx2, Lhx3 and Lhx4. The pituitary markers were expressed 10 to 100 fold greater than in placodes induced using the PIP-E6 protocol alone without supplementation. After differentiation to day 30 using the modified PIP-E6 protocol, pituitary placode cells differentiated into hormone expressing cells corresponding to derivatives of all three pituitary precursor lineages. (FIG. 64 and FIG. 65). The proportion of each of the three precursor lineages were modulated by treating the cells with an inhibitor of Notch signaling (DAPT), and to a lesser extent by CHIR (activator of Wnt). (FIG. 65).
The hormone expressing cells were responsive to external stimuli. In particular, in response to stimulation with somatocrinin, the cells released growth hormone (GH), and in response to nafarelin the cells released follicle stimulating hormone (FSH). (FIG. 66). The pituitary cells induced according to the modified PIP-E6 protocol were cultured with BMP2 and/or FGF8 to determine whether such agents could manipulate the yield of pituitary cells expressing the subtype specific markers Tbx19, Pit1, GATA2, POMC1, GH1, FDHM, and LHB. BMP2 was able to increase the yield of several subtype specific markers. (FIG. 67).

Example XXXIV

Induction of anterior pituitary gland cells: SIX1::GFP hPSCs were cultured according to a modified PIP-E6 protocol, wherein pituitary factors such as FGF8, FGF10 or SHH, etc., were included in the culture media from days 6-14. Cells were sorted based on expression of SIX1::GFP, and were replated at a concentration of 10,000 cells/cm² on PO/L/F, and were incubated with small molecule/growth factors for 2 weeks. (FIG. 68). As shown in FIG. 69, FGF2 and FGF8 may increase the number of putative pituitary stem cells, as evidenced by expression of Ki67 and Sox2. (FIG. 69).

Example XXXV

Grafting in vitro differentiated mixtures of pituitary hormone releasing cells into rat: Mixtures of pituitary hormone releasing cells derived in vitro from human PSCs using the modified PIP-E6 protocol described in the preceding two examples were grafted into unlesioned adult rat brain adjacent to the pituitary/hypothalamic site. The grafted cells survived and increased the level of detectable ACTH in the grafted animals compared to control. (FIG. 70). When the mixture of induced pituitary hormone releasing cells was grafted into hypophysectomized rats, ACTH levels appeared to increase in 2 out of 3 grafted animals. (FIG. 71).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in cellular biology, neurobiology, cancer cell biology, molecular biology, biochemistry, chemistry, organic synthesis, or related fields are intended to be within the scope of the following claims.

What is claimed is:

1. A method for inducing differentiation of pluripotent stem cells or multipotent stem cells, comprising:
   a) contacting a plurality of pluripotent stem cells or multipotent stem cells with an inhibitor of Small Mothers Against Decapentaplegic (SMAD) protein signaling; and
   b) contacting the cells with a bone morphogenetic protein (BMP) for up to about 3 days;
   wherein the cells are contacted with the inhibitor of SMAD protein signaling and the BMP in amounts effective to obtain differentiated cells expressing detectable levels of SIX1 and PAX6.

2. The method of claim 1, wherein the method further comprises at least one of the following:
   (i) the cells are contacted with the inhibitor of SMAD protein signaling for up to about 11 days;
   (ii) the cells are contacted with an activator of Wingless (Wnt) signaling in an amount effective to produce cells expressing detectable levels of SIX1 and PAX3;
   (iii) the cells are contacted with an activator of sonic hedgehog (SHH) signaling in an amount effective to produce cells expressing detectable levels of SIX1 and PITX1; and
   (iv) the cells are contacted with the BMP in an amount effective to produce cells expressing detectable levels of SIX1 and PITX3.

3. The method of claim 2, wherein the cells expressing SIX1 and PAX3 are trigeminal placode cells.

4. The method of claim 3, wherein the cells expressing SIX1 and PAX3 further express a detectable level of GD2, CD57, or a combination thereof.

5. The method of claim 4, further comprising isolating the cells expressing the detectable level of GD2, CD57, or a combination thereof from the plurality of cells.

6. The method of claim 2, wherein the cells expressing SIX1 and PITX1 are pituitary placode cells.

7. The method of claim 2, further comprising contacting the cells with at least one activator of FGF signaling in an amount effective to produce the cells expressing detectable levels of SIX1 and PITX1.

8. The method of claim 2, wherein the cells expressing SIX1 and PITX3 are lens placode cells.

9. A method of inducing differentiation of cells expressing SIX1 and PAX6, comprising contacting a plurality of cells expressing SIX1 and PAX6 with
   (i) an activator of Wnt signaling in an amount effective to obtain differentiated cells expressing detectable levels of SIX1 and PAX3;
   (ii) an activator of SHE signaling in an amount effective to obtain differentiated cells expressing detectable levels of SIX1 and PITX1; or
   (iii) a BMP in an amount effective to obtain differentiated cells expressing detectable levels of SIX1 and PITX3.

10. The method of claim 9, further comprising
    culturing the cells expressing SIX1 and PAX3 under conditions favoring differentiation of trigeminal placode cells into trigeminal neurons;
    culturing the cells expressing SIX1 and PITX1 under conditions favoring differentiation of pituitary placode cells-into pituitary cells selected from the group consisting of gonadotrophs, corticotrophs and somatotrophs; or
    culturing the cells expressing SIX1 and PAX3 under conditions favoring differentiation of lens placode cells into lens fibers.

11. The method of claim 9, wherein the cells expressing SIX1 and PAX6 further express a detectable level of TFAP2A.

12. The method of claim 9, wherein the cells expressing SIX1 and PAX3 are trigeminal placodes; wherein the cells expressing SIX1 and PITX1 are pituitary placodes; and wherein the cells expressing SIX1 and PITX3 are lens placode cells.

13. The method of claim 1, wherein the inhibitor of SMAD protein signaling blocks phosphorylation of an anaplastic lymphoma kinase (ALK).

14. The method of claim 1, wherein the inhibitor of SMAD protein signaling is 4-[4-(1,3-benzodioxol-5-yl)-5-(2-pyridinyl)-1H-imidazol-2-yl] benzamide (SB431542).

* * * * *

SEQUENCE LISTING

```
<160> NUMBER OF SEQ ID NOS: 2

<210> SEQ ID NO 1
<211> LENGTH: 240
<212> TYPE: PRT
<213> ORGANISM: Mus musculus

<400> SEQUENCE: 1

Met Glu Arg Cys Pro Ser Leu Gly Val Thr Leu Tyr Ala Leu Val Val
1               5                   10                  15

Val Leu Gly Leu Arg Ala Ala Pro Ala Gly Gly Gln His Tyr Leu His
            20                  25                  30

Ile Arg Pro Ala Pro Ser Asp Asn Leu Pro Leu Val Asp Phe Thr Leu
        35                  40                  45

Ile Glu His Pro Asp Pro Ile Phe Asp Pro Lys Glu Lys Asp Leu Asn
    50                  55                  60

Glu Thr Leu Leu Arg Ser Leu Leu Gly Gly His Tyr Asp Pro Gly Phe
65                  70                  75                  80

Met Ala Thr Ser Pro Pro Glu Asp Arg Pro Gly Gly Gly Gly Gly Pro
                85                  90                  95

Ala Gly Gly Ala Glu Asp Leu Ala Glu Leu Phe Thr Asp Gln Leu Leu
            100                 105                 110

Arg Gln Arg Pro Ser Gly Ala Met Pro Ser Glu Ile Lys Gly Leu Glu
        115                 120                 125

Phe Ser Glu Gly Leu Ala Gln Gly Lys Lys Gln Arg Leu Ser Lys Lys
    130                 135                 140

Leu Arg Arg Lys Leu Gln Met Trp Leu Trp Ser Gln Thr Phe Cys Pro
145                 150                 155                 160

Val Leu Tyr Ala Trp Asn Asp Phe Thr Leu Gly Ser Arg Phe Trp Pro
                165                 170                 175

Arg Tyr Val Lys Val Gly Ser Cys Phe Ser Lys Arg Ser Cys Ser Val
            180                 185                 190

Pro Glu Gly Met Val Cys Lys Pro Ser Lys Ser Val His Leu Thr Val
        195                 200                 205

Leu Arg Trp Arg Cys Gln Arg Arg Gly Gly Gln Arg Cys Gly Trp Ile
    210                 215                 220

Pro Ile Gln Tyr Phe Thr Pro Ile Ile Ser Glu Cys Lys Cys Ser Cys
225                 230                 235                 240
```

```
<210> SEQ ID NO 2
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctctctgctc ggccccctca cctccagtct ggtggacttg gggtcctaag tggggagg        58
```